United States Patent
Hannum

(10) Patent No.: US 10,964,409 B2
(45) Date of Patent: Mar. 30, 2021

(54) METHODS AND PROCESSES FOR NON-INVASIVE ASSESSMENT OF GENETIC VARIATIONS

(71) Applicant: SEQUENOM, INC., San Diego, CA (US)

(72) Inventor: Gregory Hannum, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 1123 days.

(21) Appl. No.: 14/505,423

(22) Filed: Oct. 2, 2014

(65) Prior Publication Data

US 2015/0100244 A1    Apr. 9, 2015

Related U.S. Application Data

(60) Provisional application No. 61/887,081, filed on Oct. 4, 2013.

(51) Int. Cl.
| | | |
|---|---|---|
| *G16B 30/00* | (2019.01) | |
| *G16B 40/00* | (2019.01) | |
| *G16B 20/10* | (2019.01) | |

(52) U.S. Cl.
CPC .............. *G16B 30/00* (2019.02); *G16B 20/10* (2019.02); *G16B 40/00* (2019.02)

(58) Field of Classification Search
CPC ........... G06F 19/22; G06F 19/18; G06F 19/24
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,075,212 A | 12/1991 | Rotbart |
| 5,091,652 A | 2/1992 | Mathies et al. |
| 5,432,054 A | 7/1995 | Saunders et al. |
| 5,445,934 A | 8/1995 | Fodor |
| 5,670,325 A | 9/1997 | Lapidus et al. |
| 5,720,928 A | 2/1998 | Schwartz et al. |
| 5,786,146 A | 7/1998 | Herman et al. |
| 5,928,870 A | 7/1999 | Lapidus et al. |
| 5,939,598 A | 8/1999 | Kucherlapati et al. |
| 6,015,714 A | 6/2000 | Baldarelli et al. |
| 6,090,550 A | 7/2000 | Collinge et al. |
| 6,100,029 A | 8/2000 | Lapidus et al. |
| 6,214,558 B1 | 4/2001 | Shuber et al. |
| 6,214,560 B1 | 4/2001 | Yguerabide et al. |
| 6,235,475 B1 | 5/2001 | Brenner et al. |
| 6,258,540 B1 | 7/2001 | Lo et al. |

(Continued)

FOREIGN PATENT DOCUMENTS

| | | |
|---|---|---|
| WO | WO 00/006770 | 2/2000 |
| WO | WO 01/032887 | 5/2001 |

(Continued)

OTHER PUBLICATIONS

Chen et al. (Prenatal Diagnosis. 2013; 33(6): 584-590 and Supp pp. 1-6). (Year: 2013).*

(Continued)

*Primary Examiner* — Olivia M. Wise
(74) *Attorney, Agent, or Firm* — Fish & Richardson P.C.

(57) ABSTRACT

Provided herein are methods, processes, systems and machines for non-invasive assessment of genetic variations.

29 Claims, 13 Drawing Sheets

(56) References Cited

U.S. PATENT DOCUMENTS

| | | |
|---|---|---|
| 6,263,286 B1 | 7/2001 | Gilmanshin et al. |
| 6,403,311 B1 | 6/2002 | Chan |
| 6,566,101 B1 | 5/2003 | Shuber et al. |
| 6,617,133 B1 | 9/2003 | Deamer |
| 6,772,070 B2 | 8/2004 | Gilmanshin et al. |
| 6,818,395 B1 | 11/2004 | Quake et al. |
| 6,927,028 B2 | 8/2005 | Dennis et al. |
| 6,936,422 B2 | 8/2005 | Akeson et al. |
| 7,005,264 B2 | 2/2006 | Su et al. |
| 7,169,560 B2 | 1/2007 | Lapidus et al. |
| 7,279,337 B2 | 10/2007 | Zhu |
| 7,282,337 B1 | 10/2007 | Harris |
| 7,947,454 B2 | 5/2011 | Akeson et al. |
| 7,960,105 B2 | 6/2011 | Schwartz et al. |
| 7,972,858 B2 | 7/2011 | Meller et al. |
| 8,688,388 B2 | 4/2014 | Dzakula et al. |
| 2001/0014850 A1 | 8/2001 | Gilmanshin et al. |
| 2001/0049102 A1 | 12/2001 | Huang et al. |
| 2002/0006621 A1 | 1/2002 | Bianchi |
| 2002/0045176 A1 | 4/2002 | Lo et al. |
| 2002/0110818 A1 | 8/2002 | Chan |
| 2002/0119469 A1 | 8/2002 | Shuber et al. |
| 2002/0164629 A1 | 11/2002 | Quake et al. |
| 2003/0013101 A1 | 1/2003 | Balasubramanian |
| 2003/0082600 A1 | 5/2003 | Olek et al. |
| 2003/0180779 A1 | 9/2003 | Lofton-Day et al. |
| 2003/0207326 A1 | 11/2003 | Su et al. |
| 2003/0232346 A1 | 12/2003 | Su |
| 2004/0081993 A1 | 4/2004 | Cantor et al. |
| 2004/0110208 A1 | 6/2004 | Chan et al. |
| 2004/0137470 A1 | 7/2004 | Dhallan et al. |
| 2005/0019784 A1 | 1/2005 | Su et al. |
| 2005/0095599 A1 | 5/2005 | Pittaro et al. |
| 2005/0112590 A1 | 5/2005 | Boom et al. |
| 2005/0147980 A1 | 7/2005 | Berlin et al. |
| 2005/0164241 A1 | 7/2005 | Hahn et al. |
| 2005/0227278 A1 | 10/2005 | Wall |
| 2005/0287592 A1 | 12/2005 | Kless |
| 2006/0046258 A1 | 3/2006 | Lapidus et al. |
| 2006/0063171 A1 | 3/2006 | Akeson et al. |
| 2006/0068440 A1 | 3/2006 | Chan et al. |
| 2006/0252071 A1 | 11/2006 | Lo et al. |
| 2007/0065823 A1 | 3/2007 | Dressman et al. |
| 2007/0202525 A1 | 8/2007 | Quake et al. |
| 2008/0020390 A1 | 1/2008 | Mitchell et al. |
| 2008/0070792 A1 | 3/2008 | Stoughton et al. |
| 2008/0081330 A1 | 4/2008 | Kahvejian et al. |
| 2008/0138809 A1 | 6/2008 | Kapur et al. |
| 2008/0187915 A1 | 8/2008 | Polonsky et al. |
| 2008/0233575 A1 | 9/2008 | Harris |
| 2009/0026082 A1 | 1/2009 | Rothberg et al. |
| 2009/0029377 A1 | 1/2009 | Lo et al. |
| 2009/0075252 A1 | 3/2009 | Harris |
| 2009/0129647 A1 | 5/2009 | Dimitrova et al. |
| 2009/0191565 A1 | 7/2009 | Lapidus et al. |
| 2009/0197257 A1 | 8/2009 | Harris |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0112575 A1 | 5/2010 | Fan et al. |
| 2010/0112590 A1 | 6/2010 | Lo et al. |
| 2010/0138165 A1 | 6/2010 | Fan et al. |
| 2010/0151471 A1 | 6/2010 | Faham et al. |
| 2010/0216151 A1 | 8/2010 | Lapidus et al. |
| 2010/0216153 A1 | 8/2010 | Lapidus et al. |
| 2010/0109197 A1 | 9/2010 | Stoddart et al. |
| 2010/0261285 A1 | 10/2010 | Goldstein et al. |
| 2010/0310421 A1 | 12/2010 | Oliver et al. |
| 2010/0330557 A1 | 12/2010 | Yakhini et al. |
| 2011/0086769 A1 | 4/2011 | Oliphant et al. |
| 2011/0159601 A1 | 6/2011 | Golovchenko et al. |
| 2011/0171634 A1 | 7/2011 | Xiao et al. |
| 2011/0174625 A1 | 7/2011 | Akeson et al. |
| 2011/0177498 A1 | 7/2011 | Clarke et al. |
| 2011/0177517 A1 | 7/2011 | Rava et al. |
| 2011/0201507 A1 | 8/2011 | Rava et al. |
| 2011/0224087 A1* | 9/2011 | Quake .................. C12Q 1/6806 506/7 |
| 2011/0230358 A1 | 9/2011 | Rava |
| 2011/0288780 A1 | 11/2011 | Rabinowitz et al. |
| 2011/0294699 A1 | 12/2011 | Lee et al. |
| 2011/0312503 A1 | 12/2011 | Chuu et al. |
| 2011/0319272 A1 | 12/2011 | Fan et al. |
| 2012/0046877 A1 | 2/2012 | Hyland et al. |
| 2012/0122701 A1 | 5/2012 | Ryan et al. |
| 2012/0165203 A1 | 6/2012 | Quake et al. |
| 2012/0184449 A1 | 7/2012 | Hixson et al. |
| 2012/0214678 A1 | 8/2012 | Rava et al. |
| 2012/0264115 A1 | 10/2012 | Rava |
| 2012/0270212 A1 | 10/2012 | Rabinowitz et al. |
| 2012/0270739 A1 | 10/2012 | Rava et al. |
| 2013/0012399 A1 | 1/2013 | Meyers |
| 2013/0022977 A1 | 1/2013 | Lapidus et al. |
| 2013/0034546 A1 | 2/2013 | Rava et al. |
| 2013/0085681 A1 | 4/2013 | Deciu et al. |
| 2013/0096011 A1 | 4/2013 | Rava et al. |
| 2013/0130921 A1 | 5/2013 | Gao et al. |
| 2013/0130923 A1 | 5/2013 | Ehrich et al. |
| 2013/0150253 A1 | 6/2013 | Deciu et al. |
| 2013/0196317 A1 | 8/2013 | Lapidus et al. |
| 2013/0237431 A1 | 9/2013 | Lo et al. |
| 2013/0245961 A1 | 9/2013 | Lo et al. |
| 2013/0261983 A1 | 10/2013 | Dzakula et al. |
| 2013/0288244 A1 | 10/2013 | Deciu et al. |
| 2013/0304392 A1 | 11/2013 | Deciu et al. |
| 2013/0309666 A1 | 11/2013 | Deciu et al. |
| 2013/0325360 A1 | 12/2013 | Deciu et al. |
| 2013/0338933 A1 | 12/2013 | Deciu et al. |
| 2014/0100792 A1 | 4/2014 | Deciu et al. |
| 2014/0180594 A1 | 6/2014 | Kim et al. |
| 2014/0235474 A1 | 8/2014 | Tang et al. |
| 2014/0242588 A1 | 8/2014 | Van Den Boom et al. |
| 2014/0322709 A1 | 10/2014 | Lapidus et al. |
| 2015/0005176 A1 | 1/2015 | Kim et al. |
| 2015/0347676 A1 | 12/2015 | Zhao et al. |
| 2016/0034640 A1 | 2/2016 | Zhao et al. |
| 2016/0110497 A1 | 4/2016 | Dzakula et al. |

FOREIGN PATENT DOCUMENTS

| | | |
|---|---|---|
| WO | WO 02/042496 | 5/2002 |
| WO | WO 03/000920 | 1/2003 |
| WO | WO 03/106620 | 12/2003 |
| WO | WO 05/023091 | 3/2005 |
| WO | WO 06/056480 | 6/2006 |
| WO | WO 2006/097049 | 9/2006 |
| WO | WO 07/140417 | 12/2007 |
| WO | WO 07/147063 | 12/2007 |
| WO | WO 08/121828 | 10/2008 |
| WO | 2008157264 A2 | 12/2008 |
| WO | WO 2008/157264 | 12/2008 |
| WO | WO 09/007743 | 1/2009 |
| WO | WO 09/032779 | 3/2009 |
| WO | WO 09/032781 | 3/2009 |
| WO | WO 09/046445 | 4/2009 |
| WO | WO 10/004265 | 1/2010 |
| WO | WO 10/033578 | 3/2010 |
| WO | WO 10/033639 | 3/2010 |
| WO | WO 10/056728 | 5/2010 |
| WO | WO 10/059731 | 5/2010 |
| WO | WO 10/065470 | 6/2010 |
| WO | WO 10/115016 | 10/2010 |
| WO | WO 11/034631 | 3/2011 |
| WO | WO 11/038327 | 3/2011 |
| WO | WO 11/050147 | 4/2011 |
| WO | WO 11/057094 | 5/2011 |
| WO | WO 11/087760 | 7/2011 |
| WO | WO 11/090556 | 7/2011 |
| WO | WO 11/090559 | 7/2011 |
| WO | WO 11/091063 | 7/2011 |
| WO | WO 11/102998 | 8/2011 |
| WO | WO 11/143659 | 11/2011 |
| WO | WO 11/146632 | 11/2011 |
| WO | WO 12/012703 | 1/2012 |

(56) References Cited

FOREIGN PATENT DOCUMENTS

| WO | WO 12/088348 | 6/2012 |
|---|---|---|
| WO | WO 12/088456 | 6/2012 |
| WO | WO 12/103031 | 8/2012 |
| WO | WO 12/108920 | 8/2012 |
| WO | WO 12/118745 | 9/2012 |
| WO | 2012141712 A1 | 10/2012 |
| WO | WO 2012/141712 | 10/2012 |
| WO | WO 12/177792 | 12/2012 |
| WO | 2013/015793 A1 | 1/2013 |
| WO | WO 13/000100 | 1/2013 |
| WO | WO 2013/015793 | 1/2013 |
| WO | WO 13/052907 | 4/2013 |
| WO | WO 13/052913 | 4/2013 |
| WO | WO 13/055817 | 4/2013 |
| WO | WO 13/109981 | 7/2013 |
| WO | WO 13/177086 | 11/2013 |
| WO | WO 13/192562 | 12/2013 |
| WO | WO 2014/039556 | 3/2014 |
| WO | WO 14/055790 | 4/2014 |
| WO | WO 14/116598 | 7/2014 |
| WO | WO 14/055774 | 10/2014 |
| WO | WO 2014/165596 | 10/2014 |
| WO | WO 2014/190286 | 11/2014 |
| WO | WO 2015/040591 | 3/2015 |
| WO | WO 2015/051163 | 4/2015 |
| WO | WO 2015/054080 | 4/2015 |
| WO | WO 2015/183872 | 12/2015 |
| WO | WO 16/019042 | 2/2016 |

OTHER PUBLICATIONS

Snyder et al. Noninvasive fetal genome sequencing: a primer. Prenatal Diagnosis. Jun. 2013, 33, pp. 547-554. (Year: 2013).*
Abyzov et al. CNVnator: An approach to discover, genotype, and characterize typical and atypical CNVs from family and population genome sequencing. Genome Research 2011, 21, pp. 974-984 (Year: 2011).*
Agarwal et al., "Commercial landscape of noninvasive prenatal testing in the United States" Prenatal Diagnosis (2013) 33(6):521-531.
Dan et al., "Clinical application of massively parallel sequencing-based prenatal noninvasive fetal trisomy test for trisomies 21 and 18 in 11,105 pregnancies with mixed risk factors" Prenatal Diagnosis (2012) 32:1225-1232.
Office Action dated Jul. 27, 2015 in U.S. Appl. No. 13/782,857, filed Mar. 1, 2013 and published as US 2013-0310260 on Nov. 21, 2013.
International Preliminary Report on Patentability dated Aug. 6, 2015 in International Application No. PCT/US2014/012369, filed Jan. 21, 2014 and published as WO 2014/116598 on Jul. 31, 2014.
Supplementary Partial European Search Report dated Aug. 10, 2015 in European Application No. EP11745050.2, filed on Feb. 9, 2011 and published as EP 2 536 852 on Dec. 26, 2012.
Office Action dated Aug. 27, 2015 in U.S. Appl. No. 13/933,935, filed Jul. 2, 2013 and published as US 2013-0304392 on Nov. 14, 2013.
Office Action dated Sep. 1, 2015 in U.S. Appl. No. 13/829,164, filed Mar. 14, 2013 and published as US 2013-0288244 on Oct. 31, 2014.
Office Action dated Sep. 8, 2015 in U.S. Appl. No. 13/669,136, filed Nov. 5, 2012 and published as US 2013-0085681 on Apr. 4, 2013.
Office Action dated Sep. 8, 2015 in U.S. Appl. No. 13/797,508, filed Mar. 12, 2013 and published as US 2013-0261983 on Oct. 3, 2013.
Office Action dated Sep. 18, 2015 in U.S. Appl. No. 12/727,824, filed Mar. 19, 2010 and published as US 2010-0216153 on Aug. 26, 2010.
Office Action dated Sep. 22, 2015 in U.S. Appl. No. 13/779,638, filed Feb. 27, 2013 and published as US 2013-0309666 on Nov. 21, 2013.
Office Action dated Sep. 28, 2015 in U.S. Appl. No. 14/187,876, filed Feb. 24, 2014 and published as US 2014-0322709 on Oct. 30, 2014.
Office Action dated Oct. 2, 2015 in U.S. Appl. No. 13/754,817, filed Jan. 30, 2013 and published as US 2013-0150253 on Jun. 13, 2013.
Office Action dated Oct. 2, 2015 in U.S. Appl. No. 13/782,883, filed Mar. 1, 2013 and published as US 2014-0180594 on Jun. 26, 2014.
International Preliminary Report on Patentability dated Oct. 15, 2015 in International Application No. PCT/US2014/032687, filed on Apr. 2, 2014 and published as WO 2014/165596 on Oct. 9, 2014.
Romiguier et al., "Contrasting GC-content dynamics across 33 mammalian genomes: relationship with life-history traits and chromosome sizes" Genome Research (2010) 20:1001-1009.
National Human Genome Research Institute, Chromosomes fact sheet , (http://www.genome.gov/26524120, downloaded Sep. 9, 2015).
Leek et al., "Tackling the widespread and critical impact of batch effects in high-throughput data" Nature Reviews Genetics (2010) 11:733-739.
The International SNP Map Working Group "A map of human genome sequence variation containing 1.42 million single nucleotide polymorphisms" Nature (2001) 409:928-933.
Fan et al., "Analysis of the size distributions of fetal and maternal cell-free DNA by paired-end sequencing" Clinical Chemistry (2010) 56(8):1279-1286.
Alkan et al., "Personalized copy number and segmental duplication maps using next-generation sequencing", Nature Genetics, vol. 41, No. 10, Oct. 30, 2009 (Oct. 30, 2009), pp. 1061-1067, and Supplementary Information 1-68.
Office Action dated Mar. 11, 2016 in U.S. Appl. No. 13/782,857, filed Mar. 1, 2013 and published as US 2013-0310260 on Nov. 21, 2013.
Office Action dated Mar. 22, 2016 in U.S. Appl. No. 12/727,824, filed Mar. 19, 2010 and published as US 2010-0216153 on Aug. 26, 2010.
Zhao et al., "Detection of fetal subchromosomal abnormalities by sequencing circulating cell-free DNA from maternal plasma" Clinical Chemistry (2015) 61(4):608-616.
Lefkowitz et al., "Clinical validation of a noninvasive prenatal test for genomewide detection of fetal copy number variants" American Journal of Obstetrics & Gynecology (Dec. 2, 2015) S0002-9378(16)00318-5. doi: 10.1016/j.ajog.2016.02.030. [Epub ahead of print].
Avent, "Refining noninvasive prenatal diagnosis with single-molecule next-generation sequencing" Clin. Chem. (2012) 58(4):657-658.
Boeva et al., "Control-free calling of copy number alterations in deep-sequencing data using GC-content normalization" Bioinformatics (2011) 27(2):268-269.
Chung et al., "Discovering transcription factor binding sites in highly repetitive regions of genomes with multi-read analysis of ChIP-Seq data" PLoS Computational Biology (2011) 7(7):e1002111.
Chandrananda et al., "Investigating and correcting plasma DNA sequencing coverage bias to enhance aneuploidy discovery" PloS One (2014) 9:e86993.
Benjamini et al., "Summarizing and correcting the GC content bias in high-throughput sequencing" Nucleic Acids Research (2012) 40(10):e72.
International Preliminary Report on Patentability dated Apr. 14, 2016 in International Application No. PCT/US2014/058885, filed on Oct. 2, 2014 and published as WO 2015/051163 on Apr. 9, 2015.
International Preliminary Report on Patentability dated Apr. 21, 2016 in International Application No. PCT/US2014/059156, filed on Oct. 3, 2014 and published as WO 2015/054080 on Apr. 16, 2015.
Yuk et al., "Genomic Analysis of Fetal Nucleic Acids in Maternal Blood" Annual Review of Genomics and Human Genetics (2012) 13:285-306.
Office Action dated Apr. 26, 2016 in U.S. Appl. No. 13/797,508, filed Mar. 12, 2013 and published as US 2013-0261983 on Oct. 3, 2013.
Office Action dated Apr. 27, 2016 in U.S. Appl. No. 13/829,164, filed Mar. 14, 2013 and published as US 2013-0288244 on Oct. 31, 2014.

(56) References Cited

OTHER PUBLICATIONS

Office Action dated Apr. 27, 2016 in U.S. Appl. No. 13/933,935, filed Jul. 2, 2013 and published as US 2013-0304392 on Nov. 14, 2013.
Hinds et al., "Whole-genome patterns of common DNA variation in three human populations" Science (2005) 307:1072-1079.
Pushkarev et al., "Single-molecule sequencing of an individual human genome" Nature Biotechnology (2009) 27(9):847-852.
Office Action dated Oct. 22, 2015 in U.S. Appl. No. 13/781,530, filed Feb. 28, 2013 and published as US 2014-0100792 on Apr. 10, 2014.
Office Action dated Oct. 27, 2015 in U.S. Appl. No. 13/333,842, filed Dec. 21, 2011 and published as US 2012/0184449 on Jul. 19, 2012.
Invitation to Pay Additional Fees and Partial International Search Report dated Oct. 14, 2015 in International Application No. PCT/US2015/042701, filed on Jul. 29, 2015.
Yu et al., "Size-based molecular diagnostics using plasma DNA for noninvasive prenatal testing" PNAS USA (2014) 111(23):8583-8588.
International Search Report and Written Opinion dated Oct. 2, 2015 in International Application No. PCT/US2015/032550, filed on May 27, 2015 and published as WO 2015/183872 on Dec. 3, 2015.
Yu et al., "Noninvasive prenatal molecular karyotyping from maternal plasma" PLoS One (2013) 8(4):e60968.
Bollen, "Bioconductor: Microarray versus next-generation sequencing tool sets" retrieved from the internet: http://dspace.library.uu.nl/bitstream/handle/1874/290489/Sander_Bollen_writing_assignment.pdf, retrieved on Sep. 23, 2015.
International Preliminary Report on Patentability dated Dec. 3, 2015 in International Application No. PCT/US2014/039389, filed on May 23, 2014 and published as WO 2014/190286 on Nov. 27, 2014.
Bianchi et al., "Isolation of fetal DNA from nucleated erythrocytes in maternal blood," PNAS, 1990,87(9): 3279-3283.
Borsenberger et al, "Chemically Labeled Nucleotides and Oligonucleotides Encode DNA for Sensing with Nanopores," J. Am. Chem. Soc., 131, 7530-7531, 2009.
Branton et al, "The potential and challenges of nanopore sequencing", Nature Biotechnology, 26:1146-1153, 2008.
Braslaysky et al., "Sequence information can be obtained from single DNA molecules," PNAS, 2003, 100(7): 3960-3964.
Brown et al. A step-by-step guide to non-linear regression analysis of experimental data using a Microsoft Excel spreadsheet Computer Methods and Programs in Biomedicine vol. 65, pp. 191-200 (2001).
Bruch et al., Trophoblast-like cells sorted from peripheral maternal blood using flow cytometry: a multiparametric study involving transmission electron microscopy and fetal DNA amplification,: Prenatal Diagnosis 11:787-798, 1991.
Cann et al., "A heterodimeric DNA polymerase: evidence that members of Euryarchaeota possess a distinct DNA polymerase." 1998, Proc. Natl. Acad. Sci. USA 95:14250.
Cariello et al., "Fidelity of Thermococcus litoralis DNA polymerase (Vent) in PCR determined by denaturing gradient gel electrophoresis," Nucleic Acids Res. Aug. 11, 1991;19(15):4193-8.
Chien et al., "Deoxyribonucleic acid polymerase from the extreme thermophile Thermus aquaticus, " 1976, J. Bacteoriol, 127: 1550-1557.
Costa et al., "Fetal RHD genotyping in maternal serum during the first trimester of pregnancy" British Journal of Haematology (2002) 119:255-260.
Cunningham et al., in Williams Obstetrics, McGraw-Hill, New York, p. 942, 2002.
Dhallan et al., "Methods to increase the percentage of free fetal DNA recovered from the maternal circulation," J. Am. Med. Soc. 291(9): 1114-1119, Mar. 2004).
Diaz and Sabino, "Accuracy of replication in the polymerase chain reaction. Comparison between Thermotoga maritima DNA polymerase and Thermus aquaticus DNA polymerase." Diaz RS, Sabino EC. 1998 Braz J. Med. Res, 31: 1239.

DNA Replication 2nd edition, Kornberg and Baker, W. H. Freeman, New York, N.Y. (1991).
Drmanac et al., "Sequencing by hybridization: towards an automated sequencing of one million M13 clones arrayed on membranes," Electrophoresis, 13(8): p. 566-573, 1992.
Herzenberg et al., "Fetal cells in the blood of pregnant women: detection and enrichment by fluorescence-activated cell sorting," PNAS 76:1453-1455, 1979.
Hinnisdaels et al., "Direct cloning of PCR products amplified with Pwo DNA polymerase," 1996, Biotechniques, 20: 186-188.
Huber et al. "High-resolution liquid chromatography of DNA fragments on non-porous poly(styrene-divinylbenzene) particles," Nucleic Acids Res. 21(5):1061-1066, 1993.
Huse et al., "Accuracy and quality of massively parallel DNA pyrosequencing" Genome Biology (2007) 8(7):R143.
Johnston et al., "Autoradiography using storage phosphor technology," Electrophoresis. May 1990;11(5):355-360.
Joos et al., "Covalent attachment of hybridizable oligonucleotides to glass supports," Analytical Biochemistry 247:96-101, 1997.
Juncosa-Ginesta et al., "Improved efficiency in site-directed mutagenesis by PCR using a *Pyrococcus* sp. GB-D polymerase," 1994, Biotechniques, 16(5): pp. 820-823.
Kato et al., "A new packing for separation of DNA restriction fragments by high performance liquid chromatography," J. Biochem, 95(1):83-86, 1984.
Khandjian, "UV crosslinking of RNA to nylon membrane enhances hybridization signals," Mol. Bio. Rep. 11: 107-115, 1986.
Kornberg and Baker, W. H. Freeman, New York, N.Y. (1991).
Lecomte and Doubleday, "Selective inactivation of the 3' to 5' exonuclease activity of *Escherichia coli* DNA polymerase I by heat," 1983, Polynucleotides Res. 11:7505-7515.
Levin, "It's prime time for reverse transcriptase," Cell 88:5-8 (1997).
Li et al., "Detection of paternally inherited fetal point mutations for beta-thalassemia using size-fractionated cell-free DNA in maternal plasma.," J. Amer. Med. Assoc. 293:843-849, 2005.
Lo et al., "Fetal DNA in maternal plasma: application to non-invasive blood group genotyping of the fetus" Transfus. Clin. Biol. (2001) 8:306-310.
Lundberg et al., "High-fidelity amplification using a thermostable DNA polymerase isolated from Pyrococcus furiosus," 1991 Gene, 108:1-6.
Mitchell & Howorka, "Chemical tags facilitate the sensing of individual DNA strands with nanopores," Angew. Chem. Int. Ed. 47:5565-5568, 2008.
Myers and Gelfand, "Reverse transcription and DNA amplification by a Thermus thermophilus DNA polymerase," Biochemistry 1991, 30:7661-7666.
Nevin, N.C., "Future direction of medical genetics", The Ulster Medical Journal, vol. 70, No. 1, (2001), pp. 1-2.
Ng et al. "The Concentration of Circulating Corticotropin-releasing Hormone mRNA in Maternal Plasma is Increased in Preeclampsia," Clinical Chemistry 49:727-731, 2003.
Nordstrom et al., "Characterization of bacteriophage T7 DNA polymerase purified to homogeneity by antithioredoxin immunoadsorbent chromatography," 1981, J. Biol. Chem. 256:3112-3117.
Oroskar et al., "Detection of immobilized amplicons by ELISA-like techniques." Clin. Chem. 42:1547-1555, 1996.
PCT International Search Report and Written Opinion of the international Searching Authority for International Application No. PCT/US11/24132, dated Aug. 8, 2011. 15 pages.
Purnell and Schmidt, "Discrimination of single base substitutions in a DNA strand immobilized in a biological nanopore," ACS Nano, 3:2533, 2009.
Sambrook, Chapter 10 of Molecular Cloning, a Laboratory Manual, 3.sup.ed Edition, J. Sambrook, and D. W. Russell, Cold Spring Harbor Press (2001).
Smid et al., "Evaluation of Different Approaches for Fetal DNA Analysis from Maternal Plasma and Nucleated Blood Cells," Clinical Chemistry, 1999, 45(9): 1570-1572.

(56) References Cited

OTHER PUBLICATIONS

Smith et al., "Direct mechanical measurements of the elasticity of single DNA molecules by using magnetic beads," Science 258:5085, pp. 1122-1126, Nov. 13, 1992.
Stenesh and McGowan, "DNA polymerase from mesophilic and thermophilic bacteria. III. Lack of fidelity in the replication of synthetic polydeoxyribonucleotides by DNA polymerase from Bacillus licheniformis and Bacillus stearothermophilus," 1977, Biochim Biophys Acta 475:32-41.
Stoddart et al, "Single-nucleotide discrimination in immobilized DNA oligonucleotides with a biological nanopore," Proc. Nat. Acad. Sci. 2009, 106(19): pp. 7702-7707.
Takagi et al., "Characterization of DNA polymerase from *Pyrococcus* sp. strain KOD1 and its application to PCR," 1997, Appl. Environ. Microbiol. 63(11): pp. 4504-4510.
Taylor et al., "Characterization of chemisorbed monolayers by surface potential measurements," J. Phys. D. Appl. Phys. 24(8):1443-1450, 1991.
Verma, "The reverse transcriptase," Biochim Biophys Acta 473(1):1-38 (Mar. 21, 1977).
Wei, Chungwen et al., "Detection and Quantification by Homogenous PCR of Cell-free Fetal DNA in Maternal Plasma", Clinical Chemistry, vol. 47, No. 2, (2001), pp. 336-338.
Wu et al., "Reverse Transcriptas," CRC Crit. Rev Biochem. 3(3): pp. 289-347 (Jan. 1975).
Yershov et al., "DNA analysis and diagnostics on oligonucleotide microchips," Proc. Natl. Acad. Sci. 93(10): pp. 4913-4918 (May 14, 1996).
Yoon et al., "Sensitive and accurate detection of copy number variants using read depth of coverage" Genome Research (2009) 19:1586-1592.
Office Action dated Aug. 22, 2013 in U.S. Appl. No. 13/619,039, filed Sep. 14, 2012 and published as: US 2013/0022977 on: Jan. 24, 2013.
Office Action dated Jan. 10, 2013 in U.S. Appl. No. 13/619,039, filed Sep. 14, 2012 and published as: US 2013/0022977 on: Jan. 24, 2013.
Office Action dated Jul. 14, 2014 in U.S. Appl. No. 12/727,824, filed Sep. 13, 2012 and published as: US 2010/0216153 on: Aug. 26, 2010.
Office Action dated Oct. 18, 2011 in U.S. Appl. No. 12/727,824, filed Sep. 13, 2012 and published as: US 2010/0216153 on: Aug. 26, 2010.
Office Action dated May 16, 2011 in U.S. Appl. No. 12/727,824, filed Sep. 13, 2012 and published as: US 2010/0216153 on: Aug. 26, 2010.
Office Action dated Feb. 25, 2015 in U.S. Appl. No. 12/727,824, filed Sep. 13, 2012 and published as: US 2010/0216153 on: Aug. 26, 2010.
Office Action dated May 29, 2015 in U.S. Appl. No. 14/187,876, filed Feb. 24, 2014 and published as US 2014-0322709 on Oct. 30, 2014.
Kim et al., "Determination of fetal DNA fraction from the plasma of pregnant women using sequence read counts" Prenat. Diagn. (2015) 35(8):810-815.
Extended European Search Report dated Dec. 2, 2015 in European Application No. EP11745050.2, filed on Feb. 9, 2011 and published as EP 2 536 852 on Dec. 26, 2012.
Omont et al., "Gene-based bin analysis of genome-wide association studies" BMC Proceedings (2008) 2 (Suppl 4):S6.
Trapnell and Salzberg, "How to map billions of short reads onto genomes" Nat. Biotechnol. (2009) 27(5):455-457.
International Search Report and Written Opinion dated Jan. 5, 2016 in International Application No. PCT/US2015/042701, filed on Jul. 29, 2015.
Office Action dated Feb. 1, 2016 in U.S. Appl. No. 13/669,136, filed Nov. 5, 2012 and published as US 2013-0085681 on Apr. 4, 2013.
Canick et al., "The impact of maternal plasma DNA fetal fraction on next generation sequencing tests for common fetal aneuploidies" Prenat. Diagn. (2013) 33(7):667-674.
Hudecova et al., "Maternal plasma fetal DNA fractions in pregnancies with low and high risks for fetal chromosomal aneuploidies" PLoS One (2014) 9(2):e88484.
Palomaki et al., "DNA sequencing of maternal plasma to detect Down syndrome: an international clinical validation study" Genet Med. (2011) 13:913-920, and Expanded Methods Appendix A, pp. 1-65.
Office Action dated Feb. 12, 2016 in U.S. Appl. No. 13/797,930, filed Mar. 12, 2013 and published as US 2013-0325360 on Dec. 5, 2013.
Forabosco et al., "Incidence of non-age-dependent chromosomal abnormalities: a population-based study on 88965 amniocenteses" European Journal of Human Genetics (2009) 17:897-903.
Grati, "Chromosomal Mosaicism in Human Feto-Placental Development: Implications for Prenatal Diagnosis" J. Clin. Med. (2014) 3:809-837.
Office Action dated Feb. 23, 2016 in U.S. Appl. No. 14/812,432, filed Jul. 29, 2015 and published as US 2016-0034640 on Feb. 4, 2016.
Office Action dated Mar. 3, 2016 in U.S. Appl. No. 13/829,373, filed Mar. 14, 2013 and published as US 2013-0338933 on Dec. 19, 2013.
Adinolfi et al., "Rapid detection of aneuploidies by microsatellite and the quantitative fluorescent polymerase chain reaction." Prenat Diagn. Dec. 1997;17(13):1299-311.
Akeson et al., "Microsecond Time-Scale Discrimination Among Polycytidylic Acid, Polyadenylic Acid, and Polyuridylic Acid as Homopolymers or as Segments Within Single RNA Molecules," Biophysical Journal vol. 77 Dec. 1999 3227-3233.
Alkan, C., et al., Personalized copy number and segmental duplication maps using nextgeneration sequencing. Nat Genet, 2009. 41(10): p. 1061-7.
Amicucci et al., "Prenatal Diagnosis of Myotonic Dystrophy Using Fetal DNA Obtained from Maternal Plasma," Clin. Chem. 46:301-302, 2000.
Anantha et al., "Porphyrin binding to quadrupled T4G4." Biochemistry. Mar. 3, 1998;37(9):2709-14.
Armour et al., "Measurement of locus copy number By hybridisation with amplifiable probes." Nucleic Acids Res. Jan. 15, 2000;28(2):605-9.
Armour et al., "The detection of large deletions or duplications in genomic DNA." Hum Mutat. Nov. 2002;20(5):325-37.
Ashkenasy et al., "Recognizing a Single Base in an Individual DNA Strand: A Step Toward Nanopore DNA Sequencing," Angew Chem Int Ed Engl. Feb. 18, 2005; 44(9): 1401-1404.
Ashoor, et al., (2012): Chromosome-selective sequencing of maternal plasma cell-free DNA for first trimester detection of trisomy 21 and trisomy 18, American Journal of Obstetrics and Gynecology, doi: 10.1016/j.ajog.2012.01.029.
Aston et al. "Optical mapping and its potential for large-scale sequencing project," (1999) Trends Biotechnol. 17(7):297-302.
Aston et al. "Optical mapping: an approach for fine mapping," (1999) Methods Enzymol. 303:55-73.
Avent et al., "Non-invasive diagnosis of fetal sex; utilization of free fetal DNA in maternal plasma and ultrasound," Prenatal Diagnosis, 2006, 26:598-603.
Beaucage and Caruthers, Tetrahedron Letts., 22:1859-1862 (1981).
Berger et al., "Universal bases for hybridization, replication and chain termination," (2000) Nucleic Acids Res. 28(15): 2911-2914.
Bergstrom et al. "Synthesis, Structure, and Deoxyribonucleic Acid Sequencing with a Universal Nucleoside: 1-(2'-Deoxy-.beta.-D-ribofuranosyl)-3-nitropyrrole," (1995) J. Am. Chem. Soc. 117, 1201-1209.
Brizot et al., "Maternal serum hCG and fetal nuchal translucency thickness for the prediction of fetal trisomies in the first trimester of pregnancy." Br J Obstet Gynaecol. Feb. 1995;102(2):127-32.
Brizot et al., "Maternal serum pregnancy-associated plasma protein A and fetal nuchal translucency thickness for the prediction of fetal trisomies in early pregnancy." Obstet Gynecol. Dec. 1994;84(6):918-22.
Brown and Lin "Synthesis and duplex stability of oligonucleotides containing adenine-guanine analogues," (1991) Carbohydrate Research 216, 129-139.

(56) References Cited

OTHER PUBLICATIONS

Brown, L., et al., Validation of QF-PCR for prenatal aneuploidy screening in the United States. Prenat Diagn, 2006. 26(11): p. 1068-74.

Brünger, "Free R value: a novel statistical quantity for assessing the accuracy of crystal structures," Nature 355, 472-475 (Jan. 30, 1992); doi:10.1038/355472a0.

Bullard et al., "Evaluation of statistical methods for normalization and differential expression in mRNA-Seq experiments," Bioinformatics 2010, 11:94, pp. 1-13.

Burlingame et al. Anal. Chem. 70:647R-716R (1998).

Campbell et al., "Identification of somatically acquired rearrangements in cancer using genome-wide massively parallel paired-end sequencing." Nat Genet. Jun. 2008;40(6):722-9. doi: 10.1038/ng.128. Epub Apr. 27, 2008.

Canick et al., "DNA sequencing of maternal plasma to identify Down syndrome and other trisomies in multiple gestations," Prenat Diagn. May 14, 2012:1-5.

Canick, et al., "A New Prenatal Blood Test for Down Syndrome (RNA)," Jul. 2012 found on the internet at: clinicaltrials.gov/show/A15NCT00877292.

Carlson et al., "Molecular Definition of 22q11 Deletions in 151 Velo-Cardio-Facial Syndrome Patients," The American Journal of Human Genetics, vol. 61, Issue 3, 620-629, Sep. 1, 1997.

Chan et al. "Size Distribution of Maternal and Fetal DNA in Maternal Plasma," (2004) Clin. Chem. 50:88-92.

Chen et al., "A method for noninvasive detection of fetal large deletions/duplications by low coverage massively parallel sequencing" Prenatal Diagnosis (2013) 33(6):584-590, and supplementary material pp. 1-6.

Chen et al., "Noninvasive Prenatal Diagnosis of Fetal Trisomy 18 and Trisomy 13 by Maternal Plasma DNA Sequencing," PLoS ONE, Jul. 2011, vol. 6, Issue 7, e21791, pp. 1-7.

Chiang et al., High-resolution mapping of copy-number alterations with massively parallel sequencing, Nat Methods. Jan. 2009 ; 6(1): 99-103.

Chim et al. (2008). "Systematic search for placental DNA-methylation markers on chromosome 21: toward a maternal plasma-based epigenetic test for fetal trisomy 21." Clin Chem 54(3): 500-11.

Chiu et al. "Maternal plasma DNA analysis with massively parallel sequencing by ligation for noninvasive prenatal diagnosis of trisomy 21." Clin Chem 56(3): 459-63.(2010).

Chiu et al. (2008). "Noninvasive prenatal diagnosis of fetal chromosomal aneuploidy by massively parallel genomic sequencing of DNA in maternal plasma." Proc Natl Acad Sci U S A 105(51): 20458-20463.

Chiu et al., "Non-invasive prenatal assessment of trisomy 21 by multiplexed maternal plasma DNA sequencing: large scale validity study," BMJ 2011;342:c7401, 1-9.

Chiu et al., "Prenatal exclusion of thalassaemia major by examination of maternal plasma," Lancet 360:998-1000, 2002.

Chu et al. (2009). "Statistical model for whole genome sequencing and its application to minimally invasive diagnosis of fetal genetic disease." Bioinformatics 25(10): 1244-50.

Cohen et al. (2005): GC Composition of the Human Genome: In Search of Isochores. Mole Biol. Evol. 22(5):1260-1272.

Costa et al., "New Strategy for Prenatal Diagnosis of X-Linked Disorders" N. Engl. J. Med. 346:1502, 2002.

Current Protocols in Molecular Biology, John Wiley & Sons, N.Y. 6.3.1-6.3.6(1989).

D'Alton ME., "Prenatal diagnostic procedures." Semin Perinatol. Jun. 1994;18(3):140-62.

Dan et al., "Prenatal detection of aneuploidy and imbalanced chromosomal arrangements by massively parallel sequencing," PLoS ONE 7(2): e27835. (2012).

Data Sheet: Illumina Sequencing: TruSeq RNA and DNA Sample Preparation Kits v2, Publication No. 970-2009-039 Apr. 27, 2011.

Davanos et al., "Relative quantitation of cell-free fetal DNA in maternal plasma using autosomal DNA markers" Clinica Chimica Acta (2011) 412:1539-1543.

Deamer et al., "Nanopores and Nucleic Acids: Prospects for ultrarapid sequencing." Focus Tibtech Apr. 2000, (vol. 18) pp. 147-151.

Derrien et al. (2012) Fast Computation and Applications of Genome Mappability. PLoS ONE 7(1): e30377, doi:10.1371/journal.pone.0030377.

Ding et al., "A high-throughput gene expression analysis technique using competitive PCR and matrix-assisted laser desorption ionization time-of-flight MS." Proc Natl Acad Sci U S A. Mar. 18, 2003;100(6):3059-64. Epub Mar. 6, 2003.

DNAcopy [online],[retrieved on Apr. 24, 2013], retrieved from the internet <URL:*>http://biocondutor.org/packages/2.12/bioc/html/DNAcopy.html.

Dohm et al., "Substantial biases in ultra-short read data sets from high-throughput DNA sequencing," Nucleic Acids Res. Sep. 2008;36(16):e105. Epub Jul. 26, 2008.

Donoho and Johnstone (1995), "WaveLab and Reproducible Research," Stanford University, Stanford CA 94305, USA, pp. 1-27.

Edelmann, L., et al., A common molecular basis for rearrangement disorders on chromosome 22q11. Hum Mol Genet, 1999. 8(7): p. 1157-67.

Egger et al., "Reverse transcription multiplex PCR for differentiation between polio- and enteroviruses from clinical and environmental samples." J Clin Microbiol. Jun. 1995;33(6):1442-7.

Ehrich et al., Noninvasive detection of fetal trisomy 21 by sequencing of DNA in maternal blood: a study in a clinical setting, American Journal of Obstetrics and Gynecology—Amer J Obstet Gynecol, vol. 204, No. 3, pp. 205.e1-205.e11, 2011 DOI: 10.1016/j.

Eiben et al., "First-trimester screening: an overview." J Histochem Cytochem. Mar. 2005;53(3):281-3.

Ensenauer, R.E., et al., Microduplication 22q11.2, an emerging syndrome: clinical, cytogenetic, and molecular analysis of thirteen patients. Am J Hum Genet, 2003. 73(5): p. 1027-40.

Fan et al., (2008). "Noninvasive diagnosis of fetal aneuploidy by shotgun sequencing DNA from maternal blood." Proc Natl Acad Sci U S A 105(42): 16266-71.

Fan et al., (2010). "Sensitivity of noninvasive prenatal detection of fetal aneuploidy from maternal plasma using shotgun sequencing is limited only by counting statistics." PLoS ONE 5(5): e10439.

Gebhard et al., "Genome-wide profiling of CpG methylation identifies novel targets of aberrant hypermethylation in myeloid leukemia." Cancer Res. Jun. 15, 2006;66(12):6118-28.

Goya, R., et al. (2010) SNVMix: predicting single nucleotide variants from nextgeneration sequencing of tumors, *Bioinformatics*, 26, 730-736.

Haar, Alfred (1910) "Zur Theorie der orthogonalen Funktionensysteme", Mathematische Annalen 69 (3): 331-371, English translation "On the Theory of Orthogonal Function Systems" 1-37.

Hahn et al., "Cell-free nucleic acids as potential markers for preeclampsia." Placenta. Feb. 2011;32 Suppl:S17-20. doi: 10.1016/j.placenta.2010.06.018.

Harris et al., "Single-molecule DNA sequencing of a viral genome." Science. Apr. 4, 2008;320(5872)106-9. doi: 10.1126/science.1150427.

Hill, Craig, "Gen-Probe Transcripediated Amplification: System Principles," Jan. 1996 www.gen-probe.com/pdfs/tma_whiteppr.pdf.

Hsu et al., "A model-based circular binary segmentation algorithm for the analysis of array CGH data" BMC Research Notes (2011) 4:394.

Hsu, S. Self, D. Grove, T. Randolph, K. Wang, J. Delrow, L. Loo, and P. Porter, "Denoising array-based comparative genomic hybridization data using wavelets", Biostatistics (Oxford, England), vol. 6, No. 2, pp. 211-226, 2005.

Hulten et al., "Rapid and simple prenatal diagnosis of common chromosome disorders: advantages and disadvantages of the molecular methods FISH and QF-PCR." Reproduction. Sep. 2003;126(3):279-97.

Human Genome Mutations, D. N. Cooper and M. Krawczak, BIOS Publishers, 1993.

Hupe,P. et al. (2004) "Analysis of array CGH data: from signal ratio to gain and loss of DNA regions", Bioinformatics, 20, 3413-3422.

(56) References Cited

OTHER PUBLICATIONS

Hudson et al., "An STS-Based Map of the Human Genome," Science, vol. 270, pp. 1945-1954 (1995).
Innis et al., PCR Protocols: A Guide to Methods and Applications, Innis et al., eds, 1990.
International Human Genome Sequencing Consortium Initial sequencing and analysis of the human genome Nature vol. 409, pp. 860-921 (2001).
James/James "Mathematics Dictionary," Fifth Edition, Chapman & Hall, International Thomson Publishing, 1992, pp. 266-267_270.
Jensen et al. "High-Throughput Massively Parallel Sequencing for Fetal Aneuploidy Detection from Maternal Plasma" Mar. 6, 2013. PLoS ONE 8(3): e57381.
Jensen et al., "Detection of microdeletion 22q11.2 in a fetus by next-generation sequencing of maternal plasma," Clin Chem. Jul. 2012;58(7):1148-1151.
Jiang et al., "FetalQuant: Deducing Fractional Fetal DNA Concentration from Massively Parallel Sequencing of DNA in Maternal Plasma," Bioinformatics, Nov. 15, 2012;28(22):2883-2890.
Jing et al. (1998) Proc Natl Acad Sci USA. 95(14):8046-51.
Jorgez et al.. "Improving Enrichment of Circulating Fetal DNA for genetic Testing: Size Fractionatiion Followed by Whole Gene Amplification." Fetal Diagnosis and Therapy, Karger Basel, CH, vol. 25, No. 3 Jan. 1, 2009, pp. 314-319.
Jurinke et al. (2004) Mol. Biotechnol. 26, 147-164.
Kalinina et al., "Nanoliter scale PCR with TaqMan detection." Nucleic Acids Res. May 15, 1997;25(10):1999-2004.
Kim et al., "Identification of significant regional genetic variations using continuous CNV values in aCGH data" Genomics (2009) 94(5):317-323.
Kitzman et al., (2012): Noninvasive whole-genome sequencing of a human fetus. Science Translational Medicine, 4 (137):137ra76.
Kulkarni et al., "Global DNA methylation patterns in placenta and its association with maternal hypertension in pre-eclampsia." DNA Cell Biol. Feb. 2011;30(2):79-84. doi: 10.1089/dna.2010.1084. Epub Nov. 2, 2010.
Lai et al. (1999) Nat Genet. 23(3):309-13.
Lai et al., (2005). Comparative analysis of algorithms for identifying amplifications and deletions in array CGH data. Bioinformatics, 21, 19:3763-70.
Langmead et al., "Ultrafast and memory-efficient alignment of short DNA sequences to the human genome." Genome Biol. 2009;10(3):R25. doi: 10.1186/gb-2009-10-3-r25. Epub Mar. 4, 2009.
Li et al., "Mapping short DNA sequencing reads and calling variants using mapping quality scores." Genome Res. Nov. 2008;18(11):1851-8. doi: 10.1101/gr.078212.108. Epub Aug. 19, 2008.
Liao et al., (2012): Noninvasive Prenatal Diagnosis of Fetal Trisomy 21 by Allelic Ratio Analysis Using Targeted Massively Parallel Sequencing of Maternal Plasma DNA. PLoS ONE, 7(5):e38154, p. 1-7.
Liao, G.J., et al., Targeted massively parallel sequencing of maternal plasma DNA permits efficient and unbiased detection of fetal alleles. Clin Chem, 2010. 57(1): p. 92-101.
Lin and Brown, (1989) Nucleic Acids Res. 17:10373-10383.
Lin and Brown, (1992) Nucleic Acids Res. 20:5149-5152.
Liu et al., "CUSHAW: a CUDA compatible short read aligner to large genomes based on the Burrows-Wheeler transform" Bioinformatics (2012) 28(14):1830-1837.
Lo "Recent advances in fetal nucleic acids in maternal plasma." J Histochem Cytochem. Mar. 2005;53(3):293-296.
Lo et al. (1997). "Presence of fetal DNA in maternal plasma and serum." Lancet 350(9076): 485-487.
Lo et al. (2007). "Digital PCR for the molecular detection of fetal chromosomal aneuploidy." Proc Natl Acad Sci U S A 104(32): 13116-21.
Lo et al. (2007). "Plasma placental RNA allelic ratio permits noninvasive prenatal chromosomal aneuploidy detection." Nat Med 13(2): 218-23.
Lo et al., "Prenatal Diagnosis of Fetal RhD Status by Molecular Analysis of Maternal Plasma," N. Engl. J. Med. 339:1734-1738, 1998.
Lo et al., "Quantative Abnormalities of Fetal NDA in Maternal Serum in Preeclampsia," Clin. Chem. 45:184-188, 1999.
Lo et al.,"Increased Fetal DNA Concentrations in the Plasma of Pregnant Women Carrying Fetuses with Trisomy 21," Clin. Chem. 45:1747-1751, 1999.
Lo YM, et al.(1998) Am J Hum Genet 62:768-775.
Lo, Y.M., et al., Maternal plasma DNA sequencing reveals the genome-wide genetic and mutational profile of the fetus. Sci Transl Med, 2010. 2(61): p. 61ra91.
Loakes and Brown (1994) Nucleic Acids Res. 22, 4039-4043.
Lun et al. (2008). "Microfluidics digital PCR reveals a higher than expected fraction of fetal DNA in maternal plasma." Clin Chem 54(10): 1664-72.
Mann et al., "Development and implementation of a new rapid aneuploidy diagnostic service within the UK National Health Service and implications for the future of prenatal diagnosis." Lancet. Sep. 29, 2001;358(9287)1057-61.
Margulies et al., "Genome sequencing in microfabricated high-density picolitre reactors." Nature. Sep. 15, 2005;437(7057):376-80. Epub Jul. 31, 2005.
Mazloom, Amin, "Gender Prediction with Bowtie Alignments using Male Specific Regions," May 10, 2012.
Metzker ML., "Sequencing technologies—the next generation." Nat Rev Genet. Jan. 2010;11(1):31-46. doi: 10.1038/nrg2626. Epub Dec. 8, 2009.
Miller et al., Consensus statement: chromosomal microarray is a first-tier clinical diagnostic test for individuals with developmental disabilities or congenital anomalies. Am J Hum Genet, 2010. 86(5): p. 749-64.
Moudrianakis et al., "Base Sequence Determination in Nucleic Acids with the Electron Microscope, III. Chemistry and Microscopy of Guanine-Labeled DNA." Proc Natl Acad Sci U S A. Mar. 1965;53:564-571.
Nakano et al., "Single-molecule PCR using water-in-oil emulsion." J Biotechnol. Apr. 24, 2003;102(2):117-1+A11024.
Nason, G.P. (2008) "Wavelet methods in Statistics", table of contents. R. Springer, New York ISBN: 978-0-387-75960-9 (Print) 978-0-387-75961-6 (Online).
Needham-VanDevanter et al., "Characterization of an adduct between CC-1065 and a defined oligodeoxynucleotide duplex." Nucleic Acids Res. Aug. 10, 1984;12(15):6159-68.
Ng et al. (2003). "mRNA of placental origin is readily detectable in maternal plasma." Proc Natl Acad Sci U S A 100(8): 4748-53.
Nguyen, Nha, "Denoising of Array-Based DNA Copy Number Data Using the Dual-tree Complex Wavelet Transform," Bioinformatics and Bioengineering, 2007. BIBE 2007. Proceedings of the 7th IEEE International Conference, Boston MA, on Oct. 14-17, 2007, pp. 137-144.
Nichols et al. "A universal nucleoside for use at ambiguous sites in DNA primers," (1994) Nature 369, 492-493.
Nicolaides et al., "One-stop clinic for assessment of risk of chromosomal defects at 12 weeks of gestation." J Matern Fetal Neonatal Med. Jul. 2002;12(1):9-18.
Nolte FS., "Branched DNA signal amplification for direct quantitation of nucleic acid sequences in clinical specimens." Adv Clin Chem. 1998;33:201-35.
Nygren, A. O., J. Dean, et al. (2010) "Quantification of fetal DNA by use of methylation-based DNA discrimination." Clin Chem 56(10): 1627-35.
Oh et al., "CAM: a web tool for combining array CGH and microarray gene expression data from multiple samples" Computers in Biology and Medicine (2009) 40(9):781-785.
Ohno, S. (1967). Sex chromosomes and Sex-linked Genes. Berlin, Springer. p. 111.
Old et al. (2007). "Candidate epigenetic biomarkers for non-invasive prenatal diagnosis of Down syndrome." Reprod Biomed Online 15(2): 227-35.
Olshen et al., "Circular binary segmentation for the analysis of array-based DNA copy number data," Biostatistics. Oct. 2004;5(4):557-572.

(56) References Cited

OTHER PUBLICATIONS

Oudejans et al. (2003). "Detection of chromosome 21-encoded mRNA of placental origin in maternal plasma." Clin Chem 49(9): 1445-9.
Palomaki et al., DNA sequencing of maternal plasma to detect Down syndrome: an international clinical validation study. Genet Med., Nov. 2011;13(11):913-920.
Palomaki, et al. "DNA sequencing of maternal plasma reliably identifies trisomy 18 and trisomy 13 as well as Down syndrome: an international collaborative study" Genet Med 2012;14:296-305.
Pandya et al., "Screening for fetal trisomies by maternal age and fetal nuchal translucency thickness at 10 to 14 weeks of gestation." Br J Obstet Gynaecol. Dec. 1995;102(12):957-62.
Pearson and Regnier, "High-Performance Anion-Exchange Chromatogrtaphy of Oligonucleotides," J. Chrom., 255:137-149, 1983.
Pekalska et al., "Classifiers for dissimilarity-based pattern recognition," 15th International Conference on Pattern Recognition (ICPR'00), vol. 2, Barcelona, Spain, Sep. 3-8, 2000, pp. 12-16.
Pertl et al., "Rapid molecular method for prenatal detection of Down's syndrome." Lancet. May 14, 1994;343(8907):1197-8.
Peters et al. "Noninvasive Prenatal Diagnosis of a Fetal Microdeletion Syndrome," Correspondence to the Editor, New England Journal of Medicine, 365:19 Nov. 10, 2011, pp. 1847-1848.
Poon et al., "Differential DNA methylation between fetus and mother as a strategy for detecting fetal DNA in maternal plasma." Clin Chem. Jan. 2002;48(1):35-41.
Product Sheet for: Nextera™ DNA Sample Prep Kit (Illumina®-Compatible) Cat. Nos. GA09115, GA091120, GA0911-50, GA0911-96, and GABC0950, from: Epicentre, an Illumina Company, Literature # 307, Jun. 2011.
Pushkarev et al., "Single-molecule sequencing of an individual human genome" Nature Biotechnology (2009) 27(9):847-850.
Qu et al., "Analysis of drug-DNA binding data." Methods Enzymol. 2000;321:353-69.
Robin, N.H. and R.J. Shprintzen, Defining the clinical spectrum of deletion 22q11.2. J Pediatr, 2005. 147(1): p. 90-6.
Romero and Rotbart in Diagnostic Molecular Biology: Principles and Applications pp. 401-406; Persing et al., eds., Mayo Foundation, Rochester, Minn., 1993.
Ross et al., "The DNA sequence of the human X chromosome." Nature. Mar. 17, 2005;434(7031):325-337.
Roth, A., et al. (2012) JointSNVMix: a probabilistic model for accurate detection of somatic mutations in normal/tumour paired next-generation sequencing data, Bioinformatics, 28, 907-913.
Saito et al., "Prenatal DNA diagnosis of a singlegene disorder from maternal plasma," Lancet 356:1170, 2000.
Sambrook and Russell, Molecular Cloning: A Laboratory Manual 3d ed., 2001.
Schouten et al., "Relative quantification of 40 nucleic acid sequences by multiplex ligation-dependent probe amplification." Nucleic Acids Res. Jun. 15, 2002;30(12):e57.
Schwinger et al., "Clinical utility gene card for: DiGeorge syndrome, velocardiofacial syndrome, Shprintzen syndrome, chromosome 22q11.2 deletion syndrome (22q11.2, TBX1)," European Journal of Human Genetics (2010) 18, published online Feb. 3, 2010.
Sehnert et al., "Optimal Detection of Fetal Chromosomal Abnormalities by Massively Parallel DNA Sequencing of Cell-Free Fetal DNA from Maternal Blood," Clinical Chemistry, 57:7, pp. 1042-1049 (2011).
Sekizawa et al., "Cell-free Fetal DNA is increased in Plasma of Women with Hyperemisis Gravidarum," Clin. Chem. 47:2164-2165, 2001.
Shah, S.P., et al. (2009) Mutational evolution in a lobular breast tumour profiled at single nucleotide resolution, Nature, 461, 809-813.
Shendure et al., "Next-generation DNA sequencing" in Nature Biotechnology (2008) 26:1135-1145.
Shen et al., "A hidden Markov model for copy number variant prediction from whole genome resequencing data". BMC Bioinformatics, 2011. 12(Suppl 6):54, p. 1-7.
Sherman, S. L., E. G. Allen, et al. (2007). "Epidemiology of Down syndrome." Ment Retard Dev Disabil Res Rev 13(3): 221-7.
Shin, M., L. M. Besser, et al. (2009). "Prevalence of Down syndrome among children and adolescents in 10 regions of the United States." Pediatrics 124(6): 1565-71.
Skaletsy et al., "The male-specific region of the human Y chromosome is a mosaic of discrete sequence classes." Nature. Jun. 19, 2003;423(6942):825-37.
Slater et al., "Rapid, high throughput prenatal detection of aneuploidy using a novel quantitative method (MLPA)." J Med Genet. Dec. 2003;40(12):907-12.
Snijders et al., "Assembly of microarrays for genome-wide measurement of DNA copy number." Nat Genet. Nov. 2001;29(3):263-4.
Snijders et al., "First-trimester ultrasound screening for chromosomal defects." Ultrasound Obstet Gynecol. Mar. 1996;7(3):216-26.
Snijders et al., "UK multicentre project on assessment of risk of trisomy 21 by maternal age and fetal nuchal-translucency thickness at 10-14 weeks of gestation. Fetal Medicine Foundation First Trimester Screening Group." Lancet. Aug. 1, 1998;352(9125):343-6.
Soni et al., "Progress toward ultrafast DNA sequencing using solid-state nanopores." Clin Chem. Nov. 2007;53(11):1996-2001. Epub Sep. 21, 2007.
Sparks et al., (2012): "Selective analysis of cell-free DNA in maternal blood for evaluation of fetal trisomy," Prenatal Diagnosis, 32, 3-9.
Sparks et al., (2012): Non-invasive Prenatal Detection and Selective Analysis of Cell-free DNA Obtained from Maternal Blood: Evaluation for Trisomy 21 and Trisomy 18, American Journal of Obstetrics and Gynecology, pp. 319.e1-319.e9, doi: 10.1016/j.ajog.2012.01.030.
Srinivasan et al., Noninvasive Detection of Fetal Subchromosome Abnormalities via Deep Sequencing of Maternal Plasma, The American Journal of Human Genetics (2013) 167-176.
Stagi et al., "Bone density and metabolism in subjects with microdeletion of chromosome 22q11 (del22q11)." Eur J Endocrinol, 2010. 163(2): p. 329-37.
Stanghellini, I., R. Bertorelli, et al. (2006). "Quantitation of fetal DNA in maternal serum during the first trimester of pregnancy by the use of a DAZ repetitive probe." Mol Hum Reprod 12(9): 587-91.
Strachan, The Human Genome, T. BIOS Scientific Publishers, 1992.
Tabor et al. (1986). "Randomised controlled trial of genetic amniocentesis in 4606 low-risk women." Lancet 1(8493): 1287-93.
Timp et al., "Nanopore Sequencing: Electrical Measurements of the Code of Life," IEEE Trans Nanotechnol. May 1, 2010; 9(3): 281-294.
Van den Berghe H, Parloir C, David G et al. A new characteristic karyotypic anomaly in lymphoproliferative disorders. Cancer 1979; 44: 188-95.
Veltman et al., "High-throughput analysis of subtelomeric chromosome rearrangements by use of array-based comparative genomic hybridization." Am J Hum Genet. May 2002;70(5):1269-76. Epub Apr. 9, 2002.
Venkatraman, ES, Olshen, AB (2007) "A faster circular binary segmentation algorithm for the analysis of array CGH data", Bioinformatics, 23, 6:657-63.
Verbeck et al. in the Journal of Biomolecular Techniques (vol. 13, Issue 2, 56-61).
Verma et al., "Rapid and simple prenatal DNA diagnosis of Down's syndrome." Lancet. Jul. 4, 1998;352(9121):9-12.
Vincent et al., "Helicase-dependent isothermal DNA amplification." EMBO Rep. Aug. 2004;5(8):795-800. Epub Jul. 9, 2004.
Voelkerding et al., "Next-generation sequencing: from basic research to diagnostics." Clin Chem. Apr. 2009;55(4):641-58. doi: 10.1373/clinchem.2008.112789. Epub Feb. 26, 2009.
Vogelstein et al., "Digital PCR." Proc Natl Acad Sci U S A. Aug. 3, 1999;96(16):9236-41.

(56) References Cited

OTHER PUBLICATIONS

Wang and S. Wang, "A novel stationary wavelet denoising algorithm for array-based DNA copy number data", International Journal of Bioinformatics Research and Applications, vol. 3, No. 2, pp. 206-222, 2007.
Wapner et al., "First-trimester screening for trisomies 21 and 18." N Engl J Med. Oct. 9, 2003;349(15):1405-13.
WaveThresh (WaveThresh : Wavelets statistics and transforms [online],[retrieved on Apr. 24, 2013], retrieved from the internet <URL:*>http://cran.r-project.org/web/packages/wavethresh/index.html<>) and a detailed description of WaveThresh ( Package 'wavethresh' [online, PDF], Apr. 2, 2013, [retrieved on Apr. 24, 2013], retrieved from the internet <URL:*>http://cran.r-project.org/web/packages/wavethresh/wavethresh.pdf<>).
Willenbrock H, Fridlyand J. A comparison study: applying segmentation to array CGH data for downstream analyses. Bioinformatics (Nov. 15, 2005);21(22):4084-91.
Wright et al., "The use of cell-free fetal nucleic acids in maternal blood for non-invasive diagnosis," Human Reproduction Update 2009, vol. 15, No. 1, pp. 139-151.
Wu et al., "Genetic and environmental influences on blood pressure and body mass index in Han Chinese: a twin study," (Feb. 2011) Hypertens Res. Hypertens Res 34: 173-179; advance online publication, Nov. 4, 2010.
Zhang et al., "A single cell level based method for copy number variation analysis by low coverage massively parallel sequencing," PLoS ONE 8(1): e54236. doi:10.1371/journal.pone.0054236 (2013).
Zhao et al., "Quantification and application of the placental epigenetic signature of the RASSF1A gene in maternal plasma." Prenat Diagn. Aug. 2010;30(8):778-82. doi: 10.1002/pd.2546.
Zhong et al., "Elevation of both maternal and fetal extracellular circulating deoxyribonucleic acid concentrations in the plasma of pregnant women with preeclampsia," Am. J. Obstet. Gynecol. 184:414-419, 2001.
Zhong et al., "Cell-free fetal DNA in the maternal circulation does not stem from the transplacental passage of fetal erythroblasts" Molecular Human Reproduction (2002) 8(9):864-870.
Zhou et al., "Recent Patents of Nanopore DNA Sequencing Technology: Progress and Challenges," Recent Patents on DNA & Gene Sequences 2010, 4, 192-201.
Zhou et al., "Detection of DNA copy number abnormality by microarray expression analysis" Hum. Genet. (2004) 114:464-467.
Zimmermann, B., X. Y. Zhong, et al. (2007). "Real-time quantitative polymerase chain reaction measurement of male fetal DNA in maternal plasma." Methods Mol Med 132: 43-9.
International Preliminary Report on Patentability and Written Opinion dated Jan. 9, 2014 in International Application No. PCT/US2012/043388, filed on Jun. 20, 2012 and published as WO 2012/177792 on Dec. 27, 2012 .
International Search Report and Written Opinion dated Apr. 5, 2013 in International Application No. PCT/US2012/043388 filed: Jun. 20, 2012 and published as: WO 12/177792 Dec. 27, 2012.
International Search Report and Written Opinion dated Jul. 4, 2013 in International Application No. PCT/US2013/022290 filed: Jan. 18, 2013, and published as: WO/2013/109981 on Jul. 25, 2013.
International Search Report and Written Opinion dated Mar. 6, 2013 in International Application No. PCT/US2012/059592 filed: Oct. 10, 2012.
International Search Report and Written Opinion dated Sep. 26, 2012 in International Application No. PCT/US2011/066639 filed: Dec. 21, 2011 and published as: WO 12/088348 Jun. 28, 2012.
Invitation to Pay Additional Fees and Partial Search Report dated Jan. 18, 2013 in International Application No. PCT/US2012/059592 filed: Oct. 10, 2012.
Invitation to Pay Additional Fees and Partial Search Report dated Jul. 3, 2013 in International Application No. PCT/US2012/059123 filed: Oct. 5, 2012 and published as: WO/2013/052913 on Apr. 11, 2013.
International Search Report and Written Opinion dated Sep. 9, 2013 in International Application No. PCT/US2012/059123, filed on Oct. 5, 2012 and published as WO/2013/052913 on Apr. 11, 2013.
International Search Report and Written Opinion dated Sep. 9, 2013 in International Application No. PCT/US2012/059114, filed on Oct. 5, 2012 and published as WO/2013/052907 on Apr. 11, 2013.
International Search Report and Written Opinion dated Sep. 18, 2013 in International Application No. PCT/US2013/047131, filed on Jun. 21, 2013 and published as WO 2013/192562 on Dec. 27, 2013.
International Search Report and Written Opinion dated Dec. 13, 2013 in International Application No. PCT/US2013/063287, filed Oct. 3, 2013.
International Preliminary Report on Patentability dated Feb. 27, 2014 in International Application No. PCT/US2012/059123, filed on Oct. 5, 2012 and published as WO 2013/052913 on Apr. 11, 2013.
Office Action dated Feb. 20, 2013 in U.S. Appl. No. 13/656,328, filed Oct. 19, 2012, not yet published.
Office Action dated Feb. 15, 2013 in U.S. Appl. No. 13/669,136, filed Nov. 5, 2012 and published as: US 2013-0085681 on Apr. 4, 2013.
Office Action dated May 7, 2013 in U.S. Appl. No. 13/754,817, filed Jan. 30, 2013.
Office Action dated May 3, 2013 in U.S. Appl. No. 13/333,842, filed Dec. 21, 2011 and published as:-2012/0184449 on: Jul. 19, 2012.
Office Action dated Aug. 22, 2013 in U.S. Appl. No. 13/797,508, filed Mar. 12, 2013.
Office Action dated Sep. 11, 2013 in U.S. Appl. No. 13/829,164, filed Mar. 14, 2013.
Office Action dated Sep. 12, 2013 in U.S. Appl. No. 13/669,136, filed Nov. 5, 2012 and published as: US 2013-0085681 on Apr. 4, 2013.
Office Action dated Sep. 12, 2013 in U.S. Appl. No. 13/656,328, filed Oct. 19, 2012 and published as US 2013-0103320 on Apr. 25, 2013.
Office Action dated Oct. 16, 2013 in U.S. Appl. No. 13/933,935, filed Jul. 2, 2013 and published as US 2013-0304392 on Nov. 14, 2013.
Office Action dated Oct. 17, 2013 in U.S. Appl. No. 13/669,136, filed Nov. 5, 2012 and published as US 2013-0085681 on Apr. 4, 2013.
Office Action dated Oct. 18, 2013 in U.S. Appl. No. 13/656,328, filed Oct. 19, 2012 and published as US 2013-0103320 on Apr. 25, 2013.
Office Action dated Dec. 26, 2013 in U.S. Appl. No. 13/797,508, filed Mar. 12, 2013 and published as US 2013-0261983 on Oct. 3, 2013.
Office Action dated Jan. 17, 2014 in U.S. Appl. No. 13/333,842, filed Dec. 21, 2011 and published as US 2012/0184449 on Jul. 19, 2012.
Office Action dated Jan. 27, 2014 in U.S. Appl. No. 13/829,164, filed Mar. 14, 2013 and published as US 2013-0288244 on Oct. 31, 2014.
Office Action dated Jan. 30, 2014 in U.S. Appl. No. 13/933,935, filed Jul. 2, 2013 and published as US 2013-0304392 on Nov. 14, 2013.
Office Action dated Apr. 7, 2014 in U.S. Appl. No. 13/754,817, filed Jan. 30, 2013 and published as US 2013-0150253 on Jun. 13, 2013.
International Preliminary Report on Patentability and Written Opinion dated Apr. 24, 2014 in International Application No. PCT/US2012/059592, filed on Oct. 10, 2012 and published as WO 2013/055817 on Apr. 18, 2013.
International Search Report and Written Opinion dated Apr. 2, 2014 in International Application No. PCT/US2013/063314, filed on Oct. 3, 2013 and published as WO 2014/055790 on Apr. 10, 2014.
International Search Report and Written Opinion dated May 9, 2014 in International Application No. PCT/US2014/012369, filed Jan. 21, 2014.
International Preliminary Report on Patentability dated Jun. 9, 2014 in International Application No. PCT/US2012/059114, filed on Oct. 5, 2012 and published as WO 2013/052907 on Apr. 11, 2013.

(56) References Cited

OTHER PUBLICATIONS

International Search Report and Written Opinion dated Jul. 14, 2014 in International Application No. PCT/US2014/032687, filed on Apr. 2, 2014.

Office Action dated Jul. 28, 2014 in U.S. Appl. No. 13/797,508, filed Mar. 12, 2013 and published as US 2013-0261983 on Oct. 3, 2013.

International Preliminary Report on Patentability dated Jul. 31, 2014 in International Application No. PCT/US2013/022290, filed on Jan. 18, 2013 and published as WO 2013/109981 on Jul. 25, 2013.

Office Action dated Aug. 13, 2014 in U.S. Appl. No. 13/829,164, filed Mar. 14, 2013 and published as US 2013-0288244 on Oct. 31, 2014.

Office Action dated Aug. 13, 2014 in U.S. Appl. No. 13/669,136, filed Nov. 5, 2012 and published as US 2013-0085681 on Apr. 4, 2013.

Office Action dated Aug. 14, 2014 in U.S. Appl. No. 13/933,935, filed Jul. 2, 2013 and published as US 2013-0304392 on Nov. 14, 2013.

International Search Report and Written Opinion dated Sep. 24, 2014 in International Application No. PCT/US2014/043497, filed on Jun. 20, 2014.

Office Action dated Oct. 6, 2014 in U.S. Appl. No. 13/754,817, filed Jan. 30, 2013 and published as US 2013-0150253 on Jun. 13, 2013.

International Search Report and Written Opinion dated Dec. 17, 2014 in International Application No. PCT/US2014/039389, filed on May 23, 2014 and published as WO 2014/190286 on Nov. 27, 2014.

International Preliminary Report on Patentability dated Dec. 31, 2014 in International Application No. PCT/US2013/047131, filed on Jun. 21, 2013 and published as WO 2013/192562 on Dec. 27, 2013.

International Search Report and Written Opinion dated Feb. 18, 2015 in International Application No. PCT/US2014/058885, filed on Oct. 2, 2014.

Office Action dated Mar. 19, 2015 in U.S. Appl. No. 13/797,508, filed Mar. 12, 2013 and published as US 2013-0261983 on Oct. 3, 2013.

Office Action dated Apr. 16, 2015 in U.S. Appl. No. 13/669,136, filed Nov. 5, 2012 and published as US 2013-0085681 on Apr. 4, 2013.

Office Action dated Apr. 16, 2015 in U.S. Appl. No. 13/933,935, filed Jul. 2, 2013 and published as US 2013-0304392 on Nov. 14, 2013.

International Preliminary Report on Patentability dated Apr. 16, 2015 in International Application No. PCT/US2013/063314, filed on Oct. 3, 2013 and published as WO 2014/055790 on Apr. 10, 2014.

International Preliminary Report on Patentability dated Apr. 16, 2015 in International Application No. PCT/US2013/063287, filed Oct. 3, 2013.

Office Action dated Apr. 17, 2015 in U.S. Appl. No. 13/829,164, filed Mar. 14, 2013 and published as US 2013-0288244 on Oct. 31, 2014.

Office Action dated Apr. 21, 2015 in U.S. Appl. No. 13/754,817, filed Jan. 30, 2013 and published as US 2013-0150253 on Jun. 13, 2013.

Office Action dated May 13, 2015 in U.S. Appl. No. 13/333,842, filed Dec. 21, 2011 and published as US 2012/0184449 on Jul. 19, 2012.

Office Action dated May 12, 2015 in U.S. Appl. No. 13/669,136, filed Nov. 5, 2012 and published as US 2013-0085681 on Apr. 4, 2013.

Fromer et al., "Discovery and statistical genotyping of copy-number variation from whole-exome sequencing depth" The American Journal of Human Genetics (2012) 91:597-607.

Krumm et al., "Copy number variation detection and genotyping from exome sequence data" Genome Research (2012) 22(8):1525-32.

Zheng et al., "Bias detection and correction in RNA-Sequencing" BMC Bioinformatics (2011) 12:290.

Zheng, et al., "Bias detection and correction in RNA-sequencing data", BMC Bioinformatics, Biomed Central, London, GB 12(1), Jul. 19, 2011, 290.

* cited by examiner

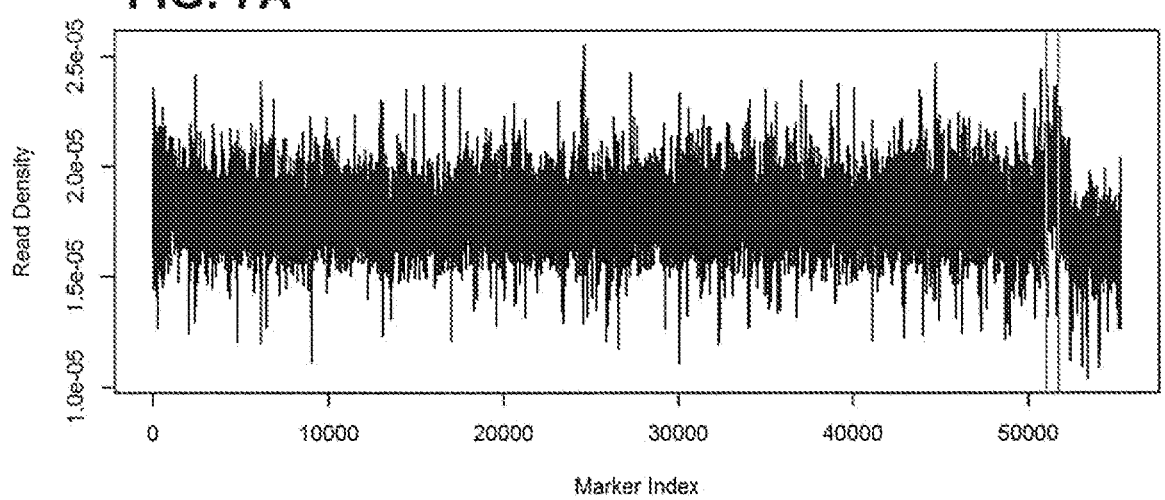
FIG. 7A Raw Read Density
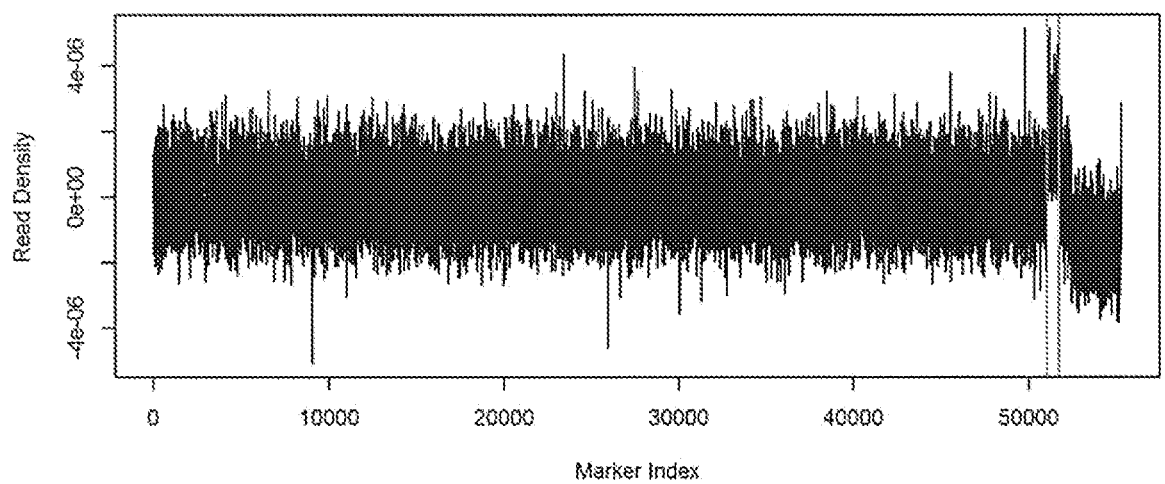
FIG. 7B Median-adjusted Read Density
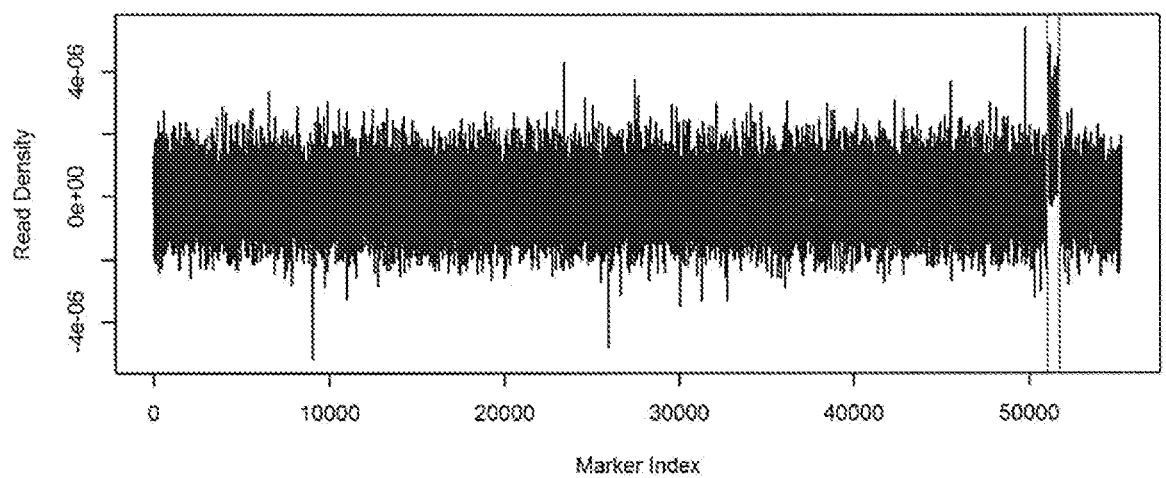
FIG. 7C Median- & PC-adjusted Read Density

METHODS AND PROCESSES FOR NON-INVASIVE ASSESSMENT OF GENETIC VARIATIONS

RELATED PATENT APPLICATIONS

This patent application claims the benefit of U.S. provisional patent application No. 61/887,081 filed on Oct. 4, 2013, entitled METHODS AND PROCESSES FOR NON-INVASIVE ASSESSMENT OF GENETIC VARIATIONS, naming Gregory Hannum as inventor. The entire content of the foregoing application is incorporated herein by reference, including all text, tables and drawings.

FIELD

Technology provided herein relates in part to methods, processes and machines for non-invasive assessment of genetic variations.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on twenty-four (24) chromosomes (see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations. Certain genetic variations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Trisomies 16 and 22, Monosomy X (Turner's Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and cancer (e.g., colorectal, breast, ovarian, lung).

Identifying one or more genetic variations or variances can lead to diagnosis of, or determining predisposition to, a particular medical condition. Identifying a genetic variance can result in facilitating a medical decision and/or employing a helpful medical procedure. In certain embodiments, identification of one or more genetic variations or variances involves the analysis of cell-free DNA. Cell-free DNA (CF-DNA) is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

SUMMARY

Provided herein, in certain aspects, is a system comprising memory and one or more microprocessors, which one or more microprocessors are configured to perform, according to instructions in the memory, a process for reducing bias in sequence reads for a sample, which process comprises (a) generating a relationship between (i) local genome bias estimates and (ii) bias frequencies for sequence reads of a test sample, thereby generating a sample bias relationship, where the sequence reads are of circulating cell-free nucleic acid from the test sample, and the sequence reads are mapped to a reference genome, (b) comparing the sample bias relationship and a reference bias relationship, thereby generating a comparison, where the reference bias relationship is between (i) local genome bias estimates and (ii) the bias frequencies for a reference and (c) normalizing counts of the sequence reads for the sample according to the comparison determined in (b), where bias in the sequence reads for the sample is reduced.

Provided herein, in certain aspects, is a system comprising memory and one or more microprocessors, which one or more microprocessors are configured to perform, according to instructions in the memory, a process for reducing bias in sequence reads for a sample, which process comprises (a) generating a relationship between (i) guanine and cytosine (GC) densities and (ii) GC density frequencies for sequence reads of a test sample, thereby generating a sample GC density relationship, where the sequence reads are of circulating cell-free nucleic acid from the test sample, and the sequence reads are mapped to a reference genome, (b) comparing the sample GC density relationship and a reference GC density relationship, thereby generating a comparison, where the reference GC density relationship is between (i) GC densities and (ii) the GC density frequencies for a reference, and (c) normalizing counts of the sequence reads for the sample according to the comparison determined in (b), whereby bias in the sequence reads for the sample is reduced.

Also provided herein, in certain aspects, is a system comprising memory and one or more microprocessors, which one or more microprocessors are configured to perform, according to instructions in the memory, a process for determining the presence or absence of an aneuploidy for a sample, which process comprises (a) filtering, according to a read density distribution, portions of a reference genome, thereby providing a read density profile for a test sample comprising read densities of filtered portions, where the read densities comprise sequence reads of circulating cell-free nucleic acid from a test sample from a pregnant female, and the read density distribution is determined for read densities of portions for multiple samples, (b) adjusting the read density profile for the test sample according to one or more principal components, which principal components are obtained from a set of known euploid samples by a principal component analysis, thereby providing a test sample profile comprising adjusted read densities, (c) comparing the test sample profile to a reference profile, thereby providing a comparison and (d) determining the presence or absence of a chromosome aneuploidy for the test sample according to the comparison.

Certain aspects of the technology are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 7A-C shows an example of a read density profile of a sample for a genome comprising a trisomy of Chromosome 21 (e.g., bracketed with two vertical lines). Relative positions of each genomic portion are shown on the x-axis. Read densities are provided on the y-axis. FIG. 7A shows a raw (e.g., not adjusted) read density profile. FIG. 7B shows the profile of 7A comprising a first adjustment comprising a subtraction of the median profile. FIG. 7C shows the profile of 7B comprising a second adjustment. The second adjustment comprises subtraction of 8× principal component profiles, weighted based on their representation found in this sample. (e.g., a model is built). For example a SampleProfile=A*PC1+B*PC2+C*PC3 . . . and a corrected profile, for example as shown in 7C=SampleProfile−A*PC1+B*PC2+C*PC3 . . . .

FIG. 8 shows a comparison of ChAI scores (y-axis) from test samples to a uniform distribution (i.e., expected distribution of p-values, x-axis). Each point represents log-p value scores of a single test sample. The samples are sorted and assigned an 'expected' value (x-axis) based on the uniform distribution. The lower dashed line represents the diagonal and the upper line represents a Bonferroni threshold. Samples that follow a uniform distribution would be expected to land on the lower diagonal (lower dashed line). The data values lie well off of the diagonals due to correlations in the portions (e.g., bias) indicating more high-scoring (low p-value) samples than expected. Methods described herein (e.g., ChAI, e.g., see Example 1) can correct for this observed bias.

DETAILED DESCRIPTION

Figure 1:
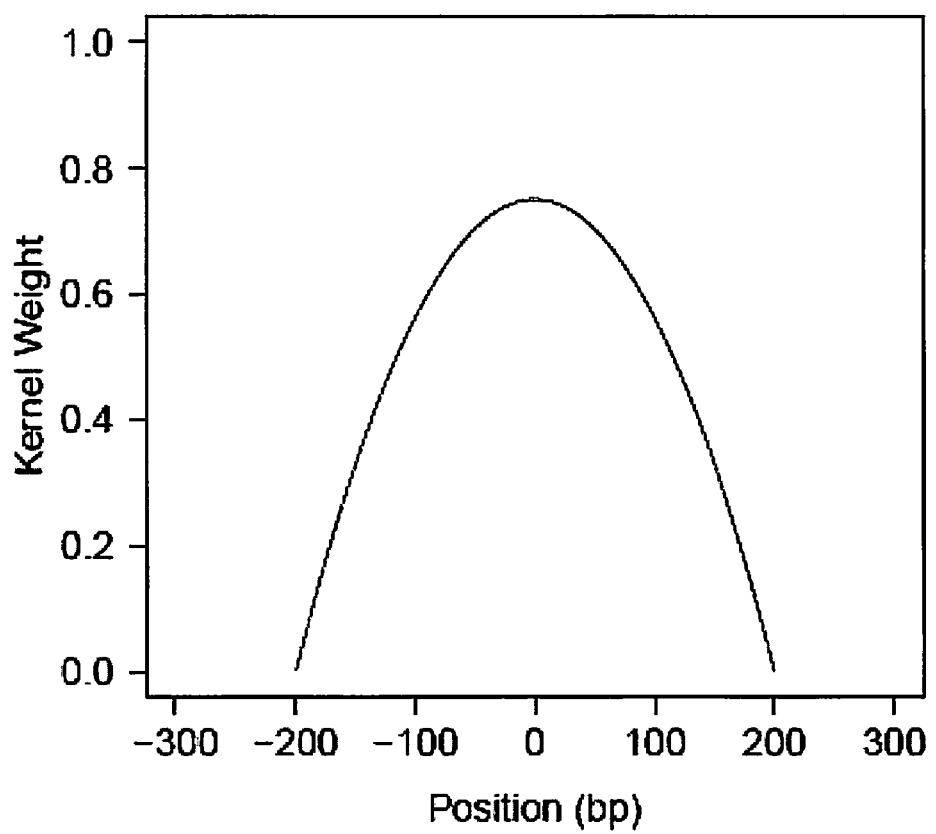
FIG. 1 shows an embodiment of a GC density provided by a Epanechnikov kernel (bandwidth=200 bp).

Next generation sequencing allows for sequencing nucleic acids on a genome-wide scale by methods that are faster and cheaper than traditional methods of sequencing. Methods, systems and products provided herein can utilize advanced sequencing technologies to locate and identify genetic variations and/or associated diseases and disorders. Methods, systems and products provided herein can often provide for a non-invasive assessment of a subjects genome (e.g., a fetal genome) using a blood sample, or part thereof, and are often safer, faster and/or less expensive than more invasive techniques (e.g., amniocentesis, biopsy). In some embodiments, provided herein are methods that comprise, in part, obtaining sequence reads of nucleic acids present in a sample, which sequence reads often are mapped to a reference sequence, processing counts of sequence reads and determining the presence or absence of a genetic variation. Systems, methods and products provided herein are useful for locating and/or identifying genetic variations and are useful for diagnosing and treating diseases, disorders and disabilities associated with certain genetic variations.

Also provided herein, in some embodiments, are data manipulation methods to reduce and/or remove sequencing bias introduced by various aspects of a sequencing technology. Sequencing bias often contributes to a non-uniform distribution of reads across a genome, or a segment thereof, and/or variations in read quality. Sequencing bias can corrupt genomic sequencing data, impair effective data analysis, taint results and preclude accurate data interpretation. Sometimes sequencing bias can be reduced by increasing sequencing coverage; however this approach often inflates sequencing costs, and has very limited effectiveness. Data manipulation methods described herein can reduce and/or remove sequencing bias thereby improving the quality of sequence read data without increasing sequencing costs. Also provided herein are systems, machines, apparatuses, products and modules that, in some embodiments, carry out methods described herein.

Samples

Provided herein are methods and compositions for analyzing nucleic acid. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, fetal vs. maternal origins, cell or tissue origins, sample origins, subject origins, and the like), or combinations thereof.

Nucleic acid or a nucleic acid mixture utilized in methods, systems, machines and/or apparatuses described herein often is isolated from a sample obtained from a subject (e.g., a test subject). A subject from which a specimen or sample is obtained is sometimes referred to herein as a test subject. A subject can be any living or non-living organism, including but not limited to a human, non-human animal, plant, bacterium, fungus, virus or protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman, a pregnant woman, a pregnant female). A subject may be any age (e.g., an embryo, a fetus, infant, child, adult).

Nucleic acid may be isolated from any type of suitable biological specimen or sample (e.g., a test sample). A sample or test sample can be any specimen that is isolated or obtained from a subject or part thereof (e.g., a human subject, a pregnant female, a fetus). A test sample is often obtained from a test subject. A test sample is often obtained from a pregnant female (e.g., a pregnant human female). Non-limiting examples of specimens include fluid or tissue from a subject, including, without limitation, blood or a blood product (e.g., serum, plasma, or the like), umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo), celocentesis sample, cells (blood cells, placental cells, embryo or fetal cells, fetal nucleated cells or fetal cellular remnants) or parts thereof (e.g., mitochondrial, nucleus, extracts, or the like), washings of female reproductive tract, urine, feces, sputum, saliva, nasal mucous, prostate fluid, lavage, semen, lymphatic fluid, bile, tears, sweat, breast milk, breast fluid, the like or combinations thereof. A test sample can comprise blood or a blood product (e.g., plasma, serum, lymphocytes, platelets, buffy coats). A test sample sometimes comprises serum obtained from a pregnant female. A test sample sometimes comprises plasma obtained from a pregnant female. In some embodiments, a biological sample is a cervical swab from a subject. In some embodiments, a biological sample may be blood and sometimes plasma or serum. The term "blood" as used herein refers to a blood sample or preparation from a subject (e.g., a test subject, e.g., a pregnant woman or a woman being tested for possible pregnancy). The term encompasses whole blood, a blood product or any fraction of blood, such as serum, plasma, buffy coat, or the like as conventionally defined. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). In certain embodiments buffy coats comprise maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted may be acellular (e.g., cell-free). In some embodiments, a fluid or tissue sample may contain cellular elements or cellular remnants. In some embodiments fetal cells or cancer cells may be included in the sample.

A sample often is heterogeneous, by which is meant that more than one type of nucleic acid species is present in the sample. For example, heterogeneous nucleic acid can include, but is not limited to, (i) fetal derived and maternal derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species is present.

For prenatal applications of technology described herein, fluid or tissue sample may be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant female between about 1 to about 45 weeks of fetal gestation (e.g., at 1-4, 4-8, 8-12, 12-16, 16-20, 20-24, 24-28, 28-32, 32-36, 36-40 or 40-44 weeks of fetal gestation), and sometimes between about 5 to about 28 weeks of fetal gestation (e.g., at 6, 7, 8, 9, 10, 11, 12, 13, 14, 15, 16, 17, 18, 19, 20, 21, 22, 23, 24, 25, 26 or 27 weeks of fetal gestation). In certain embodiments a fluid or tissue sample is collected from a pregnant female during or just after (e.g., 0 to 72 hours after) giving birth (e.g., vaginal or non-vaginal birth (e.g., surgical delivery)).

Acquisition of Blood Samples and Extraction of DNA

Methods herein often include separating, enriching and analyzing fetal DNA found in maternal blood as a non-invasive means to detect the presence or absence of a maternal and/or fetal genetic variation and/or to monitor the health of a fetus and/or a pregnant female during and sometimes after pregnancy. Thus, the first steps of practicing certain methods herein often include obtaining a blood sample from a pregnant woman and extracting DNA from a sample.

Acquisition of Blood Samples

A blood sample can be obtained from a pregnant woman at a gestational age suitable for testing using a method of the present technology. A suitable gestational age may vary depending on the disorder tested, as discussed below. Collection of blood from a woman often is performed in accordance with the standard protocol hospitals or clinics generally follow. An appropriate amount of peripheral blood, e.g., typically between 5-50 ml, often is collected and may be stored according to standard procedure prior to further preparation. Blood samples may be collected, stored or transported in a manner that minimizes degradation or the quality of nucleic acid present in the sample.

Preparation of Blood Samples

An analysis of fetal DNA found in maternal blood may be performed using, e.g., whole blood, serum, or plasma. Methods for preparing serum or plasma from maternal blood are known. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. Serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

Extraction of DNA

There are numerous known methods for extracting DNA from a biological sample including blood. The general methods of DNA preparation (e.g., described by Sambrook and Russell, Molecular Cloning: A Laboratory Manual 3d ed., 2001) can be followed; various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

In some embodiments, the sample may first be enriched or relatively enriched for fetal nucleic acid by one or more methods. For example, the discrimination of fetal and maternal DNA can be performed using the compositions and processes of the present technology alone or in combination with other discriminating factors. Examples of these factors include, but are not limited to, single nucleotide differences between chromosome X and Y, chromosome Y-specific sequences, polymorphisms located elsewhere in the genome, size differences between fetal and maternal DNA and differences in methylation pattern between maternal and fetal tissues.

Other methods for enriching a sample for a particular species of nucleic acid are described in PCT Patent Application Number PCT/US07/69991, filed May 30, 2007, PCT Patent Application Number PCT/US2007/071232, filed Jun. 15, 2007, U.S. Provisional Application Nos. 60/968,876 and 60/968,878 (assigned to the Applicant), (PCT Patent Application Number PCT/EP05/012707, filed Nov. 28, 2005) which are all hereby incorporated by reference. In certain embodiments, maternal nucleic acid is selectively removed (either partially, substantially, almost completely or completely) from the sample.

The terms "nucleic acid" and "nucleic acid molecule" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons). Deoxyribonucleotides include deoxyadenosine, deoxycytidine, deoxyguanosine and deoxythymidine. For RNA, the base cytosine is replaced with uracil. A template nucleic acid may be prepared using a nucleic acid obtained from a subject as a template.

Nucleic Acid Isolation and Processing

Nucleic acid may be derived from one or more sources (e.g., cells, serum, plasma, buffy coat, lymphatic fluid, skin, soil, and the like) by methods known in the art. Nucleic acids are often isolated from a test sample. Any suitable method can be used for isolating, extracting and/or purifying DNA from a biological sample (e.g., from blood or a blood product), non-limiting examples of which include methods of DNA preparation (e.g., described by Sambrook and Russell, Molecular Cloning: A Laboratory Manual 3d ed., 2001), various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), the like or combinations thereof.

Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 µg/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acids can include extracellular nucleic acid in certain embodiments. The term "extracellular nucleic acid" as used herein can refer to nucleic acid isolated from a source having substantially no cells and also is referred to as "cell-free" nucleic acid and/or "cell-free circulating" nucleic acid. Extracellular nucleic acid can be present in and obtained from blood (e.g., from the blood of a pregnant female). Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is fetal nucleic acid). In some embodiments, the majority of fetal nucleic acid in nucleic acid is of a length of about 500 base pairs or less, about 250 base pairs or less, about 200 base pairs or less, about 150 base pairs or less, about 100 base pairs or less, about 50 base pairs or less or about 25 base pairs or less.

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, nucleosomes comprising small fragments of fetal nucleic acid can be purified from a mixture of larger nucleosome complexes comprising larger fragments of maternal nucleic acid.

In some embodiments nucleic acids are fragmented or cleaved prior to, during or after a method described herein. Fragmented or cleaved nucleic acid may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs. Fragments can be generated by a suitable method known in the art, and the average, mean or nominal length of nucleic acid fragments can be controlled by selecting an appropriate fragment-generating procedure.

Nucleic acid fragments may contain overlapping nucleotide sequences, and such overlapping sequences can facilitate construction of a nucleotide sequence of the non-fragmented counterpart nucleic acid, or a segment thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample in certain embodiments. Nucleic acid may be partially fragmented (e.g., from an incomplete or terminated specific cleavage reaction) or fully fragmented in certain embodiments.

In some embodiments nucleic acid is fragmented or cleaved by a suitable method, non-limiting examples of which include physical methods (e.g., shearing, e.g., sonication, French press, heat, UV irradiation, the like), enzymatic processes (e.g., enzymatic cleavage agents (e.g., a suitable nuclease, a suitable restriction enzyme, a suitable methylation sensitive restriction enzyme)), chemical methods (e.g., alkylation, DMS, piperidine, acid hydrolysis, base hydrolysis, heat, the like, or combinations thereof), processes described in U.S. Patent Application Publication No. 20050112590, the like or combinations thereof.

As used herein, "fragmentation" or "cleavage" refers to a procedure or conditions in which a nucleic acid molecule, such as a nucleic acid template gene molecule or amplified product thereof, may be severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid template gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid template gene molecule or the segment of an amplified product thereof containing the corresponding nucleotide sequence of a nucleic acid template gene molecule. The term "amplified" as used herein refers to subjecting a target nucleic acid in a sample to a process that linearly or exponentially generates amplicon nucleic acids having the same or substantially the same nucleotide sequence as the target nucleic acid, or segment thereof. In certain embodiments the term "amplified" refers to a method that comprises a polymerase chain reaction (PCR). For example, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule). Accordingly, fragments can include fragments arising from segments or parts of amplified nucleic acid molecules containing, at least in part, nucleotide sequence information from or based on the representative nucleic acid template molecule.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel). The term "specific cleavage agent" as used herein refers to an agent, sometimes a chemical or an enzyme that can cleave a nucleic acid at one or more specific sites.

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any suitable form useful for conducting a suitable sequence analysis.

Nucleic acid may be single or double stranded. Single stranded DNA, for example, can be generated by denaturing double stranded DNA by heating or by treatment with alkali, for example. In certain embodiments, nucleic acid is in a D-loop structure, formed by strand invasion of a duplex DNA molecule by an oligonucleotide or a DNA-like molecule such as peptide nucleic acid (PNA). D loop formation can be facilitated by addition of *E. Coli* RecA protein and/or by alteration of salt concentration, for example, using methods known in the art.

Determining Fetal Nucleic Acid Content

The amount of fetal nucleic acid (e.g., concentration, relative amount, absolute amount, copy number, and the like) in nucleic acid is determined in some embodiments. In certain embodiments, the amount of fetal nucleic acid in a sample is referred to as "fetal fraction". In some embodiments "fetal fraction" refers to the fraction of fetal nucleic acid in circulating cell-free nucleic acid in a sample (e.g., a blood sample, a serum sample, a plasma sample) obtained from a pregnant female. In certain embodiments, the amount of fetal nucleic acid is determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation; described in further detail below) between mother and fetus, or fetal RNA markers in maternal blood plasma (see e.g., Lo, 2005, Journal of Histochemistry and Cytochemistry 53 (3): 293-296)).

Determination of fetal nucleic acid content (e.g., fetal fraction) sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample. In certain embodiments, the amount of fetal nucleic acid from a maternal sample can be determined relative to the total amount of nucleic acid present, thereby providing the percentage of fetal nucleic acid in the sample. In certain embodiments, the copy number of fetal nucleic acid can be determined in a maternal sample. In certain embodiments, the amount of fetal nucleic acid can be determined in a sequence-specific (or portion-specific) manner and sometimes with sufficient sensitivity to allow for accurate chromosomal dosage analysis (for example, to detect the presence or absence of a fetal aneuploidy).

A fetal quantifier assay (FQA) can be performed in conjunction with any of the methods described herein. Such an assay can be performed by any method known in the art and/or described in U.S. Patent Application Publication No.

2010/0105049, such as, for example, by a method that can distinguish between maternal and fetal DNA based on differential methylation status, and quantify (e.g., determine the amount of) the fetal DNA. Methods for differentiating nucleic acid based on methylation status include, but are not limited to, methylation sensitive capture, for example, using a MBD2-Fc fragment in which the methyl binding domain of MBD2 is fused to the Fc fragment of an antibody (MBD-FC) (Gebhard et al. (2006) Cancer Res. 66(12):6118-28); methylation specific antibodies; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes (e.g., digestion of maternal DNA in a maternal sample using one or more methylation sensitive restriction enzymes thereby enriching the fetal DNA). Methyl-sensitive enzymes also can be used to differentiate nucleic acid based on methylation status, which, for example, can preferentially or substantially cleave or digest at their DNA recognition sequence if the latter is non-methylated.

Thus, an unmethylated DNA sample will be cut into smaller fragments than a methylated DNA sample and a hypermethylated DNA sample will not be cleaved. Except where explicitly stated, any method for differentiating nucleic acid based on methylation status can be used with the compositions and methods of the technology herein. The amount of fetal DNA can be determined, for example, by introducing one or more competitors at known concentrations during an amplification reaction. Determining the amount of fetal DNA also can be done, for example, by RT-PCR, primer extension, sequencing and/or counting. In certain instances, the amount of nucleic acid can be determined using BEAMing technology as described in U.S. Patent Application Publication No. 2007/0065823. In certain embodiments, the restriction efficiency can be determined and the efficiency rate is used to further determine the amount of fetal DNA.

In certain embodiments, a fetal quantifier assay (FQA) can be used to determine the concentration of fetal DNA in a maternal sample, for example, by the following method: a) determine the total amount of DNA present in a maternal sample; b) selectively digest the maternal DNA in a maternal sample using one or more methylation sensitive restriction enzymes thereby enriching the fetal DNA; c) determine the amount of fetal DNA from step b); and d) compare the amount of fetal DNA from step c) to the total amount of DNA from step a), thereby determining the concentration of fetal DNA in the maternal sample. In certain embodiments, the absolute copy number of fetal nucleic acid in a maternal sample can be determined, for example, using mass spectrometry and/or a system that uses a competitive PCR approach for absolute copy number measurements. See for example, Ding and Cantor (2003) PNAS, USA 100:3059-3064, and U.S. Patent Application Publication No. 2004/0081993, both of which are hereby incorporated by reference.

In certain embodiments, fetal fraction can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome. In certain embodiments, fetal alleles are identified, for example, by their relative minor contribution to the mixture of fetal and maternal nucleic acids in the sample when compared to the major contribution to the mixture by the maternal nucleic acids. Accordingly, the relative abundance of fetal nucleic acid in a maternal sample can be determined as a parameter of the total number of unique sequence reads mapped to a target nucleic acid sequence on a reference genome for each of the two alleles of a polymorphic site.

In certain embodiments, fetal fraction can be determined based on one or more levels. Fetal fraction determination according to a level is described, for example, in International Application Publication No. WO 2014/055774, the entire content of which is incorporated herein by reference, including all text, tables, equations and drawings. In some embodiments, a fetal fraction is determined according to a level categorized as representative of a maternal and/or fetal copy number variation. For example, determining fetal fraction can comprises assessing an expected level for a maternal and/or fetal copy number variation utilized for the determination of fetal fraction. In some embodiments, a fetal fraction is determined for a level (e.g., a first level) categorized as representative of a copy number variation according to an expected level range determined for the same type of copy number variation. A fetal fraction can determined according to an observed level that falls within an expected level range and is thereby categorized as a maternal and/or fetal copy number variation. In some embodiments, a fetal fraction is determined when an observed level (e.g., a first level) categorized as a maternal and/or fetal copy number variation is different than the expected level determined for the same maternal and/or fetal copy number variation. Fetal fraction can be provided as a percent. For example, a fetal fraction can be divided by 100 thereby providing a percent value. For example, for a first level representative of a maternal homozygous duplication and having a level of 155 and an expected level for a maternal homozygous duplication having a level of 150, a fetal fraction can be determined as 10% (e.g., (fetal fraction=2×(155−150)).

The amount of fetal nucleic acid in extracellular nucleic acid can be quantified and used in conjunction with a method provided herein. Thus, in certain embodiments, methods of the technology described herein comprise an additional step of determining the amount of fetal nucleic acid. The amount of fetal nucleic acid can be determined in a nucleic acid sample from a subject before or after processing to prepare sample nucleic acid. In certain embodiments, the amount of fetal nucleic acid is determined in a sample after sample nucleic acid is processed and prepared, which amount is utilized for further assessment. In some embodiments, an outcome comprises factoring the fraction of fetal nucleic acid in the sample nucleic acid (e.g., adjusting counts, removing samples, making a call or not making a call). In certain embodiments, a method provided herein can be used in conjunction with a method for determining fetal fraction. For example, methods for determining fetal fraction that include a normalization process may comprise one or more normalization methods provided herein (e.g., a principal component normalization).

The determination step can be performed before, during, at any one point in a method described herein, or after certain (e.g., aneuploidy detection, fetal gender determination) methods described herein. For example, to achieve a fetal gender or aneuploidy determination method with a given sensitivity or specificity, a fetal nucleic acid quantification method may be implemented prior to, during or after fetal gender or aneuploidy determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more fetal nucleic acid. In some embodiments, samples determined as having a certain threshold amount of fetal nucleic acid (e.g., about 15% or more fetal nucleic acid; about 4% or more fetal nucleic acid) are further analyzed for fetal gender or aneuploidy determination, or the presence or absence of aneuploidy or genetic variation, for example. In certain embodiments, determinations of, for example, fetal gender or the presence or absence of aneuploidy are selected (e.g., selected and communicated to a patient) only for samples having a certain threshold amount of fetal nucleic acid (e.g., about 15% or more fetal nucleic acid; about 4% or more fetal nucleic acid).

In some embodiments, the determination of fetal fraction or determining the amount of fetal nucleic acid is not required or necessary for identifying the presence or absence of a chromosome aneuploidy. In some embodiments, identifying the presence or absence of a chromosome aneuploidy does not require the sequence differentiation of fetal versus maternal DNA. In certain embodiments this is because the summed contribution of both maternal and fetal sequences in a particular chromosome, chromosome portion or segment thereof is analyzed. In some embodiments, identifying the presence or absence of a chromosome aneuploidy does not rely on a priori sequence information that would distinguish fetal DNA from maternal DNA.

Enriching Nucleic Acids

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with a method provided herein. Thus, in certain embodiments, methods of the technology comprise an additional step of enriching for a subpopulation of nucleic acid in a sample, such as, for example, fetal nucleic acid. In certain embodiments, a method for determining fetal fraction described above also can be used to enrich for fetal nucleic acid. In certain embodiments, maternal nucleic acid is selectively removed (partially, substantially, almost completely or completely) from the sample. In certain embodiments, enriching for a particular low copy number species nucleic acid (e.g., fetal nucleic acid) may improve quantitative sensitivity. Methods for enriching a sample for a particular species of nucleic acid are described, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639, International Patent Application Publication No. WO2011/034631, International Patent Application Publication No. WO2006/056480, and International Patent Application Publication No. WO2011/143659, the entire content of each is incorporated herein by reference, including all text, tables, equations and drawings.

In some embodiments, nucleic acid is enriched for certain target fragment species and/or reference fragment species. In certain embodiments, nucleic acid is enriched for a specific nucleic acid fragment length or range of fragment lengths using one or more length-based separation methods described below. In certain embodiments, nucleic acid is enriched for fragments from a select genomic region (e.g., chromosome) using one or more sequence-based separation methods described herein and/or known in the art. Certain methods for enriching for a nucleic acid subpopulation (e.g., fetal nucleic acid) in a sample are described in detail below.

Some methods for enriching for a nucleic acid subpopulation (e.g., fetal nucleic acid) that can be used with a method described herein include methods that exploit epigenetic differences between maternal and fetal nucleic acid. For example, fetal nucleic acid can be differentiated and separated from maternal nucleic acid based on methylation differences. Methylation-based fetal nucleic acid enrichment methods are described in U.S. Patent Application Publication No. 2010/0105049, which is incorporated by reference herein. Such methods sometimes involve binding a sample nucleic acid to a methylation-specific binding agent (methyl-CpG binding protein (MBD), methylation specific antibodies, and the like) and separating bound nucleic acid from unbound nucleic acid based on differential methylation status. Such methods also can include the use of methylation-sensitive restriction enzymes (as described above; e.g., HhaI and HpaII), which allow for the enrichment of fetal nucleic acid regions in a maternal sample by selectively digesting nucleic acid from the maternal sample with an enzyme that selectively and completely or substantially digests the maternal nucleic acid to enrich the sample for at least one fetal nucleic acid region.

Another method for enriching for a nucleic acid subpopulation (e.g., fetal nucleic acid) that can be used with a method described herein is a restriction endonuclease enhanced polymorphic sequence approach, such as a method described in U.S. Patent Application Publication No. 2009/0317818, which is incorporated by reference herein. Such methods include cleavage of nucleic acid comprising a non-target allele with a restriction endonuclease that recognizes the nucleic acid comprising the non-target allele but not the target allele; and amplification of uncleaved nucleic acid but not cleaved nucleic acid, where the uncleaved, amplified nucleic acid represents enriched target nucleic acid (e.g., fetal nucleic acid) relative to non-target nucleic acid (e.g., maternal nucleic acid). In certain embodiments, nucleic acid may be selected such that it comprises an allele having a polymorphic site that is susceptible to selective digestion by a cleavage agent, for example.

Some methods for enriching for a nucleic acid subpopulation (e.g., fetal nucleic acid) that can be used with a method described herein include selective enzymatic degradation approaches. Such methods involve protecting target sequences from exonuclease digestion thereby facilitating the elimination in a sample of undesired sequences (e.g., maternal DNA). For example, in one approach, sample nucleic acid is denatured to generate single stranded nucleic acid, single stranded nucleic acid is contacted with at least one target-specific primer pair under suitable annealing conditions, annealed primers are extended by nucleotide polymerization generating double stranded target sequences, and digesting single stranded nucleic acid using a nuclease that digests single stranded (e.g., non-target) nucleic acid. In certain embodiments, the method can be repeated for at least one additional cycle. In certain embodiments, the same target-specific primer pair is used to prime each of the first and second cycles of extension, and In certain embodiments, different target-specific primer pairs are used for the first and second cycles.

Some methods for enriching for a nucleic acid subpopulation (e.g., fetal nucleic acid) that can be used with a method described herein include massively parallel signature sequencing (MPSS) approaches. MPSS typically is a solid phase method that uses adapter (e.g., tag) ligation, followed by adapter decoding, and reading of the nucleic acid sequence in small increments. Tagged PCR products are typically amplified such that each nucleic acid generates a PCR product with a unique tag. Tags are often used to attach the PCR products to microbeads. After several rounds of ligation-based sequence determination, for example, a sequence signature can be identified from each bead. Each signature sequence (MPSS tag) in a MPSS dataset is analyzed, compared with all other signatures, and all identical signatures are counted.

In certain embodiments, certain enrichment methods (e.g., certain MPS and/or MPSS-based enrichment methods) can include amplification (e.g., PCR)-based approaches. In certain embodiments, loci-specific amplification methods can be used (e.g., using loci-specific amplification primers). In certain embodiments, a multiplex SNP allele PCR approach can be used. In certain embodiments, a multiplex SNP allele PCR approach can be used in combination with uniplex sequencing. For example, such an approach can involve the use of multiplex PCR (e.g., MASSARRAY system) and incorporation of capture probe sequences into the amplicons followed by sequencing using, for example, the Illumina MPSS system. In certain embodiments, a multiplex SNP allele PCR approach can be used in combination with a three-primer system and indexed sequencing. For example, such an approach can involve the use of multiplex PCR (e.g., MASSARRAY system) with primers having a first capture probe incorporated into certain loci-specific forward PCR primers and adapter sequences incorporated into loci-specific reverse PCR primers, to thereby generate amplicons, followed by a secondary PCR to incorporate reverse capture sequences and molecular index barcodes for sequencing using, for example, the Illumina MPSS system. In certain embodiments, a multiplex SNP allele PCR approach can be used in combination with a four-primer system and indexed sequencing. For example, such an approach can involve the use of multiplex PCR (e.g., MASSARRAY system) with primers having adaptor sequences incorporated into both loci-specific forward and loci-specific reverse PCR primers, followed by a secondary PCR to incorporate both forward and reverse capture sequences and molecular index barcodes for sequencing using, for example, the Illumina MPSS system. In certain embodiments, a microfluidics approach can be used. In certain embodiments, an array-based microfluidics approach can be used. For example, such an approach can involve the use of a microfluidics array (e.g., Fluidigm) for amplification at low plex and incorporation of index and capture probes, followed by sequencing. In certain embodiments, an emulsion microfluidics approach can be used, such as, for example, digital droplet PCR.

In certain embodiments, universal amplification methods can be used (e.g., using universal or non-loci-specific amplification primers). In certain embodiments, universal amplification methods can be used in combination with pull-down approaches. In certain embodiments, a method can include biotinylated ultramer pull-down (e.g., biotinylated pull-down assays from Agilent or IDT) from a universally amplified sequencing library. For example, such an approach can involve preparation of a standard library, enrichment for selected regions by a pull-down assay, and a secondary universal amplification step. In certain embodiments, pull-down approaches can be used in combination with ligation-based methods. In certain embodiments, a method can include biotinylated ultramer pull down with sequence specific adapter ligation (e.g., HALOPLEX PCR, Halo Genomics). For example, such an approach can involve the use of selector probes to capture restriction enzyme-digested fragments, followed by ligation of captured products to an adaptor, and universal amplification followed by sequencing. In certain embodiments, pull-down approaches can be used in combination with extension and ligation-based methods. In certain embodiments, a method can include molecular inversion probe (MIP) extension and ligation. For example, such an approach can involve the use of molecular inversion probes in combination with sequence adapters followed by universal amplification and sequencing. In certain embodiments, complementary DNA can be synthesized and sequenced without amplification.

In certain embodiments, extension and ligation approaches can be performed without a pull-down component. In certain embodiments, a method can include loci-specific forward and reverse primer hybridization, extension and ligation. Such methods can further include universal amplification or complementary DNA synthesis without amplification, followed by sequencing. Such methods can reduce or exclude background sequences during analysis, in certain embodiments.

In certain embodiments, pull-down approaches can be used with an optional amplification component or with no amplification component. In certain embodiments, a method can include a modified pull-down assay and ligation with full incorporation of capture probes without universal amplification. For example, such an approach can involve the use of modified selector probes to capture restriction enzyme-digested fragments, followed by ligation of captured products to an adaptor, optional amplification, and sequencing. In certain embodiments, a method can include a biotinylated pull-down assay with extension and ligation of adaptor sequence in combination with circular single stranded ligation. For example, such an approach can involve the use of selector probes to capture regions of interest (e.g., target sequences), extension of the probes, adaptor ligation, single stranded circular ligation, optional amplification, and sequencing. In certain embodiments, the analysis of the sequencing result can separate target sequences form background.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments often are isolated away from the remaining fragments in the nucleic acid sample. In certain embodiments, the separated target fragments and the separated reference fragments also are isolated away from each other (e.g., isolated in separate assay compartments). In certain embodiments, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from the nucleic acid sample. Commercially available nucleic acid capture systems include, for example, Nimblegen sequence capture system (Roche NimbleGen, Madison, Wis.); Illumina BEADARRAY platform (Illumina, San Diego, Calif.); Affymetrix GENECHIP platform (Affymetrix, Santa Clara, Calif.); Agilent SureSelect Target Enrichment System (Agilent Technologies, Santa Clara, Calif.); and related platforms. Such methods typically involve hybridization of a capture oligonucleotide to a segment or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome). In certain embodiments, a hybridization-based method (e.g., using oligonucleotide arrays) can be used to enrich for nucleic acid sequences from certain chromosomes (e.g., a potentially aneuploid chromosome, reference chromosome or other chromosome of interest) or segments of interest thereof.

In some embodiments, nucleic acid is enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In certain embodiments, length-based separation approaches can include fragment circularization, chemical treatment (e.g., formaldehyde, polyethylene glycol (PEG)), mass spectrometry and/or size-specific nucleic acid amplification, for example.

Certain length-based separation methods that can be used with methods described herein employ a selective sequence tagging approach, for example. The term "sequence tagging" refers to incorporating a recognizable and distinct sequence into a nucleic acid or population of nucleic acids. The term "sequence tagging" as used herein has a different meaning than the term "sequence tag" described later herein. In such sequence tagging methods, a fragment size species (e.g., short fragments) nucleic acids are subjected to selective sequence tagging in a sample that includes long and short nucleic acids. Such methods typically involve performing a nucleic acid amplification reaction using a set of nested primers which include inner primers and outer primers. In certain embodiments, one or both of the inner can be tagged to thereby introduce a tag onto the target amplification product. The outer primers generally do not anneal to the short fragments that carry the (inner) target sequence. The inner primers can anneal to the short fragments and generate an amplification product that carries a tag and the target sequence. Typically, tagging of the long fragments is inhibited through a combination of mechanisms which include, for example, blocked extension of the inner primers by the prior annealing and extension of the outer primers. Enrichment for tagged fragments can be accomplished by any of a variety of methods, including for example, exonuclease digestion of single stranded nucleic acid and amplification of the tagged fragments using amplification primers specific for at least one tag.

Another length-based separation method that can be used with methods described herein involves subjecting a nucleic acid sample to polyethylene glycol (PEG) precipitation. Examples of methods include those described in International Patent Application Publication Nos. WO2007/140417 and WO2010/115016, the entire content of each is incorporated herein by reference, including all text, tables, equations and drawings. This method in general entails contacting a nucleic acid sample with PEG in the presence of one or more monovalent salts under conditions sufficient to substantially precipitate large nucleic acids without substantially precipitating small (e.g., less than 300 nucleotides) nucleic acids.

Another size-based enrichment method that can be used with methods described herein involves circularization by ligation, for example, using circligase. Short nucleic acid fragments typically can be circularized with higher efficiency than long fragments. Non-circularized sequences can be separated from circularized sequences, and the enriched short fragments can be used for further analysis.

Nucleic Acid Library

In some embodiments a nucleic acid library is a plurality of polynucleotide molecules (e.g., a sample of nucleic acids) that are prepared, assemble and/or modified for a specific process, non-limiting examples of which include immobilization on a solid phase (e.g., a solid support, e.g., a flow cell, a bead), enrichment, amplification, cloning, detection and/or for nucleic acid sequencing. In certain embodiments, a nucleic acid library is prepared prior to or during a sequencing process. A nucleic acid library (e.g., sequencing library) can be prepared by a suitable method as known in the art. A nucleic acid library can be prepared by a targeted or a non-targeted preparation process.

In some embodiments a library of nucleic acids is modified to comprise a chemical moiety (e.g., a functional group) configured for immobilization of nucleic acids to a solid support. In some embodiments a library of nucleic acids is modified to comprise a biomolecule (e.g., a functional group) and/or member of a binding pair configured for immobilization of the library to a solid support, non-limiting examples of which include thyroxin-binding globulin, steroid-binding proteins, antibodies, antigens, haptens, enzymes, lectins, nucleic acids, repressors, protein A, protein G, avidin, streptavidin, biotin, complement component C1q, nucleic acid-binding proteins, receptors, carbohydrates, oligonucleotides, polynucleotides, complementary nucleic acid sequences, the like and combinations thereof. Some examples of specific binding pairs include, without limitation: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; an oligonucleotide or polynucleotide and its corresponding complement; the like or combinations thereof.

In some embodiments a library of nucleic acids is modified to comprise one or more polynucleotides of known composition, non-limiting examples of which include an identifier (e.g., a tag, an indexing tag), a capture sequence, a label, an adapter, a restriction enzyme site, a promoter, an enhancer, an origin of replication, a stem loop, a complimentary sequence (e.g., a primer binding site, an annealing site), a suitable integration site (e.g., a transposon, a viral integration site), a modified nucleotide, the like or combinations thereof. Polynucleotides of known sequence can be added at a suitable position, for example on the 5' end, 3' end or within a nucleic acid sequence. Polynucleotides of known sequence can be the same or different sequences. In some embodiments a polynucleotide of known sequence is configured to hybridize to one or more oligonucleotides immobilized on a surface (e.g., a surface in flow cell). For example, a nucleic acid molecule comprising a 5' known sequence may hybridize to a first plurality of oligonucleotides while the 3' known sequence may hybridize to a second plurality of oligonucleotides. In some embodiments a library of nucleic acid can comprise chromosome-specific tags, capture sequences, labels and/or adaptors. In some embodiments, a library of nucleic acids comprises one or more detectable labels. In some embodiments one or more detectable labels may be incorporated into a nucleic acid library at a 5' end, at a 3' end, and/or at any nucleotide position within a nucleic acid in the library. In some embodiments a library of nucleic acids comprises hybridized oligonucleotides. In certain embodiments hybridized oligonucleotides are labeled probes. In some embodiments a library of nucleic acids comprises hybridized oligonucleotide probes prior to immobilization on a solid phase.

In some embodiments a polynucleotide of known sequence comprises a universal sequence. A universal sequence is a specific nucleotide acid sequence that is integrated into two or more nucleic acid molecules or two or more subsets of nucleic acid molecules where the universal sequence is the same for all molecules or subsets of molecules that it is integrated into. A universal sequence is often designed to hybridize to and/or amplify a plurality of different sequences using a single universal primer that is complementary to a universal sequence. In some embodiments two (e.g., a pair) or more universal sequences and/or universal primers are used. A universal primer often comprises a universal sequence. In some embodiments adapters (e.g., universal adapters) comprise universal sequences. In some embodiments one or more universal sequences are used to capture, identify and/or detect multiple species or subsets of nucleic acids.

In certain embodiments of preparing a nucleic acid library, (e.g., in certain sequencing by synthesis procedures), nucleic acids are size selected and/or fragmented into lengths of several hundred base pairs, or less (e.g., in preparation for library generation). In some embodiments, library preparation is performed without fragmentation (e.g., when using ccfDNA).

In certain embodiments, a ligation-based library preparation method is used (e.g., ILLUMINA TRUSEQ, Illumina, San Diego Calif.). Ligation-based library preparation methods often make use of an adaptor (e.g., a methylated adaptor) design which can incorporate an index sequence at the initial ligation step and often can be used to prepare samples for single-read sequencing, paired-end sequencing and multiplexed sequencing. For example, sometimes nucleic acids (e.g., fragmented nucleic acids or ccfDNA) are end repaired by a fill-in reaction, an exonuclease reaction or a combination thereof. In some embodiments the resulting blunt-end repaired nucleic acid can then be extended by a single nucleotide, which is complementary to a single nucleotide overhang on the 3' end of an adapter/primer. Any nucleotide can be used for the extension/overhang nucleotides. In some embodiments nucleic acid library preparation comprises ligating an adapter oligonucleotide. Adapter oligonucleotides are often complementary to flow-cell anchors, and sometimes are utilized to immobilize a nucleic acid library to a solid support, such as the inside surface of a flow cell, for example. In some embodiments, an adapter oligonucleotide comprises an identifier, one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing).

An identifier can be a suitable detectable label incorporated into or attached to a nucleic acid (e.g., a polynucleotide) that allows detection and/or identification of nucleic acids that comprise the identifier. In some embodiments an identifier is incorporated into or attached to a nucleic acid during a sequencing method (e.g., by a polymerase). Non-limiting examples of identifiers include nucleic acid tags, nucleic acid indexes or barcodes, a radiolabel (e.g., an isotope), metallic label, a fluorescent label, a chemiluminescent label, a phosphorescent label, a fluorophore quencher, a dye, a protein (e.g., an enzyme, an antibody or part thereof, a linker, a member of a binding pair), the like or combinations thereof. In some embodiments an identifier (e.g., a nucleic acid index or barcode) is a unique, known and/or identifiable sequence of nucleotides or nucleotide analogues. In some embodiments identifiers are six or more contiguous nucleotides. A multitude of fluorophores are available with a variety of different excitation and emission spectra. Any suitable type and/or number of fluorophores can be used as an identifier. In some embodiments 1 or more, 2 or more, 3 or more, 4 or more, 5 or more, 6 or more, 7 or more, 8 or more, 9 or more, 10 or more, 20 or more, 30 or more or 50 or more different identifiers are utilized in a method described herein (e.g., a nucleic acid detection and/or sequencing method). In some embodiments, one or two types of identifiers (e.g., fluorescent labels) are linked to each nucleic acid in a library. Detection and/or quantification of an identifier can be performed by a suitable method, machine or apparatus, non-limiting examples of which include flow cytometry, quantitative polymerase chain reaction (qPCR), gel electrophoresis, a luminometer, a fluorometer, a spectrophotometer, a suitable gene-chip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof.

In some embodiments, a transposon-based library preparation method is used (e.g., EPICENTRE NEXTERA, Epicentre, Madison Wis.). Transposon-based methods typically use in vitro transposition to simultaneously fragment and tag DNA in a single-tube reaction (often allowing incorporation of platform-specific tags and optional barcodes), and prepare sequencer-ready libraries.

In some embodiments a nucleic acid library or parts thereof are amplified (e.g., amplified by a PCR-based method). In some embodiments a sequencing method comprises amplification of a nucleic acid library. A nucleic acid library can be amplified prior to or after immobilization on a solid support (e.g., a solid support in a flow cell). Nucleic acid amplification includes the process of amplifying or increasing the numbers of a nucleic acid template and/or of a complement thereof that are present (e.g., in a nucleic acid library), by producing one or more copies of the template and/or its complement. Amplification can be carried out by a suitable method. A nucleic acid library can be amplified by a thermocycling method or by an isothermal amplification method. In some embodiments a rolling circle amplification method is used. In some embodiments amplification takes place on a solid support (e.g., within a flow cell) where a nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge amplification, emulsion PCR, WildFire amplification (e.g., US patent publication US20130012399), the like or combinations thereof.

Sequencing

In some embodiments, nucleic acids (e.g., nucleic acid fragments, sample nucleic acid, cell-free nucleic acid) are sequenced. In certain embodiments, a full or substantially full sequence is obtained and sometimes a partial sequence is obtained.

In some embodiments some or all nucleic acids in a sample are enriched and/or amplified (e.g., non-specifically, e.g., by a PCR based method) prior to or during sequencing. In certain embodiments specific nucleic acid portions or subsets in a sample are enriched and/or amplified prior to or during sequencing. In some embodiments, a portion or subset of a pre-selected pool of nucleic acids is sequenced randomly. In some embodiments, nucleic acids in a sample are not enriched and/or amplified prior to or during sequencing.

As used herein, "reads" (e.g., "a read", "a sequence read") are short nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads).

The length of a sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, sequence reads are of a mean, median, average or absolute length of about 15 bp to about 900 bp long. In certain embodiments sequence reads are of a mean, median, average or absolute length about 1000 bp or more.

In some embodiments the nominal, average, mean or absolute length of single-end reads sometimes is about 15 contiguous nucleotides to about 50 or more contiguous nucleotides, about 15 contiguous nucleotides to about 40 or more contiguous nucleotides, and sometimes about 15 contiguous nucleotides or about 36 or more contiguous nucleotides. In certain embodiments the nominal, average, mean or absolute length of single-end reads is about 20 to about 30 bases, or about 24 to about 28 bases in length. In certain embodiments the nominal, average, mean or absolute length of single-end reads is about 1, 2, 3, 4, 5, 6, 7, 8, 9, 10, 11, 12, 13, 14, 15, 16, 17, 18, 19, 21, 22, 23, 24, 25, 26, 27, 28 or about 29 bases or more in length.

In certain embodiments, the nominal, average, mean or absolute length of the paired-end reads sometimes is about 10 contiguous nucleotides to about 25 contiguous nucleotides or more (e.g., about 10, 11, 12, 13, 14, 15, 16, 17, 18, 19, 20, 21, 22, 23, 24 or 25 nucleotides in length or more), about 15 contiguous nucleotides to about 20 contiguous nucleotides or more, and sometimes is about 17 contiguous nucleotides or about 18 contiguous nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from the blood of a pregnant female can be reads from a mixture of fetal and maternal nucleic acid. A mixture of relatively short reads can be transformed by processes described herein into a representation of a genomic nucleic acid present in the pregnant female and/or in the fetus. A mixture of relatively short reads can be transformed into a representation of a copy number variation (e.g., a maternal and/or fetal copy number variation), genetic variation or an aneuploidy, for example. Reads of a mixture of maternal and fetal nucleic acid can be transformed into a representation of a composite chromosome or a segment thereof comprising features of one or both maternal and fetal chromosomes. In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, a representative fraction of a genome is sequenced and is sometimes referred to as "coverage" or "fold coverage". For example, a 1-fold coverage indicates that roughly 100% of the nucleotide sequences of the genome are represented by reads. In some embodiments "fold coverage" is a relative term referring to a prior sequencing run as a reference. For example, a second sequencing run may have 2-fold less coverage than a first sequencing run. In some embodiments a genome is sequenced with redundancy, where a given region of the genome can be covered by two or more reads or overlapping reads (e.g., a "fold coverage" greater than 1, e.g., a 2-fold coverage).

In some embodiments, one nucleic acid sample from one individual is sequenced. In certain embodiments, nucleic acids from each of two or more samples are sequenced, where samples are from one individual or from different individuals. In certain embodiments, nucleic acid samples from two or more biological samples are pooled, where each biological sample is from one individual or two or more individuals, and the pool is sequenced. In the latter embodiments, a nucleic acid sample from each biological sample often is identified by one or more unique identifiers.

In some embodiments a sequencing method utilizes identifiers that allow multiplexing of sequence reactions in a sequencing process. The greater the number of unique identifiers, the greater the number of samples and/or chromosomes for detection, for example, that can be multiplexed in a sequencing process. A sequencing process can be performed using any suitable number of unique identifiers (e.g., 4, 8, 12, 24, 48, 96, or more).

A sequencing process sometimes makes use of a solid phase, and sometimes the solid phase comprises a flow cell on which nucleic acid from a library can be attached and reagents can be flowed and contacted with the attached nucleic acid. A flow cell sometimes includes flow cell lanes, and use of identifiers can facilitate analyzing a number of samples in each lane. A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs. In some embodiments the number of samples analyzed in a given flow cell lane are dependent on the number of unique identifiers utilized during library preparation and/or probe design. single flow cell lane. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell. Non-limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively).

Any suitable method of sequencing nucleic acids can be used, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments sequencing technologies that include the use of nucleic acid imaging technologies (e.g., transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS). In some embodiments MPS sequencing methods utilize a targeted approach, where specific chromosomes, genes or regions of interest are sequences. In certain embodiments a non-targeted approach is used where most or all nucleic acids in a sample are sequenced, amplified and/or captured randomly.

In some embodiments a targeted enrichment, amplification and/or sequencing approach is used. A targeted approach often isolates, selects and/or enriches a subset of nucleic acids in a sample for further processing by use of sequence-specific oligonucleotides. In some embodiments a library of sequence-specific oligonucleotides are utilized to target (e.g., hybridize to) one or more sets of nucleic acids in a sample. Sequence-specific oligonucleotides and/or primers are often selective for particular sequences (e.g., unique nucleic acid sequences) present in one or more chromosomes, genes, exons, introns, and/or regulatory regions of interest. Any suitable method or combination of methods can be used for enrichment, amplification and/or sequencing of one or more subsets of targeted nucleic acids. In some embodiments targeted sequences are isolated and/or enriched by capture to a solid phase (e.g., a flow cell, a bead) using one or more sequence-specific anchors. In some embodiments targeted sequences are enriched and/or amplified by a polymerase-based method (e.g., a PCR-based method, by any suitable polymerase based extension) using sequence-specific primers and/or primer sets. Sequence specific anchors often can be used as sequence-specific primers.

MPS sequencing sometimes makes use of sequencing by synthesis and certain imaging processes. A nucleic acid sequencing technology that may be used in a method described herein is sequencing-by-synthesis and reversible terminator-based sequencing (e.g., Illumina's Genome Analyzer; Genome Analyzer II; HISEQ 2000; HISEQ 2500 (Illumina, San Diego Calif.)). With this technology, millions of nucleic acid (e.g., DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs.

Sequencing by synthesis, in some embodiments, comprises iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEMFET sensor), the like or combinations thereof. Other sequencing methods that may be used to conduct methods herein include digital PCR and sequencing by hybridization.

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g., fetal alleles and maternal alleles). Alleles can be enumerated to determine copy number.

In certain embodiments, sequencing by hybridization can be used. The method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, nanopore sequencing can be used in a method described herein. Nanopore sequencing is a single-molecule sequencing technology whereby a single nucleic acid molecule (e.g., DNA) is sequenced directly as it passes through a nanopore.

A suitable MPS method, system or technology platform for conducting methods described herein can be used to obtain nucleic acid sequence reads. Non-limiting examples of MPS platforms include Illumina/Solex/HiSeq (e.g., Illumina's Genome Analyzer; Genome Analyzer II; HISEQ 2000; HISEQ), SOLiD, Roche/454, PACBIO and/or SMRT, Helicos True Single Molecule Sequencing, Ion Torrent and Ion semiconductor-based sequencing (e.g., as developed by Life Technologies), WildFire, 5500, 5500xl W and/or 5500xl W Genetic Analyzer based technologies (e.g., as developed and sold by Life Technologies, US patent publication no. US20130012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing, the like or combinations thereof.

In some embodiments, chromosome-specific sequencing is performed. In some embodiments, chromosome-specific sequencing is performed utilizing DANSR (digital analysis of selected regions). Digital analysis of selected regions enables simultaneous quantification of hundreds of loci by cfDNA-dependent catenation of two locus-specific oligonucleotides via an intervening 'bridge' oligonucleotide to form a PCR template. In some embodiments, chromosome-specific sequencing is performed by generating a library enriched in chromosome-specific sequences. In some embodiments, sequence reads are obtained only for a selected set of chromosomes. In some embodiments, sequence reads are obtained only for chromosomes 21, 18 and 13. In some embodiments sequence reads are obtained for and/or and mapped to an entire reference genome or a segment of a genome.

In some embodiments, sequence reads are generated, obtained, gathered, assembled, manipulated, transformed, processed, and/or provided by a sequence module. A machine comprising a sequence module can be a suitable machine and/or apparatus that determines the sequence of a nucleic acid utilizing a sequencing technology known in the art. In some embodiments a sequence module can align, assemble, fragment, complement, reverse complement, and/or error check (e.g., error correct sequence reads).

In some embodiments, nucleotide sequence reads obtained from a sample are partial nucleotide sequence reads. As used herein, "partial nucleotide sequence reads" refers to sequence reads of any length with incomplete sequence information, also referred to as sequence ambiguity. Partial nucleotide sequence reads may lack information regarding nucleobase identity and/or nucleobase position or order. Partial nucleotide sequence reads generally do not include sequence reads in which the only incomplete sequence information (or in which less than all of the bases are sequenced or determined) is from inadvertent or unintentional sequencing errors. Such sequencing errors can be inherent to certain sequencing processes and include, for example, incorrect calls for nucleobase identity, and missing or extra nucleobases. Thus, for partial nucleotide sequence reads herein, certain information about the sequence is often deliberately excluded. That is, one deliberately obtains sequence information with respect to less than all of the nucleobases or which might otherwise be characterized as or be a sequencing error. In some embodiments, a partial nucleotide sequence read can span a portion of a nucleic acid fragment. In some embodiments, a partial nucleotide sequence read can span the entire length of a nucleic acid fragment. Partial nucleotide sequence reads are described, for example, in International Patent Application Publication no. WO2013/052907, the entire content of which is incorporated herein by reference, including all text, tables, equations and drawings.

Mapping Reads

Sequence reads can be mapped. Any suitable mapping method (e.g., process, algorithm, program, software, module, the like or combination thereof) can be used and certain aspects of mapping processes are described hereafter.

Mapping nucleotide sequence reads (e.g., sequence information from a fragment whose physical genomic position is unknown) can be performed in a number of ways, and often comprises alignment of the obtained sequence reads with a matching sequence in a reference genome. In such alignments, sequence reads generally are aligned to a reference sequence and those that align are designated as being "mapped", "a mapped sequence read" or "a mapped read".

As used herein, the terms "aligned", "alignment", or "aligning" refer to two or more nucleic acid sequences that can be identified as a match (e.g., 100% identity) or partial match. Alignments can be done manually or by a computer (e.g., a software, program, module, or algorithm), non-limiting examples of which include the Efficient Local Alignment of Nucleotide Data (ELAND) computer program distributed as part of the Illumina Genomics Analysis pipeline. Alignment of a sequence read can be a 100% sequence match. In some cases, an alignment is less than a 100% sequence match (e.g., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand. In certain embodiments a nucleic acid sequence is aligned with the reverse complement of another nucleic acid sequence.

Various computational methods can be used to map and/or align sequence reads to a reference genome. Non-limiting examples of computer algorithms that can be used to align sequences include, without limitation, BLAST, BLITZ, FASTA, BOWTIE 1, BOWTIE 2, ELAND, MAQ, PROBEMATCH, SOAP or SEQMAP, or variations thereof or combinations thereof. In some embodiments, sequence reads can be aligned with reference sequences and/or sequences in a reference genome. In some embodiments, the sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search the identified sequences against a sequence database.

In some embodiments mapped sequence reads and/or information associated with a mapped sequence read are stored on and/or accessed from a non-transitory computer-readable storage medium in a suitable computer-readable format. A "computer-readable format" is sometimes referred to generally herein as a format. In some embodiments mapped sequence reads are stored and/or accessed in a suitable binary format, a text format, the like or a combination thereof. A binary format is sometimes a BAM format. A text format is sometimes a sequence alignment/map (SAM) format. Non-limiting examples of binary and/or text formats include BAM, SAM, SRF, FASTQ, Gzip, the like, or combinations thereof. In some embodiments mapped sequence reads are stored in and/or are converted to a format that requires less storage space (e.g., less bytes) than a traditional format (e.g., a SAM format or a BAM format). In some embodiments mapped sequence reads in a first format are compressed into a second format requiring less storage space than the first format. The term "compressed" as used herein refers to a process of data compression, source coding, and/or bit-rate reduction where a computer readable data file is reduced in size. In some embodiments mapped sequence reads are compressed from a SAM format in a binary format. Some data sometimes is lost after a file is compressed. Sometimes no data is lost in a compression process. In some file compression embodiments, some data is replaced with an index and/or a reference to another data file comprising information regarding a mapped sequence read. In some embodiments a mapped sequence read is stored in a binary format comprising or consisting of a read count, a chromosome identifier (e.g., that identifies a chromosome to which a read is mapped) and a chromosome position identifier (e.g., that identifies a position on a chromosome to which a read is mapped). In some embodiments a binary format comprises a 20 byte array, a 16 byte array, an 8 byte array, a 4 byte array or a 2 byte array. In some embodiments mapped read information is stored in an array in a 10 byte format, 9 byte format, 8 byte format, 7 byte format, 6 byte format, 5 byte format, 4 byte format, 3 byte format or 2 byte format. Sometimes mapped read data is stored in a 4 byte array comprising a 5 byte format. In some embodiments a binary format comprises a 5-byte format comprising a 1-byte chromosome ordinal and a 4-byte chromosome position. In some embodiments mapped reads are stored in a compressed binary format that is about 100 times, about 90 times, about 80 times, about 70 times, about 60 times, about 55 times, about 50 times, about 45 times, about 40 times or about 30 times smaller than a sequence alignment/map (SAM) format. In some embodiments mapped reads are stored in a compress binary format that is about 2 times smaller to about 50 times smaller than (e.g., about 30, 25, 20, 19, 18, 17, 16, 15, 14, 13, 12, 11, 10, 9, 8, 7, 6, or about 5 times smaller than) a GZip format.

Figure 10A:
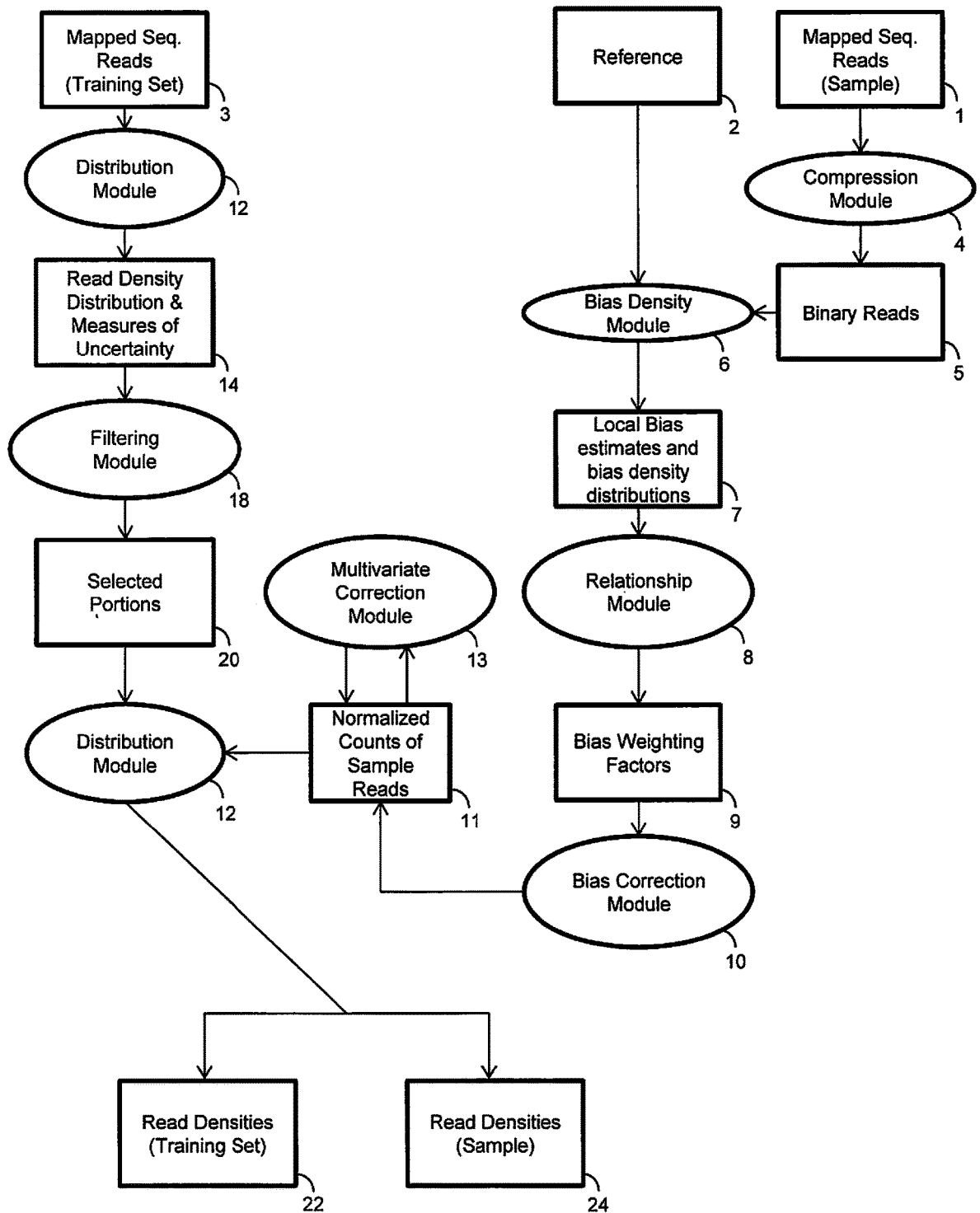
FIG. 10A-10B shows an embodiment of a system.

In some embodiments a system comprises a compression module (e.g., 4, FIG. 10A). In some embodiments mapped sequence read information stored on a non-transitory computer-readable storage medium in a computer-readable format is compressed by a compression module. A compression module sometimes converts mapped sequence reads to and from a suitable format. A compression module can accept mapped sequence reads in a first format (e.g., 1), convert them into a compressed format (e.g., a binary format, 5) and transfer the compressed reads to another module (e.g., a bias density module 6) in some embodiments. A compression module often provides sequence reads in a binary format 5 (e.g., a BReads format). Non-limiting examples of a compression module include GZIP, BGZF, and BAM, the like or modifications thereof).

The following provides an example of converting an integer into a 4-byte array using Java:

```
public static final byte[ ]
convertToByteArray(int value)
{
return new byte[ ] {
(byte)(value >>> 24),
(byte)(value >>> 16),
(byte)(value >>> 8),
(byte)value};
}
```

In some embodiments, a read may uniquely or non-uniquely map to a reference genome. A read is considered as "uniquely mapped" if it aligns with a single sequence in the reference genome. A read is considered as "non-uniquely mapped" if it aligns with two or more sequences in a reference genome. In some embodiments, non-uniquely mapped reads are eliminated from further analysis (e.g., quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read mapped to a reference sequence.

As used herein, the term "reference genome" can refer to any particular known, sequenced or characterized genome, whether partial or complete, of any organism or virus which may be used to reference identified sequences from a subject. A reference genome sometimes refers to a segment of a reference genome (e.g., a chromosome or part thereof, e.g., one or more portions of a reference genome). Human genomes, human genome assemblies and/or genomes from any other organisms can be used as a reference genome. One or more human genomes, human genome assemblies as well as genomes of other organisms can be found at the National Center for Biotechnology Information at www.ncbi.nlm.nih.gov. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes. The term "reference sequence" as used herein refers to one or more polynucleotide sequences of one or more reference samples. In some embodiments reference sequences comprise sequence reads obtained from a reference sample. In some embodiments reference sequences comprise sequence reads, an assembly of reads, a consensus DNA sequence (e.g., a sequence contig), read densities and/or read density profiles obtained from one or more reference samples. A read density profile obtained from a reference sample is sometimes referred to herein as a reference profile. A read density profile obtained from a test sample and/or test subject is sometimes referred to herein as a test profile. In some embodiments a reference sample is obtained from a reference subject substantially free of a genetic variation (e.g., a genetic variation in question). In some embodiments a reference sample is obtained from a reference subject comprising a known genetic variation. The term "reference" as used herein can refer to a reference genome, a reference sequence, reference sample and/or a reference subject.

In certain embodiments, where a sample nucleic acid is from a pregnant female, a reference sequence sometimes is not from the fetus, the mother of the fetus or the father of the fetus, and is referred to herein as an "external reference." A maternal reference may be prepared and used in some embodiments. When a reference from the pregnant female is prepared ("maternal reference sequence") based on an external reference, reads from DNA of the pregnant female that contains substantially no fetal DNA often are mapped to the external reference sequence and assembled. In certain embodiments the external reference is from DNA of an individual having substantially the same ethnicity as the pregnant female. A maternal reference sequence may not completely cover the maternal genomic DNA (e.g., it may cover about 50%, 60%, 70%, 80%, 90% or more of the maternal genomic DNA), and the maternal reference may not perfectly match the maternal genomic DNA sequence (e.g., the maternal reference sequence may include multiple mismatches).

In certain embodiments, mappability is assessed for a genomic region (e.g., portions, genomic portions). Mappability is the ability to unambiguously align a nucleotide sequence read to a portion of a reference genome, typically up to a specified number of mismatches, including, for example, 0, 1, 2 or more mismatches. In some embodiments, mappability is provided as a score or value where the score or value is generated by a suitable mapping algorithm or computer mapping software. For a given genomic region, the expected mappability can be estimated using a sliding-window approach of a preset read length and averaging the resulting read-level mappability values. Genomic regions comprising stretches of unique nucleotide sequence sometimes have a high mappability value.

Sequence reads can be mapped by a mapping module or by a machine comprising a mapping module, which mapping module generally maps reads to a reference genome or segment thereof. A mapping module can map sequence reads by a suitable method known in the art. In some embodiments, a mapping module or a machine comprising a mapping module is required to provide mapped sequence reads.

Counts

Sequence reads that are mapped can be quantified to determine the number of reads that are mapped to a region or portion of a reference genome. In certain embodiments a read that maps to a reference genome, or a region, portion or segment thereof, is termed a count. In some embodiments a count comprises a value. In certain embodiments a count value is determined by a mathematical process. A count can be determined by a suitable method, operation or mathematical process. In certain embodiments a count is weighted, removed, filtered, normalized, adjusted, averaged, added, or subtracted or processed by a combination thereof. In certain embodiments a count is derived from a sequence read that is processed or manipulated by a suitable method, operation or mathematical process described herein or known in the art. For example, a count is often normalized and/or weighted according to one or more biases associated with a sequence read. In some embodiments a count is normalized and/or weighted according GC bias associated with a sequence read. In some embodiments, a count is derived from raw sequence reads and/or filtered sequence reads. In some embodiments one or more counts are not mathematically manipulated. The term "raw count" and "raw counts" as used herein refers to a one or more counts that have not been mathematically manipulated.

In some embodiments a count is determined for some or all of the sequence reads mapped to a reference genome, or a region, portion or segment thereof. In certain embodiments, counts are determined from a pre-defined subset of mapped sequence reads. Pre-defined subsets (e.g., selected subsets) of mapped sequence reads can be defined or selected utilizing any suitable feature or variable. In some embodiments, pre-defined subsets of mapped sequence reads can include from 1 to n sequence reads, where n represents a number equal to the sum of all sequence reads generated from a test subject or reference subject sample.

Counts are often derived from sequence reads obtained from a subject (e.g., a test subject). Counts are sometimes derived from sequence reads obtained from a nucleic acid sample from a pregnant female bearing a fetus. Counts of nucleic acid sequence reads often are counts representative of both a fetus and a mother of a fetus (e.g., for a pregnant female subject). In certain embodiments, where a subject is a pregnant female, some counts are derived from a fetal genome and some counts are derived from a maternal genome.

Read Density

Counts of sequence reads (e.g., weighted counts) are often represented as a read density. A read density is often determined and/or generated for one or more portions of a genome. In certain embodiments, a read density is determined and/or generated for one or more chromosomes. In some embodiments a read density comprises a quantitative measure of counts of sequence reads mapped to a portion of a reference genome. A read density can be determined by a suitable process. In some embodiments a read density is determined by a suitable distribution and/or a suitable distribution function. Non-limiting examples of a distribution function include a probability function, probability distribution function, probability density function (PDF), a kernel density function (kernel density estimation), a cumulative distribution function, probability mass function, discrete probability distribution, an absolutely continuous univariate distribution, the like, any suitable distribution, or combinations thereof. In certain embodiments, a PDF comprises a kernel density function (kernel density estimation). Non-limiting examples of a kernel density function that can be used for generating a local genome bias estimate include a uniform kernel density function (uniform kernel), a Gaussian kernel density function (Gaussian kernel), a triangular kernel density function (triangular kernel), a biweight kernel density function (biweight kernel), a tricube kernel density function (tricube kernel), a triweight kernel density function (triweight kernel), cosine kernel functions (cosine kernel), an Epanechnikov kernel density function (Epanechnikov kernel), a normal kernel density function (normal kernel), the like or a combination thereof. A read density is often a density estimation derived from a suitable probability density function. A density estimation is the construction of an estimate, based on observed data, of an underlying probability density function. In some embodiments a read density comprises a density estimation (e.g., a probability density estimation, a kernel density estimation). A density estimation often comprises a kernel density estimation. In some embodiments a read density is a kernel density estimate, determined according to a kernel density function. A read density is often generated according to a process comprising generating a density estimation for each of the one or more portions of a genome where each portion comprises counts of sequence reads. A read density is often generated for normalized and/or weighted counts mapped to a portion. In some embodiments each read mapped to a portion often contributes to a read density, a value (e.g., a count) equal to its weight obtained from a normalization process described herein. In some embodiments read densities for one or more portions are adjusted. Read densities can be adjusted by a suitable method. For example, read densities for one or more portions can be weighted and/or normalized.

In some embodiments a system comprises a distribution module 12. A distribution module often generates and/or provides read densities (e.g., 22, 24) for portions (e.g., filtered portions) of a genome. A distribution module can provide read densities, read density distributions 14 and/or an associated measure of uncertainty (e.g., a MAD, a quantile) for one or more reference samples, a training set (e.g., 3) and/or a test sample. A distribution module can accept, retrieve, and/or store sequence reads (e.g., 1, 3, 5) and/or counts (e.g., normalized counts 11, weighted counts). A distribution module often accepts (e.g., user inputs and user parameters for portions), retrieves, generates and/or stores portions (e.g., unfiltered or filtered portions). Sometimes a distribution module accepts and/or retrieves portions (e.g., filtered portions and/or selected portions 20) from a filtering module 18. In some embodiments a distribution module comprises instructions for a microprocessor (e.g., an algorithm, a script) in the form of code and/or source code (e.g., a collection of standard or custom scripts) and/or one or more software packages (e.g., statistical software packages) that carry out the functions of a distribution module. In some embodiments a distribution module comprises code (e.g., script) written in java, S or R that utilizes a suitable package (e.g., an S package, an R package). A non-limiting example of a distribution module is provided in Example 2.

In some embodiments a read density profile is determined. In some embodiments a read density profile comprises at least one read density, and often comprises two or more read densities (e.g., a read density profile often comprises multiple read densities). In some embodiments, a read density profile comprises a suitable quantitative value (e.g., a mean, a median, a Z-score, or the like). A read density profile often comprises values resulting from one or more read densities. A read density profile sometimes comprises values resulting from one or more manipulations of read densities based on one or more adjustments (e.g., normalizations). In some embodiments a read density profile comprises unmanipulated read densities. In some embodiments, one or more read density profiles are generated from various aspects of a data set comprising read densities, or a derivation thereof (e.g., product of one or more mathematical and/or statistical data processing steps known in the art and/or described herein). In certain embodiments, a read density profile comprises normalized read densities. In some embodiments a read density profile comprises adjusted read densities. In certain embodiments a read density profile comprises raw read densities (e.g., unmanipulated, not adjusted or normalized), normalized read densities, weighted read densities, read densities of filtered portions, z-scores of read densities, p-values of read densities, integral values of read densities (e.g., area under the curve), average, mean or median read densities, principle components, the like, or combinations thereof. Often read densities of a read density profile and/or a read density profile is associated with a measure of uncertainty (e.g., a MAD). In certain embodiments, a read density profile comprises a distribution of median read densities. In some embodiments a read density profile comprises a relationship (e.g., a fitted relationship, a regression, or the like) of a plurality of read densities. For example, sometimes a read density profile comprises a relationship between read densities (e.g., read densities value) and genomic locations (e.g., portions, portion locations). In some embodiments, a read density profile is generated using a static window process, and in certain embodiments, a read density profile is generated using a sliding window process. The term "density read profile" as used herein refers to a product of a mathematical and/or statistical manipulation of read densities that can facilitate identification of patterns and/or correlations in large quantities of sequence read data. In some embodiments a read density profile is sometimes printed and/or displayed (e.g., displayed as a visual representation, e.g., a plot or a graph).

A read density profile often comprises multiple data points, where each data point represents a quantitative value of one or more read densities. Any suitable number of data points may be included in a read density profile depending on the nature and/or complexity of a data set. In certain embodiments, read density profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, 100,000 or more data points, or 1,000,000 or more data points. In some embodiments a data point is a quantitative value and/or estimate of counts of sequence reads mapped to or associated with one or more portions. In some embodiments, a data point in a read density profile comprises the results of a data manipulation of counts mapped to one or more portions. In certain embodiments, a data point is often a quantitative value and/or estimate of a one or more read densities (e.g., a mean read density). A read density profile often comprises multiple read densities associated with and/or mapped to multiple portions of a reference genome. In some embodiments, a read density profile comprises read densities from 2 to about 1,000,000 portions. In some embodiments, read densities from 2 to about 500,000, 2 to about 100,000, 2 to about 50,000, 2 to about 40,000, 2 to about 30,000, 2 to about 20,000, 2 to about 10,000, 2 to about 5000, 2 to about 2500, 2 to about 1250, 2 to about 1000, 2 to about 500, 2 to about 250, 2 to about 100 or 2 to about 60 portions determine a read density profile. In some embodiments read densities from about 10 to about 50 portions determine a read density profile.

In some embodiments, a read density profile corresponds to a set of portions (e.g., a set of portions of a reference genome, a set of portions of a chromosome or a subset of portions of a segment of a chromosome). In some embodiments a read density profile comprises read densities and/or counts associated with a collection (e.g., a set, a subset) of portions. In some embodiments, a read density profile is determined for read densities of portions that are contiguous. In some embodiments contiguous portions comprise gaps comprising segments of a reference sequence and/or sequence reads that are not included in a density profile (e.g., portions removed by a filtering). Sometimes portions (e.g., a set of portions) that are contiguous represent neighboring segments of a genome or neighboring segments of a chromosome or gene. For example, two or more contiguous portions, when aligned by merging the portions end to end, can represent a sequence assembly of a DNA sequence longer than each portion. For example two or more contiguous portions can represent an intact genome, chromosome, gene, intron, exon or segment thereof. Sometimes a read density profile is determined from a collection (e.g., a set, a subset) of contiguous portions and/or non-contiguous portions. In some cases, a read density profile comprises one or more portions, which portions can be weighted, removed, filtered, normalized, adjusted, averaged, derived as a mean, added, subtracted, processed or transformed by any combination thereof.

In some embodiments a read density profile comprises read densities for portions of a genome comprising a genetic variation. In some embodiments a read density profile comprises read densities for portions of a genome that do not comprise a genetic variation (e.g., portions of a genome that are substantially free of a genetic variation). In certain embodiments, a read density profile comprises read densities for portions of a genome comprising a genetic variation and read densities for portions of a genome that are substantially free of a genetic variation.

A read density profile is often determined for a sample and/or a reference (e.g., a reference sample). A read density profile is sometimes generated for an entire genome, one or more chromosomes, or for a part or segment of a genome or a chromosome. In some embodiments one or more read density profiles are determined for a genome or segments thereof. In some embodiments, a read density profile is representative of the entirety of a set of read densities of a sample, and in certain embodiments, a read density profile is representative of a part or subset of read densities of a sample. That is, sometimes a read density profile comprises or is generated from read densities representative of data that has not been filtered to remove any data, and sometimes a read density profile includes or is generated from data points representative of data that has been filtered to remove unwanted data.

In some embodiments a read density profile is determined for a reference (e.g., a reference sample, a training set). A read density profile for a reference is sometimes referred to herein as a reference profile. In some embodiments a reference profile comprises a read densities obtained from a one or more references (e.g., reference sequences, reference samples). In some embodiments a reference profile comprises read densities determined for one or more (e.g., a set of) known euploid samples. In some embodiments a reference profile comprises read densities of filtered portions. In some embodiments a reference profile comprises read densities adjusted according to the one or more principle components.

In some embodiments a system comprises a profile generation module (e.g., 26). A profile generation module often accepts, retrieves and/or stores read densities (e.g., 22, 24). A profile generation module can accept and/or retrieve read densities (e.g., adjusted, weighted, normalized, mean, averaged, median, and/or integrated read densities) from another suitable module (e.g., a distribution module). A profile generation module can accept and/or retrieve read densities from a suitable source (e.g., one or more reference subjects, a training set, one or more test subjects, and the like). A profile generation module often generates and/or provides read density profiles (e.g., 32, 30, 28) to another suitable module (e.g., a PCA statistics module 33, a portion weighting module 42, a scoring module 46) and/or to a user (e.g., by plotting, graphing and/or printing). An example of a profile generation module, or part thereof, is provided in Example 2.

Portions

In some embodiments, mapped sequence reads and/or counts are grouped together according to various parameters and assigned to particular segments and/or regions of a reference genome termed herein as "portions" or "a portion". In some embodiments a portion is an entire chromosome, a segment of a chromosome, a segment of a reference genome, a segment spanning multiple chromosome, multiple chromosome segments, and/or combinations thereof. In some embodiments, a portion is predefined based on specific parameters (e.g., predetermined lengths, predetermined spacing, a predetermined GC content, or any other suitable parameter). In some embodiments, a portion is arbitrarily defined based on partitioning of a genome (e.g., partitioned by size, GC content, contiguous regions, contiguous regions of an arbitrarily defined size, and the like). In some embodiments, a portion is delineated based on one or more parameters which include, for example, length or a particular feature or features of the sequence. In some embodiments, a portion is based on a particular length of genomic sequence. Portions can be approximately the same length or portions can be different lengths. In some embodiments, portions are of about equal length. In some embodiments portions of different lengths are adjusted or weighted. A portion can be any suitable length. In some embodiments, a portion is about 10 kilobases (kb) to about 100 kb, about 20 kb to about 80 kb, about 30 kb to about 70 kb, about 40 kb to about 60 kb, and sometimes about 50 kb. In some embodiments, a portion is about 10 kb to about 20 kb. A portion is not limited to contiguous runs of sequence. Thus, portions can be made up of contiguous and/or non-contiguous sequences.

In some embodiments, a portion comprises a window comprising a pre-selected number of bases. A window may comprise any suitable number of bases determined by a portion length. In some embodiments a genome, or segments thereof, is partitioned into a plurality of windows. Windows encompassing regions of a genome may or may not overlap.

In some embodiments windows are positioned at equal distances from each other. In some embodiments windows are positioned at different distances from each other. In certain embodiment a genome, or segment thereof is partitioned into a plurality of sliding windows, where a window is slid incrementally across a genome, or segment thereof, where each window at each increment represents a portion. A window can be slid across a genome at any suitable increment or according to any numerical pattern or athematic defined sequence. In some embodiments windows are slid across a genome, or a segment thereof, at an increment of about 100,000 bp or less, about 50,000 bp or less, about 25,000 bp or less, about 10,000 bp or less, about 5,000 bp or less, about 1,000 bp or less, about 500 bp or less, or about 100 bp or less. For example a window may comprise about 100,000 bp and may be slid across a genome in increments of 50,000 bp.

In some embodiments, portions can be particular chromosome segments in a chromosome of interest, such as, for example, a chromosome where a genetic variation is assessed (e.g., an aneuploidy of chromosomes 13, 18 and/or 21 or a sex chromosome). A portion is not limited to a single chromosome. In some embodiments, one or more portions include all or part of one chromosome or all or part of two or more chromosomes. In some embodiments, one or more portions may span one, two, or more entire chromosomes. In addition, portions may span jointed or disjointed regions of multiple chromosomes. Portions can be a genes, gene fragments, regulatory sequences, introns, exons, and the like.

In some embodiments, certain regions of a genome are filtered prior to partitioning a genome, or segment thereof, into portions. Regions of a genome may be selected for exclusion from a partitioning process using any suitable method. Often regions comprising similar regions (e.g., identical or homologous regions or sequences, e.g., repetitive regions) are removed and/or filtered. Sometimes unmappable regions are excluded. In some embodiments only unique regions are retained. Regions removed during partitioning may be within a single chromosome or may span multiple chromosomes. In some embodiments a partitioned genome is trimmed down and optimized for faster alignment, often allowing for focus on uniquely identifiable sequences. In some embodiments, partitioning of a genome into regions (e.g., regions transcending chromosomes) may be based on information gain produced in the context of classification. For example, information content may be quantified using a p-value profile measuring the significance of particular genomic locations for distinguishing between groups of confirmed normal and abnormal subjects (e.g., euploid and trisomy subjects, respectively). In some embodiments, partitioning of a genome into regions (e.g., regions transcending chromosomes) may be based on any other criterion, such as, for example, speed/convenience while aligning reads, GC content (e.g., high or low GC content), uniformity of GC content, other measures of sequence content (e.g., fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, measure of uncertainty assigned to individual portions of a reference genome, and/or a targeted search for particular features.

A "segment" of a genome is sometimes a region comprising one or more chromosomes, or a part of a chromosome. A "segment" is typically a different part of a genome than a portion. A "segment" of a genome and/or a chromosome is sometimes in a different region of a genome or chromosome than a portion, sometimes does not share a polynucleotide with a portion, and sometimes includes a polynucleotide that is in a portion. A segment of a genome or chromosome often contains a larger number of nucleotides than a portion (e.g., a segment sometimes includes one or more portions), and sometimes a segment of a chromosome contains a smaller number of nucleotides than a portion (e.g., a segment sometimes is within a portion).

Filtering Portions

Figure 5A:
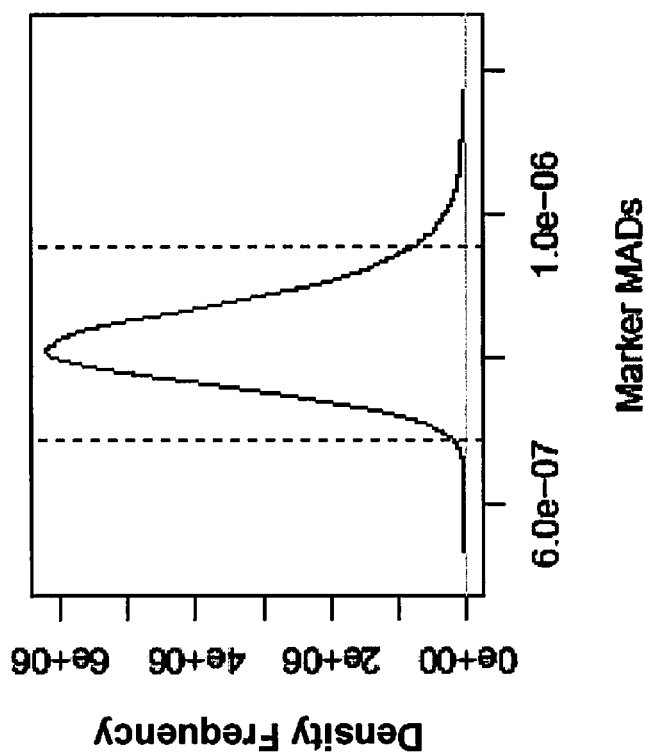
FIG. 5A shows a distribution of median GC densities (x-axis) for all portions of a genome.
Figure 5B:
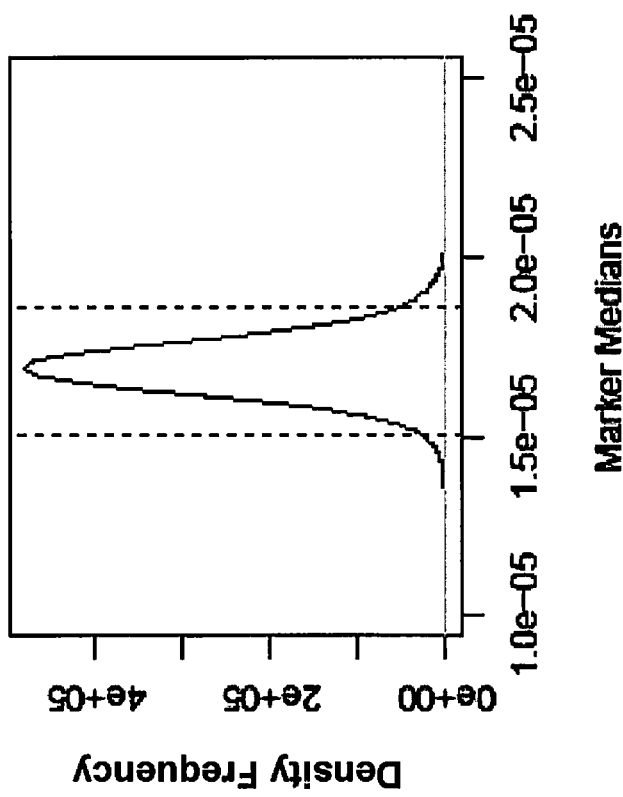
FIG. 5B shows median absolute deviation (MAD) values (x-axis) determined according to the GC density distributions for multiple samples. GC density frequencies are shown on the y-axis. Portions were filtered according to median GC density distributions for multiple reference samples (e.g., a training set) and MAD values determined according to GC density distributions of multiple samples. Portions comprising GC densities outside of an established threshold (e.g., four times the inter-quartile range of MAD) were removed from consideration according to the filtering process.

In certain embodiments one or more portions (e.g., portions of a genome) are removed from consideration by a filtering process. In certain embodiments one or more portions are filtered (e.g., subjected to a filtering process) thereby providing filtered portions. In some embodiments a filtering process removes certain portions and retains portions (e.g., a subset of portions). Following a filtering process, retained portions are often referred to herein as filtered portions. In some embodiments portions of a reference genome are filtered. In some embodiments portions of a reference genome that are removed by a filtering process are not included in a determination of the presence or absence of a genetic variation (e.g., a chromosome aneuploidy). In some embodiments portions of a chromosome in a reference genome are filtered. In some embodiments portions associated with read densities (e.g., where a read density is for a portion) are removed by a filtering process and read densities associated with removed portions are not included in a determination of the presence or absence of a genetic variation (e.g., a chromosome aneuploidy). In some embodiments a read density profile comprises and/or consist of read densities of filtered portions. Portions can be selected, filtered, and/or removed from consideration using any suitable criteria and/or method known in the art or described herein. Non-limiting examples of criteria used for filtering portions include redundant data (e.g., redundant or overlapping mapped reads), non-informative data (e.g., portions of a reference genome with zero mapped counts), portions of a reference genome with over represented or under represented sequences, GC content, noisy data, mappability, counts, count variability, read density, variability of read density, a measure of uncertainty, a repeatability measure, the like, or combinations of the foregoing. Portions are sometimes filtered according to a distribution of counts and/or a distribution of read densities. In some embodiments portions are filtered according to a distribution of counts and/or read densities where the counts and/or read densities are obtained from one or more reference samples. One or more reference samples is sometimes referred to herein as a training set. In some embodiments portions are filtered according to a distribution of counts and/or read densities where the counts and/or read densities are obtained from one or more test samples. In some embodiments portions are filtered according to a measure of uncertainty for a read density distribution. In certain embodiments, portions that demonstrate a large deviation in read densities are removed by a filtering process. For example, a distribution of read densities (e.g., a distribution of average mean, or median read densities e.g., FIG. 5A) can be determined, where each read density in the distribution maps to the same portion. A measure of uncertainty (e.g., a MAD) can be determined by comparing a distribution of read densities for multiple samples where each portion of a genome is associated with measure of uncertainty. According to the foregoing example, portions can be filtered according to a measure of uncertainty (e.g., a standard deviation (SD), a MAD) associated with each portion and a predetermined threshold. FIG. 5B shows a distribution of MAD values for portions, determined according to read density distributions for multiple samples. A predetermined threshold is indicated by the dashed vertical lines enclosing a range of acceptable MAD values. In the example of FIG. 5B, portions comprising MAD values within the acceptable range are retained and portions comprising MAD values outside of the acceptable range are removed from consideration by a filtering process. In some embodiments, according to the foregoing example, portions comprising read densities values (e.g., median, average or mean read densities) outside a pre-determined measure of uncertainty are often removed from consideration by a filtering process. In some embodiments portions comprising read densities values (e.g., median, average or mean read densities) outside an inter-quartile range of a distribution are removed from consideration by a filtering process. In some embodiments portions comprising read densities values outside more than 2 times, 3 times, 4 times or 5 times an inter-quartile range of a distribution are removed from consideration by a filtering process. In some embodiments portions comprising read densities values outside more than 2 sigma, 3 sigma, 4 sigma, 5 sigma, 6 sigma, 7 sigma or 8 sigma (e.g., where sigma is a range defined by a standard deviation) are removed from consideration by a filtering process.

In some embodiments a system comprises a filtering module 18. A filtering module often accepts, retrieves and/or stores portions (e.g., portions of pre-determined sizes and/or overlap, portion locations within a reference genome) and read densities associated with portions, often from another suitable module (e.g., a distribution module 12). In some embodiments selected portions (e.g., 20, e.g., filtered portions) are provided by a filtering module. In some embodiments, a filtering module is required to provide filtered portions and/or to remove portions from consideration. In certain embodiments a filtering module removes read densities from consideration where read densities are associated with removed portions. A filtering module often provides selected portions (e.g., filtered portions) to another suitable module (e.g., a distribution module 21). A non-limiting example of a filtering module is provided in Example 3.

Bias Estimates

Sequencing technologies can be vulnerable to multiple sources of bias. Sometimes sequencing bias is a local bias (e.g., a local genome bias). Local bias often is manifested at the level of a sequence read. A local genome bias can be any suitable local bias. Non-limiting examples of a local bias include sequence bias (e.g., GC bias, AT bias, and the like), bias correlated with DNase I sensitivity, entropy, repetitive sequence bias, chromatin structure bias, polymerase error-rate bias, palindrome bias, inverted repeat bias, PCR related bias, the like or combinations thereof. In some embodiments the source of a local bias is not determined or known.

In some embodiments a local genome bias estimate is determined. A local genome bias estimate is sometimes referred to herein as a local genome bias estimation. A local genome bias estimate can be determined for a reference genome, a segment or a portion thereof. In certain embodiments, a local genome bias estimate is determined for one or more chromosomes in a reference genome. In some embodiments a local genome bias estimate is determined for one or more sequence reads (e.g., some or all sequence reads of a sample). A local genome bias estimate is often determined for a sequence read according to a local genome bias estimation for a corresponding location and/or position of a reference (e.g., a reference genome, a chromosome in a reference genome). In some embodiments a local genome bias estimate comprises a quantitative measure of bias of a sequence (e.g., a sequence read, a sequence of a reference genome). A local genome bias estimation can be determined by a suitable method or mathematical process. In some embodiments a local genome bias estimate is determined by a suitable distribution and/or a suitable distribution function (e.g., a PDF). In some embodiments a local genome bias estimate comprises a quantitative representation of a PDF. In some embodiments a local genome bias estimate (e.g., a probability density estimation (PDE), a kernel density estimation) is determined by a probability density function (e.g., a PDF, e.g., a kernel density function) of a local bias content. In some embodiments a density estimation comprises a kernel density estimation. A local genome bias estimate is sometimes expressed as an average, mean, or median of a distribution. Sometimes a local genome bias estimate is expressed as a sum or an integral (e.g., an area under a curve (AUC) of a suitable distribution.

A PDF (e.g., a kernel density function, e.g., an Epanechnikov kernel density function) often comprises a bandwidth variable (e.g., a bandwidth). A bandwidth variable often defines the size and/or length of a window from which a probability density estimate (PDE) is derived when using a PDF. A window from which a PDE is derived often comprises a defined length of polynucleotides. In some embodiments a window from which a PDE is derived is a portion. A portion (e.g., a portion size, a portion length) is often determined according to a bandwidth variable. A bandwidth variable determines the length or size of the window used to determine a local genome bias estimate. a length of a polynucleotide segment (e.g., a contiguous segment of nucleotide bases) from which a local genome bias estimate is determined. A PDE (e.g., read density, local genome bias estimate (e.g., a GC density)) can be determined using any suitable bandwidth, non-limiting examples of which include a bandwidth of about 5 bases to about 100,000 bases, about 5 bases to about 50,000 bases, about 5 bases to about 25,000 bases, about 5 bases to about 10,000 bases, about 5 bases to about 5,000 bases, about 5 bases to about 2,500 bases, about 5 bases to about 1000 bases, about 5 bases to about 500 bases, about 5 bases to about 250 bases, about 20 bases to about 250 bases, or the like. In some embodiments a local genome bias estimate (e.g., a GC density) is determined using a bandwidth of about 400 bases or less, about 350 bases or less, about 300 bases or less, about 250 bases or less, about 225 bases or less, about 200 bases or less, about 175 bases or less, about 150 bases or less, about 125 bases or less, about 100 bases or less, about 75 bases or less, about 50 bases or less or about 25 bases or less. In certain embodiments a local genome bias estimate (e.g., a GC density) is determined using a bandwidth determined according to an average, mean, median, or maximum read length of sequence reads obtained for a given subject and/or sample. Sometimes a local genome bias estimate (e.g., a GC density) is determined using a bandwidth about equal to an average, mean, median, or maximum read length of sequence reads obtained for a given subject and/or sample. In some embodiments a local genome bias estimate (e.g., a GC density) is determined using a bandwidth of about 250, 240, 230, 220, 210, 200, 190, 180, 160, 150, 140, 130, 120, 110, 100, 90, 80, 70, 60, 50, 40, 30, 20 or about 10 bases.

A local genome bias estimate can be determined at a single base resolution, although local genome bias estimates (e.g., local GC content) can be determined at a lower resolution. In some embodiments a local genome bias estimate is determined for a local bias content. A local genome bias estimate (e.g., as determined using a PDF) often is determined using a window. In some embodiments, a local genome bias estimate comprises use of a window comprising a pre-selected number of bases. Sometimes a window comprises a segment of contiguous bases. Sometimes a window comprises one or more portions of non-contiguous bases. Sometimes a window comprises one or more portions (e.g., portions of a genome). A window size or length is often determined by a bandwidth and according to a PDF. In some embodiments a window is about 10 or more, 8 or more, 7 or more, 6 or more, 5 or more, 4 or more, 3 or more, or about 2 or more times the length of a bandwidth. A window is sometimes twice the length of a selected bandwidth when a PDF (e.g., a kernel density function) is used to determine a density estimate. A window may comprise any suitable number of bases. In some embodiments a window comprises about 5 bases to about 100,000 bases, about 5 bases to about 50,000 bases, about 5 bases to about 25,000 bases, about 5 bases to about 10,000 bases, about 5 bases to about 5,000 bases, about 5 bases to about 2,500 bases, about 5 bases to about 1000 bases, about 5 bases to about 500 bases, about 5 bases to about 250 bases, or about 20 bases to about 250 bases. In some embodiments a genome, or segments thereof, is partitioned into a plurality of windows. Windows encompassing regions of a genome may or may not overlap. In some embodiments windows are positioned at equal distances from each other. In some embodiments windows are positioned at different distances from each other. In certain embodiment a genome, or segment thereof, is partitioned into a plurality of sliding windows, where a window is slid incrementally across a genome, or segment thereof, where each window at each increment comprises a local genome bias estimate (e.g., a local GC density). A window can be slid across a genome at any suitable increment, according to any numerical pattern or according to any athematic defined sequence. In some embodiments, for a local genome bias estimate determination, a window is slid across a genome, or a segment thereof, at an increment of about 10,000 bp or more about 5,000 bp or more, about 2,500 bp or more, about 1,000 bp or more, about 750 bp or more, about 500 bp or more, about 400 bases or more, about 250 bp or more, about 100 bp or more, about 50 bp or more, or about 25 bp or more. In some embodiments, for a local genome bias estimate determination, a window is slid across a genome, or a segment thereof, at an increment of about 25, 24, 23, 22, 21, 20, 19, 18, 17, 16, 15, 14, 13, 12, 11, 10, 9, 8, 7, 6, 5, 4, 3, 2, or about 1 bp. For example, for a local genome bias estimate determination, a window may comprise about 400 bp (e.g., a bandwidth of 200 bp) and may be slid across a genome in increments of 1 bp. In some embodiments, a local genome bias estimate is determined for each base in a genome, or segment thereof, using a kernel density function and a bandwidth of about 200 bp.

In some embodiments a local genome bias estimate is a local GC content and/or a representation of local GC content. The term "local" as used herein (e.g., as used to describe a local bias, local bias estimate, local bias content, local genome bias, local GC content, and the like) refers to a polynucleotide segment of 10,000 bp or less. In some embodiments the term "local" refers to a polynucleotide segment of 5000 bp or less, 4000 bp or less, 3000 bp or less, 2000 bp or less, 1000 bp or less, 500 bp or less, 250 bp or less, 200 bp or less, 175 bp or less, 150 bp or less, 100 bp or less, 75 bp or less, or 50 bp or less. A local GC content is often a representation (e.g., a mathematical, a quantitative representation) of GC content for a local segment of a genome, sequence read, sequence read assembly (e.g., a contig, a profile, and the like). For example, a local GC content can be a local GC bias estimate or a GC density.

One or more GC densities are often determined for polynucleotides of a reference or sample (e.g., a test sample). In some embodiments a GC density is a representation (e.g., a mathematical, a quantitative representation) of local GC content (e.g., for a polynucleotide segment of 5000 bp or less). In some embodiments a GC density is a local genome bias estimate. A GC density can be determined using a suitable process described herein and/or known in the art. A GC density can be determined using a suitable PDF (e.g., a kernel density function (e.g., an Epanechnikov kernel density function, e.g., see FIG. 1)). In some embodiments a GC density is a PDE (e.g., a kernel density estimation). In certain embodiments, a GC density is defined by the presence or absence of one or more guanine (G) and/or cytosine (C) nucleotides. Inversely, in some embodiments, a GC density can be defined by the presence or absence of one or more a adenine (A) and/or thymidine (T) nucleotides. GC densities for local GC content, in some embodiments, are normalized according to GC densities determined for an entire genome, or segment thereof (e.g., autosomes, set of chromosomes, single chromosome, a gene e.g., see FIG. 2). One or more GC densities can be determined for polynucleotides of a sample (e.g., a test sample) or a reference sample. A GC density often is determined for a reference genome. In some embodiments a GC density is determined for a sequence read according to a reference genome. A GC density of a read is often determined according to a GC density determined for a corresponding location and/or position of a reference genome to which a read is mapped. In some embodiments a GC density determined for a location on a reference genome is assigned and/or provided for a read, where the read, or a segment thereof, maps to the same location on the reference genome. Any suitable method can be used to determine a location of a mapped read on a reference genome for the purpose of generating a GC density for a read. In some embodiments a median position of a mapped read determines a location on a reference genome from which a GC density for the read is determined. For example, where the median position of a read maps to Chromosome 12 at base number x of a reference genome, the GC density of the read is often provided as the GC density determined by a kernel density estimation for a position located on Chromosome 12 at or near base number x of the reference genome. In some embodiments a GC density is determined for some or all base positions of a read according to a reference genome. Sometimes a GC density of a read comprises an average, sum, median or integral of two or more GC densities determined for a plurality of base positions on a reference genome.

In some embodiments a local genome bias estimation (e.g., a GC density) is quantitated and/or is provided a value. A local genome bias estimation (e.g., a GC density) is sometimes expressed as an average, mean, and/or median. A local genome bias estimation (e.g., a GC density) is sometimes expressed as a maximum peak height of a PDE. Sometimes a local genome bias estimation (e.g., a GC density) is expressed as a sum or an integral (e.g., an area under a curve (AUC)) of a suitable PDE. In some embodiments a GC density comprises a kernel weight. In certain embodiments a GC density of a read comprises a value about equal to an average, mean, sum, median, maximum peak height or integral of a kernel weight.

Bias Frequencies

Bias frequencies are sometimes determined according to one or more local genome bias estimates (e.g., GC densities). A bias frequency is sometimes a count or sum of the number of occurrences of a local genome bias estimate for a sample, reference (e.g., a reference genome, a reference sequence, a chromosome in a reference genome) or part thereof. A bias frequency is sometimes a count or sum of the number of occurrences of a local genome bias estimate (e.g., each local genome bias estimate) for a sample, reference, or part thereof. In some embodiments a bias frequency is a GC density frequency. A GC density frequency is often determined according to one or more GC densities. For example, a GC density frequency may represent the number of times a GC density of value x is represented over an entire genome, or a segment thereof. A bias frequency is often a distribution of local genome bias estimates, where the number of occurrences of each local genome bias estimate is represented as a bias frequency (e.g., see FIG. 3). Bias frequencies are sometimes mathematically manipulated and/or normalized. Bias frequencies can be mathematically manipulated and/or normalized by a suitable method. In some embodiments, bias frequencies are normalized according to a representation (e.g., a fraction, a percentage) of each local genome bias estimate for a sample, reference or part thereof (e.g., autosomes, a subset of chromosomes, a single chromosome, or reads thereof). Bias frequencies can be determined for some or all local genome bias estimates of a sample or reference. In some embodiments bias frequencies can be determined for local genome bias estimates for some or all sequence reads of a test sample.

In some embodiments a system comprises a bias density module 6. A bias density module can accept, retrieve and/or store mapped sequence reads 5 and reference sequences 2 in any suitable format and generate local genome bias estimates, local genome bias distributions, bias frequencies, GC densities, GC density distributions and/or GC density frequencies (collectively represented by box 7). In some embodiments a bias density module transfers data and/or information (e.g., 7) to another suitable module (e.g., a relationship module 8).

Relationships

In some embodiments one or more relationships are generated between local genome bias estimates and bias frequencies. The term "relationship" as use herein refers to a mathematical and/or a graphical relationship between two or more variables or values. A relationship can be generated by a suitable mathematical and/or graphical process. Non-limiting examples of a relationship include a mathematical and/or graphical representation of a function, a correlation, a distribution, a linear or non-linear equation, a line, a regression, a fitted regression, the like or a combination thereof. Sometimes a relationship comprises a fitted relationship. In some embodiments a fitted relationship comprises a fitted regression. Sometimes a relationship comprises two or more variables or values that are weighted. In some embodiments a relationship comprise a fitted regression where one or more variables or values of the relationship a weighted. Sometimes a regression is fitted in a weighted fashion. Sometimes a regression is fitted without weighting. In certain embodiments, generating a relationship comprises plotting or graphing.

In some embodiments a suitable relationship is determined between local genome bias estimates and bias frequencies. In some embodiments generating a relationship between (i) local genome bias estimates and (ii) bias frequencies for a sample provides a sample bias relationship. In some embodiments generating a relationship between (i) local genome bias estimates and (ii) bias frequencies for a reference provides a reference bias relationship. In certain embodiments, a relationship is generated between GC densities and GC density frequencies. In some embodiments generating a relationship between (i) GC densities and (ii) GC density frequencies for a sample provides a sample GC density relationship. In some embodiments generating a relationship between (i) GC densities and (ii) GC density frequencies for a reference provides a reference GC density relationship. In some embodiments, where local genome bias estimates are GC densities, a sample bias relationship is a sample GC density relationship and a reference bias relationship is a reference GC density relationship. GC densities of a reference GC density relationship and/or a sample GC density relationship are often representations (e.g., mathematical or quantitative representation) of local GC content. In some embodiments a relationship between local genome bias estimates and bias frequencies comprises a distribution. In some embodiments a relationship between local genome bias estimates and bias frequencies comprises a fitted relationship (e.g., a fitted regression). In some embodiments a relationship between local genome bias estimates and bias frequencies comprises a fitted linear or non-linear regression (e.g., a polynomial regression). In certain embodiments a relationship between local genome bias estimates and bias frequencies comprises a weighted relationship where local genome bias estimates and/or bias frequencies are weighted by a suitable process. In some embodiments a weighted fitted relationship (e.g., a weighted fitting) can be obtained by a process comprising a quantile regression, parameterized distributions or an empirical distribution with interpolation. In certain embodiments a relationship between local genome bias estimates and bias frequencies for a test sample, a reference or part thereof, comprises a polynomial regression where local genome bias estimates are weighted. In some embodiments a weighed fitted model comprises weighting values of a distribution. Values of a distribution can be weighted by a suitable process. In some embodiments, values located near tails of a distribution are provided less weight than values closer to the median of the distribution. For example, for a distribution between local genome bias estimates (e.g., GC densities) and bias frequencies (e.g., GC density frequencies), a weight is determined according to the bias frequency for a given local genome bias estimate, where local genome bias estimates comprising bias frequencies closer to the mean of a distribution are provided greater weight than local genome bias estimates comprising bias frequencies further from the mean.

In some embodiments a system comprises a relationship module 8. A relationship module can generate relationships as well as functions, coefficients, constants and variables that define a relationship. A relationship module can accept, store and/or retrieve data and/or information (e.g., 7) from a suitable module (e.g., a bias density module 6) and generate a relationship. A relationship module often generates and compares distributions of local genome bias estimates. A relationship module can compare data sets and sometimes generate regressions and/or fitted relationships. In some embodiments a relationship module compares one or more distributions (e.g., distributions of local genome bias estimates of samples and/or references) and provides weighting factors and/or weighting assignments 9 for counts of sequence reads to another suitable module (e.g., a bias correction module). Sometimes a relationship module provides normalized counts of sequence reads directly to a distribution module 21 where the counts are normalized according to a relationship and/or a comparison.

Generating a Comparison and Use Thereof

In some embodiments a process for reducing local bias in sequence reads comprises normalizing counts of sequence reads. Counts of sequence reads are often normalized according to a comparison of a test sample to a reference. For example, sometimes counts of sequence reads are normalized by comparing local genome bias estimates of sequence reads of a test sample to local genome bias estimates of a reference (e.g., a reference genome, or part thereof). In some embodiments counts of sequence reads are normalized by comparing bias frequencies of local genome bias estimates of a test sample to bias frequencies of local genome bias estimates of a reference. In some embodiments counts of sequence reads are normalized by comparing a sample bias relationship and a reference bias relationship, thereby generating a comparison.

Counts of sequence reads are often normalized according to a comparison of two or more relationships. In certain embodiments two or more relationships are compared thereby providing a comparison that is used for reducing local bias in sequence reads (e.g., normalizing counts). Two or more relationships can be compared by a suitable method. In some embodiments a comparison comprises adding, subtracting, multiplying and/or dividing a first relationship from a second relationship. In certain embodiments comparing two or more relationships comprises a use of a suitable linear regression and/or a non-linear regression. In certain embodiments comparing two or more relationships comprises a suitable polynomial regression (e.g., a $3^{rd}$ order polynomial regression). In some embodiments a comparison comprises adding, subtracting, multiplying and/or dividing a first regression from a second regression. In some embodiments two or more relationships are compared by a process comprising an inferential framework of multiple regressions. In some embodiments two or more relationships are compared by a process comprising a suitable multivariate analysis. In some embodiments two or more relationships are compared by a process comprising a basis function (e.g., a blending function, e.g., polynomial bases, Fourier bases, or the like), splines, a radial basis function and/or wavelets.

In certain embodiments a distribution of local genome bias estimates comprising bias frequencies for a test sample and a reference is compared by a process comprising a polynomial regression where local genome bias estimates are weighted. In some embodiments a polynomial regression is generated between (i) ratios, each of which ratios comprises bias frequencies of local genome bias estimates of a reference and bias frequencies of local genome bias estimates of a sample and (ii) local genome bias estimates. In some embodiments a polynomial regression is generated between (i) a ratio of bias frequencies of local genome bias estimates of a reference to bias frequencies of local genome bias estimates of a sample and (ii) local genome bias estimates. In some embodiments a comparison of a distribution of local genome bias estimates for reads of a test sample and a reference comprises determining a log ratio (e.g., a log 2 ratio) of bias frequencies of local genome bias estimates for the reference and the sample. In some embodiments a comparison of a distribution of local genome bias estimates comprises dividing a log ratio (e.g., a log 2 ratio) of bias frequencies of local genome bias estimates for the reference by a log ratio (e.g., a log 2 ratio) of bias frequencies of local genome bias estimates for the sample (e.g., see Example 1 and FIG. 4).

Normalizing counts according to a comparison typically adjusts some counts and not others. Normalizing counts sometimes adjusts all counts and sometimes does not adjust any counts of sequence reads. A count for a sequence read sometimes is normalized by a process that comprises determining a weighting factor and sometimes the process does not include directly generating and utilizing a weighting factor. Normalizing counts according to a comparison sometimes comprises determining a weighting factor for each count of a sequence read. A weighting factor is often specific to a sequence read and is applied to a count of a specific sequence read. A weighting factor is often determined according to a comparison of two or more bias relationships (e.g., a sample bias relationship compared to a reference bias relationship). A normalized count is often determined by adjusting a count value according to a weighting factor. Adjusting a count according to a weighting factor sometimes includes adding, subtracting, multiplying and/or dividing a count for a sequence read by a weighting factor. A weighting factor and/or a normalized count is sometimes determined from a regression (e.g., a regression line). A normalized count is sometimes obtained directly from a regression line (e.g., a fitted regression line) resulting from a comparison between bias frequencies of local genome bias estimates of a reference (e.g., a reference genome, a chromosome in a reference genome) and a test sample. In some embodiments each count of a read of a sample is provided a normalized count value according to a comparison of (i) bias frequencies of a local genome bias estimates of reads compared to (ii) bias frequencies of a local genome bias estimates of a reference. In certain embodiments, counts of sequence reads obtained for a sample are normalized and bias in the sequence reads is reduced.

Sometimes a system comprises a bias correction module 10. In some embodiments, functions of a bias correction module are performed by a relationship modeling module 8. A bias correction module can accept, retrieve, and/or store mapped sequence reads and weighting factors (e.g., 9) from a suitable module (e.g., a relationship module 8, a compression module 4). In some embodiments a bias correction module provides a count to mapped reads. In some embodiments a bias correction module applies weighting assignments and/or bias correction factors to counts of sequence reads thereby providing normalized and/or adjusted counts. A bias correction module often provides normalized counts to a another suitable module (e.g., a distribution module 21).

In certain embodiments normalizing counts comprises factoring one or more features in addition to GC density, and normalizing counts of the sequence reads. In certain embodiments normalizing counts comprises factoring one or more different local genome bias estimates, and normalizing counts of the sequence reads. In certain embodiments counts of sequence reads are weighted according to a weighting determined according to one or more features (e.g., one or more biases). In some embodiments counts are normalized according to one or more combined weights. Sometimes factoring one or more features and/or normalizing counts according to one or more combined weights is by a process comprising use of a multivariate model. Any suitable multivariate model can be used to normalize counts. Non-limiting examples of a multivariate model include a multivariate linear regression, multivariate quantile regression, a multivariate interpolation of empirical data, a non-linear multivariate model, the like, or a combination thereof.

In some embodiments a system comprises a multivariate correction module 13. A multivariate correction module can perform functions of a bias density module 6, relationship module 8 and/or a bias correction module 10 multiple times thereby adjusting counts for multiple biases. In some embodiments a multivariate correction module comprises one or more bias density modules 6, relationship modules 8 and/or bias correction modules 10. Sometimes a multivariate correction module provides normalized counts 11 to another suitable module (e.g., a distribution module 21).

Weighted Portions

In some embodiments portions are weighted. In some embodiments one or more portions are weighted thereby providing weighted portions. Weighting portions sometimes removes portion dependencies. Portions can be weighted by a suitable process. In some embodiments one or more portions are weighted by an eigen function (e.g., an eigenfunction). In some embodiments an eigen function comprises replacing portions with orthogonal eigen-portions. In some embodiments a system comprises a portion weighting module 42. In some embodiments a weighting module accepts, retrieves and/or stores read densities, read density profiles, and/or adjusted read density profiles. In some embodiments weighted portions are provided by a portion weighting module. In some embodiments, a weighting module is required to weight portions. A weighting module can weight portions by one or more weighting methods known in the art or described herein. A weighting module often provides weighted portions to another suitable module (e.g., a scoring module 46, a PCA statistics module 33, a profile generation module 26 and the like).

Principal Component Analysis

In some embodiments a read density profile (e.g., a read density profile of a test sample (e.g., FIG. 7A) is adjusted according to a principal component analysis (PCA). A read density profile of one or more reference samples and/or a read density profile of a test subject can be adjusted according to a PCA. A read density profile for a genome, part of a genome, a chromosome, or a segment of a chromosome can be adjusted according to a PCA. Removing bias from a read density profile by a PCA related process is sometimes referred to herein as adjusting a profile. A PCA can be performed by a suitable PCA method, or a variation thereof. Non-limiting examples of a PCA method include a canonical correlation analysis (CCA), a Karhunen-Loève transform (KLT), a Hotelling transform, a proper orthogonal decomposition (POD), a singular value decomposition (SVD) of X, an eigenvalue decomposition (EVD) of XTX, a factor analysis, an Eckart-Young theorem, a Schmidt-Mirsky theorem, empirical orthogonal functions (EOF), an empirical eigenfunction decomposition, an empirical component analysis, quasiharmonic modes, a spectral decomposition, an empirical modal analysis, the like, variations or combinations thereof. A PCA often identifies one or more biases in a read density profile. A bias identified by a PCA is sometimes referred to herein as a principal component. In some embodiments one or more biases can be removed by adjusting a read density profile according to one or more principal component using a suitable method. A read density profile can be adjusted by adding, subtracting, multiplying and/or dividing one or more principal components from a read density profile. In some embodiments one or more biases can be removed from a read density profile by subtracting one or more principal components from a read density profile. Although bias in a read density profile is often identified and/or quantitated by a PCA of a profile, principal components are often subtracted from a profile at the level of read densities. Biases or features in a read density profile that are identified and/or quantitated by a PCA of a profile include, but are not limited to, fetal gender, sequence bias (e.g., guanine and cytosine (GC) bias), fetal fraction, bias correlated with DNase I sensitivity, entropy, repetitive sequence bias, chromatin structure bias, polymerase error-rate bias, palindrome bias, inverted repeat bias, PCR amplification bias, and hidden copy number variation.

Figure 6A:
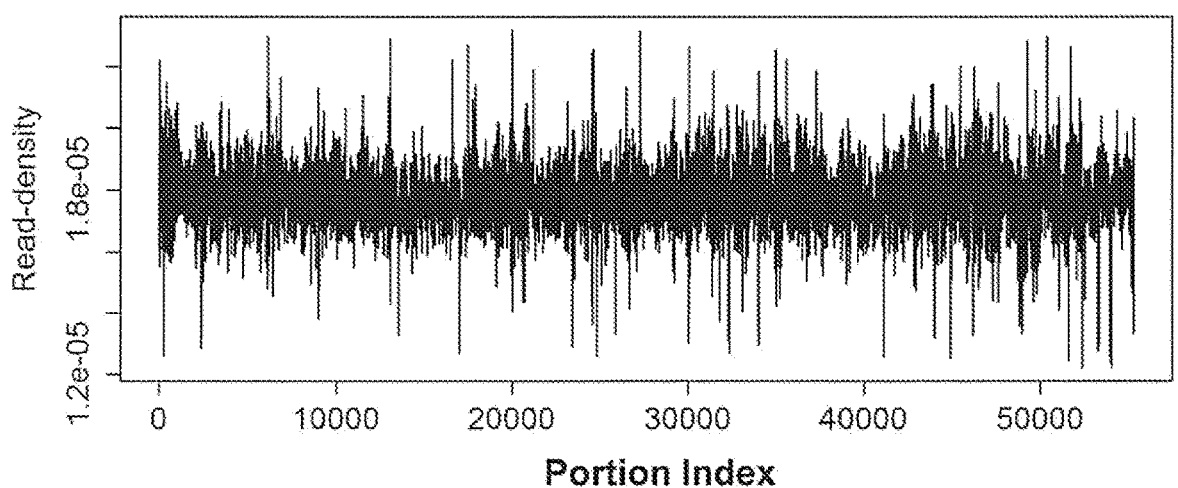
FIG. 6A shows a read density profile of a sample for a genome comprising median read densities (y-axis, e.g., read density/portion) and relative positions of each genomic portion (x-axis, portion index) within a genome.
Figure 6B:
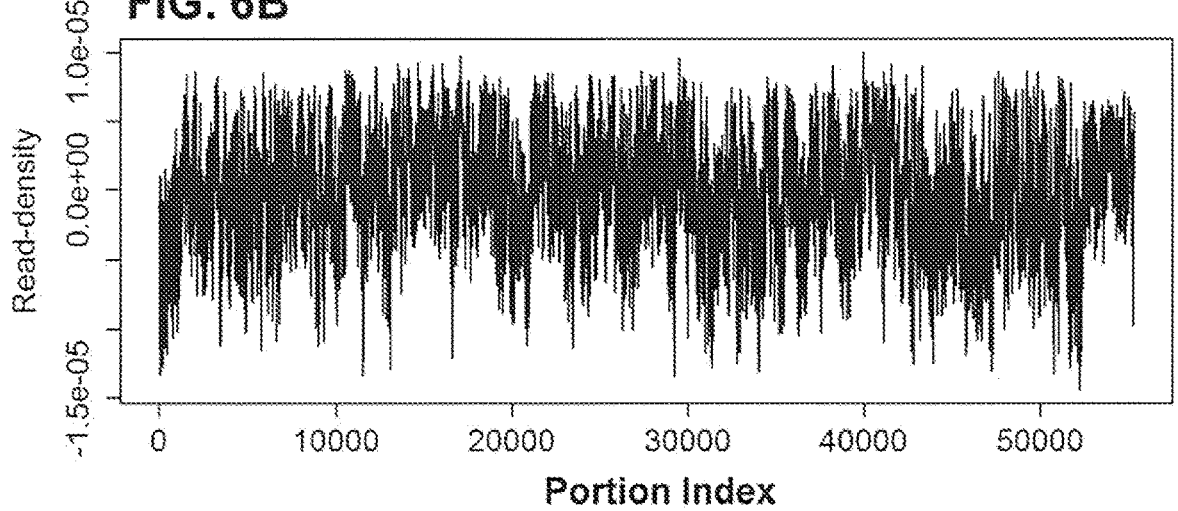
FIG. 6B shows a first principal component (PC1) and FIG. 6C shows a second principal component (PC2) obtained from a principal component analysis of read density profiles obtained from a training set of 500 euploids.
Figure 6C:
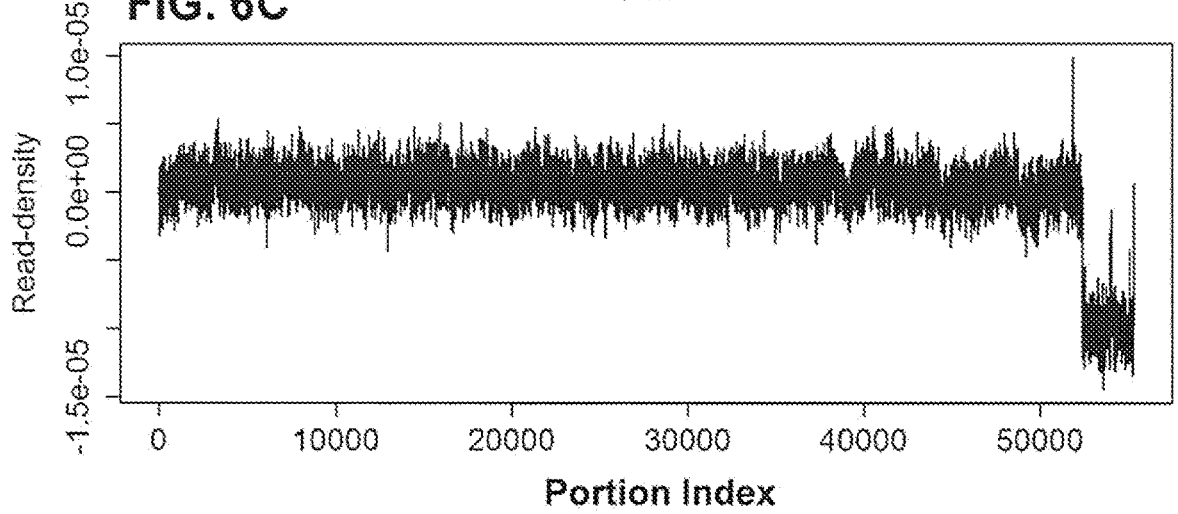

A PCA often identifies one or more principal components. In some embodiments a PCA identifies a $1^{st}$, $2^{nd}$, $3^{rd}$, $4^{th}$, $5^{th}$, $6^{th}$, $7^{th}$, $8^{th}$, $9^{th}$, and a $10^{th}$ or more principal components. In certain embodiments 1, 2, 3, 4, 5, 6, 7, 8, 9, 10 or more principal components are used to adjust a profile. In certain embodiments 5 principal components are used to adjust a profile. Often, principal components are used to adjust a profile in the order of their appearance in a PCA. For example, where three principal components are subtracted from a read density profile, a $1^{st}$, $2^{nd}$ and $3^{rd}$ principal component are used. Sometimes a bias identified by a principal component comprises a feature of a profile that is not used to adjust a profile. For example, a PCA may identify a genetic variation (e.g., an aneuploidy, deletion, translocation, insertion) and/or a gender difference (e.g., as seen in FIG. 6C) as a principal component. Thus, in some embodiments, one or more principal components are not used to adjust a profile. For example, sometimes a $1^{st}$, $2^{nd}$ and $4^{th}$ principal component are used to adjust a profile where a $3^{rd}$ principal component is not used to adjust a profile. A principal component can be obtained from a PCA using any suitable sample or reference. In some embodiments principal components are obtained from a test sample (e.g., a test subject). In some embodiments principal components are obtained from one or more references (e.g., reference samples, reference sequences, a reference set). As shown, for example, in FIG. 6 a PCA is performed on a median read density profile obtained from a training set (FIG. 6A) comprising multiple samples resulting in the identification of a $1^{st}$ principal component (FIG. 6B) and a second principal component (FIG. 6C). In some embodiments principal components are obtained from a set of subjects known to be devoid of a genetic variation in question. In some embodiments principal components are obtained from a set of known euploids. Principal component are often identified according to a PCA performed using one or more read density profiles of a reference (e.g., a training set). One or more principal components obtained from a reference are often subtracted from a read density profile of a test subject (e.g., FIG. 7B) thereby providing an adjusted profile (e.g., FIG. 7C).

In some embodiments a system comprises a PCA statistics module 33. A PCA statistics module can accepts and/or retrieve read density profiles from another suitable module (e.g., a profile generation module 26). A PCA is often performed by a PCA statistics module. A PCA statistics module often accepts, retrieves and/or stores read density profiles and processes read density profiles from a reference set 32, training set 30 and/or from one or more test subjects 28. A PCA statistics module can generate and/or provide principal components and/or adjust read density profiles according to one or more principal components. Adjusted read density profiles (e.g., 40, 38) are often provided by a PCA statistics module. A PCA statistics module can provide and/or transfer adjusted read density profiles (e.g., 38, 40) to another suitable module (e.g., a portion weighting module 42, a scoring module 46). In some embodiments a PCA statistics module can provide a gender call 36. A gender call is sometimes a determination of fetal gender determined according to a PCA and/or according to one or more principal components. In some embodiments a PCA statistics module comprises some, all or a modification of the R code shown below. An R code for computing principal components generally starts with cleaning the data (e.g., subtracting median, filtering portions, and trimming extreme values):

```
#Clean the data outliers for PCA
dclean <- (dat - m)[mask,]
for (j in 1:ncol(dclean))
{
q <- quantile(dclean[,j],c(.25,.75))
qmin <- q[1] - 4*(q[2]-q[1])
qmax <- q[2] + 4*(q[2]-q[1])
dclean[dclean[,j] < qmin,j] <- qmin
dclean[dclean[,j] > qmax,j] <- qmax
}
```

Then the principal components are computed:

```
#Compute principal components
pc <- prcomp(dclean)$x
```

Finally, each sample's PCA-adjusted profile can be computed with:

```
#Compute residuals
mm <- model.matrix(~pc[,1:numpc])
for (j in 1:ncol(dclean))
dclean[,j] <- dclean[,j] - predict(lm(dclean[,j]~mm))
```

Comparing Profiles

In some embodiments, determining an outcome comprises a comparison. In certain embodiments, a read density profile, or a portion thereof, is utilized to provide an outcome. In certain embodiments, a read density profile for a genome, part of a genome, a chromosome, or a segment of a chromosome is utilized to provide an outcome. In some embodiments determining an outcome (e.g., a determination of the presence or absence of a genetic variation) comprises a comparison of two or more read density profiles. Comparing read density profiles often comprises comparing read density profiles generated for a selected segment of a genome. For example, a test profile is often compared to a reference profile where the test and reference profiles were determined for a segment of a genome (e.g., a reference genome) that is substantially the same segment. Comparing read density profiles sometimes comprises comparing two or more subsets of portions of a read density profile. A subset of portions of a read density profile may represent a segment of a genome (e.g., a chromosome, or segment thereof). A read density profile can comprise any amount of subsets of portions. Sometimes a read density profile comprises two or more, three or more, four or more, or five or more subsets. In certain embodiments a read density profile comprises two subsets of portions where each portion represents segments of a reference genome that are adjacent. In some embodiments a test profile can be compared to a reference profile where the test profile and reference profile both comprise a first subset of portions and a second subset of portions where the first and second subsets represent different segments of a genome. Some subsets of portions of a read density profile may comprise genetic variations and other subsets of portions are sometimes substantially free of genetic variations. Sometimes all subsets of portions of a profile (e.g., a test profile) are substantially free of a genetic variation. Sometimes all subsets of portions of a profile (e.g., a test profile) comprise a genetic variation. In some embodiments a test profile can comprise a first subset of portions that comprise a genetic variation and a second subset of portions that are substantially free of a genetic variation.

In some embodiments methods described herein comprise preforming a comparison (e.g., comparing a test profile to a reference profile). Two or more data sets, two or more relationships and/or two or more profiles can be compared by a suitable method. Non-limiting examples of statistical methods suitable for comparing data sets, relationships and/or profiles include Behrens-Fisher approach, bootstrapping, Fisher's method for combining independent tests of significance, Neyman-Pearson testing, confirmatory data analysis, exploratory data analysis, exact test, F-test, Z-test, T-test, calculating and/or comparing a measure of uncertainty, a null hypothesis, counternulls and the like, a chi-square test, omnibus test, calculating and/or comparing level of significance (e.g., statistical significance), a meta analysis, a multivariate analysis, a regression, simple linear regression, robust linear regression, the like or combinations of the foregoing. In certain embodiments comparing two or more data sets, relationships and/or profiles comprises determining and/or comparing a measure of uncertainty. A "measure of uncertainty" as used herein refers to a measure of significance (e.g., statistical significance), a measure of error, a measure of variance, a measure of confidence, the like or a combination thereof. A measure of uncertainty can be a value (e.g., a threshold) or a range of values (e.g., an interval, a confidence interval, a Bayesian confidence interval, a threshold range). Non-limiting examples of a measure of uncertainty include p-values, a suitable measure of deviation (e.g., standard deviation, sigma, absolute deviation, mean absolute deviation, the like), a suitable measure of error (e.g., standard error, mean squared error, root mean squared error, the like), a suitable measure of variance, a suitable standard score (e.g., standard deviations, cumulative percentages, percentile equivalents, Z-scores, T-scores, R-scores, standard nine (stanine), percent in stanine, the like), the like or combinations thereof. In some embodiments determining the level of significance comprises determining a measure of uncertainty (e.g., a p-value). In certain embodiments, two or more data sets, relationships and/or profiles can be analyzed and/or compared by utilizing multiple (e.g., 2 or more) statistical methods (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or any suitable mathematical and/or statistical manipulations (e.g., referred to herein as manipulations).

In certain embodiments comparing two or more read density profiles comprises determining and/or comparing a measure of uncertainty for two or more read density profiles. Read density profiles and/or associated measures of uncertainty are sometimes compared to facilitate interpretation of mathematical and/or statistical manipulations of a data set and/or to provide an outcome. A read density profile generated for a test subject sometimes is compared to a read density profile generated for one or more references (e.g., reference samples, reference subjects, and the like). In some embodiments an outcome is provided by comparing a read density profile from a test subject to a read density profile from a reference for a chromosome, portions or segments thereof, where a reference read density profile is obtained from a set of reference subjects known not to possess a genetic variation (e.g., a reference). In some embodiments an outcome is provided by comparing a read density profile from a test subject to a read density profile from a reference for a chromosome, portions or segments thereof, where a reference read density profile is obtained from a set of reference subjects known to possess a specific genetic variation (e.g., a chromosome aneuploidy, a trisomy).

In certain embodiments, a read density profile of a test subject is compared to a predetermined value representative of the absence of a genetic variation, and sometimes deviates from a predetermined value at one or more genomic locations (e.g., portions) corresponding to a genomic location in which a genetic variation is located. For example, in test subjects (e.g., subjects at risk for, or suffering from a medical condition associated with a genetic variation), read density profiles are expected to differ significantly from read density profiles of a reference (e.g., a reference sequence, reference subject, reference set) for selected portions when a test subject comprises a genetic variation in question. Read density profiles of a test subject are often substantially the same as read density profiles of a reference (e.g., a reference sequence, reference subject, reference set) for selected portions when a test subject does not comprise a genetic variation in question. Read density profiles are often compared to a predetermined threshold and/or threshold range (e.g., see FIG. 8). The term "threshold" as used herein refers to any number that is calculated using a qualifying data set and serves as a limit of diagnosis of a genetic variation (e.g., a copy number variation, an aneuploidy, a chromosomal aberration, and the like). In certain embodiments a threshold is exceeded by results obtained by methods described herein and a subject is diagnosed with a genetic variation (e.g., a trisomy). In some embodiments a threshold value or range of values often is calculated by mathematically and/or statistically manipulating sequence read data (e.g., from a reference and/or subject). A predetermined threshold or threshold range of values indicative of the presence or absence of a genetic variation can vary while still providing an outcome useful for determining the presence or absence of a genetic variation. In certain embodiments, a read density profile comprising normalized read densities and/or normalized counts is generated to facilitate classification and/or providing an outcome. An outcome can be provided based on a plot of a read density profile comprising normalized counts (e.g., using a plot of such a read density profile).

In some embodiments a system comprises a scoring module 46. A scoring module can accept, retrieve and/or store read density profiles (e.g., adjusted, normalized read density profiles) from another suitable module (e.g., a profile generation module 26, a PCA statistics module 33, a portion weighting module 42, and the like). A scoring module can accept, retrieve, store and/or compare two or more read density profiles (e.g., test profiles, reference profiles, training sets, test subjects). A scoring module can often provide a score (e.g., a plot, profile statistics, a comparison (e.g., a difference between two or more profiles), a Z-score, a measure of uncertainty, a call zone, a sample call 50 (e.g., a determination of the presence or absence of a genetic variation), and/or an outcome). A scoring module can provide a score to an end user and/or to another suitable module (e.g., a display, printer, the like). In some embodiments a scoring module comprises some, all or a modification of the R code shown below which comprises an R function for computing Chi-square statistics for a specific test (e.g., High-chr21 counts).

The three parameters are:

```
x = sample read data (portion x sample)
m = median values for portions
y = test vector (Ex. False for all portions except True for chr21)
getChisqP <- function(x,m,y)
{
ahigh <- apply(x[!y,],2,function(x) sum((x>m[!y])))
alow <- sum((!y))-ahigh
bhigh <- apply(x[y,],2,function(x) sum((x>m[y])))
blow <- sum(y)-bhigh
p <- sapply(1:length(ahigh), function(i) {
p <- chisq.test(matrix(c(ahigh[i],alow[i],bhigh[i],blow[i]),2))$p.value/2
if (ahigh[i]/alow[i] > bhigh[i]/blow[i]) p <- max(p,1-p)
else p <- min(p,1-p); p})
return(p)
```

Experimental Conditions

In certain embodiments, a principal component normalization process can adjust for biases associated with experimental conditions. Data processing in view of experimental conditions is described, for example, in International Patent Application Publication No. WO2013/109981, the entire content of which is incorporated herein by reference, including all text, tables, equations and drawings.

In certain instances, samples can be affected by common experimental conditions. Samples processed at substantially the same time or using substantially the same conditions and/or reagents sometimes exhibit similar experimental condition (e.g., common experimental condition) induced data variability (e.g., bias) when compared to other samples processed at a different time and/or at the same time using different conditions and/or reagents. There often are practical considerations that limit the number of samples that can be prepared, processed and/or analyzed at any given time during an experimental procedure. In certain embodiments, the time frame for processing a sample from raw material to generating an outcome sometimes is days, weeks or even months. Due to the time between isolation and final analysis, high through-put experiments that analyze large numbers of samples sometimes generate batch effects or experimental condition-induced data variability. Experimental condition-induced data variability often includes any data variability that is a result of sample isolation, storage, preparation and/or analysis. Non-limiting examples of experimental condition induced variability include flow-cell based variability and/or plate based variability that includes: over or under representation of sequences; noisy data; spurious or outlier data points, reagent effects, personnel effects, laboratory condition effects and the like. Experimental condition induced variability sometimes occurs to subpopulations of samples in a data set (e.g., batch effect). A batch often is samples processed using substantially the same reagents, samples processed in the same sample preparation plate (e.g., microwell plate used for sample preparation; nucleic acid isolation, for example), samples staged for analysis in the same staging plate (e.g., microwell plate used to organize samples prior to loading onto a flow cell), samples processed at substantially the same time, samples processed by the same personnel, and/or samples processed under substantially the same experimental conditions (e.g., temperature, $CO_2$ levels, ozone levels, the like or combinations thereof). Experimental condition batch effects sometimes affect samples analyzed on the same flow cell, prepared in the same reagent plate or microwell plate and/or staged for analysis (e.g., preparing a nucleic acid library for sequencing) in the same reagent plate or microwell plate. Additional sources of variability can include, quality of nucleic acid isolated, amount of nucleic acid isolated, time to storage after nucleic acid isolation, time in storage, storage temperature, the like and combinations thereof. Variability of data points in a batch (e.g., subpopulation of samples in a data set which are processed at the same time and/or using the same reagents and/or experimental conditions) sometimes is greater than variability of data points seen between batches. This data variability sometimes includes spurious or outlier data whose magnitude can effect interpretation of some or all other data in a data set. A portion or all of a data set can be adjusted for experimental conditions using data processing steps described herein and known in the art; normalization to the median absolute deviation calculated for all samples analyzed in a flow cell, or processed in a microwell plate, for example. Data processing in view of experimental conditions is described, for example, in International Patent Application Publication No. WO2013/109981, the entire content of which is incorporated herein by reference, including all text, tables, equations and drawings.

Aneuploidy Detection Using Comparisons

In some embodiments, a principal component normalization process is used in conjunction with a method for determining the presence or absence of an aneuploidy according to a comparison. Aneuploidy detection using comparisons is described, for example, in International Patent Application Publication No. WO 2014/116598, the entire content of which is incorporated herein by reference, including all text, tables, equations and drawings.

In this section, a comparison of ratios or ratios or ratio values, ploidy assessment and ploidy assessment value collectively are referred to as a "comparison." In some embodiments the presence or absence of a chromosome aneuploidy in a subject is determined according to one or more comparisons. In some embodiments, the presence or absence of a chromosome aneuploidy in a subject is determined according to one or more comparisons for three selected autosomes (e.g., where one or more of the three selected autosomes is a test chromosome). In some embodiments, the presence or absence of a chromosome aneuploidy is determined according to one or more comparisons generated for a set of distinct chromosomes, a euploid region, an aneuploid region or a euploid region and an aneuploid region. In some embodiments, the presence or absence of a chromosome aneuploidy (e.g., a chromosome aneuploidy in a fetus) is determined according to a comparison obtained for a subject and a euploid region and/or an aneuploid region (e.g., a euploid region and an aneuploid region determined for a reference set). In certain embodiments the presence or absence of a chromosome aneuploidy is determined according to a relation between a comparison obtained for a subject and a euploid region and/or an aneuploid region. For example, the presence or absence of a chromosome aneuploidy is determined according to whether a comparison is in a euploid region or aneuploid region, or how far away a ploidy assessment value is from a euploid region or aneuploid region, in some embodiments. In some embodiments a relation is a proximity or a distance (e.g., a mathematical difference and/or a graphical distance, e.g., a distance between a point and a region). A relation can be determined by a suitable method known in the art or described herein, non-limiting examples of which include probability distribution, probability density function, cumulative distribution function, likelihood function, Bayesian model comparison, Bayes factor, Deviance information criterion, chi-squared tests, Euclidean distance, spatial analysis, mahalanobis distance, Manhattan distance, Chebyshev distance, Minkowski distance, Bregman divergence, Bhattacharyya distance, Hellinger distance, metric space, Canberra distance, convex hull (e.g., even-odd winding rule), the like or combinations thereof.

In some embodiments, the absence of a chromosome aneuploidy is determined according to a comparison and a euploid region. In some embodiments, the absence of a chromosome aneuploidy is determined according to a relation between a comparison and a euploid region. In some embodiments, a comparison that falls within, in or near a euploid region is a determination of a euploid chromosome (e.g., an absence of an aneuploid chromosome). In some embodiments, a comparison that is in or near a euploid region indicates that each chromosome, from which the comparison was determined, is euploid. For example, sometimes a comparison generated according to counts mapped to ChrA, ChrB and ChrC falls within a euploid region (e.g., a euploid region determined according to counts mapped to ChrA, ChrB and ChrC) and an absence of a chromosome aneuploidy is determined. In some embodiments the absence of a chromosome aneuploidy, as determined according to a comparison, indicates that each chromosome (e.g., each chromosome from which the ploidy assessment value was derived) is euploid (e.g., euploid in a mother and/or fetus).

In some embodiments, a comparison that falls outside an aneuploid region is a determination of one or more euploid chromosomes. In some embodiments, a comparison that is outside a euploid region indicates that one or more chromosomes, from which the comparison was determined, are euploid. For example, sometimes a comparison generated according to counts mapped to ChrA, ChrB and ChrC falls outside a euploid region (e.g., a euploid region determined according to counts mapped to ChrA, ChrB and ChrC) and an absence of a chromosome aneuploidy is determined. In some embodiments, a comparison that is outside a euploid region indicates that two of three chromosomes used for the comparison or assessment, and from which the comparison was determined, are euploid.

In some embodiments a comparison falls within an aneuploid region and one or more chromosomes, from which the comparison was determined, are euploid. For example, sometimes a comparison generated according to counts mapped to ChrA, ChrB and ChrC falls within an aneuploid region (e.g., an aneuploid region determined according to counts mapped to ChrA, ChrB and ChrC) and an absence of a chromosome aneuploidy is determined for two of the three chromosomes.

In some embodiments, the presence of a chromosome aneuploidy is determined according to a comparison and a euploid region. In certain embodiments, the presence of a chromosome aneuploidy is determined according to a relation between a comparison and a euploid region. In some embodiments, a comparison that falls outside a euploid region is a determination of an aneuploid chromosome (e.g., the presence of an aneuploid chromosome). In some embodiments, a comparison that falls outside a euploid region indicates that one or more chromosomes, from which the comparison was determined, is aneuploid. For example, sometimes a comparison generated according to counts mapped to ChrA, ChrB and ChrC falls outside a euploid region (e.g., a euploid region determined according to counts mapped to ChrA, ChrB and ChrC) and the presence of a chromosome aneuploidy is determined.

In some embodiments, a comparison that falls within, in or near a aneuploid region is a determination of an aneuploid chromosome (e.g., a presence of an aneuploid chromosome). In some embodiments, a comparison that is in or near an aneuploid region indicates that one or more chromosomes, from which the ploidy assessment value was determined, is aneuploid. In some embodiments, a comparison that is in or near an aneuploid region indicates that 1, 2, 3, 4, and/or 5 chromosomes, from which the comparison was determined, are aneuploid. In some embodiments, a comparison that is in or near an aneuploid region indicates that one of three chromosomes, from which the comparison was determined, is aneuploid. For example, sometimes a comparison generated according to counts mapped to ChrA, ChrB and ChrC falls within an aneuploid region (e.g., an aneuploid region determined according to counts mapped to ChrA, ChrB and ChrC) and one of the chromosomes is an aneuploid chromosome.

In some embodiments, a comparison that falls near an aneuploid region is a determination of an aneuploid chromosome (e.g., a presence of an aneuploid chromosome). In some embodiments, a comparison that is near a aneuploid region indicates that one or more chromosomes, from which the comparison was determined, is aneuploid. In some embodiments, a reference plot comprises a defined euploid region and three defined aneuploid regions (e.g., aneuploid for Chr13, Chr18 or Chr21) and a determination of the presence of an aneuploidy is made according to a comparison that falls closest to one of the aneuploid regions. For example, a comparison that is closer to an aneuploid region for Chr21 than to another region (e.g., an aneuploid region for Chr13 or Chr18, or a euploid region) can indicate the presence of an aneuploidy for Chr21.

In some embodiments a comparison generated according to counts mapped to Chr13, Chr18 and Chr21 falls within an aneuploid region (e.g., an aneuploid region determined according to counts mapped to Chr13, Chr18 and Chr21) and one of the chromosomes is an aneuploid chromosome. In some embodiments a comparison generated according to counts mapped to Chr13, Chr18 and Chr21 falls within an aneuploid region (e.g., an aneuploid region determined according to counts mapped to Chr13, Chr18 and Chr21), Chr18 and Chr21 are determined to be euploid and Chr13 is determined to be aneuploid. In some embodiments a comparison generated according to counts mapped to Chr13, Chr18 and Chr21 falls within an aneuploid region (e.g., an aneuploid region determined according to counts mapped to Chr13, Chr18 and Chr21), Chr13 and Chr21 are determined to be euploid and Chr18 is determined to be aneuploid. In some embodiments a comparison generated according to counts mapped to Chr13, Chr18 and Chr21 falls within an aneuploid region (e.g., an aneuploid region determined according to counts mapped to Chr13, Chr18 and Chr21), Chr18 and Chr13 are determined to be euploid and Chr21 is determined to be aneuploid.

In some embodiments the presence or absence of a chromosome aneuploidy is determined according to a first comparison and a second comparison where both comparisons where generated from sequence reads mapped to the same set of two or more chromosomes. In some embodiments, the presence or absence of a chromosome aneuploidy in a subject is determined according to a relation (e.g., a distance) between a first comparison generated for a subject and a second comparison generated for a second subject. In some embodiments, a second comparison is a set of comparisons (e.g., a region) generated for one or more subjects. In some embodiments the presence or absence of a chromosome aneuploidy in a subject is determined according to a relation (e.g., a distance) between a first comparison generated for the subject and a reference set of comparisons generated for one or more subjects. In some embodiments a first comparison is a comparison for a subject and a second comparison is a comparison or a set of comparisons representing one or more euploid fetuses. In some embodiments a second comparison is a value or set of values (e.g., a region) expected for a euploid fetus. In some embodiments a second comparison is a value or set of values generated for a subject (e.g., a pregnant female subject) where a fetus is known to be euploid for one or more of the chromosomes from which the comparison was generated. In some embodiments, the distance is determined according to an uncertainty value (e.g., a standard deviation or MAD). In some embodiments the distance between a first and a second comparison (e.g., a second comparison representative of one or more euploid subjects) is 1, 2, 3, 4, 5, 6 or more times an associated uncertainty and the first comparison is determined to be aneuploid. In some embodiments, the distance between a first and a second comparison (e.g., a second comparison representative of one or more euploid subjects) is 3 or more times an associated uncertainty and the first comparison is determined to represent an aneuploid chromosome.

In some embodiments the presence or absence of a chromosome aneuploid is determined according to a comparison generated according to counts mapped to one or more specific chromosomes and a euploid region, an aneuploid region, or a euploid region and an aneuploid region. In some embodiments the presence or absence of a chromosome aneuploid is determined according to a comparison generated according to sequence reads mapped to one or more specific chromosomes and sequence reads mapped to other chromosomes are not required for the determination. In some embodiments the presence or absence of a chromosome aneuploid is determined according to a comparison generated according to sequence reads mapped to 2, 3, 4, 5 or 6 distinct chromosomes and counts mapped to other chromosomes are not obtained or required for the determination. In some embodiments, the presence or absence of a chromosome aneuploid is determined according to a comparison generated according to three distinct chromosomes or segments thereof and the determination is not based on a chromosome other than one of the three distinct chromosomes. For example, where ChrA, ChrB and ChrC represent three distinct chromosomes or segments thereof, the presence or absence of a chromosome aneuploid is sometimes determined according to a comparison generated according to ChrA, ChrB and ChrC and the determination is not based on a chromosome other than ChrA, ChrB or ChrC. In some embodiments, ChrA, ChrB and ChrC represent Chr13, Chr21 and Chr18 respectively.

Sex Chromosome Karyotype

In some embodiments, a principal component normalization process is used in conjunction with a method for determining a sex chromosome karyotype. Methods for determining sex chromosome karyotype are described, for example, in International Patent Application Publication No. WO 2013/192562, the entire content of which is incorporated herein by reference, including all text, tables, equations and drawings.

In some embodiments, sequence read counts that map to one or more sex chromosomes (i.e., chromosome X, chromosome Y) are normalized. In some embodiments, normalization comprises a principal component normalization. In some embodiments, normalization involves determining an experimental bias for portions of a reference genome. In some embodiments, experimental bias can be determined for multiple samples from a first fitted relation (e.g., fitted linear relation, fitted non-linear relation) for each sample between counts of sequence reads mapped to each of the portions of a reference genome and a mapping feature (e.g., GC content) for each of the portions. The slope of a fitted relation (e.g., linear relation) generally is determined by linear regression. In some embodiments, each experimental bias is represented by an experimental bias coefficient. Experimental bias coefficient is the slope of a linear relationship between, for example, (i) counts of sequence reads mapped to each of the portions of a reference genome, and (ii) a mapping feature for each of the portions. In some embodiments, experimental bias can comprise an experimental bias curvature estimation.

In some embodiments, a method further comprises calculating a genomic section level (e.g., an elevation, a level) for each of the genomic portions from a second fitted relation (e.g., fitted linear relation, fitted non-linear relation) between the experimental bias and the counts of sequence reads mapped to each of the portions and the slope of the relation can be determined by linear regression. For example, if the first fitted relation is linear and the second fitted relation is linear, genomic section level $L_i$ can be determined for each of the portions of the reference genome according to Equation α:

$$L_i = (m_i - G_i S) I^{-1} \qquad \text{Equation } \alpha$$

where $G_i$ is the experimental bias, I is the intercept of the second fitted relation, S is the slope of the second relation, $m_i$ is measured counts mapped to each portion of the reference genome and i is a sample.

In some embodiments, a secondary normalization process is applied to one or more calculated genomic section levels. In some embodiments, the secondary normalization comprises GC normalization and sometimes comprises use of the PERUN methodology. In some embodiments, the secondary normalization comprises a principal component normalization.

Fetal Ploidy Determination

In some embodiments, a principal component normalization process is used in conjunction with a method for determining fetal ploidy. Methods for determining fetal ploidy are described, for example, in U.S. Patent Application Publication No. US 2013/0288244, the entire content of which is incorporated herein by reference, including all text, tables, equations and drawings.

A fetal ploidy can be determined, in part, from a measure of fetal fraction and the fetal ploidy determination is used to make a determination of the presence or absence of a genetic variation (e.g., a chromosome aneuploidy, a trisomy). A fetal ploidy can be determined, in part, from a measure of fetal fraction determined by any suitable method of fetal fraction determination including methods described herein. In some embodiments, the method requires a calculated reference count $F_i$ (sometimes represented as $f_i$) determined for a portion (i.e. a bin, i) of a genome for multiple samples where the ploidy of the fetus for portion i of the genome is known to be euploid. In some embodiments an uncertainty value (e.g., a standard deviation, σ) is determined for the reference count $f_i$. In some embodiments a reference count $f_i$, an uncertainty value, a test sample count and/or a measured fetal fraction (F) are used to determine fetal ploidy. In some embodiments a reference count (e.g., an average, mean or median reference count) is normalized by a principal component normalization and/or other normalization such as, for example, bin-wise normalization, normalization by GC content, linear and nonlinear least squares regression, LOESS, GC LOESS, LOWESS, PERUN, RM, GCRM and/or combinations thereof. In some embodiments a reference count of a segment of a genome known to be euploid is equal to 1 when the reference count is normalized by principal component normalization. In some embodiments both the reference count (e.g., for a fetus known to be euploid) and the counts of a test sample for a portion or segment of a genome are normalized by principal component normalization and the reference count is equal to 1. In some embodiments a reference count of a segment of a genome known to be euploid is equal to 1 when the reference count is normalized by PERUN. In some embodiments both the reference count (e.g., for a fetus known to be euploid) and the counts of a test sample for a portion or segment of a genome are normalized by PERUN and the reference count is equal to 1. Likewise, in some embodiments, a reference count of a portion or segment of a genome known to be euploid is equal to 1 when the counts are normalized by (i.e., divided by) a median of the reference count. For example, in some embodiments both the reference count (e.g., for a fetus known to be euploid) and the counts of a test sample for a portion or segment of a genome are normalized by a median reference count, the normalized reference count is equal to 1 and the test sample count is normalized (e.g., divided by) the median reference count. In some embodiments both the reference count (e.g., for a fetus known to be euploid) and the counts of a test sample for a portion or segment of a genome are normalized by principal component normalization, GCRM, GC, RM or a suitable method. In some embodiments a reference count is an average, mean or median reference count. A reference count is often a normalized count for a bin (e.g., a normalized genomic section level). In some embodiments a reference count and the counts for a test sample are raw counts. A reference count, in some embodiments, is determined from an average, mean or median count profile. In some embodiments, a reference count is a calculated genomic section level. In some embodiments a reference count of a reference sample and a count of a test sample (e.g., a patient sample, e.g., $y_i$) are normalized by the same method or process.

Additional Data Processing and Normalization

Mapped sequence reads that have been counted are referred to herein as raw data, since the data represents unmanipulated counts (e.g., raw counts). In some embodiments, sequence read data in a data set can be processed further (e.g., mathematically and/or statistically manipulated) and/or displayed to facilitate providing an outcome. In certain embodiments, data sets, including larger data sets, may benefit from pre-processing to facilitate further analysis. Pre-processing of data sets sometimes involves removal of redundant and/or uninformative portions or portions of a reference genome (e.g., portions of a reference genome with uninformative data, redundant mapped reads, portions with zero median counts, over represented or under represented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing". Processing can render data more amenable to further analysis, and can generate an outcome in some embodiments. In some embodiments one or more or all processing methods (e.g., normalization methods, portion filtering, mapping, validation, the like or combinations thereof) are performed by a processor, a micro-processor, a computer, in conjunction with memory and/or by a microprocessor controlled apparatus.

The term "noisy data" as used herein refers to (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing or replicating DNA used to generate sequence reads. In certain embodiments, noise results from certain sequences being over represented when prepared using PCR-based methods. Methods described herein can reduce or eliminate the contribution of noisy data, and therefore reduce the effect of noisy data on the provided outcome.

The terms "uninformative data", "uninformative portions of a reference genome", and "uninformative portions" as used herein refer to portions, or data derived therefrom, having a numerical value that is significantly different from a predetermined threshold value or falls outside a predetermined cutoff range of values. The terms "threshold" and "threshold value" herein refer to any number that is calculated using a qualifying data set and serves as a limit of diagnosis of a genetic variation (e.g. a copy number variation, an aneuploidy, a microduplication, a microdeletion, a chromosomal aberration, and the like). In certain embodiments a threshold is exceeded by results obtained by methods described herein and a subject is diagnosed with a genetic variation (e.g. trisomy 21). A threshold value or range of values often is calculated by mathematically and/or statistically manipulating sequence read data (e.g., from a reference and/or subject), in some embodiments, and in certain embodiments, sequence read data manipulated to generate a threshold value or range of values is sequence read data (e.g., from a reference and/or subject). In some embodiments, an uncertainty value is determined. An uncertainty value generally is a measure of variance or error and can be any suitable measure of variance or error. In some embodiments an uncertainty value is a standard deviation, standard error, calculated variance, p-value, or mean absolute deviation (MAD). In some embodiments an uncertainty value can be calculated according to a formula described herein.

Any suitable procedure can be utilized for processing data sets described herein. Non-limiting examples of procedures suitable for use for processing data sets include filtering, normalizing, weighting, monitoring peak heights, monitoring peak areas, monitoring peak edges, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set.

In some embodiments, one or more processing steps can comprise one or more filtering steps. The term "filtering" as used herein refers to removing portions or portions of a reference genome from consideration. Portions of a reference genome can be selected for removal based on any suitable criteria, including but not limited to redundant data (e.g., redundant or overlapping mapped reads), non-informative data (e.g., portions of a reference genome with zero median counts), portions of a reference genome with over represented or under represented sequences, noisy data, the like, or combinations of the foregoing. A filtering process often involves removing one or more portions of a reference genome from consideration and subtracting the counts in the one or more portions of a reference genome selected for removal from the counted or summed counts for the portions of a reference genome, chromosome or chromosomes, or genome under consideration. In some embodiments, portions of a reference genome can be removed successively (e.g., one at a time to allow evaluation of the effect of removal of each individual portion), and in certain embodiments all portions of a reference genome marked for removal can be removed at the same time. In some embodiments, portions of a reference genome characterized by a variance above or below a certain level are removed, which sometimes is referred to herein as filtering "noisy" portions of a reference genome. In certain embodiments, a filtering process comprises obtaining data points from a data set that deviate from the mean profile level of a portion, a chromosome, or segment of a chromosome by a predetermined multiple of the profile variance, and in certain embodiments, a filtering process comprises removing data points from a data set that do not deviate from the mean profile level of a portion, a chromosome or segment of a chromosome by a predetermined multiple of the profile variance. In some embodiments, a filtering process is utilized to reduce the number of candidate portions of a reference genome analyzed for the presence or absence of a genetic variation.

Reducing the number of candidate portions of a reference genome analyzed for the presence or absence of a genetic variation (e.g., micro-deletion, micro-duplication) often reduces the complexity and/or dimensionality of a data set, and sometimes increases the speed of searching for and/or identifying genetic variations and/or genetic aberrations by two or more orders of magnitude.

In some embodiments one or more processing steps can comprise one or more normalization steps. Normalization can be performed by a suitable method described herein or known in the art. In certain embodiments normalization comprises adjusting values measured on different scales to a notionally common scale. In certain embodiments normalization comprises a sophisticated mathematical adjustment to bring probability distributions of adjusted values into alignment. In some embodiments normalization comprises aligning distributions to a normal distribution. In certain embodiments normalization comprises mathematical adjustments that allow comparison of corresponding normalized values for different datasets in a way that eliminates the effects of certain gross influences (e.g., error and anomalies). In certain embodiments normalization comprises scaling. Normalization sometimes comprises division of one or more data sets by a predetermined variable or formula. Normalization sometimes comprises subtraction of one or more data sets by a predetermined variable or formula. Non-limiting examples of normalization methods include portion-wise normalization, normalization by GC content, median count (median bin count, median portion count) normalization, linear and nonlinear least squares regression, LOESS, GC LOESS, LOWESS (locally weighted scatterplot smoothing), PERUN, ChAI, principal component normalization, repeat masking (RM), GC-normalization and repeat masking (GCRM), cQn and/or combinations thereof. In some embodiments, the determination of a presence or absence of a genetic variation (e.g., an aneuploidy, a microduplication, a microdeletion) utilizes a normalization method (e.g., portion-wise normalization, normalization by GC content, median count (median bin count, median portion count) normalization, linear and nonlinear least squares regression, LOESS, GC LOESS, LOWESS (locally weighted scatterplot smoothing), PERUN, ChAI, principal component normalization, repeat masking (RM), GC-normalization and repeat masking (GCRM), cQn, a normalization method known in the art and/or a combination thereof). In some embodiments, the determination of a presence or absence of a genetic variation (e.g., an aneuploidy, a microduplication, a microdeletion) utilizes one or more of LOESS, median count (median bin count, median portion count) normalization, and principal component normalization. In some embodiments, the determination of a presence or absence of a genetic variation utilizes LOESS followed by median count (median bin count, median portion count) normalization. In some embodiments, the determination of a presence or absence of a genetic variation utilizes LOESS followed by median count (median bin count, median portion count) normalization followed by principal component normalization.

Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference portions to the total number of counts mapped to the chromosome or the entire genome on which the selected portion or sections are mapped; normalizing raw count data for one or more selected portions to a median reference count for one or more portions or the chromosome on which a selected portion or segments is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data. Normalizing portions, or portions of a reference genome, with respect to a normalizing value sometimes is referred to as "portion-wise normalization".

In certain embodiments, a processing step comprising normalization includes normalizing to a static window, and in some embodiments, a processing step comprising normalization includes normalizing to a moving or sliding window. The term "window" as used herein refers to one or more portions chosen for analysis, and sometimes used as a reference for comparison (e.g., used for normalization and/or other mathematical or statistical manipulation). The term "normalizing to a static window" as used herein refers to a normalization process using one or more portions selected for comparison between a test subject and reference subject data set. In some embodiments the selected portions are utilized to generate a profile. A static window generally includes a predetermined set of portions that do not change during manipulations and/or analysis. The terms "normalizing to a moving window" and "normalizing to a sliding window" as used herein refer to normalizations performed to portions localized to the genomic region (e.g., immediate genetic surrounding, adjacent portion or sections, and the like) of a selected test portion, where one or more selected test portions are normalized to portions immediately surrounding the selected test portion. In certain embodiments, the selected portions are utilized to generate a profile. A sliding or moving window normalization often includes repeatedly moving or sliding to an adjacent test portion, and normalizing the newly selected test portion to portions immediately surrounding or adjacent to the newly selected test portion, where adjacent windows have one or more portions in common. In certain embodiments, a plurality of selected test portions and/or chromosomes can be analyzed by a sliding window process.

In some embodiments, normalizing to a sliding or moving window can generate one or more values, where each value represents normalization to a different set of reference portions selected from different regions of a genome (e.g., chromosome). In certain embodiments, the one or more values generated are cumulative sums (e.g., a numerical estimate of the integral of the normalized count profile over the selected portion, domain (e.g., part of chromosome), or chromosome). The values generated by the sliding or moving window process can be used to generate a profile and facilitate arriving at an outcome. In some embodiments, cumulative sums of one or more portions can be displayed as a function of genomic position. Moving or sliding window analysis sometimes is used to analyze a genome for the presence or absence of micro-deletions and/or micro-insertions. In certain embodiments, displaying cumulative sums of one or more portions is used to identify the presence or absence of regions of genetic variation (e.g., micro-deletions, micro-duplications). In some embodiments, moving or sliding window analysis is used to identify genomic regions containing micro-deletions and in certain embodiments, moving or sliding window analysis is used to identify genomic regions containing micro-duplications.

Described in greater detail hereafter are certain examples of normalization processes that can be utilized, such as LOESS, PERUN, ChAI and principal component normalization methods, for example.

In some embodiments, a processing step comprises a weighting. The terms "weighted", "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more portions or portions of a reference genome, based on the quality or usefulness of the data in the selected portion or portions of a reference genome). A weighting function can be used to increase the influence of data with a relatively small measurement variance, and/or to decrease the influence of data with a relatively large measurement variance, in some embodiments. For example, portions of a reference genome with under represented or low quality sequence data can be "down weighted" to minimize the influence on a data set, whereas selected portions of a reference genome can be "up weighted" to increase the influence on a data set. A non-limiting example of a weighting function is $[1/(\text{standard deviation})^2]$. A weighting step sometimes is performed in a manner substantially similar to a normalizing step. In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak levels, determination of peak edge locations, calculation of peak area ratios, analysis of median chromosomal level, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median levels, mean levels, count distribution within a genomic region, relative representation of nucleic acid species, the like or combinations thereof.

In some embodiments, a processing step can comprise the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median levels, mean levels, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation, depending on the genetic status of the reference samples (e.g., positive or negative for a selected genetic variation). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation or medical condition.

After data sets have been counted, optionally filtered and normalized, the processed data sets can be further manipulated by one or more filtering and/or normalizing procedures, in some embodiments. A data set that has been further manipulated by one or more filtering and/or normalizing procedures can be used to generate a profile, in certain embodiments. The one or more filtering and/or normalizing procedures sometimes can reduce data set complexity and/or dimensionality, in some embodiments. An outcome can be provided based on a data set of reduced complexity and/or dimensionality.

In some embodiments portions may be filtered according to a measure of error (e.g., standard deviation, standard error, calculated variance, p-value, mean absolute error (MAE), average absolute deviation and/or mean absolute deviation (MAD). In certain embodiments a measure of error refers to count variability. In some embodiments portions are filtered according to count variability. In certain embodiments count variability is a measure of error determined for counts mapped to a portion (i.e., portion) of a reference genome for multiple samples (e.g., multiple sample obtained from multiple subjects, e.g., 50 or more, 100 or more, 500 or more 1000 or more, 5000 or more or 10,000 or more subjects). In some embodiments portions with a count variability above a pre-determined upper range are filtered (e.g., excluded from consideration). In some embodiments a pre-determined upper range is a MAD value equal to or greater than about 50, about 52, about 54, about 56, about 58, about 60, about 62, about 64, about 66, about 68, about 70, about 72, about 74 or equal to or greater than about 76. In some embodiments portions with a count variability below a pre-determined lower range are filtered (e.g., excluded from consideration). In some embodiments a pre-determined lower range is a MAD value equal to or less than about 40, about 35, about 30, about 25, about 20, about 15, about 10, about 5, about 1, or equal to or less than about 0. In some embodiments portions with a count variability outside a pre-determined range are filtered (e.g., excluded from consideration). In some embodiments a pre-determined range is a MAD value greater than zero and less than about 76, less than about 74, less than about 73, less than about 72, less than about 71, less than about 70, less than about 69, less than about 68, less than about 67, less than about 66, less than about 65, less than about 64, less than about 62, less than about 60, less than about 58, less than about 56, less than about 54, less than about 52 or less than about 50. In some embodiments a pre-determined range is a MAD value greater than zero and less than about 67.7. In some embodiments portions with a count variability within a pre-determined range are selected (e.g., used for determining the presence or absence of a genetic variation).

In some embodiments the count variability of portions represents a distribution (e.g., a normal distribution). In some embodiments portions are selected within a quantile of the distribution. In some embodiments portions within a quantile equal to or less than about 99.9%, 99.8%, 99.7%, 99.6%, 99.5%, 99.4%, 99.3%, 99.2%, 99.1%, 99.0%, 98.9%, 98.8%, 98.7%, 98.6%, 98.5%, 98.4%, 98.3%, 98.2%, 98.1%, 98.0%, 97%, 96%, 95%, 94%, 93%, 92%, 91%, 90%, 85%, 80%, or equal to or less than a quantile of about 75% for the distribution are selected. In some embodiments portions within a 99% quantile of the distribution of count variability are selected. In some embodiments portions with a MAD>0 and a MAD<67.725 a within the 99% quantile and are selected, resulting in the identification of a set of stable portions of a reference genome.

Non-limiting examples of portion filtering with respect to PERUN, for example, is provided herein and in international patent application no. PCT/US12/59123 (WO2013/052913) the entire content of which is incorporated herein by reference, including all text, tables, equations and drawings. Portions may be filtered based on, or based on part on, a measure of error. A measure of error comprising absolute values of deviation, such as an R-factor, can be used for portion removal or weighting in certain embodiments. An R-factor, in some embodiments, is defined as the sum of the absolute deviations of the predicted count values from the actual measurements divided by the predicted count values from the actual measurements. While a measure of error comprising absolute values of deviation may be used, a suitable measure of error may be alternatively employed. In certain embodiments, a measure of error not comprising absolute values of deviation, such as a dispersion based on squares, may be utilized. In some embodiments, portions are filtered or weighted according to a measure of mappability (e.g., a mappability score). A portion sometimes is filtered or weighted according to a relatively low number of sequence reads mapped to the portion (e.g., 0, 1, 2, 3, 4, 5 reads mapped to the portion). Portions can be filtered or weighted according to the type of analysis being performed. For example, for chromosome 13, 18 and/or 21 aneuploidy analysis, sex chromosomes may be filtered, and only autosomes, or a subset of autosomes, may be analyzed.

In particular embodiments, the following filtering process may be employed. The same set of portions (e.g., portions of a reference genome) within a given chromosome (e.g., chromosome 21) is selected and the number of reads in affected and unaffected samples are compared. The gap relates trisomy 21 and euploid samples and it involves a set of portions covering most of chromosome 21. The set of portions is the same between euploid and T21 samples. The distinction between a set of portions and a single section is not crucial, as a portion can be defined. The same genomic region is compared in different patients. This process can be utilized for a trisomy analysis, such as for T13 or T18 in addition to, or instead of, T21.

After data sets have been counted, optionally filtered and normalized, the processed data sets can be manipulated by weighting, in some embodiments. One or more portions can be selected for weighting to reduce the influence of data (e.g., noisy data, uninformative data) contained in the selected portions, in certain embodiments, and in some embodiments, one or more portions can be selected for weighting to enhance or augment the influence of data (e.g., data with small measured variance) contained in the selected portions. In some embodiments, a data set is weighted utilizing a single weighting function that decreases the influence of data with large variances and increases the influence of data with small variances. A weighting function sometimes is used to reduce the influence of data with large variances and augment the influence of data with small variances (e.g., $[1/(\text{standard deviation})^2]$). In some embodiments, a profile plot of processed data further manipulated by weighting is generated to facilitate classification and/or providing an outcome. An outcome can be provided based on a profile plot of weighted data.

Filtering or weighting of portions can be performed at one or more suitable points in an analysis. For example, portions may be filtered or weighted before or after sequence reads are mapped to portions of a reference genome. Portions may be filtered or weighted before or after an experimental bias for individual genome portions is determined in some embodiments. In certain embodiments, portions may be filtered or weighted before or after genomic section levels are calculated.

After data sets have been counted, optionally filtered, normalized, and optionally weighted, the processed data sets can be manipulated by one or more mathematical and/or statistical (e.g., statistical functions or statistical algorithm) manipulations, in some embodiments. In certain embodiments, processed data sets can be further manipulated by calculating Z-scores for one or more selected portions, chromosomes, or portions of chromosomes. In some embodiments, processed data sets can be further manipulated by calculating P-values. In certain embodiments, mathematical and/or statistical manipulations include one or more assumptions pertaining to ploidy and/or fetal fraction. In some embodiments, a profile plot of processed data further manipulated by one or more statistical and/or mathematical manipulations is generated to facilitate classification and/or providing an outcome. An outcome can be provided based on a profile plot of statistically and/or mathematically manipulated data. An outcome provided based on a profile plot of statistically and/or mathematically manipulated data often includes one or more assumptions pertaining to ploidy and/or fetal fraction.

In certain embodiments, multiple manipulations are performed on processed data sets to generate an N-dimensional space and/or N-dimensional point, after data sets have been counted, optionally filtered and normalized. An outcome can be provided based on a profile plot of data sets analyzed in N-dimensions.

In some embodiments, data sets are processed utilizing one or more peak level analysis, peak width analysis, peak edge location analysis, peak lateral tolerances, the like, derivations thereof, or combinations of the foregoing, as part of or after data sets have processed and/or manipulated. In some embodiments, a profile plot of data processed utilizing one or more peak level analysis, peak width analysis, peak edge location analysis, peak lateral tolerances, the like, derivations thereof, or combinations of the foregoing is generated to facilitate classification and/or providing an outcome. An outcome can be provided based on a profile plot of data that has been processed utilizing one or more peak level analysis, peak width analysis, peak edge location analysis, peak lateral tolerances, the like, derivations thereof, or combinations of the foregoing.

In some embodiments, the use of one or more reference samples that are substantially free of a genetic variation in question can be used to generate a reference median count profile, which may result in a predetermined value representative of the absence of the genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for the selected portion or sections is expected to vary significantly from the predetermined value for non-affected genomic locations. In certain embodiments, the use of one or more reference samples known to carry the genetic variation in question can be used to generate a reference median count profile, which may result in a predetermined value representative of the presence of the genetic variation, and often deviates from a predetermined value in areas corresponding to the genomic location in which a test subject does not carry the genetic variation. In test subjects not at risk for, or suffering from a medical condition associated with a genetic variation, the numerical value for the selected portion or sections is expected to vary significantly from the predetermined value for affected genomic locations.

In some embodiments, analysis and processing of data can include the use of one or more assumptions. A suitable number or type of assumptions can be utilized to analyze or process a data set. Non-limiting examples of assumptions that can be used for data processing and/or analysis include maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a fetal quantifier assay (e.g., FQA), assumptions regarding twins (e.g., if 2 twins and only 1 is affected the effective fetal fraction is only 50% of the total measured fetal fraction (similarly for triplets, quadruplets and the like)), fetal cell free DNA (e.g., cfDNA) uniformly covers the entire genome, the like and combinations thereof.

In those instances where the quality and/or depth of mapped sequence reads does not permit an outcome prediction of the presence or absence of a genetic variation at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

LOESS Normalization

LOESS is a regression modeling method known in the art that combines multiple regression models in a k-nearest-neighbor-based meta-model. LOESS is sometimes referred to as a locally weighted polynomial regression. GC LOESS, in some embodiments, applies an LOESS model to the relationship between fragment count (e.g., sequence reads, counts) and GC composition for portions of a reference genome. Plotting a smooth curve through a set of data points using LOESS is sometimes called an LOESS curve, particularly when each smoothed value is given by a weighted quadratic least squares regression over the span of values of the y-axis scattergram criterion variable. For each point in a data set, the LOESS method fits a low-degree polynomial to a subset of the data, with explanatory variable values near the point whose response is being estimated. The polynomial is fitted using weighted least squares, giving more weight to points near the point whose response is being estimated and less weight to points further away. The value of the regression function for a point is then obtained by evaluating the local polynomial using the explanatory variable values for that data point. The LOESS fit is sometimes considered complete after regression function values have been computed for each of the data points. Many of the details of this method, such as the degree of the polynomial model and the weights, are flexible.

PERUN Normalization

A normalization methodology for reducing error associated with nucleic acid indicators is referred to herein as Parameterized Error Removal and Unbiased Normalization (PERUN) described herein and in International Patent Application Publication No. WO2013/052913, the entire content of which is incorporated herein by reference, including all text, tables, equations and drawings. PERUN methodology can be applied to a variety of nucleic acid indicators (e.g., nucleic acid sequence reads) for the purpose of reducing effects of error that confound predictions based on such indicators.

In certain embodiments, PERUN methodology includes calculating a genomic section level for portions of a reference genome from (a) sequence read counts mapped to a portion of a reference genome for a test sample, (b) experimental bias (e.g., GC bias) for the test sample, and (c) one or more fit parameters (e.g., estimates of fit) for a fitted relationship between (i) experimental bias for a portion of a reference genome to which sequence reads are mapped and (ii) counts of sequence reads mapped to the portion. Experimental bias for each of the portions of a reference genome can be determined across multiple samples according to a fitted relationship for each sample between (i) the counts of sequence reads mapped to each of the portions of a reference genome, and (ii) a mapping feature for each of the portions of a reference genome. This fitted relationship for each sample can be assembled for multiple samples in three dimensions. The assembly can be ordered according to the experimental bias in certain embodiments, although PERUN methodology may be practiced without ordering the assembly according to the experimental bias. The fitted relationship for each sample and the fitted relationship for each portion of the reference genome can be fitted independently to a linear function or non-linear function by a suitable fitting process known in the art.

Hybrid Regression Normalization

In some embodiments a hybrid normalization method is used. In some embodiments a hybrid normalization method reduces bias (e.g., GC bias). A hybrid normalization, in some embodiments, comprises (i) an analysis of a relationship of two variables (e.g., counts and GC content) and (ii) selection and application of a normalization method according to the analysis. A hybrid normalization, in certain embodiments, comprises (i) a regression (e.g., a regression analysis) and (ii) selection and application of a normalization method according to the regression. In some embodiments counts obtained for a first sample (e.g., a first set of samples) are normalized by a different method than counts obtained from another sample (e.g., a second set of samples). In some embodiments counts obtained for a first sample (e.g., a first set of samples) are normalized by a first normalization method and counts obtained from a second sample (e.g., a second set of samples) are normalized by a second normalization method. For example, in certain embodiments a first normalization method comprises use of a linear regression and a second normalization method comprises use of a non-linear regression (e.g., a LOESS, GC-LOESS, LOWESS regression, LOESS smoothing).

In some embodiments a hybrid normalization method is used to normalize sequence reads mapped to portions of a genome or chromosome (e.g., counts, mapped counts, mapped reads). In certain embodiments raw counts are normalized and in some embodiments adjusted, weighted, filtered or previously normalized counts are normalized by a hybrid normalization method. In certain embodiments, genomic section levels or Z-scores are normalized. In some embodiments counts mapped to selected portions of a genome or chromosome are normalized by a hybrid normalization approach. Counts can refer to a suitable measure of sequence reads mapped to portions of a genome, non-limiting examples of which include raw counts (e.g., unprocessed counts), normalized counts (e.g., normalized by PERUN, ChAI, principal component normalization, or a suitable method), portion levels (e.g., average levels, mean levels, median levels, or the like), Z-scores, the like, or combinations thereof. The counts can be raw counts or processed counts from one or more samples (e.g., a test sample, a sample from a pregnant female). In some embodiments counts are obtained from one or more samples obtained from one or more subjects.

In some embodiments a normalization method (e.g., the type of normalization method) is selected according to a regression (e.g., a regression analysis) and/or a correlation coefficient. A regression analysis refers to a statistical technique for estimating a relationship among variables (e.g., counts and GC content). In some embodiments a regression is generated according to counts and a measure of GC content for each portion of multiple portions of a reference genome. A suitable measure of GC content can be used, non-limiting examples of which include a measure of guanine, cytosine, adenine, thymine, purine (GC), or pyrimidine (AT or ATU) content, melting temperature ($T_m$) (e.g., denaturation temperature, annealing temperature, hybridization temperature), a measure of free energy, the like or combinations thereof. A measure of guanine (G), cytosine (C), adenine (A), thymine (T), purine (GC), or pyrimidine (AT or ATU) content can be expressed as a ratio or a percentage. In some embodiments any suitable ratio or percentage is used, non-limiting examples of which include GC/AT, GC/total nucleotide, GC/A, GC/T, AT/total nucleotide, AT/GC, AT/G, AT/C, G/A, C/A, G/T, G/A, G/AT, C/T, the like or combinations thereof. In some embodiments a measure of GC content is a ratio or percentage of GC to total nucleotide content. In some embodiments a measure of GC content is a ratio or percentage of GC to total nucleotide content for sequence reads mapped to a portion of reference genome. In certain embodiments the GC content is determined according to and/or from sequence reads mapped to each portion of a reference genome and the sequence reads are obtained from a sample (e.g., a sample obtained from a pregnant female). In some embodiments a measure of GC content is not determined according to and/or from sequence reads. In certain embodiments, a measure of GC content is determined for one or more samples obtained from one or more subjects.

In some embodiments generating a regression comprises generating a regression analysis or a correlation analysis. A suitable regression can be used, non-limiting examples of which include a regression analysis, (e.g., a linear regression analysis), a goodness of fit analysis, a Pearson's correlation analysis, a rank correlation, a fraction of variance unexplained, Nash-Sutcliffe model efficiency analysis, regression model validation, proportional reduction in loss, root mean square deviation, the like or a combination thereof. In some embodiments a regression line is generated. In certain embodiments generating a regression comprises generating a linear regression. In certain embodiments generating a regression comprises generating a non-linear regression (e.g., an LOESS regression, an LOWESS regression).

In some embodiments a regression determines the presence or absence of a correlation (e.g., a linear correlation), for example between counts and a measure of GC content. In some embodiments a regression (e.g., a linear regression) is generated and a correlation coefficient is determined. In some embodiments a suitable correlation coefficient is determined, non-limiting examples of which include a coefficient of determination, an $R^2$ value, a Pearson's correlation coefficient, or the like.

In some embodiments goodness of fit is determined for a regression (e.g., a regression analysis, a linear regression). Goodness of fit sometimes is determined by visual or mathematical analysis. An assessment sometimes includes determining whether the goodness of fit is greater for a non-linear regression or for a linear regression. In some embodiments a correlation coefficient is a measure of a goodness of fit. In some embodiments an assessment of a goodness of fit for a regression is determined according to a correlation coefficient and/or a correlation coefficient cutoff value. In some embodiments an assessment of a goodness of fit comprises comparing a correlation coefficient to a correlation coefficient cutoff value. In some embodiments an assessment of a goodness of fit for a regression is indicative of a linear regression. For example, in certain embodiments, a goodness of fit is greater for a linear regression than for a non-linear regression and the assessment of the goodness of fit is indicative of a linear regression. In some embodiments an assessment is indicative of a linear regression and a linear regression is used to normalized the counts. In some embodiments an assessment of a goodness of fit for a regression is indicative of a non-linear regression. For example, in certain embodiments, a goodness of fit is greater for a non-linear regression than for a linear regression and the assessment of the goodness of fit is indicative of a non-linear regression. In some embodiments an assessment is indicative of a non-linear regression and a non-linear regression is used to normalized the counts.

In some embodiments an assessment of a goodness of fit is indicative of a linear regression when a correlation coefficient is equal to or greater than a correlation coefficient cutoff. In some embodiments an assessment of a goodness of fit is indicative of a non-linear regression when a correlation coefficient is less than a correlation coefficient cutoff. In some embodiments a correlation coefficient cutoff is pre-determined. In some embodiments a correlation coefficient cut-off is about 0.5 or greater, about 0.55 or greater, about 0.6 or greater, about 0.65 or greater, about 0.7 or greater, about 0.75 or greater, about 0.8 or greater or about 0.85 or greater.

For example, in certain embodiments, a normalization method comprising a linear regression is used when a correlation coefficient is equal to or greater than about 0.6. In certain embodiments, counts of a sample (e.g., counts per portion of a reference genome, counts per portion) are normalized according to a linear regression when a correlation coefficient is equal to or greater than a correlation coefficient cut-off of 0.6, otherwise the counts are normalized according to a non-linear regression (e.g., when the coefficient is less than a correlation coefficient cut-off of 0.6). In some embodiments a normalization process comprises generating a linear regression or non-linear regression for the (i) the counts and (ii) the GC content, for each portion of multiple portions of a reference genome. In certain embodiments, a normalization method comprising a non-linear regression (e.g., a LOWESS, a LOESS) is used when a correlation coefficient is less than a correlation coefficient cut-off of 0.6. In some embodiments a normalization method comprising a non-linear regression (e.g., a LOWESS) is used when a correlation coefficient (e.g., a correlation coefficient) is less than a correlation coefficient cut-off of about 0.7, less than about 0.65, less than about 0.6, less than about 0.55 or less than about 0.5. For example, in some embodiments a normalization method comprising a non-linear regression (e.g., a LOWESS, a LOESS) is used when a correlation coefficient is less than a correlation coefficient cut-off of about 0.6.

In some embodiments a specific type of regression is selected (e.g., a linear or non-linear regression) and, after the regression is generated, counts are normalized by subtracting the regression from the counts. In some embodiments subtracting a regression from the counts provides normalized counts with reduced bias (e.g., GC bias). In some embodiments a linear regression is subtracted from the counts. In some embodiments a non-linear regression (e.g., a LOESS, GC-LOESS, LOWESS regression) is subtracted from the counts. Any suitable method can be used to subtract a regression line from the counts. For example, if counts x are derived from portion i (e.g., a portion i) comprising a GC content of 0.5 and a regression line determines counts y at a GC content of 0.5, then x-y=normalized counts for portion i. In some embodiments counts are normalized prior to and/or after subtracting a regression. In some embodiments, counts normalized by a hybrid normalization approach are used to generate genomic section levels, Z-cores, levels and/or profiles of a genome or a segment thereof. In certain embodiments, counts normalized by a hybrid normalization approach are analyzed by methods described herein to determine the presence or absence of a genetic variation (e.g., in a fetus).

In some embodiments a hybrid normalization method comprises filtering or weighting one or more portions before or after normalization. A suitable method of filtering portions, including methods of filtering portions (e.g., portions of a reference genome) described herein can be used. In some embodiments, portions (e.g., portions of a reference genome) are filtered prior to applying a hybrid normalization method. In some embodiments, only counts of sequencing reads mapped to selected portions (e.g., portions selected according to count variability) are normalized by a hybrid normalization. In some embodiments counts of sequencing reads mapped to filtered portions of a reference genome (e.g., portions filtered according to count variability) are removed prior to utilizing a hybrid normalization method. In some embodiments a hybrid normalization method comprises selecting or filtering portions (e.g., portions of a reference genome) according to a suitable method (e.g., a method described herein). In some embodiments a hybrid normalization method comprises selecting or filtering portions (e.g., portions of a reference genome) according to an uncertainty value for counts mapped to each of the portions for multiple test samples. In some embodiments a hybrid normalization method comprises selecting or filtering portions (e.g., portions of a reference genome) according to count variability. In some embodiments a hybrid normalization method comprises selecting or filtering portions (e.g., portions of a reference genome) according to GC content, repetitive elements, repetitive sequences, introns, exons, the like or a combination thereof.

For example, in some embodiments multiple samples from multiple pregnant female subjects are analyzed and a subset of portions (e.g., portions of a reference genome) is selected according to count variability. In certain embodiments a linear regression is used to determine a correlation coefficient for (i) counts and (ii) GC content, for each of the selected portions for a sample obtained from a pregnant female subject. In some embodiments a correlation coefficient is determined that is greater than a pre-determined correlation cutoff value (e.g., of about 0.6), an assessment of the goodness of fit is indicative of a linear regression and the counts are normalized by subtracting the linear regression from the counts. In certain embodiments a correlation coefficient is determined that is less than a pre-determined correlation cutoff value (e.g., of about 0.6), an assessment of the goodness of fit is indicative of a non-linear regression, an LOESS regression is generated and the counts are normalized by subtracting the LOESS regression from the counts.

Profiles

In some embodiments, a processing step can comprise generating one or more profiles (e.g., profile plot) from various aspects of a data set or derivation thereof (e.g., product of one or more mathematical and/or statistical data processing steps known in the art and/or described herein). The term "profile" as used herein refers to a product of a mathematical and/or statistical manipulation of data that can facilitate identification of patterns and/or correlations in large quantities of data. A "profile" often includes values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a part or subset of a data set. That is, a profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a portion. In certain embodiments, a data point in a profile includes results of data manipulation for groups of portions. In some embodiments, groups of portions may be adjacent to one another, and in certain embodiments, groups of portions may be from different parts of a chromosome or genome.

Data points in a profile derived from a data set can be representative of any suitable data categorization. Non-limiting examples of categories into which data can be grouped to generate profile data points include: portions based on size, portions based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile (e.g., a genomic profile, a chromosome profile, a profile of a segment of a chromosome) often is a collection of normalized or non-normalized counts for two or more portions. A profile often includes at least one level (e.g., a genomic section level), and often comprises two or more levels (e.g., a profile often has multiple levels). A level generally is for a set of portions having about the same counts or normalized counts. Levels are described in greater detail herein. In certain embodiments, a profile comprises one or more portions, which portions can be weighted, removed, filtered, normalized, adjusted, averaged, derived as a mean, added, subtracted, processed or transformed by any combination thereof. A profile often comprises normalized counts mapped to portions defining two or more levels, where the counts are further normalized according to one of the levels by a suitable method. Often counts of a profile (e.g., a profile level) are associated with an uncertainty value.

A profile comprising one or more levels is sometimes padded (e.g., hole padding). Padding (e.g., hole padding) refers to a process of identifying and adjusting levels in a profile that are due to maternal microdeletions or maternal duplications (e.g., copy number variations). In some embodiments levels are padded that are due to fetal microduplications or fetal microdeletions. Microduplications or microdeletions in a profile can, in some embodiments, artificially raise or lower the overall level of a profile (e.g., a profile of a chromosome) leading to false positive or false negative determinations of a chromosome aneuploidy (e.g., a trisomy). In some embodiments levels in a profile that are due to microduplications and/or deletions are identified and adjusted (e.g., padded and/or removed) by a process sometimes referred to as padding or hole padding. In certain embodiments a profile comprises one or more first levels that are significantly different than a second level within the profile, each of the one or more first levels comprise a maternal copy number variation, fetal copy number variation, or a maternal copy number variation and a fetal copy number variation and one or more of the first levels are adjusted.

A profile comprising one or more levels can include a first level and a second level. In some embodiments a first level is different (e.g., significantly different) than a second level. In some embodiments a first level comprises a first set of portions, a second level comprises a second set of portions and the first set of portions is not a subset of the second set of portions. In certain embodiments, a first set of portions is different than a second set of portions from which a first and second level are determined. In some embodiments a profile can have multiple first levels that are different (e.g., significantly different, e.g., have a significantly different value) than a second level within the profile. In some embodiments a profile comprises one or more first levels that are significantly different than a second level within the profile and one or more of the first levels are adjusted. In some embodiments a profile comprises one or more first levels that are significantly different than a second level within the profile, each of the one or more first levels comprise a maternal copy number variation, fetal copy number variation, or a maternal copy number variation and a fetal copy number variation and one or more of the first levels are adjusted. In some embodiments a first level within a profile is removed from the profile or adjusted (e.g., padded). A profile can comprise multiple levels that include one or more first levels significantly different than one or more second levels and often the majority of levels in a profile are second levels, which second levels are about equal to one another. In some embodiments greater than 50%, greater than 60%, greater than 70%, greater than 80%, greater than 90% or greater than 95% of the levels in a profile are second levels.

A profile sometimes is displayed as a plot. For example, one or more levels representing counts (e.g., normalized counts) of portions can be plotted and visualized. Non-limiting examples of profile plots that can be generated include raw count (e.g., raw count profile or raw profile), normalized count, portion-weighted, z-score, p-value, area ratio versus fitted ploidy, median level versus ratio between fitted and measured fetal fraction, principle components, the like, or combinations thereof. Profile plots allow visualization of the manipulated data, in some embodiments. In certain embodiments, a profile plot can be utilized to provide an outcome (e.g., area ratio versus fitted ploidy, median level versus ratio between fitted and measured fetal fraction, principle components). The terms "raw count profile plot" or "raw profile plot" as used herein refer to a plot of counts in each portion in a region normalized to total counts in a region (e.g., genome, portion, chromosome, chromosome portions of a reference genome or a segment of a chromosome). In some embodiments, a profile can be generated using a static window process, and in certain embodiments, a profile can be generated using a sliding window process.

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions (e.g., maternal contribution of nucleic acid (e.g., maternal fraction), fetal contribution of nucleic acid (e.g., fetal fraction), ploidy of reference sample, the like or combinations thereof). In certain embodiments, a test profile often centers around a predetermined value representative of the absence of a genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for a selected portion is expected to vary significantly from the predetermined value for non-affected genomic locations. Depending on starting assumptions (e.g., fixed ploidy or optimized ploidy, fixed fetal fraction or optimized fetal fraction or combinations thereof) the predetermined threshold or cutoff value or threshold range of values indicative of the presence or absence of a genetic variation can vary while still providing an outcome useful for determining the presence or absence of a genetic variation. In some embodiments, a profile is indicative of and/or representative of a phenotype.

By way of a non-limiting example, normalized sample and/or reference count profiles can be obtained from raw sequence read data by (a) calculating reference median counts for selected chromosomes, portions or segments thereof from a set of references known not to carry a genetic variation, (b) removal of uninformative portions from the reference sample raw counts (e.g., filtering); (c) normalizing the reference counts for all remaining portions of a reference genome to the total residual number of counts (e.g., sum of remaining counts after removal of uninformative portions of a reference genome) for the reference sample selected chromosome or selected genomic location, thereby generating a normalized reference subject profile; (d) removing the corresponding portions from the test subject sample; and (e) normalizing the remaining test subject counts for one or more selected genomic locations to the sum of the residual reference median counts for the chromosome or chromosomes containing the selected genomic locations, thereby generating a normalized test subject profile. In certain embodiments, an additional normalizing step with respect to the entire genome, reduced by the filtered portions in (b), can be included between (c) and (d).

A data set profile can be generated by one or more manipulations of counted mapped sequence read data. Some embodiments include the following. Sequence reads are mapped and the number of sequence tags mapping to each genomic portion are determined (e.g., counted). A raw count profile is generated from the mapped sequence reads that are counted. An outcome is provided by comparing a raw count profile from a test subject to a reference median count profile for chromosomes, portions or segments thereof from a set of reference subjects known not to possess a genetic variation, in certain embodiments.

In some embodiments, sequence read data is optionally filtered to remove noisy data or uninformative portions. After filtering, the remaining counts typically are summed to generate a filtered data set. A filtered count profile is generated from a filtered data set, in certain embodiments.

After sequence read data have been counted and optionally filtered, data sets can be normalized to generate levels or profiles. A data set can be normalized by normalizing one or more selected portions to a suitable normalizing reference value. In some embodiments, a normalizing reference value is representative of the total counts for the chromosome or chromosomes from which portions are selected. In certain embodiments, a normalizing reference value is representative of one or more corresponding portions, portions of chromosomes or chromosomes from a reference data set prepared from a set of reference subjects known not to possess a genetic variation. In some embodiments, a normalizing reference value is representative of one or more corresponding portions, portions of chromosomes or chromosomes from a test subject data set prepared from a test subject being analyzed for the presence or absence of a genetic variation. In certain embodiments, the normalizing process is performed utilizing a static window approach, and in some embodiments the normalizing process is performed utilizing a moving or sliding window approach. In certain embodiments, a profile comprising normalized counts is generated to facilitate classification and/or providing an outcome. An outcome can be provided based on a plot of a profile comprising normalized counts (e.g., using a plot of such a profile).

Levels

In some embodiments, a value (e.g., a number, a quantitative value) is ascribed to a level. A level can be determined by a suitable method, operation or mathematical process (e.g., a processed level). A level often is, or is derived from, counts (e.g., normalized counts) for a set of portions. In some embodiments a level of a portion is substantially equal to the total number of counts mapped to a portion (e.g., counts, normalized counts). Often a level is determined from counts that are processed, transformed or manipulated by a suitable method, operation or mathematical process known in the art. In some embodiments a level is derived from counts that are processed and non-limiting examples of processed counts include weighted, removed, filtered, normalized, adjusted, averaged, derived as a mean (e.g., mean level), added, subtracted, transformed counts or combination thereof. In some embodiments a level comprises counts that are normalized (e.g., normalized counts of portions). A level can be for counts normalized by a suitable process, non-limiting examples of which include portion-wise normalization, normalization by GC content, median count normalization, linear and nonlinear least squares regression, LOESS (e.g., GC LOESS), LOWESS, PERUN, ChAI, principal component normalization, RM, GCRM, cQn, the like and/or combinations thereof. A level can comprise normalized counts or relative amounts of counts. In some embodiments a level is for counts or normalized counts of two or more portions that are averaged and the level is referred to as an average level. In some embodiments a level is for a set of portions having a mean count or mean of normalized counts which is referred to as a mean level. In some embodiments a level is derived for portions that comprise raw and/or filtered counts. In some embodiments, a level is based on counts that are raw. In some embodiments a level is associated with an uncertainty value (e.g., a standard deviation, a MAD). In some embodiments a level is represented by a Z-score or p-value. A level for one or more portions is synonymous with a "genomic section level" herein.

A level for one or more portions is synonymous with a "genomic section level" herein. The term "level" as used herein is sometimes synonymous with the term "elevation". A determination of the meaning of the term "level" can be determined from the context in which it is used. For example, the term "level", when used in the context of genomic sections, profiles, reads and/or counts often means an elevation. The term "level", when used in the context of a substance or composition (e.g., level of RNA, plexing level) often refers to an amount. The term "level", when used in the context of uncertainty (e.g., level of error, level of confidence, level of deviation, level of uncertainty) often refers to an amount.

Normalized or non-normalized counts for two or more levels (e.g., two or more levels in a profile) can sometimes be mathematically manipulated (e.g., added, multiplied, averaged, normalized, the like or combination thereof) according to levels. For example, normalized or non-normalized counts for two or more levels can be normalized according to one, some or all of the levels in a profile. In some embodiments normalized or non-normalized counts of all levels in a profile are normalized according to one level in the profile. In some embodiments normalized or non-normalized counts of a first level in a profile are normalized according to normalized or non-normalized counts of a second level in the profile.

Non-limiting examples of a level (e.g., a first level, a second level) are a level for a set of portions comprising processed counts, a level for a set of portions comprising a mean, median or average of counts, a level for a set of portions comprising normalized counts, the like or any combination thereof. In some embodiments, a first level and a second level in a profile are derived from counts of portions mapped to the same chromosome. In some embodiments, a first level and a second level in a profile are derived from counts of portions mapped to different chromosomes.

In some embodiments a level is determined from normalized or non-normalized counts mapped to one or more portions. In some embodiments, a level is determined from normalized or non-normalized counts mapped to two or more portions, where the normalized counts for each portion often are about the same. There can be variation in counts (e.g., normalized counts) in a set of portions for a level. In a set of portions for a level there can be one or more portions having counts that are significantly different than in other portions of the set (e.g., peaks and/or dips). Any suitable number of normalized or non-normalized counts associated with any suitable number of portions can define a level.

In some embodiments one or more levels can be determined from normalized or non-normalized counts of all or some of the portions of a genome. Often a level can be determined from all or some of the normalized or non-normalized counts of a chromosome, or segment thereof. In some embodiments, two or more counts derived from two or more portions (e.g., a set of portions) determine a level. In some embodiments two or more counts (e.g., counts from two or more portions) determine a level. In some embodiments, counts from 2 to about 100,000 portions determine a level. In some embodiments, counts from 2 to about 50,000, 2 to about 40,000, 2 to about 30,000, 2 to about 20,000, 2 to about 10,000, 2 to about 5000, 2 to about 2500, 2 to about 1250, 2 to about 1000, 2 to about 500, 2 to about 250, 2 to about 100 or 2 to about 60 portions determine a level. In some embodiments counts from about 10 to about 50 portions determine a level. In some embodiments counts from about 20 to about 40 or more portions determine a level. In some embodiments, a level comprises counts from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60 or more portions. In some embodiments, a level corresponds to a set of portions (e.g., a set of portions of a reference genome, a set of portions of a chromosome or a set of portions of a segment of a chromosome).

In some embodiments, a level is determined for normalized or non-normalized counts of portions that are contiguous. In some embodiments portions (e.g., a set of portions) that are contiguous represent neighboring segments of a genome or neighboring segments of a chromosome or gene. For example, two or more contiguous portions, when aligned by merging the portions end to end, can represent a sequence assembly of a DNA sequence longer than each portion. For example two or more contiguous portions can represent of an intact genome, chromosome, gene, intron, exon or segment thereof. In some embodiments a level is determined from a collection (e.g., a set) of contiguous portions and/or non-contiguous portions.

Outcome

Methods described herein can provide a determination of the presence or absence of a genetic variation (e.g., fetal aneuploidy) for a sample, thereby providing an outcome (e.g., thereby providing an outcome determinative of the presence or absence of a genetic variation (e.g., fetal aneuploidy)). A genetic variation often includes a gain, a loss and/or alteration (e.g., duplication, deletion, fusion, insertion, mutation, reorganization, substitution or aberrant methylation) of genetic information (e.g., chromosomes, segments of chromosomes, polymorphic regions, translocated regions, altered nucleotide sequence, the like or combinations of the foregoing) that results in a detectable change in the genome or genetic information of a test subject with respect to a reference. Presence or absence of a genetic variation can be determined by transforming, analyzing and/or manipulating sequence reads that have been mapped to portions (e.g., counts, counts of genomic portions of a reference genome). Determining an outcome, in some embodiments, comprises analyzing nucleic acid from a pregnant female. In certain embodiments, an outcome is determined according to counts (e.g., normalized counts, read densities, read density profiles) obtained from a pregnant female where the counts are from nucleic acid obtained from the pregnant female.

Methods described herein sometimes determine presence or absence of a fetal aneuploidy (e.g., full chromosome aneuploidy, partial chromosome aneuploidy or segmental chromosomal aberration (e.g., mosaicism, deletion and/or insertion)) for a test sample from a pregnant female bearing a fetus. In certain embodiments methods described herein detect euploidy or lack of euploidy (non-euploidy) for a sample from a pregnant female bearing a fetus. Methods described herein sometimes detect trisomy for one or more chromosomes (e.g., chromosome 13, chromosome 18, chromosome 21 or combination thereof) or segment thereof.

In some embodiments, presence or absence of a genetic variation (e.g., a fetal aneuploidy) is determined by a method described herein, by a method known in the art or by a combination thereof. Presence or absence of a genetic variation generally is determined from counts of sequence reads mapped to portions of a reference genome.

Read densities from a reference sometimes are for a nucleic acid sample from the same pregnant female from which a test sample is obtained. In certain embodiments read densities from a reference are for a nucleic acid sample from one or more pregnant females different than the female from which a test sample was obtained. In some embodiments, read densities and/or read density profiles from a first set of portions form a test subject are compared to read densities and/or read density profiles from a second set of portions, where the second set of portions is different than the first set of portions. In some embodiments read densities and/or read density profiles from a first set of portions form a test subject are compared to read densities and/or read density profiles from a second set of portions, where the second set of portion is from the test subject or from a reference subject that is not the test subject. In a non-limiting example, where a first set of portions is in chromosome 21 or segment thereof, a second set of portions often is in another chromosome (e.g., chromosome 1, chromosome 13, chromosome 14, chromosome 18, chromosome 19, segment thereof or combination of the foregoing). A reference often is located in a chromosome or segment thereof that is typically euploid. For example, chromosome 1 and chromosome 19 often are euploid in fetuses owing to a high rate of early fetal mortality associated with chromosome 1 and chromosome 19 aneuploidies. A measure of uncertainty between the read densities and/or read density profiles from a test subject and a reference can be generated and/or compared. Presence or absence of a genetic variation (e.g., fetal aneuploidy) sometimes is determined without comparing read densities and/or read density profiles from a test subject to a reference.

In certain embodiments a reference comprises read densities and/or a read profile for the same set of portions as for a test subject, where the read densities for the reference are from one or more reference samples (e.g., often multiple reference samples from multiple reference subjects). A reference sample often is from one or more pregnant females different than a female from which a test sample is obtained.

A measure of uncertainty for read densities and/or read profiles of a test subject and/or reference can be generated. In some embodiments a measure of uncertainty is determined for read densities and/or read profiles of a test subject. In some embodiments a measure of uncertainty is determined for read densities and/or read profiles of a reference subject. In some embodiments a measure of uncertainty is determined from an entire read density profile or a subset of portions within a read density profile.

In some embodiments, reference samples are euploid for a selected segment of a genome, and a measure of uncertainty between a test profile and a reference profile is assessed for the selected segment. In some embodiments a determination of the presence or absence of a genetic variation is according to the number of deviations (e.g., measures of deviations, MAD) between a test profile and a reference profile for a selected segment of a genome (e.g., a chromosome, or segment thereof). In some embodiments the presence of a genetic variation is determined when the number of deviations between a test profile and a reference profile is greater than about 1, greater than about 1.5, greater than about 2, greater than about 2.5, greater than about 2.6, greater than about 2.7, greater than about 2.8, greater than about 2.9, greater than about 3, greater than about 3.1, greater than about 3.2, greater than about 3.3, greater than about 3.4, greater than about 3.5, greater than about 4, greater than about 5, or greater than about 6. For example, sometimes a test profile and a reference profile differ by more than 3 measures of deviation (e.g., 3 sigma, 3 MAD) and the presence of a genetic variation is determined. In some embodiments a test profile obtained from a pregnant female is larger than a reference profile by more than 3 measures of deviation (e.g., 3 sigma, 3 MAD) and the presence of a fetal chromosome aneuploidy (e.g., a fetal trisomy) is determined. A deviation of greater than three between a test profile and a reference profile often is indicative of a non-euploid test subject (e.g., presence of a genetic variation) for a selected segment of a genome. A test profile significantly greater than a reference profile for a selected segment of a genome, which reference is euploid for the selected segment, sometimes is determinative of a trisomy. In some embodiments a read density profile obtained from a pregnant female is less than a reference profile for a selected segment, by more than 3 measures of deviation (e.g., 3 sigma, 3 MAD) and the presence of a fetal chromosome aneuploidy (e.g., a fetal monosomy) is determined. Test profiles significantly below a reference profile, which reference profile is indicative of euploidy, sometimes are determinative of a monosomy.

In some embodiments the absence of a genetic variation is determined when the number of deviations between a test profile and reference profile for a selected segment of a genome is less than about 3.5, less than about 3.4, less than about 3.3, less than about 3.2, less than about 3.1, less than about 3.0, less than about 2.9, less than about 2.8, less than about 2.7, less than about 2.6, less than about 2.5, less than about 2.0, less than about 1.5, or less than about 1.0. For example, sometimes a test profile differs from a reference profile by less than 3 measures of deviation (e.g., 3 sigma, 3 MAD) and the absence of a genetic variation is determined. In some embodiments a test profile obtained from a pregnant female differs from a reference profile by less than 3 measures of deviation (e.g., 3 sigma, 3 MAD) and the absence of a fetal chromosome aneuploidy (e.g., a fetal euploid) is determined. In some embodiments (e.g., deviation of less than three between test profiles and reference profiles (e.g., 3-sigma for standard deviation) often is indicative of a segment of a genome that is euploid (e.g., absence of a genetic variation). A measure of deviation between test profiles for a test sample and reference profiles for one or more reference subjects can be plotted and visualized (e.g., z-score plot).

Any other suitable reference can be factored with test profiles for determining presence or absence of a genetic variation (or determination of euploid or non-euploid) for a test region (e.g., a segment of a genome that is tested) of a test sample. In some embodiments a fetal fraction determination can be factored with counts of sequence reads (e.g., read densities) to determine the presence or absence of a genetic variation. For example, read densities and/or read density profiles can be normalized according to fetal fraction prior to a comparison and/or determining an outcome. A suitable process for quantifying fetal fraction can be utilized, non-limiting examples of which include a mass spectrometric process, sequencing process or combination thereof.

In some embodiments a determination of the presence or absence of a genetic variation (e.g., a fetal aneuploidy) is determined according to a call zone. In certain embodiments a call is made (e.g., a call determining the presence or absence of a genetic variation, e.g., an outcome) when a value (e.g., a read density profile and/or a measure of uncertainty) or collection of values falls within a pre-defined range (e.g., a zone, a call zone). In some embodiments a call zone is defined according to a collection of values (e.g., read density profiles and/or measures of uncertainty) that are obtained from the same patient sample. In certain embodiments a call zone is defined according to a collection of values that are derived from the same chromosome or segment thereof. In some embodiments a call zone based on a genetic variation determination is defined according a measure of uncertainty (e.g., high level of confidence, e.g., low measure of uncertainty) and/or a fetal fraction.

In some embodiments a call zone is defined according to a determination of a genetic variation and a fetal fraction of about 2.0% or greater, about 2.5% or greater, about 3% or greater, about 3.25% or greater, about 3.5% or greater, about 3.75% or greater, or about 4.0% or greater. For example, in some embodiments a call is made that a fetus comprises a trisomy 21 based on a comparison of a test profile and a reference profile where a test sample, from which the test profile was derived, comprises a fetal fraction determination of 2% or greater or 4% or greater for a test sample obtained from a pregnant female bearing a fetus. For example, in some embodiments a call is made that a fetus is euploid based on a comparison of a test profile and a reference profile where a test sample, from which the test profile was derived, comprises a fetal fraction determination of 2% or greater or 4% or greater for a test sample obtained from a pregnant female bearing a fetus. In some embodiments a call zone is defined by a confidence level of about 99% or greater, about 99.1% or greater, about 99.2% or greater, about 99.3% or greater, about 99.4% or greater, about 99.5% or greater, about 99.6% or greater, about 99.7% or greater, about 99.8% or greater or about 99.9% or greater. In some embodiments a call is made without using a call zone. In some embodiments a call is made using a call zone and additional data or information. In some embodiments a call is made based on a comparison without the use of a call zone. In some embodiments a call is made based on visual inspection of a profile (e.g., visual inspection of read densities).

In some embodiments a no-call zone is where a call is not made. In some embodiments a no-call zone is defined by a value or collection of values that indicate low accuracy, high risk, high error, low level of confidence, high measure of uncertainty, the like or a combination thereof. In some embodiments a no-call zone is defined, in part, by a fetal fraction of about 5% or less, about 4% or less, about 3% or less, about 2.5% or less, about 2.0% or less, about 1.5% or less or about 1.0% or less.

A genetic variation sometimes is associated with medical condition. An outcome determinative of a genetic variation is sometimes an outcome determinative of the presence or absence of a condition (e.g., a medical condition), disease, syndrome or abnormality, or includes, detection of a condition, disease, syndrome or abnormality (e.g., non-limiting examples listed in Table 1). In certain embodiments a diagnosis comprises assessment of an outcome. An outcome determinative of the presence or absence of a condition (e.g., a medical condition), disease, syndrome or abnormality by methods described herein can sometimes be independently verified by further testing (e.g., by karyotyping and/or amniocentesis). Analysis and processing of data can provide one or more outcomes. The term "outcome" as used herein can refer to a result of data processing that facilitates determining the presence or absence of a genetic variation (e.g., an aneuploidy, a copy number variation). In certain embodiments the term "outcome" as used herein refers to a conclusion that predicts and/or determines the presence or absence of a genetic variation (e.g., an aneuploidy, a copy number variation). In certain embodiments the term "outcome" as used herein refers to a conclusion that predicts and/or determines a risk or probability of the presence or absence of a genetic variation (e.g., an aneuploidy, a copy number variation) in a subject (e.g., a fetus). A diagnosis sometimes comprises use of an outcome. For example, a health practitioner may analyze an outcome and provide a diagnosis bases on, or based in part on, the outcome. In some embodiments, determination, detection or diagnosis of a condition, syndrome or abnormality (e.g., listed in Table 1) comprises use of an outcome determinative of the presence or absence of a genetic variation. In some embodiments, an outcome based on counted mapped sequence reads or transformations thereof is determinative of the presence or absence of a genetic variation. In certain embodiments, an outcome generated utilizing one or more methods (e.g., data processing methods) described herein is determinative of the presence or absence of one or more conditions, syndromes or abnormalities listed in Table 1. In certain embodiments a diagnosis comprises a determination of a presence or absence of a condition, syndrome or abnormality. Often a diagnosis comprises a determination of a genetic variation as the nature and/or cause of a condition, syndrome or abnormality. In certain embodiments an outcome is not a diagnosis. An outcome often comprises one or more numerical values generated using a processing method described herein in the context of one or more considerations of probability. A consideration of risk or probability can include, but is not limited to: a measure of uncertainty, a confidence level, sensitivity, specificity, standard deviation, coefficient of variation (CV) and/or confidence level, Z-scores, Chi values, Phi values, ploidy values, fitted fetal fraction, area ratios, median level, the like or combinations thereof. A consideration of probability can facilitate determining whether a subject is at risk of having, or has, a genetic variation, and an outcome determinative of a presence or absence of a genetic disorder often includes such a consideration.

An outcome sometimes is a phenotype. An outcome sometimes is a phenotype with an associated level of confidence (e.g., a measure of uncertainty, e.g., a fetus is positive for trisomy 21 with a confidence level of 99%, a test subject is negative for a cancer associated with a genetic variation at a confidence level of 95%). Different methods of generating outcome values sometimes can produce different types of results. Generally, there are four types of possible scores or calls that can be made based on outcome values generated using methods described herein: true positive, false positive, true negative and false negative. The terms "score", "scores", "call" and "calls" as used herein refer to calculating the probability that a particular genetic variation is present or absent in a subject/sample. The value of a score may be used to determine, for example, a variation, difference, or ratio of mapped sequence reads that may correspond to a genetic variation. For example, calculating a positive score for a selected genetic variation or portion from a data set, with respect to a reference genome can lead to an identification of the presence or absence of a genetic variation, which genetic variation sometimes is associated with a medical condition (e.g., cancer, preeclampsia, trisomy, monosomy, and the like). In some embodiments, an outcome comprises a read density, a read density profile and/or a plot (e.g., a profile plot). In those embodiments in which an outcome comprises a profile, a suitable profile or combination of profiles can be used for an outcome. Non-limiting examples of profiles that can be used for an outcome include z-score profiles, p-value profiles, chi value profiles, phi value profiles, the like, and combinations thereof.

An outcome generated for determining the presence or absence of a genetic variation sometimes includes a null result (e.g., a data point between two clusters, a numerical value with a standard deviation that encompasses values for both the presence and absence of a genetic variation, a data set with a profile plot that is not similar to profile plots for subjects having or free from the genetic variation being investigated). In some embodiments, an outcome indicative of a null result still is a determinative result, and the determination can include the need for additional information and/or a repeat of the data generation and/or analysis for determining the presence or absence of a genetic variation.

An outcome can be generated after performing one or more processing steps described herein, in some embodiments. In certain embodiments, an outcome is generated as a result of one of the processing steps described herein, and in some embodiments, an outcome can be generated after each statistical and/or mathematical manipulation of a data set is performed. An outcome pertaining to the determination of the presence or absence of a genetic variation can be expressed in a suitable form, which form comprises without limitation, a probability (e.g., odds ratio, p-value), likelihood, value in or out of a cluster, value over or under a threshold value, value within a range (e.g., a threshold range), value with a measure of variance or confidence, or risk factor, associated with the presence or absence of a genetic variation for a subject or sample. In certain embodiments, comparison between samples allows confirmation of sample identity (e.g., allows identification of repeated samples and/or samples that have been mixed up (e.g., mislabeled, combined, and the like)).

In some embodiments, an outcome comprises a value above or below a predetermined threshold or cutoff value and/or a measure of uncertainty or a confidence level associated with the value. In certain embodiments a predetermined threshold or cutoff value is an expected level or an expected level range. An outcome also can describe an assumption used in data processing. In certain embodiments, an outcome comprises a value that falls within or outside a predetermined range of values (e.g., a threshold range) and the associated uncertainty or confidence level for that value being inside or outside the range. In some embodiments, an outcome comprises a value that is equal to a predetermined value (e.g., equal to 1, equal to zero), or is equal to a value within a predetermined value range, and its associated uncertainty or confidence level for that value being equal or within or outside a range. An outcome sometimes is graphically represented as a plot (e.g., profile plot).

As noted above, an outcome can be characterized as a true positive, true negative, false positive or false negative. The term "true positive" as used herein refers to a subject correctly diagnosed as having a genetic variation. The term "false positive" as used herein refers to a subject wrongly identified as having a genetic variation. The term "true negative" as used herein refers to a subject correctly identified as not having a genetic variation. The term "false negative" as used herein refers to a subject wrongly identified as not having a genetic variation. Two measures of performance for any given method can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome is not due to chance) in certain embodiments is expressed as a Z-score, a p-value, or the results of a t-test. In some embodiments, a measured variance, confidence interval, sensitivity, specificity and the like (e.g., referred to collectively as confidence parameters) for an outcome can be generated using one or more data processing manipulations described herein. Specific examples of generating outcomes and associated confidence levels are described in the Examples section and in international patent application no. PCT/US12/59123 (WO2013/052913) the entire content of which is incorporated herein by reference, including all text, tables, equations and drawings.

The term "sensitivity" as used herein refers to the number of true positives divided by the number of true positives plus the number of false negatives, where sensitivity (sens) may be within the range of $0 \leq sens \leq 1$. The term "specificity" as used herein refers to the number of true negatives divided by the number of true negatives plus the number of false positives, where sensitivity (spec) may be within the range of $0 \leq spec \leq 1$. In some embodiments a method that has sensitivity and specificity equal to one, or 100%, or near one (e.g., between about 90% to about 99%) sometimes is selected. In some embodiments, a method having a sensitivity equaling 1, or 100% is selected, and in certain embodiments, a method having a sensitivity near 1 is selected (e.g., a sensitivity of about 90%, a sensitivity of about 91%, a sensitivity of about 92%, a sensitivity of about 93%, a sensitivity of about 94%, a sensitivity of about 95%, a sensitivity of about 96%, a sensitivity of about 97%, a sensitivity of about 98%, or a sensitivity of about 99%). In some embodiments, a method having a specificity equaling 1, or 100% is selected, and in certain embodiments, a method having a specificity near 1 is selected (e.g., a specificity of about 90%, a specificity of about 91%, a specificity of about 92%, a specificity of about 93%, a specificity of about 94%, a specificity of about 95%, a specificity of about 96%, a specificity of about 97%, a specificity of about 98%, or a specificity of about 99%).

In some embodiments, presence or absence of a genetic variation (e.g., chromosome aneuploidy) is determined for a fetus. In such embodiments, presence or absence of a fetal genetic variation (e.g., fetal chromosome aneuploidy) is determined.

In certain embodiments, presence or absence of a genetic variation (e.g., chromosome aneuploidy) is determined for a sample. In such embodiments, presence or absence of a genetic variation in sample nucleic acid (e.g., chromosome aneuploidy) is determined. In some embodiments, a variation detected or not detected resides in sample nucleic acid from one source but not in sample nucleic acid from another source. Non-limiting examples of sources include placental nucleic acid, fetal nucleic acid, maternal nucleic acid, cancer cell nucleic acid, non-cancer cell nucleic acid, the like and combinations thereof. In non-limiting examples, a particular genetic variation detected or not detected (i) resides in placental nucleic acid but not in fetal nucleic acid and not in maternal nucleic acid; (ii) resides in fetal nucleic acid but not maternal nucleic acid; or (iii) resides in maternal nucleic acid but not fetal nucleic acid.

The presence or absence of a genetic variation and/or associated medical condition (e.g., an outcome) is often provided by an outcome module. The presence or absence of a genetic variation (e.g., an aneuploidy, a fetal aneuploidy, a copy number variation) is, in some embodiments, identified by an outcome module or by a machine comprising an outcome module. An outcome module can be specialized for determining a specific genetic variation (e.g., a trisomy, a trisomy 21, a trisomy 18). For example, an outcome module that identifies a trisomy 21 can be different than and/or distinct from an outcome module that identifies a trisomy 18. In some embodiments, an outcome module or a machine comprising an outcome module is required to identify a genetic variation or an outcome determinative of a genetic variation (e.g., an aneuploidy, a copy number variation). In certain embodiments an outcome is transferred from an outcome module to a display module where an outcome is provided by the display module.

A genetic variation or an outcome determinative of a genetic variation identified by methods described herein can be independently verified by further testing (e.g., by targeted sequencing of maternal and/or fetal nucleic acid). An outcome typically is provided to a health care professional (e.g., laboratory technician or manager; physician or assistant). In certain embodiments an outcome is provided on a suitable visual medium (e.g., a peripheral or component of a machine, e.g., a printer or display). In some embodiments, an outcome determinative of the presence or absence of a genetic variation is provided to a healthcare professional in the form of a report, and in certain embodiments the report comprises a display of an outcome value and an associated confidence parameter. Generally, an outcome can be displayed in a suitable format that facilitates determination of the presence or absence of a genetic variation and/or medical condition. Non-limiting examples of formats suitable for use for reporting and/or displaying data sets or reporting an outcome include digital data, a graph, a 2D graph, a 3D graph, and 4D graph, a picture (e.g., a jpg, bitmap (e.g., bmp), pdf, tiff, gif, raw, png, the like or suitable format), a pictograph, a chart, a table, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing. Various examples of outcome representations are shown in the drawings and are described in the Examples.

Generating an outcome can be viewed as a transformation of nucleic acid sequence read data, or the like, into a representation of a subject's cellular nucleic acid, in certain embodiments. For example, analyzing sequence reads of nucleic acid from a subject and generating a chromosome profile and/or outcome can be viewed as a transformation of relatively small sequence read fragments to a representation of relatively large chromosome structure. In some embodiments, an outcome results from a transformation of sequence reads from a subject (e.g., a pregnant female), into a representation of an existing structure (e.g., a genome, a chromosome or segment thereof) present in the subject (e.g., a maternal and/or fetal nucleic acid). In some embodiments, an outcome comprises a transformation of sequence reads from a first subject (e.g., a pregnant female), into a composite representation of structures (e.g., a genome, a chromosome or segment thereof), and a second transformation of the composite representation that yields a representation of a structure present in a first subject (e.g., a pregnant female) and/or a second subject (e.g., a fetus).

Outcome Pertaining to Sex Chromosomes

In some embodiments, an outcome pertains to a genetic variation of a sex chromosome. Genetic variations of sex chromosomes are described, for example, in International Patent Application Publication No. WO 2013/192562, the entire content of which is incorporated herein by reference, including all text, tables, equations and drawings. In some embodiments, an outcome is a determination of sex chromosome karyotype, detection of a sex chromosome aneuploidy and/or determination of fetal gender. Some sex chromosome aneuploidy (SCA) conditions include, but are not limited to, Turner syndrome [45,X], Trisomy X [47,XXX], Klinefelter syndrome [47,XXY], and [47,XYY] syndrome (sometimes referred to as Jacobs syndrome).

Assessments of sex chromosome variations, in some embodiments, are based on a segregation of sequence read count transformations for chromosome X and chromosome Y. Sequence read count transformations may include, for example, chromosome X representations and chromosome Y representations and/or Z-scores based on such representations. A two dimensional plot of nucleotide sequence read count transformations (e.g., Z scores based on PERUN normalized read counts or principal component normalized read counts) for chromosome X versus chromosome Y for a group of samples having various karyotypes (e.g., XX, XY, XXX, X, XXY, XYY) generates a planar field of plot points that can be carved into regions, each specific for a particular karyotype. Determination of a sex chromosome karyotype, for example, for a given sample may be achieved by determining in which region of the planar field the plot point for that sample falls.

Certain methods described herein can be useful for generating plots having well-defined regions (e.g., with sharp boundaries, high resolution) for particular karyotype variations. Methods that can help generate high resolution plots include sequence read count normalization, selection of informative portions (i.e., bins) for chromosome X and chromosome Y, establishment of non-reportable (i.e., "no call" zones), and additional normalization of chromosome X and chromosome Y levels. Normalization of sequence reads and further normalization of levels is described herein and may include PERUN normalization and/or principal component normalization, for example, of sequence reads mapped to chromosome X and/or chromosome Y and/or levels (e.g., chromosome representations) for chromosome X and/or Y. Selection of informative portions for chromosome X and chromosome Y is described, for example, in International Patent Application Publication No. WO 2013/192562, and may include, for example, evaluation of filtering parameters such as cross-validation parameters, mappability, repeatability and/or male versus female separation.

Use of Outcomes

A health care professional, or other qualified individual, receiving a report comprising one or more outcomes determinative of the presence or absence of a genetic variation can use the displayed data in the report to make a call regarding the status of the test subject or patient. The healthcare professional can make a recommendation based on the provided outcome, in some embodiments. A health care professional or qualified individual can provide a test subject or patient with a call or score with regards to the presence or absence of the genetic variation based on the outcome value or values and associated confidence parameters provided in a report, in some embodiments. In certain embodiments, a score or call is made manually by a healthcare professional or qualified individual, using visual observation of the provided report. In certain embodiments, a score or call is made by an automated routine, sometimes embedded in software, and reviewed by a healthcare professional or qualified individual for accuracy prior to providing information to a test subject or patient. The term "receiving a report" as used herein refers to obtaining, by a communication means, a written and/or graphical representation comprising an outcome, which upon review allows a healthcare professional or other qualified individual to make a determination as to the presence or absence of a genetic variation in a test subject or patient. The report may be generated by a computer or by human data entry, and can be communicated using electronic means (e.g., over the internet, via computer, via fax, from one network location to another location at the same or different physical sites), or by a other method of sending or receiving data (e.g., mail service, courier service and the like). In some embodiments the outcome is transmitted to a health care professional in a suitable medium, including, without limitation, in verbal, document, or file form. The file may be, for example, but not limited to, an auditory file, a computer readable file, a paper file, a laboratory file or a medical record file.

The term "providing an outcome" and grammatical equivalents thereof, as used herein also can refer to a method for obtaining such information, including, without limitation, obtaining the information from a laboratory (e.g., a laboratory file). A laboratory file can be generated by a laboratory that carried out one or more assays or one or more data processing steps to determine the presence or absence of the medical condition. The laboratory may be in the same location or different location (e.g., in another country) as the personnel identifying the presence or absence of the medical condition from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

In some embodiments, an outcome can be provided to a health care professional, physician or qualified individual from a laboratory and the health care professional, physician or qualified individual can make a diagnosis based on the outcome. In some embodiments, an outcome can be provided to a health care professional, physician or qualified individual from a laboratory and the health care professional, physician or qualified individual can make a diagnosis based, in part, on the outcome along with additional data and/or information and other outcomes.

A healthcare professional or qualified individual, can provide a suitable recommendation based on the outcome or outcomes provided in the report. Non-limiting examples of recommendations that can be provided based on the provided outcome report includes, surgery, radiation therapy, chemotherapy, genetic counseling, after birth treatment solutions (e.g., life planning, long term assisted care, medicaments, symptomatic treatments), pregnancy termination, organ transplant, blood transfusion, the like or combinations of the foregoing. In some embodiments the recommendation is dependent on the outcome based classification provided (e.g., Down's syndrome, Turner syndrome, medical conditions associated with genetic variations in T13, medical conditions associated with genetic variations in T18).

Laboratory personnel (e.g., a laboratory manager) can analyze values (e.g., test profiles, reference profiles, level of deviation) underlying a determination of the presence or absence of a genetic variation (or determination of euploid or non-euploid for a test region). For calls pertaining to presence or absence of a genetic variation that are close or questionable, laboratory personnel can re-order the same test, and/or order a different test (e.g., karyotyping and/or amniocentesis in the case of fetal aneuploidy determinations), that makes use of the same or different sample nucleic acid from a test subject.

Genetic Variations and Medical Conditions

The presence or absence of a genetic variance can be determined using a method, machine or apparatus described herein. In certain embodiments, the presence or absence of one or more genetic variations is determined according to an outcome provided by methods, machines and apparatuses described herein. A genetic variation generally is a particular genetic phenotype present in certain individuals, and often a genetic variation is present in a statistically significant sub-population of individuals. In some embodiments, a genetic variation is a chromosome abnormality (e.g., aneuploidy, duplication of one or more chromosomes, loss of one or more chromosomes), partial chromosome abnormality or mosaicism (e.g., loss or gain of one or more segments of a chromosome), translocations, inversions, each of which is described in greater detail herein. Non-limiting examples of genetic variations include one or more deletions (e.g., micro-deletions), duplications (e.g., micro-duplications), insertions, mutations, polymorphisms (e.g., single-nucleotide polymorphisms), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 50,000 kilobases (kb) in length (e.g., about 10 bp, 50 bp, 100 bp, 500 bp, 1 kb, 5 kb, 10 kb, 50 kb, 100 kb, 500 kb, 1000 kb, 5000 kb or 10,000 kb in length).

A genetic variation is sometime a deletion. In certain embodiments a deletion is a mutation (e.g., a genetic aberration) in which a part of a chromosome or a sequence of DNA is missing. A deletion is often the loss of genetic material. Any number of nucleotides can be deleted. A deletion can comprise the deletion of one or more entire chromosomes, a segment of a chromosome, an allele, a gene, an intron, an exon, any non-coding region, any coding region, a segment thereof or combination thereof. A deletion can comprise a microdeletion. A deletion can comprise the deletion of a single base.

A genetic variation is sometimes a genetic duplication. In certain embodiments a duplication is a mutation (e.g., a genetic aberration) in which a part of a chromosome or a sequence of DNA is copied and inserted back into the genome. In certain embodiments a genetic duplication (e.g., duplication) is any duplication of a region of DNA. In some embodiments a duplication is a nucleic acid sequence that is repeated, often in tandem, within a genome or chromosome. In some embodiments a duplication can comprise a copy of one or more entire chromosomes, a segment of a chromosome, an allele, a gene, an intron, an exon, any non-coding region, any coding region, segment thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation is sometimes an insertion. An insertion is sometimes the addition of one or more nucleotide base pairs into a nucleic acid sequence. An insertion is sometimes a microinsertion. In certain embodiments an insertion comprises the addition of a segment of a chromosome into a genome, chromosome, or segment thereof. In certain embodiments an insertion comprises the addition of an allele, a gene, an intron, an exon, any non-coding region, any coding region, segment thereof or combination thereof into a genome or segment thereof. In certain embodiments an insertion comprises the addition (e.g., insertion) of nucleic acid of unknown origin into a genome, chromosome, or segment thereof. In certain embodiments an insertion comprises the addition (e.g., insertion) of a single base.

As used herein a "copy number variation" generally is a class or type of genetic variation or chromosomal aberration. A copy number variation can be a deletion (e.g., microdeletion), duplication (e.g., a micro-duplication) or insertion (e.g., a micro-insertion). Often, the prefix "micro" as used herein sometimes is a segment of nucleic acid less than 5 Mb in length. A copy number variation can include one or more deletions (e.g., micro-deletion), duplications and/or insertions (e.g., a micro-duplication, micro-insertion) of a segment of a chromosome. In certain embodiments a duplication comprises an insertion. In certain embodiments an insertion is a duplication. In certain embodiments an insertion is not a duplication.

In some embodiments a copy number variation is a fetal copy number variation. Often, a fetal copy number variation is a copy number variation in the genome of a fetus. In some embodiments a copy number variation is a maternal and/or fetal copy number variation. In certain embodiments a maternal and/or fetal copy number variation is a copy number variation within the genome of a pregnant female (e.g., a female subject bearing a fetus), a female subject that gave birth or a female capable of bearing a fetus. A copy number variation can be a heterozygous copy number variation where the variation (e.g., a duplication or deletion) is present on one allele of a genome. A copy number variation can be a homozygous copy number variation where the variation is present on both alleles of a genome. In some embodiments a copy number variation is a heterozygous or homozygous fetal copy number variation. In some embodiments a copy number variation is a heterozygous or homozygous maternal and/or fetal copy number variation. A copy number variation sometimes is present in a maternal genome and a fetal genome, a maternal genome and not a fetal genome, or a fetal genome and not a maternal genome.

"Ploidy" is a reference to the number of chromosomes present in a fetus or mother. In certain embodiments "Ploidy" is the same as "chromosome ploidy". In humans, for example, autosomal chromosomes are often present in pairs. For example, in the absence of a genetic variation, most humans have two of each autosomal chromosome (e.g., chromosomes 1-22). The presence of the normal complement of 2 autosomal chromosomes in a human is often referred to as euploid or diploid. "Microploidy" is similar in meaning to ploidy. "Microploidy" often refers to the ploidy of a segment of a chromosome. The term "microploidy" sometimes is a reference to the presence or absence of a copy number variation (e.g., a deletion, duplication and/or an insertion) within a chromosome (e.g., a homozygous or heterozygous deletion, duplication, or insertion, the like or absence thereof).

In certain embodiments the microploidy of a fetus matches the microploidy of the mother of the fetus (e.g., the pregnant female subject). In certain embodiments the microploidy of a fetus matches the microploidy of the mother of the fetus and both the mother and fetus carry the same heterozygous copy number variation, homozygous copy number variation or both are euploid. In certain embodiments the microploidy of a fetus is different than the microploidy of the mother of the fetus. For example, sometimes the microploidy of a fetus is heterozygous for a copy number variation, the mother is homozygous for a copy number variation and the microploidy of the fetus does not match (e.g., does not equal) the microploidy of the mother for the specified copy number variation.

A genetic variation for which the presence or absence is identified for a subject is associated with a medical condition in certain embodiments. Thus, technology described herein can be used to identify the presence or absence of one or more genetic variations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations, medical conditions and states are described hereafter.

Fetal Gender

In some embodiments, the prediction of a fetal gender or gender related disorder (e.g., sex chromosome aneuploidy) can be determined by a method, machine and/or apparatus described herein. Gender determination generally is based on a sex chromosome. In humans, there are two sex chromosomes, the X and Y chromosomes. The Y chromosome contains a gene, SRY, which triggers embryonic development as a male. The Y chromosomes of humans and other mammals also contain other genes needed for normal sperm production. Individuals with XX are female and XY are male and non-limiting variations, often referred to as sex chromosome aneuploidies, include X0, XYY, XXX and XXY. In certain embodiments, males have two X chromosomes and one Y chromosome (XXY; Klinefelter's Syndrome), or one X chromosome and two Y chromosomes (XYY syndrome; Jacobs Syndrome), and some females have three X chromosomes (XXX; Triple X Syndrome) or a single X chromosome instead of two (X0; Turner Syndrome). In certain embodiments, only a portion of cells in an individual are affected by a sex chromosome aneuploidy which may be referred to as a mosaicism (e.g., Turner mosaicism). Other cases include those where SRY is damaged (leading to an XY female), or copied to the X (leading to an XX male).

In certain cases, it can be beneficial to determine the gender of a fetus in utero. For example, a patient (e.g., pregnant female) with a family history of one or more sex-linked disorders may wish to determine the gender of the fetus she is carrying to help assess the risk of the fetus inheriting such a disorder. Sex-linked disorders include, without limitation, X-linked and Y-linked disorders. X-linked disorders include X-linked recessive and X-linked dominant disorders. Examples of X-linked recessive disorders include, without limitation, immune disorders (e.g., chronic granulomatous disease (CYBB), Wiskott-Aldrich syndrome, X-linked severe combined immunodeficiency, X-linked agammaglobulinemia, hyper-IgM syndrome type 1, IPEX, X-linked lymphoproliferative disease, Properdin deficiency), hematologic disorders (e.g., Hemophilia A, Hemophilia B, X-linked sideroblastic anemia), endocrine disorders (e.g., androgen insensitivity syndrome/Kennedy disease, KAL1 Kallmann syndrome, X-linked adrenal hypoplasia congenital), metabolic disorders (e.g., ornithine transcarbamylase deficiency, oculocerebrorenal syndrome, adrenoleukodystrophy, glucose-6-phosphate dehydrogenase deficiency, pyruvate dehydrogenase deficiency, Danon disease/glycogen storage disease Type IIb, Fabry's disease, Hunter syndrome, Lesch-Nyhan syndrome, Menkes disease/occipital horn syndrome), nervous system disorders (e.g., Coffin-Lowry syndrome, MASA syndrome, X-linked alpha thalassemia mental retardation syndrome, Siderius X-linked mental retardation syndrome, color blindness, ocular albinism, Norrie disease, choroideremia, Charcot-Marie-Tooth disease (CMTX2-3), Pelizaeus-Merzbacher disease, SMAX2), skin and related tissue disorders (e.g., dyskeratosis congenital, hypohidrotic ectodermal dysplasia (EDA), X-linked ichthyosis, X-linked endothelial corneal dystrophy), neuromuscular disorders (e.g., Becker's muscular dystrophy/Duchenne, centronuclear myopathy (MTM1), Conradi-Hünermann syndrome, Emery-Dreifuss muscular dystrophy 1), urologic disorders (e.g., Alport syndrome, Dent's disease, X-linked nephrogenic diabetes insipidus), bone/tooth disorders (e.g., AMELX Amelogenesis imperfecta), and other disorders (e.g., Barth syndrome, McLeod syndrome, Smith-Fineman-Myers syndrome, Simpson-Golabi-Behmel syndrome, Mohr-Tranebjrg syndrome, Nasodigitoacoustic syndrome). Examples of X-linked dominant disorders include, without limitation, X-linked hypophosphatemia, Focal dermal hypoplasia, Fragile X syndrome, Aicardi syndrome, Incontinentia pigmenti, Rett syndrome, CHILD syndrome, Lujan-Fryns syndrome, and Orofaciodigital syndrome 1. Examples of Y-linked disorders include, without limitation, male infertility, retinitis pigmentosa, and azoospermia.

Chromosome Abnormalities

In some embodiments, the presence or absence of a fetal chromosome abnormality can be determined by using a method, machine and/or apparatus described herein. Chromosome abnormalities include, without limitation, a gain or loss of an entire chromosome or a region of a chromosome comprising one or more genes. Chromosome abnormalities include monosomies, trisomies, polysomies, loss of heterozygosity, translocations, deletions and/or duplications of one or more nucleotide sequences (e.g., one or more genes), including deletions and duplications caused by unbalanced translocations. The term "chromosomal abnormality" or "aneuploidy" as used herein refers to a deviation between the structure of the subject chromosome and a normal homologous chromosome. The term "normal" refers to the predominate karyotype or banding pattern found in healthy individuals of a particular species, for example, a euploid genome (e.g., diploid in humans, e.g., 46,XX or 46,XY). As different organisms have widely varying chromosome complements, the term "aneuploidy" does not refer to a particular number of chromosomes, but rather to the situation in which the chromosome content within a given cell or cells of an organism is abnormal. In some embodiments, the term "aneuploidy" herein refers to an imbalance of genetic material caused by a loss or gain of a whole chromosome, or part of a chromosome. An "aneuploidy" can refer to one or more deletions and/or insertions of a segment of a chromosome. The term "euploid", in some embodiments, refers a normal complement of chromosomes.

The term "monosomy" as used herein refers to lack of one chromosome of the normal complement. Partial monosomy can occur in unbalanced translocations or deletions, in which only a segment of the chromosome is present in a single copy. Monosomy of sex chromosomes (45, X) causes Turner syndrome, for example. The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47,XYY in Jacobs Syndrome). In some embodiments, a trisomy is a duplication of most or all of an autosome. In certain embodiments a trisomy is a whole chromosome aneuploidy resulting in three instances (e.g., three copies) of a particular type of chromosome (e.g., instead of two instances (e.g., a pair) of a particular type of chromosome for a euploid).

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing non-disjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

The terms "partial monosomy" and "partial trisomy" as used herein refer to an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the segment that exists on the derivative chromosome) and only one copy of part of the other chromosome involved in the derivative chromosome.

The term "mosaicism" as used herein refers to aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and protocols described herein can identify presence or absence of non-mosaic and mosaic chromosome abnormalities.

Tables 1A and 1B present a non-limiting list of chromosome conditions, syndromes and/or abnormalities that can be potentially identified by methods, machines and/or an apparatus described herein. Table 1B is from the DECIPHER database as of Oct. 6, 2011 (e.g., version 5.1, based on positions mapped to GRCh37; available at uniform resource locator (URL) dechipher.sanger.ac.uk).

TABLE 1A

| Chromosome | Abnormality | Disease Association |
|---|---|---|
| X | XO | Turner's Syndrome |
| Y | XXY | Klinefelter syndrome |
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymphoproliferative disease |
| 1 | 1p (somatic) monosomy trisomy | neuroblastoma |
| 2 | monosomy trisomy 2q | growth retardation, developmental and mental delay, and minor physical abnormalities |
| 3 | monosomy trisomy (somatic) | Non-Hodgkin's lymphoma |
| 4 | monosomy trisomy (somatic) | Acute non lymphocytic leukemia (ANLL) |
| 5 | 5p | Cri du chat; Lejeune syndrome |
| 5 | 5q (somatic) monosomy trisomy | myelodysplastic syndrome |
| 6 | monosomy trisomy (somatic) | clear-cell sarcoma |
| 7 | 7q11.23 deletion | William's syndrome |
| 7 | monosomy trisomy | monosomy 7 syndrome of childhood; somatic: renal cortical adenomas; myelodysplastic syndrome |
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |
| 9 | monosomy 9p partial trisomy | Rethore syndrome |
| 9 | trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobsen Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |
| 14 | monosomy trisomy (somatic) | myeloid disorders (MDS, ANLL, atypical CML) |
| 15 | 15q11-q13 deletion monosomy | Prader-Willi, Angelman's syndrome |
| 15 | trisomy (somatic) | myeloid and lymphoid lineages affected, e.g., MDS, ANLL, ALL, CLL) |
| 16 | trisomy | Full Trisomy 16 Mosaic Trisomy 16 |
| 16 | 16q13.3 deletion | Rubenstein-Taybi |
| 3 | monosomy trisomy (somatic) | papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |

TABLE 1A-continued

| Chromosome | Abnormality | Disease Association |
|---|---|---|
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |
| 18 | 18q- | Grouchy Lamy Salmon Landry Syndrome |
| 18 | monosomy trisomy | Edwards Syndrome |
| 19 | monosomy trisomy | |
| 20 | 20p- | trisomy 20p syndrome |
| 20 | 20p11.2-12 deletion | Alagille |
| 20 | 20q- | somatic: MDS, ANLL, polycythemia vera, chronic neutrophilic leukemia |
| 20 | monosomy trisomy (somatic) | papillary renal cell carcinomas (malignant) |
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

TABLE 1B

| Syndrome | Chromosome | Start | End | Interval (Mb) | Grade |
|---|---|---|---|---|---|
| 12q14 microdeletion syndrome | 12 | 65,071,919 | 68,645,525 | 3.57 | |
| 15q13.3 microdeletion syndrome | 15 | 30,769,995 | 32,701,482 | 1.93 | |
| 15q24 recurrent microdeletion syndrome | 15 | 74,377,174 | 76,162,277 | 1.79 | |
| 15q26 overgrowth syndrome | 15 | 99,357,970 | 102,521,392 | 3.16 | |
| 16p11.2 microduplication syndrome | 16 | 29,501,198 | 30,202,572 | 0.70 | |
| 16p11.2-p12.2 microdeletion syndrome | 16 | 21,613,956 | 29,042,192 | 7.43 | |
| 16p13.11 recurrent microdeletion (neurocognitive disorder susceptibility locus) | 16 | 15,504,454 | 16,284,248 | 0.78 | |
| 16p13.11 recurrent microduplication (neurocognitive disorder susceptibility locus) | 16 | 15,504,454 | 16,284,248 | 0.78 | |
| 17q21.3 recurrent microdeletion syndrome | 17 | 43,632,466 | 44,210,205 | 0.58 | 1 |
| 1p36 microdeletion syndrome | 1 | 10,001 | 5,408,761 | 5.40 | 1 |
| 1q21.1 recurrent microdeletion (susceptibility locus for neurodevelopmental disorders) | 1 | 146,512,930 | 147,737,500 | 1.22 | 3 |

TABLE 1B-continued

| Syndrome | Chromosome | Start | End | Interval (Mb) | Grade |
|---|---|---|---|---|---|
| 1q21.1 recurrent microduplication (possible susceptibility locus for neurodevelopmental disorders) | 1 | 146,512,930 | 147,737,500 | 1.22 | 3 |
| 1q21.1 susceptibility locus for Thrombocytopenia-Absent Radius (TAR) syndrome | 1 | 145,401,253 | 145,928,123 | 0.53 | 3 |
| 22q11 deletion syndrome (Velocardiofacial/DiGeorge syndrome) | 22 | 18,546,349 | 22,336,469 | 3.79 | 1 |
| 22q11 duplication syndrome | 22 | 18,546,349 | 22,336,469 | 3.79 | 3 |
| 22q11.2 distal deletion syndrome | 22 | 22,115,848 | 23,696,229 | 1.58 | |
| 22q13 deletion syndrome (Phelan-Mcdermid syndrome) | 22 | 51,045,516 | 51,187,844 | 0.14 | 1 |
| 2p15-16.1 microdeletion syndrome | 2 | 57,741,796 | 61,738,334 | 4.00 | |
| 2q33.1 deletion syndrome | 2 | 196,925,089 | 205,206,940 | 8.28 | 1 |
| 2q37 monosomy | 2 | 239,954,693 | 243,102,476 | 3.15 | 1 |
| 3q29 microdeletion syndrome | 3 | 195,672,229 | 197,497,869 | 1.83 | |
| 3q29 microduplication syndrome | 3 | 195,672,229 | 197,497,869 | 1.83 | |
| 7q11.23 duplication syndrome | 7 | 72,332,743 | 74,616,901 | 2.28 | |
| 8p23.1 deletion syndrome | 8 | 8,119,295 | 11,765,719 | 3.65 | |
| 9q subtelomeric deletion syndrome | 9 | 140,403,363 | 141,153,431 | 0.75 | 1 |
| Adult-onset autosomal dominant leukodystrophy (ADLD) | 5 | 126,063,045 | 126,204,952 | 0.14 | |
| Angelman syndrome (Type 1) | 15 | 22,876,632 | 28,557,186 | 5.68 | 1 |
| Angelman syndrome (Type 2) | 15 | 23,758,390 | 28,557,186 | 4.80 | 1 |
| ATR-16 syndrome | 16 | 60,001 | 834,372 | 0.77 | 1 |
| AZFa | Y | 14,352,761 | 15,154,862 | 0.80 | |
| AZFb | Y | 20,118,045 | 26,065,197 | 5.95 | |
| AZFb + AZFc | Y | 19,964,826 | 27,793,830 | 7.83 | |
| AZFc | Y | 24,977,425 | 28,033,929 | 3.06 | |
| Cat-Eye Syndrome (Type I) | 22 | 1 | 16,971,860 | 16.97 | |
| Charcot-Marie-Tooth syndrome type 1A (CMT1A) | 17 | 13,968,607 | 15,434,038 | 1.47 | 1 |
| Cri du Chat Syndrome (5p deletion) | 5 | 10,001 | 11,723,854 | 11.71 | 1 |
| Early-onset Alzheimer disease with cerebral amyloid angiopathy | 21 | 27,037,956 | 27,548,479 | 0.51 | |
| Familial Adenomatous Polyposis | 5 | 112,101,596 | 112,221,377 | 0.12 | |
| Hereditary Liability to Pressure Palsies (HNPP) | 17 | 13,968,607 | 15,434,038 | 1.47 | 1 |
| Leri-Weill dyschondrostosis (LWD) - SHOX deletion | X | 751,878 | 867,875 | 0.12 | |

TABLE 1B-continued

| Syndrome | Chromosome | Start | End | Interval (Mb) | Grade |
|---|---|---|---|---|---|
| Leri-Weill dyschondrostosis (LWD) - SHOX deletion | X | 460,558 | 753,877 | 0.29 | |
| Miller-Dieker syndrome (MDS) | 17 | 1 | 2,545,429 | 2.55 | 1 |
| NF1-microdeletion syndrome | 17 | 29,162,822 | 30,218,667 | 1.06 | 1 |
| Pelizaeus-Merzbacher disease | X | 102,642,051 | 103,131,767 | 0.49 | |
| Potocki-Lupski syndrome (17p11.2 duplication syndrome) | 17 | 16,706,021 | 20,482,061 | 3.78 | |
| Potocki-Shaffer syndrome | 11 | 43,985,277 | 46,064,560 | 2.08 | 1 |
| Prader-Willi syndrome (Type 1) | 15 | 22,876,632 | 28,557,186 | 5.68 | 1 |
| Prader-Willi Syndrome (Type 2) | 15 | 23,758,390 | 28,557,186 | 4.80 | 1 |
| RCAD (renal cysts and diabetes) | 17 | 34,907,366 | 36,076,803 | 1.17 | |
| Rubinstein-Taybi Syndrome | 16 | 3,781,464 | 3,861,246 | 0.08 | 1 |
| Smith-Magenis Syndrome | 17 | 16,706,021 | 20,482,061 | 3.78 | 1 |
| Sotos syndrome | 5 | 175,130,402 | 177,456,545 | 2.33 | 1 |
| Split hand/foot malformation 1 (SHFM1) | 7 | 95,533,860 | 96,779,486 | 1.25 | |
| Steroid sulphatase deficiency (STS) | X | 6,441,957 | 8,167,697 | 1.73 | |
| WAGR 11p13 deletion syndrome | 11 | 31,803,509 | 32,510,988 | 0.71 | |
| Williams-Beuren Syndrome (WBS) | 7 | 72,332,743 | 74,616,901 | 2.28 | 1 |
| Wolf-Hirschhorn Syndrome | 4 | 10,001 | 2,073,670 | 2.06 | 1 |
| Xq28 (MECP2) duplication | X | 152,749,900 | 153,390,999 | 0.64 | |

Grade 1 conditions often have one or more of the following characteristics; pathogenic anomaly; strong agreement amongst geneticists; highly penetrant; may still have variable phenotype but some common features; all cases in the literature have a clinical phenotype; no cases of healthy individuals with the anomaly; not reported on DVG databases or found in healthy population; functional data confirming single gene or multi-gene dosage effect; confirmed or strong candidate genes; clinical management implications defined; known cancer risk with implication for surveillance; multiple sources of information (OMIM, Gene reviews, Orphanet, Unique, Wikipedia); and/or available for diagnostic use (reproductive counseling).

Grade 2 conditions often have one or more of the following characteristics; likely pathogenic anomaly; highly penetrant; variable phenotype with no consistent features other than DD; small number of cases/reports in the literature; all reported cases have a clinical phenotype; no functional data or confirmed pathogenic genes; multiple sources of information (OMIM, Gene reviews, Orphanet, Unique, Wikipedia); and/or may be used for diagnostic purposes and reproductive counseling.

Grade 3 conditions often have one or more of the following characteristics; susceptibility locus; healthy individuals or unaffected parents of a proband described; present in control populations; non penetrant; phenotype mild and not specific; features less consistent; no functional data or confirmed pathogenic genes; more limited sources of data; possibility of second diagnosis remains a possibility for cases deviating from the majority or if novel clinical finding present; and/or caution when using for diagnostic purposes and guarded advice for reproductive counseling.

Preeclampsia

In some embodiments, the presence or absence of preeclampsia is determined by using a method, machine or apparatus described herein. Preeclampsia is a condition in which hypertension arises in pregnancy (e.g., pregnancy-induced hypertension) and is associated with significant amounts of protein in the urine. In certain embodiments, preeclampsia also is associated with elevated levels of extracellular nucleic acid and/or alterations in methylation patterns. For example, a positive correlation between extracellular fetal-derived hypermethylated RASSF1A levels and the severity of pre-eclampsia has been observed. In certain examples, increased DNA methylation is observed for the H19 gene in preeclamptic placentas compared to normal controls.

Preeclampsia is one of the leading causes of maternal and fetal/neonatal mortality and morbidity worldwide. Circulating cell-free nucleic acids in plasma and serum are novel biomarkers with promising clinical applications in different medical fields, including prenatal diagnosis. Quantitative changes of cell-free fetal (cff)DNA in maternal plasma as an indicator for impending preeclampsia have been reported in different studies, for example, using real-time quantitative PCR for the male-specific SRY or DYS 14 loci. In cases of early onset preeclampsia, elevated levels may be seen in the first trimester. The increased levels of cffDNA before the onset of symptoms may be due to hypoxia/reoxygenation within the intervillous space leading to tissue oxidative stress and increased placental apoptosis and necrosis. In addition to the evidence for increased shedding of cffDNA into the maternal circulation, there is also evidence for reduced renal clearance of cffDNA in preeclampsia. As the amount of fetal DNA is currently determined by quantifying Y-chromosome specific sequences, alternative approaches such as measurement of total cell-free DNA or the use of gender-independent fetal epigenetic markers, such as DNA methylation, offer an alternative. Cell-free RNA of placental origin is another alternative biomarker that may be used for screening and diagnosing preeclampsia in clinical practice. Fetal RNA is associated with subcellular placental particles that protect it from degradation. Fetal RNA levels sometimes are ten-fold higher in pregnant females with preeclampsia compared to controls, and therefore is an alternative biomarker that may be used for screening and diagnosing preeclampsia in clinical practice.

Pathogens

In some embodiments, the presence or absence of a pathogenic condition is determined by a method, machine or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods, machines and apparatus provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g., strain).

Cancers

In some embodiments, the presence or absence of a cell proliferation disorder (e.g., a cancer) is determined by using a method, machine or apparatus described herein. For example, levels of cell-free nucleic acid in serum can be elevated in patients with various types of cancer compared with healthy patients. Patients with metastatic diseases, for example, can sometimes have serum DNA levels approximately twice as high as non-metastatic patients. Patients with metastatic diseases may also be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Thus, it is further contemplated that a method provided herein can be used to identify a particular type of cancer.

Software can be used to perform one or more steps in the processes described herein, including but not limited to; counting, data processing, generating an outcome, and/or providing one or more recommendations based on generated outcomes, as described in greater detail hereafter.

Machines, Software and Interfaces

Certain processes and methods described herein often cannot be performed without a computer, processor, software, module or other apparatus. Methods described herein typically are computer-implemented methods, and one or more portions of a method sometimes are performed by one or more processors (e.g., microprocessors), computers, or microprocessor controlled apparatuses. In some embodiments one or more or all processing methods known or described herein (e.g., mapping, data compression, local genome bias estimate determinations, relationship determinations, relationship comparisons, count normalization, read density and/or read density profile generations, PCA, profile adjustments, portion filtering, portion weighting, profile comparisons, profile scoring, determination of an outcome, the like or combinations thereof) are performed by a processor, a micro-processor, a computer, in conjunction with memory and/or by a microprocessor controlled apparatus. Embodiments pertaining to methods described in this document generally are applicable to the same or related processes implemented by instructions in systems, apparatus and computer program products described herein. In some embodiments, processes and methods described herein (e.g., quantifying, counting and/or determining sequence reads, counts, levels and/or profiles) are performed by automated methods. In some embodiments one or more steps and a method described herein is carried out by a processor and/or computer, and/or carried out in conjunction with memory. In some embodiments, an automated method is embodied in software, modules, processors, peripherals and/or a machine comprising the like, that determine sequence reads, counts, mapping, mapped sequence tags, levels, profiles, normalizations, comparisons, range setting, categorization, adjustments, plotting, outcomes, transformations and identifications. As used herein, software refers to computer readable program instructions that, when executed by a processor, perform computer operations, as described herein.

Sequence reads, counts, read densities, and read density profiles derived from a test subject (e.g., a patient, a pregnant female) and/or from a reference subject can be further analyzed and processed to determine the presence or absence of a genetic variation. Sequence reads, counts, levels and/or profiles sometimes are referred to as "data" or "data sets". In some embodiments, data or data sets can be characterized by one or more features or variables (e.g., sequence based [e.g., GC content, specific nucleotide sequence, the like], function specific [e.g., expressed genes, cancer genes, the like], location based [genome specific, chromosome specific, portion or portion specific], the like and combinations thereof). In certain embodiments, data or data sets can be organized into a matrix having two or more dimensions based on one or more features or variables. Data organized into matrices can be organized using any suitable features or variables. A non-limiting example of data in a matrix includes data that is organized by maternal age, maternal ploidy, and fetal contribution. In certain embodiments, data sets characterized by one or more features or variables sometimes are processed after counting.

Apparatuses (multiple apparatuses, also referred to herein in plural as apparatus), software and interfaces may be used to conduct methods described herein. Using apparatuses, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical variance algorithms, comparisons, iterative steps, validation algorithms, and graphical representations, for example. In some embodiments, a data set may be entered by a user as input information, a user may download one or more data sets by a suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A system typically comprises one or more apparatuses. In some embodiments an apparatus is a machine. In some embodiments an apparatus comprises a machine. An apparatus can comprise one or more of memory, one or more processors, and/or instructions. Where a system includes two or more apparatuses, some or all of the apparatuses may be located at the same location, some or all of the apparatuses may be located at different locations, all of the apparatuses may be located at one location and/or all of the apparatuses may be located at different locations. Where a system includes two or more apparatus, some or all of the apparatuses may be located at the same location as a user, some or all of the apparatuses may be located at a location different than a user, all of the apparatuses may be located at the same location as the user, and/or all of the apparatuses may be located at one or more locations different than the user. Apparatuses of a system described herein can interface with one or more remote computing servers and/or computers (e.g., a cloud, a cloud computing service) by a suitable method. The term "cloud" as used herein refers to, in part, two or more computers (e.g., often a plurality of computers) connected through a real-time communication network (e.g., an internet) that can perform a centralized function (e.g., a method described herein) where portions of the function are shared by a plurality of computers in a network. A "cloud" can often run one or more programs (e.g., software programs, modules) on a plurality of connected computers at the same time. In some embodiments a system and/or an apparatus described herein comprises a cloud (e.g., a cloud server, a cloud computer, a cloud computing service). One or more functions of a system and/or an apparatus described herein can be performed by a cloud. Data and/or information can be transferred to, and/or from an apparatus and a cloud using a suitable method. The term "computer" as used herein refers to an electrical, man-made device comprising a microprocessor that can perform arithmetical and logical operations. A computer sometimes comprises instructions, software (e.g., modules), memory, a display, one or more peripherals and/or a storage medium. In some embodiments a machine comprises a computer. In some embodiments a machine is a computer. A computer often interfaces and/or is connected to other computers (e.g., an internet, a network, a cloud).

A system sometimes comprises a computing apparatus or a sequencing apparatus, or a computing apparatus and a sequencing apparatus (i.e., sequencing machine and/or computing machine). A sequencing apparatus generally is configured to receive physical nucleic acid and generate signals corresponding to nucleotide bases of the nucleic acid. A sequencing apparatus is often "loaded" with a sample comprising nucleic acid and the nucleic acid of the sample loaded in the sequencing apparatus generally is subjected to a nucleic acid sequencing process. The term "loading a sequence apparatus" as used herein refers to contacting a portion of a sequencing apparatus (e.g., a flow cell) with a nucleic acid sample, which portion of the sequencing apparatus is configured to receive a sample for conducting a nucleic acid sequencing process. In some embodiments a sequencing apparatus is loaded with a variant of a sample nucleic acid. A variant sometimes is produced by a process that modifies the sample nucleic acid to a form suitable for sequencing the nucleic acid (e.g., by ligation (e.g., adding adaptors to ends of sample nucleic acid by ligation), amplification, restriction digest, the like or combinations thereof). A sequencing apparatus is often configured, in part, to perform a suitable DNA sequencing method that generates signals (e.g., electronic signals, detector signals, images, the like, or combinations thereof) corresponding to nucleotide bases of the loaded nucleic acid.

One or more signals corresponding to each base of a DNA sequence are often processed and/or transformed into base calls (e.g., a specific nucleotide base, e.g., guanine, cytosine, thymine, uracil, adenine, and the like) by a suitable process. A collection of base calls derived from a loaded nucleic acid often are processed and/or assembled into one or more sequence reads. In embodiments in which multiple sample nucleic acids are sequenced at one time (i.e., multiplexing), a suitable de-multiplexing process can be utilized to associated particular reads with the sample nucleic acid from which they originated. Sequence reads can be aligned by a suitable process to a reference genome and reads aligned to portions of the reference genome can be counted, as described herein.

A sequencing apparatus sometimes is associated with and/or comprises one or more computing apparatus in a system. The one or more computing apparatus sometimes are configured to perform one or more of the following processes: generating base calls from sequencing apparatus signals, assembling reads (e.g., generating reads), de-multiplexing reads, aligning reads to a reference genome, counting reads aligned to genomic portions in the reference genome, and the like. The one or more computing apparatus sometimes are configured to perform one or more of the following additional processes: normalize read counts (e.g., reduce or remove bias), generate one or more determinations (e.g., determine fetal fraction, fetal ploidy, fetal sex, fetal chromosome count, outcome, presence or absence of a genetic variation (e.g., presence or absence of a fetal chromosome aneuploidy (e.g., chromosome 13, 18 and/or 21 trisomy)), and the like.

In some embodiments, one computing apparatus is associated with a sequencing apparatus, and in certain embodiments, the one computing apparatus performs the majority or all of the following processes: generate base calls from sequencing apparatus signals, assemble reads, de-multiplex reads, align reads and count the reads aligned to genomic portions of a reference genome, normalize read counts and generate one or more outcomes (e.g., fetal fraction, presence or absence of a particular genetic variation). In the latter embodiments, in which one computing apparatus is associated with a sequencing apparatus, the computing apparatus often includes one or more processors (e.g., microprocessors) and memory having instructions that are carried out by the one or more processors to perform the processes. In some embodiments, the one computing apparatus can be a single or multi-core computing device local to the sequencing apparatus (e.g., located in the same location (e.g., the same address, the same building, same floor, same room or the like)). In some embodiments the one computing apparatus is integrated with the sequencing apparatus.

In some embodiments, multiple computing apparatus in a system are associated with a sequencing apparatus, and a subset of the total processes performed by the system may be allocated to or divided among particular computing apparatus in the system. Subsets of the total number of processes can be divided among two or more computing apparatus, or groups thereof, in any suitable combination. In certain embodiments, generating base calls from sequencing apparatus signals, assembling reads and de-multiplexing reads are performed by a first computing apparatus or group thereof, aligning and counting reads mapped to portions of a reference genome are performed by a second computing apparatus or group thereof, and normalizing read counts and providing one or more outcomes are performed by a third computing apparatus or group thereof. In systems comprising two or more computing apparatus or groups thereof, each particular computing apparatus may include memory, one or more processors or a combination thereof. A multi-computing apparatus system sometimes includes one or more suitable servers local to a sequencing apparatus, and sometimes includes one or more suitable servers not local to the sequencing apparatus (e.g., web servers, on-line servers, application servers, remote file servers, cloud servers (e.g., cloud environment, cloud computing)).

Apparatus in different system configurations can generate different types of output data. For example, a sequencing apparatus can output base signals and the base signal output data can be transferred to a computing apparatus that converts the base signal data to base calls. In some embodiments, the base calls are output data from one computing apparatus and are transferred to another computing apparatus for generating sequence reads. In certain embodiments, base calls are not output data from a particular apparatus, and instead, are utilized in the same apparatus that received sequencing apparatus base signals to generate sequence reads. In some embodiments, one apparatus receives sequencing apparatus base signals, generates base calls, sequence reads and de-multiplexes sequence reads, and outputs de-multiplexed sequence reads for a sample that can be transferred to another apparatus or group thereof that aligns the sequence reads to a reference genome. In some embodiments, one apparatus or group thereof can output aligned sequence reads mapped to portions of a reference genome (e.g., SAM or BAM files), and such output data can be transferred to a second computing apparatus or group thereof that normalizes the sequence reads (e.g., normalizes the counts of the sequence reads) and generates an outcome (e.g., fetal fraction and/or presence or absence of a fetal trisomy). Output data from one apparatus can be transferred to a second apparatus in any suitable manner. For example, output data from one apparatus sometimes is placed on a physical storage device and the storage device is transported and connected to a second apparatus to which the output data is transferred. Output data sometimes is stored by one apparatus in a database, and a second apparatus accesses the output data from the same database.

A system sometimes comprises a bias reduction machine. A bias reduction machine sometimes comprises one or more computers. In some embodiments a bias reduction machine maps sequence reads and/or compresses reads (e.g., mapped sequence reads). A bias reduction machine sometimes compresses sequence reads into a suitable compressed format (e.g., a BReads format). In some embodiments a bias reduction machine generates read densities, density profiles, adjusted read density profiles and/or outcomes. One or more function of a bias reduction machine may be performed by a network and/or a cloud (e.g., cloud computing network). A bias reduction machine can interface with multiple servers (e.g., cloud servers) comprising microprocessors, memory and storage media, modules, data and/or information (e.g., references, reference sequence reads, reference read densities, reference density profiles, and the like) and/or software. A bias reduction machine can transfer data and/or information to a cloud where one or more functions of a bias reduction machine are performed. Processed data and/or information can be transferred to a bias reduction machine from a cloud.

A system sometimes comprises a sequencing machine and a bias reduction machine where a sequencing machine generates sequence reads from sample nucleic acid, sometimes maps sequence reads, and provides and/or transfers unmapped or mapped sequence reads to a bias reduction machine. A sequencing machine can provide or transfer reads to a bias reduction machine by any suitable method. A sequencing machine and bias reduction machine are sometimes connected together by a suitable hardware interface. In some embodiments a sequencing machine and bias reduction machine are connected to a network and/or a cloud. In some embodiments a sequencing machine and bias reduction machine are connected together by network and/or a cloud. Some or all methods and/or functions of a sequencing machine and/or a bias reduction machine can be performed by a cloud. A sequencing machine can transfer reads by use of a transitory and/or a non-transitory computer readable medium to a bias reduction machine. For example, sequence reads can be transferred by digital or analogue signals transmitted by wired cables and/or wireless signals. In some embodiments sequence reads are transferred from a sequencing machine to a bias reduction machine using non-transitory computer readable storage medium.

A bias reduction machine may comprise one or more modules described herein that can carry out some or all of the functions of a bias reduction machine. In some embodiments a bias reduction machine comprises a compression module and carries out the function of a compression module. In some embodiments a bias reduction machine comprises one or more of a bias density module, relationship module, bias correction module and/or a multivariate correction module. A bias correction machine can use one or more modules to remove bias (e.g., GC bias) from reads and/or provide normalized counts of sample reads. In some embodiments a bias correction machine comprises one or more of a distribution module, a filtering module and/or a profile generation module. A bias correction machine can often process sequence reads from a training set or reference as well as sequence reads from a test sample. In some embodiments a bias correction machine comprises one or more of a PCA statistics module and/or a portion weighting module. A bias correction machine often utilizes mapped reads and multiple modules and provides read densities, density profiles and/or adjusted read density profiles to a scoring module, an end user, a computer peripheral (e.g., a display, a printer), or to an outcome generator machine. In some embodiments a bias reduction machine provides an outcome. Sometimes a bias reduction machine does not provide an outcome. In some embodiments a bias reduction machine comprises an outcome generator machine. Sometimes a bias reduction machine transfers normalized reads, read densities, density profiles and/or adjusted read density profiles to an outcome generator machine. A bias reduction machine can transfer data and/or information (e.g., read density profiles) to an outcome generator machine by any suitable method. In some embodiments a system comprises one or more of a sequencing machine, a bias reduction machine and/or an outcome generator machine. An outcome generator machine can receive normalized counts of reads, read densities, density profiles and/or adjusted read density profiles from a bias correction machine. An outcome generator machine often provides a call or an outcome (e.g., a determination of the presence or absence of a genetic variation). An outcome generator machine often provides a call or an outcome to an end user and/or a computer peripheral (e.g., a display, a printer). An outcome generator machine sometimes comprises one or more of a filtering module, distribution module, a profile generation module, PCA statistics module, portion weighting module, scoring module and/or one or more other suitable modules.

In some embodiments a user interacts with an apparatus (e.g., a computing apparatus, a sequencing apparatus). In some embodiments a user may place a query to a system, computer or module which then may acquire a data set via internet access (e.g., a cloud), and in certain embodiments, a programmable processor may be prompted to acquire a suitable data set based on given parameters. A programmable processor also may prompt a user to select one or more data set options selected by the processor based on given parameters. A programmable processor may prompt a user to select one or more data set options selected by the processor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, apparatuses, or computer programs.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report). In some embodiments a display module processes, transforms and/or transfers data and/or information into a suitable visual medium for presentation on a suitable display (e.g., a monitor, LED, LCD, CRT, the like or combinations thereof), a printer, a suitable peripheral or device. In certain embodiments a display module provides a visual display of a relationship, profile or outcome. Non-limiting examples of a suitable visual medium and/or display include a chart, plot, graph, the like or combinations thereof. In some embodiments a display module processes, transforms data and/or information into a visual representation of a fetal and/or maternal genome, or a segment thereof (e.g., a chromosome or part thereof). In some embodiments, a display module or a machine comprising a display module is required to provide a suitable visual display.

In a system, input and output means may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus may serve as data that can be input via an input device. In certain embodiments, mapped sequence reads may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process described herein, and software can include one or more modules for performing such processes (e.g., sequencing module, bias correction module, display module). The term "software" refers to computer readable program instructions that, when executed by a computer, perform computer operations. Instructions executable by the one or more processors sometimes are provided as executable code, that when executed, can cause one or more processors to implement a method described herein. A module described herein can exist as software, and instructions (e.g., processes, routines, subroutines) embodied in the software can be implemented or performed by a processor. For example, a module (e.g., a software module) can be a part of a program that performs a particular process or task. The term "module" refers to a self-contained functional unit that can be used in a larger apparatus or software system. A module can comprise a set of instructions for carrying out a function of the module by one or more microprocessors. Instructions of a module can be implemented in a computing environment by use of a suitable programming language, suitable software, and/or code written in a suitable language (e.g., a computer programming language known in the art) and/or operating system, non-limiting examples of which include UNIX, Linux, oracle, windows, Ubuntu, ActionScript, C, C++, C#, Haskell, Java, JavaScript, Objective-C, Pen, Python, Ruby, Smalltalk, SQL, Visual Basic, COBOL, Fortran, UML, HTML (e.g., with PHP), PGP, G, R, S, the like or combinations thereof. In some embodiments a module described herein comprises code (e.g., script) written in S or R that utilizes a suitable package (e.g., an S package, an R package). R, R source code, R programs, R packages and R documentation are available for download from a CRAN or CRAN mirror site (The Comprehensive R Archive Network (CRAN)[online], [retrieved on 2013 Apr. 24], retrieved from the internet <URL:*>http://cran.us.r-project.org/< >). CRAN is a network of ftp and web servers around the world that store identical, up-to-date, versions of code and documentation for R.

A module can transform data and/or information. Data and/or information can be in a suitable form. For example, data and/or information can be digital or analogue. In certain embodiments, data and/or information can be packets, bytes, characters, or bits. In some embodiments, data and/or information can be any gathered, assembled or usable data or information. Non-limiting examples of data and/or information include a suitable media, files, pictures, video, sound (e.g., frequencies, audible or non-audible), numbers, constants, values, objects, time, text, functions, instructions, computer code, maps, references, sequences, reads, mapped reads, read densities, read density profiles, ranges, thresholds, displays, representations, outcomes, transformations, the like or combinations thereof. A module can accept or receive data and/or information, transform the data and/or information into a second form, and provide or transfer the second form to a machine, peripheral, component or another module. A module can perform one or more of the following non-limiting functions: mapping sequence reads, compressing a file (e.g., mapped read data), filtering portions, selecting portions, performing a PCA, providing principal components, adjusting read densities and/or read density profiles, weighting portions, scoring, providing counts, assembling portions, normalizing counts, providing local genome bias estimate local genome bias estimates, providing bias frequencies, providing read densities, providing read density profiles, providing a call zone and/or a no call zone, providing a measure of uncertainty, providing or determining expected ranges (e.g., threshold ranges and threshold levels), plotting, and/or determining an outcome, for example. A processor can, in certain embodiments, carry out the instructions in a module. In some embodiments, one or more processors are required to carry out instructions in a module or group of modules. A module can provide data and/or information to another module, apparatus or source and can receive data and/or information from another module, apparatus or source.

A non-transitory computer-readable storage medium sometimes comprises an executable program stored thereon and sometimes the program instructs a microprocessor to perform a function (e.g., a method described herein). A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and processor capable of implementing instructions from a module can be located in a machine or in different apparatus. A module and/or processor capable of implementing an instruction for a module can be located in the same location as a user (e.g., local network) or in a different location from a user (e.g., remote network, cloud system). In embodiments in which a method is carried out in conjunction with two or more modules, the modules can be located in the same apparatus, one or more modules can be located in different apparatus in the same physical location, and one or more modules may be located in different apparatus in different physical locations.

A machine, in some embodiments, comprises at least one processor for carrying out the instructions in a module. Counts of sequence reads mapped to portions of a reference genome sometimes are accessed by a processor that executes instructions configured to carry out a method described herein. Counts that are accessed by a processor can be within memory of a system, and the counts can be accessed and placed into the memory of the system after they are obtained. In some embodiments, a machine includes a processor (e.g., one or more processors) which processor can perform and/or implement one or more instructions (e.g., processes, routines and/or subroutines) from a module. In some embodiments, a machine includes multiple processors, such as processors coordinated and working in parallel. In some embodiments, a machine operates with one or more external processors (e.g., an internal or external network, server, storage device and/or storage network (e.g., a cloud)). In some embodiments, a machine comprises a module. In certain embodiments a machine comprises one or more modules. A machine comprising a module often can receive and transfer one or more of data and/or information to and from other modules. In certain embodiments, a machine comprises peripherals and/or components. In certain embodiments a machine can comprise one or more peripherals or components that can transfer data and/or information to and from other modules, peripherals and/or components. In certain embodiments a machine interacts with a peripheral and/or component that provides data and/or information. In certain embodiments peripherals and components assist a machine in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a processor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like), the world wide web (www), the internet, a computer and/or another module.

Software often is provided on a program product containing program instructions recorded on a computer readable medium (e.g., a non-transitory computer readable medium), including, but not limited to, magnetic media including floppy disks, hard disks, and magnetic tape; and optical media including CD-ROM discs, DVD discs, magneto-optical discs, solid state drives, flash drives, RAM, ROM, BUS, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Pert, R, S, Python, Fortran, and the like. In some embodiments, an algorithm can be configured or modified to include margin of errors, statistical analysis, statistical significance, a measure of uncertainty and/or comparisons to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of an identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more processors in certain embodiments. A processor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A processor may implement software in a system. In some embodiments, a processor may be programmed to automatically perform a task described herein that a user could perform. Accordingly, a processor, or algorithm conducted by such a processor, can require little to no supervision or input from a user (e.g., software may be programmed to implement a function automatically). In some embodiments, the complexity of a process is so large that a single person or group of persons could not perform the process in a timeframe short enough for determining the presence or absence of a genetic variation.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

One entity can generate counts of sequence reads, map the sequence reads to portions, count the mapped reads, and utilize the counted mapped reads in a method, system, machine or computer program product described herein, in some embodiments. Counts of sequence reads mapped to portions sometimes are transferred by one entity to a second entity for use by the second entity in a method, system, machine or computer program product described herein, in certain embodiments.

In some embodiments, one entity generates sequence reads and a second entity maps those sequence reads to portions in a reference genome in some embodiments. The second entity sometimes counts the mapped reads and utilizes the counted mapped reads in a method, system, machine or computer program product described herein. In certain embodiments the second entity transfers the mapped reads to a third entity, and the third entity counts the mapped reads and utilizes the mapped reads in a method, system, machine or computer program product described herein. In certain embodiments the second entity counts the mapped reads and transfers the counted mapped reads to a third entity, and the third entity utilizes the counted mapped reads in a method, system, machine or computer program product described herein. In embodiments involving a third entity, the third entity sometimes is the same as the first entity. That is, the first entity sometimes transfers sequence reads to a second entity, which second entity can map sequence reads to portions in a reference genome and/or count the mapped reads, and the second entity can transfer the mapped and/or counted reads to a third entity. A third entity sometimes can utilize the mapped and/or counted reads in a method, system, machine or computer program product described herein, where the third entity sometimes is the same as the first entity, and sometimes the third entity is different from the first or second entity.

In some embodiments, one entity obtains blood from a pregnant female, optionally isolates nucleic acid from the blood (e.g., from the plasma or serum), and transfers the blood or nucleic acid to a second entity that generates sequence reads from the nucleic acid.

Figure 11:
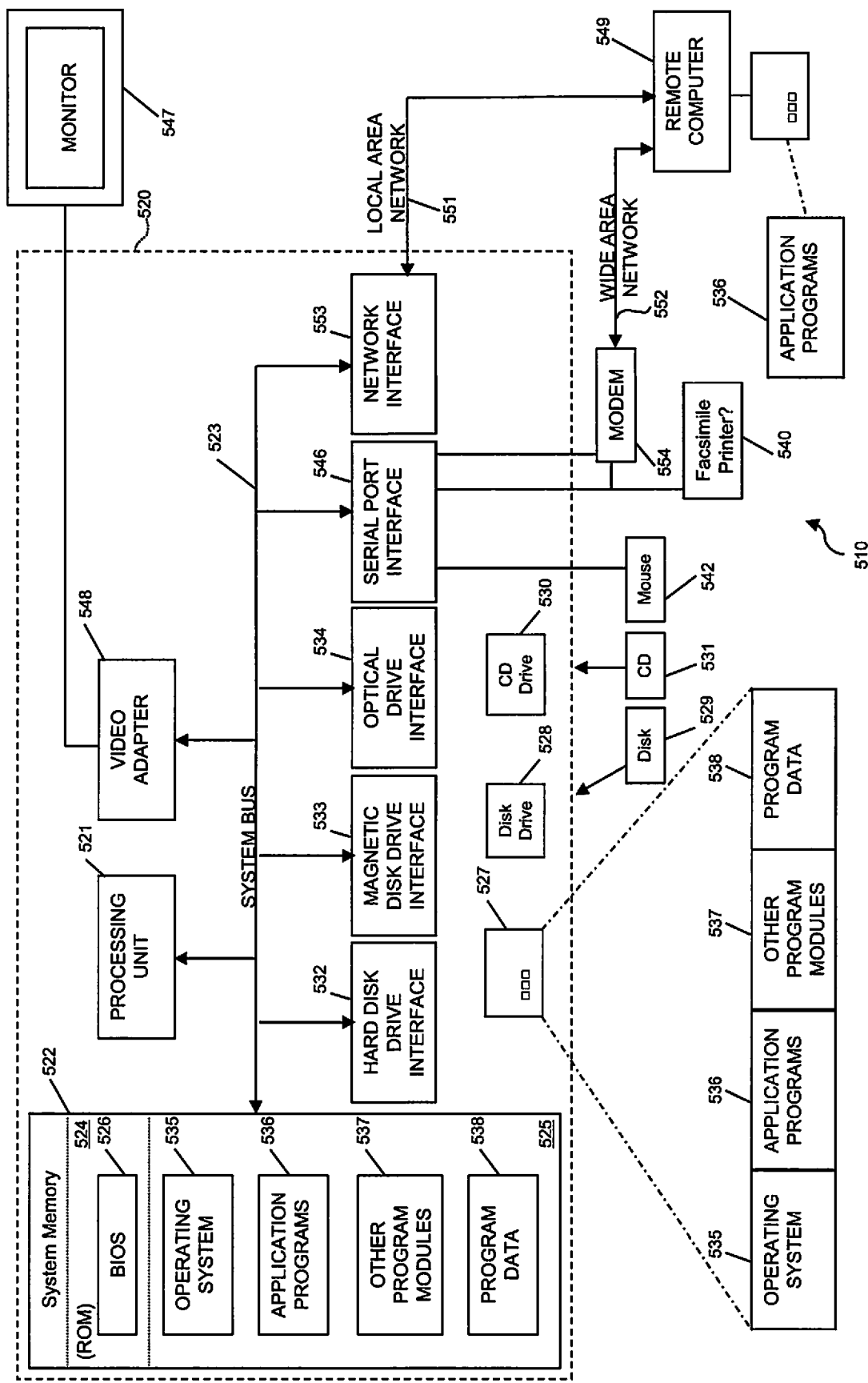
FIG. 11 shows an embodiment of a system.
Figure 12:
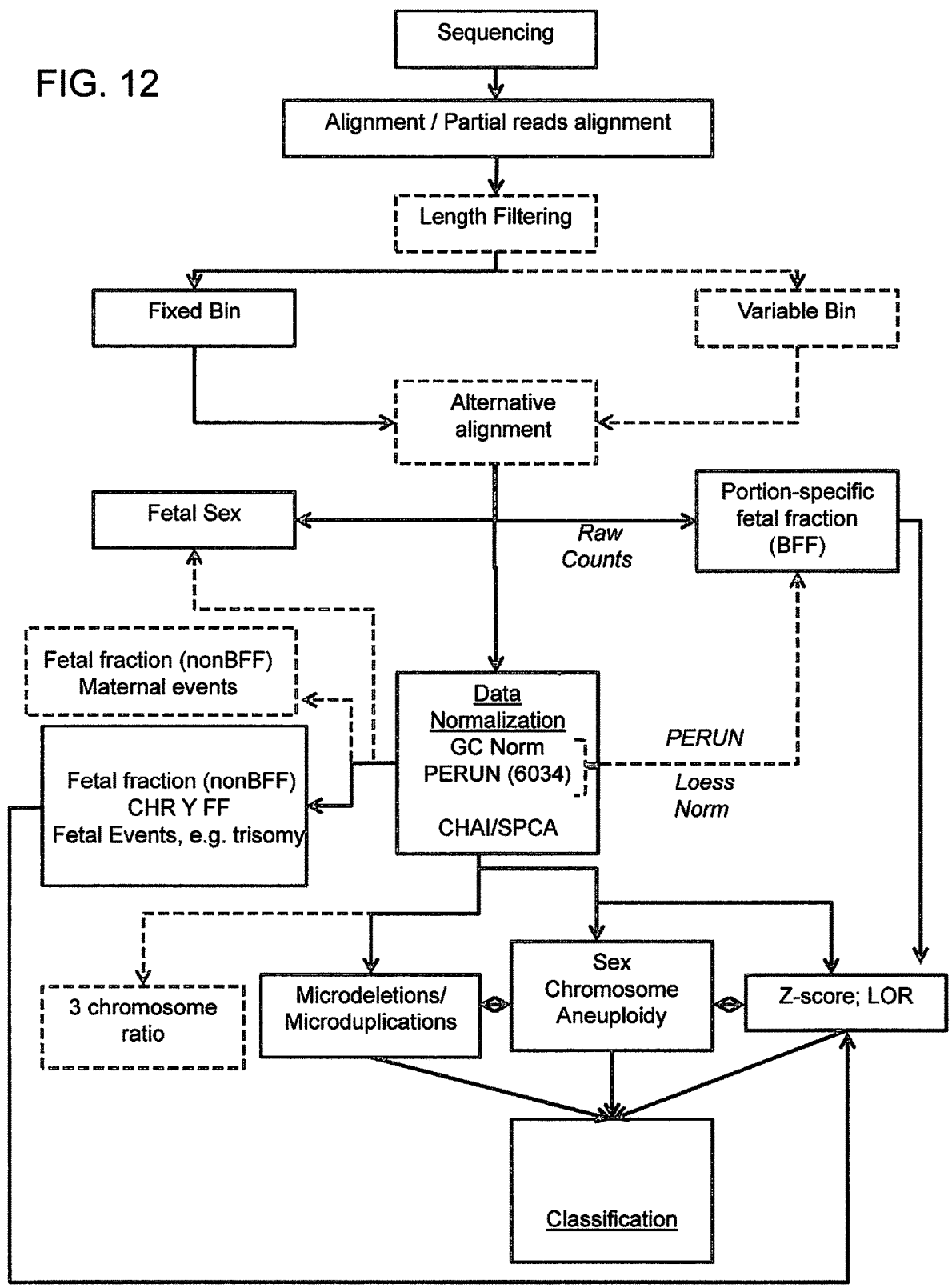
FIG. 12 shows an embodiment of a method provided herein.

FIG. 11 illustrates a non-limiting example of a computing environment 510 in which various systems, methods, algorithms, and data structures described herein may be implemented. The computing environment 510 is only one example of a suitable computing environment and is not intended to suggest any limitation as to the scope of use or functionality of the systems, methods, and data structures described herein. Neither should computing environment 510 be interpreted as having any dependency or requirement relating to any one or combination of components illustrated in computing environment 510. A subset of systems, methods, and data structures shown in FIG. 11 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 510 of FIG. 11 includes a general purpose computing device in the form of a computer 520, including a processing unit 521, a system memory 522, and a system bus 523 that operatively couples various system components including the system memory 522 to the processing unit 521. There may be only one or there may be more than one processing unit 521, such that the processor of computer 520 includes a single central-processing unit (CPU), or a plurality of processing units, commonly referred to as a parallel processing environment. The computer 520 may be a conventional computer, a distributed computer, or any other type of computer.

The system bus 523 may be any of several types of bus structures including a memory bus or memory controller, a peripheral bus, and a local bus using any of a variety of bus architectures. The system memory may also be referred to as simply the memory, and includes read only memory (ROM) 524 and random access memory (RAM). A basic input/output system (BIOS) 526, containing the basic routines that help to transfer information between elements within the computer 520, such as during start-up, is stored in ROM 524. The computer 520 may further include a hard disk drive interface 527 for reading from and writing to a hard disk, not shown, a magnetic disk drive 528 for reading from or writing to a removable magnetic disk 529, and an optical disk drive 530 for reading from or writing to a removable optical disk 531 such as a CD ROM or other optical media.

The hard disk drive 527, magnetic disk drive 528, and optical disk drive 530 are connected to the system bus 523 by a hard disk drive interface 532, a magnetic disk drive interface 533, and an optical disk drive interface 534, respectively. The drives and their associated computer-readable media provide nonvolatile storage of computer-readable instructions, data structures, program modules and other data for the computer 520. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 529, optical disk 531, ROM 524, or RAM, including an operating system 535, one or more application programs 536, other program modules 537, and program data 538. A user may enter commands and information into the personal computer 520 through input devices such as a keyboard 540 and pointing device 542. Other input devices (not shown) may include a microphone, joystick, game pad, satellite dish, scanner, or the like. These and other input devices are often connected to the processing unit 521 through a serial port interface 546 that is coupled to the system bus, but may be connected by other interfaces, such as a parallel port, game port, or a universal serial bus (USB). A monitor 547 or other type of display device is also connected to the system bus 523 via an interface, such as a video adapter 548. In addition to the monitor, computers typically include other peripheral output devices (not shown), such as speakers and printers.

The computer 520 may operate in a networked environment using logical connections to one or more remote computers, such as remote computer 549. These logical connections may be achieved by a communication device coupled to or a part of the computer 520, or in other manners. The remote computer 549 may be another computer, a server, a router, a network PC, a client, a peer device or other common network node, and typically includes many or all of the elements described above relative to the computer 520, although only a memory storage device 550 has been illustrated in FIG. 11. The logical connections depicted in FIG. 11 include a local-area network (LAN) 551 and a wide-area network (WAN) 552. Such networking environments are commonplace in office networks, enterprise-wide computer networks, intranets and the Internet, which all are types of networks.

When used in a LAN-networking environment, the computer 520 is connected to the local network 551 through a network interface or adapter 553, which is one type of communications device. When used in a WAN-networking environment, the computer 520 often includes a modem 554, a type of communications device, or any other type of communications device for establishing communications over the wide area network 552. The modem 554, which may be internal or external, is connected to the system bus 523 via the serial port interface 546. In a networked environment, program modules depicted relative to the personal computer 520, or portions thereof, may be stored in the remote memory storage device. It is appreciated that the network connections shown are non-limiting examples and other communications devices for establishing a communications link between computers may be used.

In some embodiments a system comprises one or more microprocessors and memory, which memory comprises instructions executable by the one or more microprocessors and which instructions executable by the one or more microprocessors are configured to (a) generate a relationship between (i) local genome bias estimates and (ii) bias frequencies for sequence reads of a test sample, thereby generating a sample bias relationship, where the sequence reads are of circulating cell-free nucleic acid from the test sample, and the sequence reads are mapped to a reference genome, (b) compare the sample bias relationship and a reference bias relationship, thereby generating a comparison, where the reference bias relationship is between (i) local genome bias estimates and (ii) the bias frequencies for a reference and (c) normalize counts of the sequence reads for the sample according to the comparison determined in (b), whereby bias in the sequence reads for the sample is reduced.

In some embodiments a system comprises one or more microprocessors and memory, which memory comprises instructions executable by the one or more microprocessors and which instructions executable by the one or more microprocessors are configured to (a) generate a relationship between (i) guanine and cytosine (GC) densities and (ii) GC density frequencies for sequence reads of a test sample, thereby generating a sample GC density relationship, where the sequence reads are of circulating cell-free nucleic acid from the test sample, and the sequence reads are mapped to a reference genome, (b) compare the sample GC density relationship and a reference GC density relationship, thereby generating a comparison, where, the reference GC density relationship is between (i) GC densities and (ii) the GC density frequencies for a reference and (c) normalize counts of the sequence reads for the sample according to the comparison determined in (b), whereby bias in the sequence reads for the sample is reduced.

In some embodiments a system comprises one or more microprocessors and memory, which memory comprises instructions executable by the one or more microprocessors and which instructions executable by the one or more microprocessors are configured to (a) filter, according to a read density distribution, portions of a reference genome, thereby providing a read density profile for a test sample comprising read densities of filtered portions, where the read densities are determined using sequence reads of circulating cell-free nucleic acid from a test sample from a pregnant female mapped to a reference genome and the read density distribution is determined for read densities of portions for multiple samples, (b) adjust, using a microprocessor, the read density profile for the test sample according to one or more principal components, which principal components are obtained from a set of known euploid samples by a principal component analysis, thereby providing a test sample profile comprising adjusted read densities, (c) compare the test sample profile to a reference profile, thereby providing a comparison and (d) determine the presence or absence of a chromosome aneuploidy for the test sample according to the comparison.

In some embodiments, presented herein, is a non-transitory computer-readable storage medium comprising an executable program stored thereon. In some embodiments a non-transitory computer-readable storage medium comprising an executable program stored thereon comprises a computer program product. In some embodiments a non-transitory computer-readable storage medium comprising an executable program stored thereon refers to software. A computer program product is often software. In some embodiments presented herein is a non-transitory computer-readable storage medium comprising an executable program stored thereon, where the program instructs a microprocessor to perform the following: (a) generate a relationship between (i) guanine and cytosine (GC) densities and (ii) GC density frequencies for sequence reads of a test sample, thereby generating a sample GC density relationship, where the sequence reads are of circulating cell-free nucleic acid from the test sample, and the sequence reads are mapped to a reference genome, (b) compare the sample GC density relationship and a reference GC density relationship, thereby generating a comparison, where, the reference GC density relationship is between (i) GC densities and (ii) the GC density frequencies for a reference, and (c) normalizing counts of the sequence reads for the sample according to the comparison determined in (b), whereby bias in the sequence reads for the sample is reduced.

Also presented herein, in some embodiments, is a non-transitory computer-readable storage medium with comprising an executable program stored thereon, where the program instructs a microprocessor to perform the following: (a) filter, according to a read density distribution, portions of a reference genome, thereby providing a read density profile for a test sample comprising read densities of filtered portions, where the read densities comprise sequence reads of circulating cell-free nucleic acid from a test sample from a pregnant female, and the read density distribution is determined for read densities of portions for multiple samples, (b) adjust the read density profile for the test sample according to one or more principal components, which principal components are obtained from a set of known euploid samples by a principal component analysis, thereby providing a test sample profile comprising adjusted read densities, (c) compare the test sample profile to a reference profile, thereby providing a comparison and (d) determine the presence or absence of a chromosome aneuploidy for the test sample according to the comparison.

Modules

One or more modules can be utilized in a method described herein, non-limiting examples of which include a compression module, sequencing module, mapping module, filtering module, bias density module, relationship module, bias correction module, multivariate correction module, distribution module, profile generation module, PCA statistics module, portion weighting module, scoring module, outcome module, display module, the like or combination thereof. In some embodiments a module is a non-transitory computer readable medium comprising a set of instruction (e.g., a computer program product, e.g., software, a program), where the set of instruction directs one or more microprocessors to perform a function. In some embodiments a module comprises instructions in the form of suitable computer code (e.g., source code). A source code sometimes comprises a program. Computer code sometimes comprises one or more files (e.g., text files). Computer code can be stored on a suitable non-transitory storage medium (e.g., in memory, e.g., on a computer's hard disk). Computer code files often are arranged into a directory tree (e.g., a source tree). Computer code of a module can be written in a suitable programming language non-limiting examples of which include C programming language, basic, R, R++, S, Java, HTML, the like, or combinations thereof. In some embodiments a suitable main program acts as an interpreter for a computer code. In some embodiments a module comprises and/or has access to memory. Modules are sometimes controlled by a microprocessor. In certain embodiments a module or a machine comprising one or more modules, gathers, assembles, receives, obtains, accesses, recovers, provides and/or transfers data and/or information to or from another module, machine, component, peripheral or operator of a machine. In some embodiments, data and/or information (e.g., sequence reads, counts, etc.) are provided to a module by a machine comprising one or more of the following: one or more flow cells, a camera, a detector (e.g., a photo detector, a photo cell, an electrical detector (e.g., an amplitude modulation detector, a frequency and phase modulation detector, a phase-locked loop detector), a counter, a sensor (e.g., a sensor of pressure, temperature, volume, flow, weight), a fluid handling device, a printer, a display (e.g., an LED, LCT or CRT), the like or combinations thereof. Sometimes an operator of a machine provides a constant, a threshold value, a formula or a predetermined value to a module. A module is often configured to transfer data and/or information to or from another module or machine. A module can receive data and/or information from another module, non-limiting examples of which include a compression module, sequencing module, mapping module, filtering module, bias density module, relationship module, bias correction module, multivariate correction module, distribution module, profile generation module, PCA statistics module, portion weighting module, scoring module, outcome module, display module, the like or combination thereof. A module can manipulate and/or transform data and/or information. Data and/or information derived from or transformed by a module can be transferred to another suitable machine and/or module, non-limiting examples of which include a compression module, sequencing module, mapping module, filtering module, bias density module, relationship module, bias correction module, multivariate correction module, distribution module, profile generation module, PCA statistics module, portion weighting module, scoring module, outcome module, display module, the like or combination thereof. A machine comprising a module can comprise at least one processor. In some embodiments, data and/or information are received by and/or provided by a machine comprising a module. A machine comprising a module can include a processor (e.g., one or more processors) which processor can perform and/or implement one or more instructions (e.g., processes, routines and/or subroutines) of a module. In some embodiments, a module operates with one or more external processors (e.g., an internal or external network, server, storage device and/or storage network (e.g., a cloud)). In some embodiments a system, (e.g., an embodiment of a system shown in FIG. 10) comprises one or more of a compression module, sequencing module, mapping module, filtering module, bias density module, relationship module, bias correction module, multivariate correction module, distribution module, profile generation module, PCA statistics module, portion weighting module, scoring module, outcome module, display module, the like or combination thereof.

Transformations

As noted above, data sometimes is transformed from one form into another form. The terms "transformed", "transformation", and grammatical derivations or equivalents thereof, as used herein refer to an alteration of data from a physical starting material (e.g., test subject and/or reference subject sample nucleic acid) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent and/or visually represent the presence or absence of a genomic insertion, duplication or deletion; represent the presence or absence of a variation in the physical amount of a sequence associated with medical conditions). A virtual representation sometimes is further transformed into one or more numerical values or graphical representations of the digital representation of the starting material. These methods can transform physical starting material into a numerical value or graphical representation, or a representation of the physical appearance of a test subject's genome.

In some embodiments methods and systems herein transform a mixture of a multitude of polynucleotide fragments found in the blood of a pregnant female into one or more representations of specific microscopic and/or submicroscopic structures (e.g., a chromosome, or segment thereof) present in fetal, maternal or placental cells. These polynucleotide fragments generally originate from different cells and tissues (e.g., maternal, placental, fetal, e.g., muscle, heart, liver, lymphocytes, tumor), different chromosomes, and different genetic elements and/or locations (e.g., centromeric regions, repetitive elements, GC rich regions, hypervariable regions, different genes, different regulatory elements, introns, exons, and the like). In some embodiments a system described herein transforms polynucleotide fragments, by use of a sequencing machine, into sequence reads. In some embodiments a system described herein transforms sequence reads, which sequence reads comprise bias, to normalized sequence counts, read densities and/or profiles. Sequence reads are often transformed into normalized sequence counts, read densities and/or profiles in which bias is significantly reduced, often by use of a bias reduction machine and/or one or more suitable processes and/or modules (e.g., a mapping module, bias density module, relationship module, bias correction module, and/or multivariate correction module). Normalized sequence reads and read densities and/or read density profiles generated from normalized sequence reads having reduced bias are useful for generating a more confident outcome. Sequence reads are often altered by a transformation that changes specific sequence read parameters and reduces bias, thereby providing normalized sequence reads which are sometimes transformed into profiles and outcomes.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fetal gender prediction, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principle component analysis of derived quantities; and the like or combinations thereof.

EXAMPLES

The following examples are provided by way of illustration only and not by way of limitation. Thus, the examples set forth below illustrate certain embodiments and do not limit the technology. Those of skill in the art will readily recognize a variety of non-critical parameters that could be changed or modified to yield essentially the same or similar results.

Example 1

ChAl

Figure 10B:
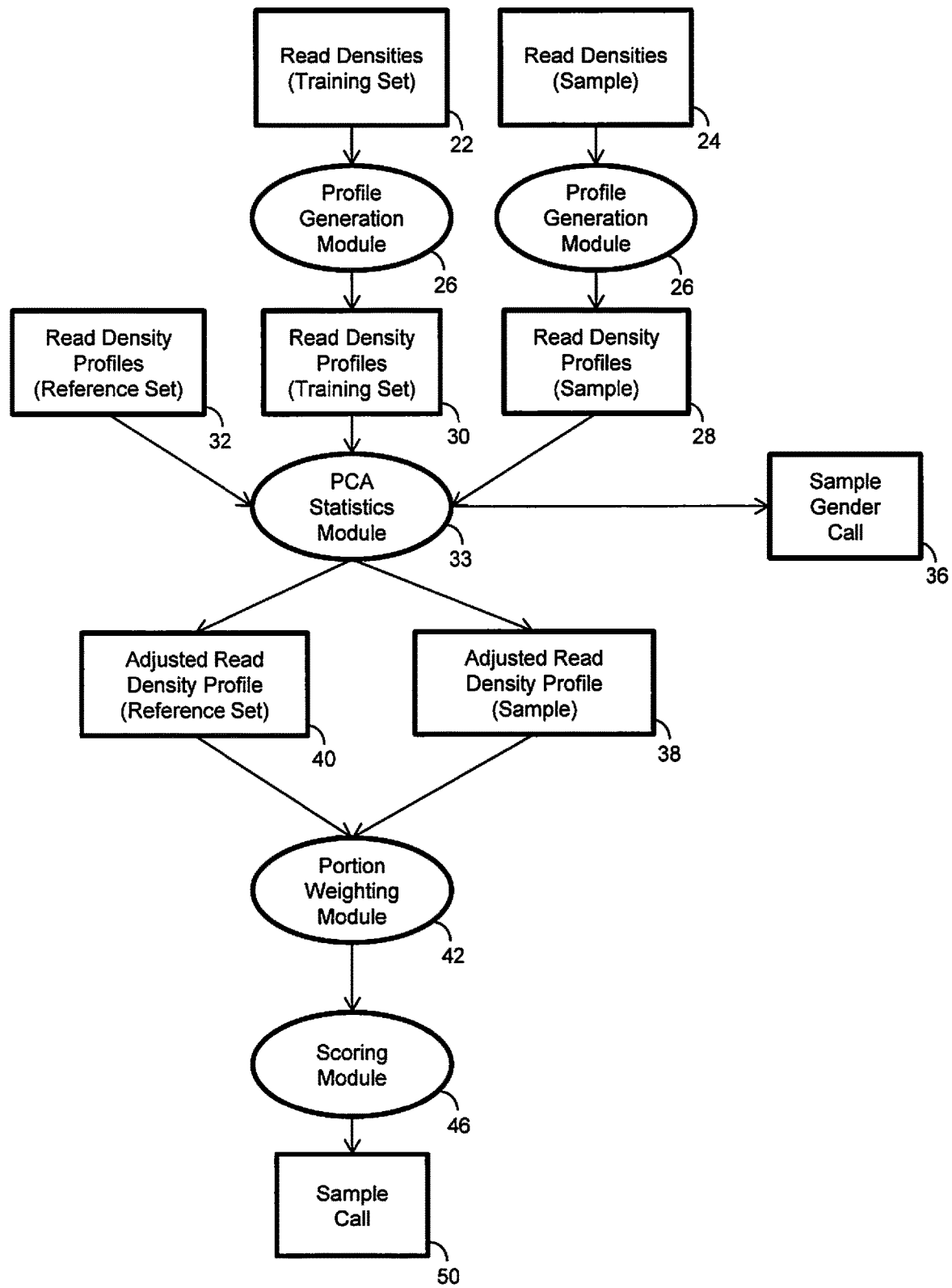

ChAl is an exemplary system for determining the presence or absence of a chromosome aneuploidy in a fetus from sequence reads obtained from a test subject (e.g., a pregnant female). An example of a system flow chart for ChAl is shown in FIGS. 10A and 10B. Sequence read were obtained from a pregnant female test subject and one or more reference subjects sometimes referred to herein as a training set. Pregnant female subjects of the training set had fetuses that were euploid as confirmed by other testing methods.

Sequence reads were first compressed from a SAM or BAM format to a binary-reads format (BReads format) which allowed ChAl to run much more quickly. The BReads format stores the genomic location of each read, including a chromosome and base pair position determined according to a reference genome and discards other information. A BReads file begins with a count of the reads contained. This improves loading times by eliminating the need for memory reallocations. The value was stored on disk as a four-byte array. Reads were then stored using a 5-byte format, one for the chromosome ordinal (zero-index of 1-22,X,Y,M), and four for the chromosome position. BReads files were loaded by first reading the sequence read count from the first four bytes. Each sequence read is then loaded five bytes at a time, with the first byte indicating a chromosome ordinal and the next four converting to the integer position. Random sampling of reads can be performed quickly by using disk-skip commands to specific read indexes.

As an example, the disk usage of different formats is compared to the disk usage of Breads format in Table I for 17,673,732 mapped reads.

TABLE 1

Disk usage for different formats based on a sample with 17,673,732 reads.

| Format | Space Usage |
|---|---|
| SAM | 4.0 GB |
| Mapped read positions | 247 MB |
| GZip read positions | 97 MB |
| BReads | 85 MB |

The BReads format was roughly 50× smaller than the original SAM file and used about 12% less space than a GZip format. BReads also had the advantage of storing the number of reads at the head for one-time memory allocation, and can be quickly sampled since reads do not have to be read in order. These features were not possible with the other formats.

Modeling GC Bias

GC-bias models were then learned for each sample. Samples which were designated for training were used, in part, to create a portion filter and to learn other genome biases which are not well accounted for by GC bias alone. Finally, the training statistics were used to filter and score test samples.

ChAl modeled GC bias using density estimates of local GC content. GC density was estimated from a reference genome using a kernel function such as the Epanechnikov kernel (FIG. 1). Other kernels are also appropriate, including a Gaussian or a triweight kernel. The bandwidth was selected as 200 bp, however the bandwidth parameter is flexible.

Figure 2:
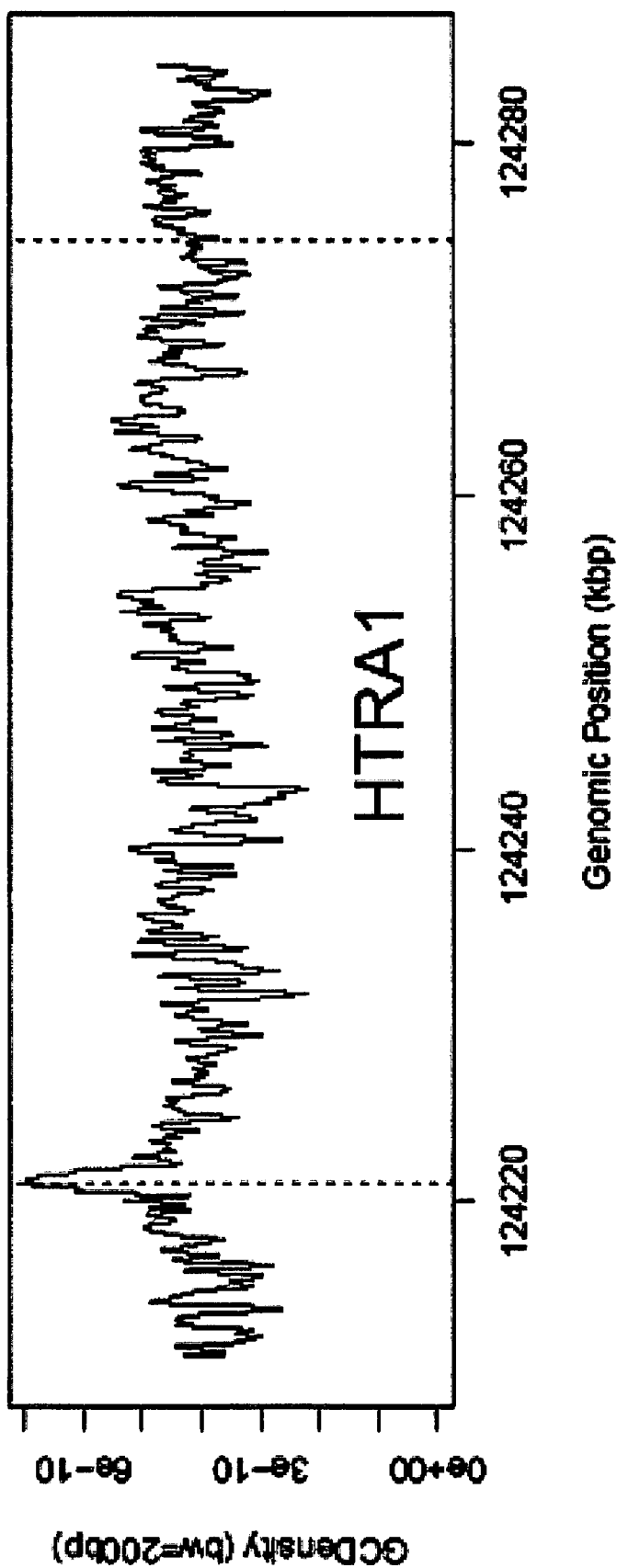
FIG. 2 shows a plot of GC densities (y-axis) for the HTRA1 gene where GC densities are normalized across an entire genome. Genomic positions are shown on the x-axis.
Figure 3:
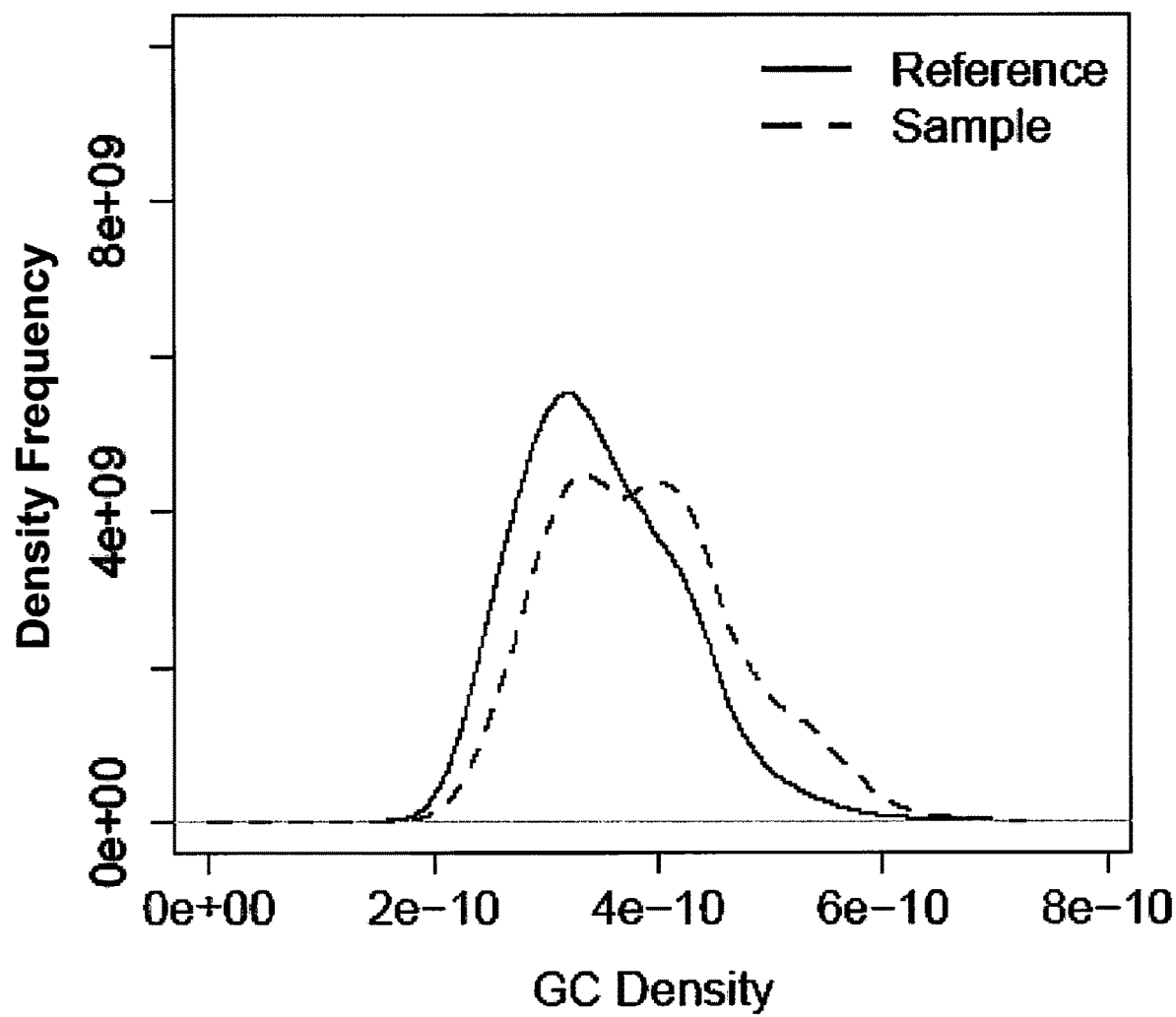
FIG. 3 shows a distribution of local genome bias estimates (e.g., GC Density, x-axis) for a reference genome (solid line) and for sequence reads obtained from a sample (dashed line). Bias frequencies (e.g., Density Frequency) are shown on the y-axis. GC density estimates are normalized across an entire genome. In this example, the sample has more reads with high GC content than would be expected from the reference.
Figure 4:
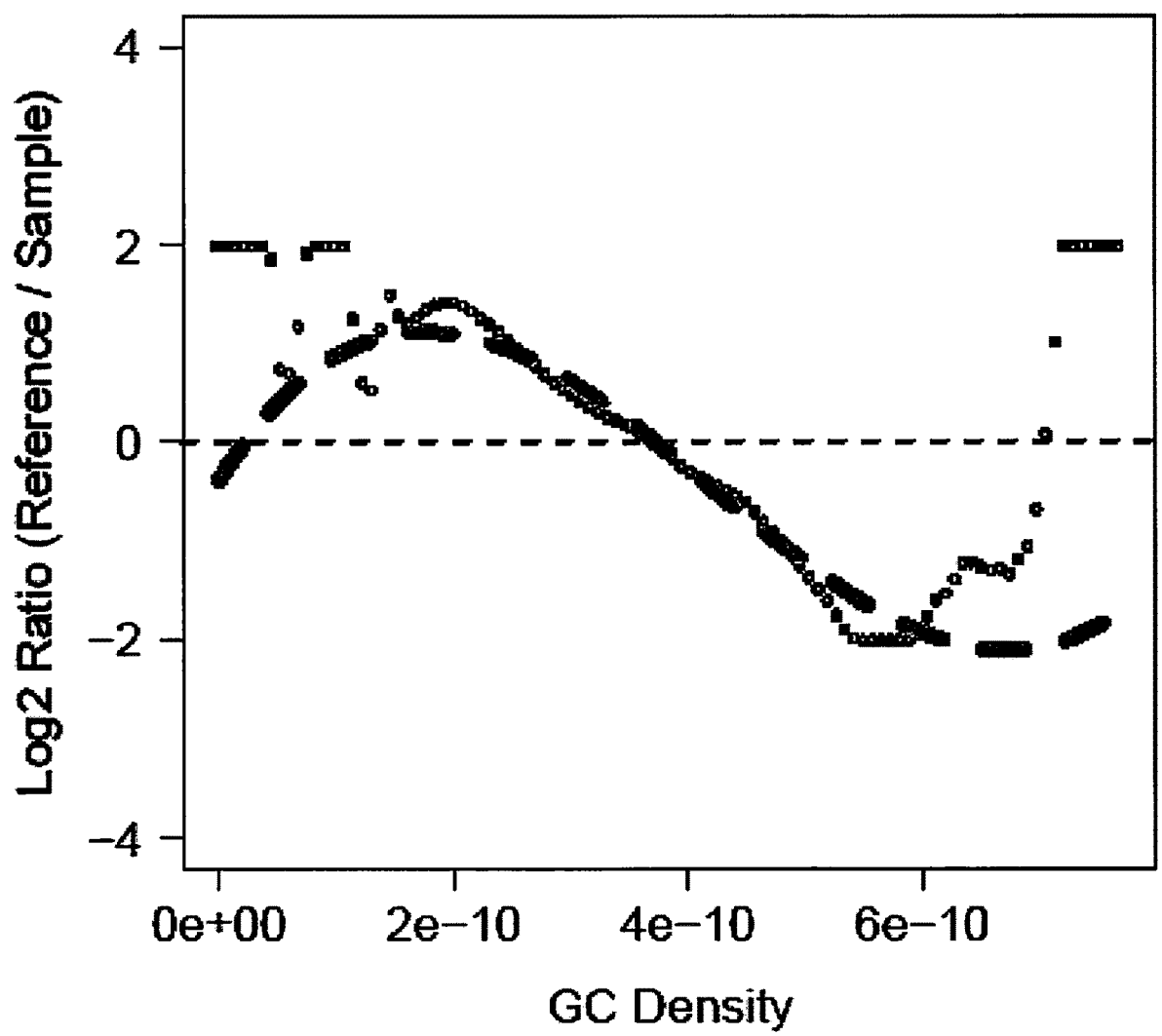
FIG. 4 shows a comparison of a distribution of GC density estimates for a reference genome and GC density estimates of sequence reads for a sample using a weighted $3^{rd}$ order polynomial fitted relationship. GC density estimates (x-axis) were normalized across an entire genome. GC density frequencies are represented on the y-axis as a log 2 ratio of density frequencies of the reference divided by those of the sample

Using a kernel, GC density was estimated at base-pair resolution on a reference genome (e.g., as shown in FIG. 2). Using the GC density estimates of the reference, the local GC content of each read from a sample was determined. The distribution of GC density estimates for the sample was then compared to the distribution across the whole reference genome to determine GC bias (FIG. 3). Reads and reference values which map to AT-rich regions (GC density=0) were discarded. The difference between a sample's GC-density distribution and a reference was modeled using a polynomial, fit on a log-ratio of the density of the reference distribution divided by the density of the sample's distribution (FIG. 4). The model was fit in a weighted fashion, with each weight taken as the sample's distribution-density value for a given GC-density value. This ensured that the tails of the distribution did not excessively drive the fit. Other fitting models, such as a quantile regression model or parameterized distributions can be used as is appropriate for the bias's distribution.

Using the fit GC model, each count of a sequence read for a sample was weighted to adjust for its over- or under-representation as compared to the reference. By incorporating these weights into the estimation of read-density, the ChAl algorithm was able to correct for GC biases.

Multidimensional Bias Correction

GC Bias was only one of several biases affecting read patterns in a genome. Additional biases were sometimes modeled and corrected for using a generalized multivariate model to estimate read weights. This correction was performed as follows:

1. N bias values were estimated for a test sample and a reference genome at each of a subset of genomic positions.

2. Density of the bias values was modeled using an N-dimensional smoothing kernel or an appropriate parametric function.
3. The log-ratio was calculated for a set of density values taken from the reference and test densities.
4. The log-ratio of density was modeled using the chosen points with a multivariate model (e.g., weighted 3rd order polynomial for each dimension).
5. The model was used to estimate the ratio of the frequency of a given read compared to the reference, and the appropriate weight was assigned.

Portion Filtering

Samples were scored for chromosomal abnormalities based on the representation of sequence reads (e.g., counts) on the genome. This representation was determined using a density function, similar to the one used for local GC estimation. The read-density kernel generally has a much larger bandwidth, with the default being 50,000 bp. Each count of a read contributes to the density a value equal to its weight from the GC-bias model. The read-density can be evaluated at any or all base-pairs, but for computational performance only certain locations were used. These positions were termed "portions". Portions can be located wherever it is most important to estimate read-density. For the classification of chromosomal aneuploidies portions were initially (e.g., before filtering) spaced evenly across the genome. Each portion comprised of a 50,000 bp window and, prior to filtering, overlapped the next adjacent portion by 25,000 bp.

Some portions include poorly mapped genomic regions which led to extreme perturbations in read-density from sample to sample. ChAI identified and removed these portions by a filtering process using a training set. Portions which showed large deviations in median (e.g., FIG. 5A) and/or MAD values (e.g., FIG. 5B) were removed from consideration. The threshold of these deviations was taken as any value outside the training population quartiles by more than four times the inter-quartile range (FIG. 5). This threshold can be fine-tuned to maximize test performance for a specific set of ChAI parameters.

Training and Scoring

Using only reads which map to filtered portions, each sample's genome read-density profile was calculated. Samples which were part of the training set were then used to estimate training statistics which were used for scoring the test set. These statistics consisted of portion medians, principal-components, and null distributions for the scoring test statistic. The portion medians and principal components were used for modeling genome-wide read biases which may be present from any number of biological and technical artifacts (FIG. 6A-C). To minimize the impact of extreme portion values on the rest of the sample, each value which was outside of 4xIQR across the other portions in a sample was trimmed to 4xIQR.

Test samples were corrected for hidden biases by first subtracting the trained median values from the test portion values. The components of the sample values which correlate with the top trained principal components were also removed. This was done by modeling the portion values using multivariate linear regression based on the principal component terms (FIG. 7). The values predicted by the model were subtracted from the sample values, leaving only the unbiased residuals. The number of principal components used is optional, with the default being eight.

After corrections, samples were scored using a Fisher-exact test. This test compared the number of portions whose values were greater or less than the trained median in the chromosomal region of interest. These counts were evaluated against the rest of the portions in the genome. The scoring statistic was taken as the negative log 10 p-value. Other scoring statistics can be used in this step, such as a Wilcoxon signed-rank test or an F-test.

Figure 8:
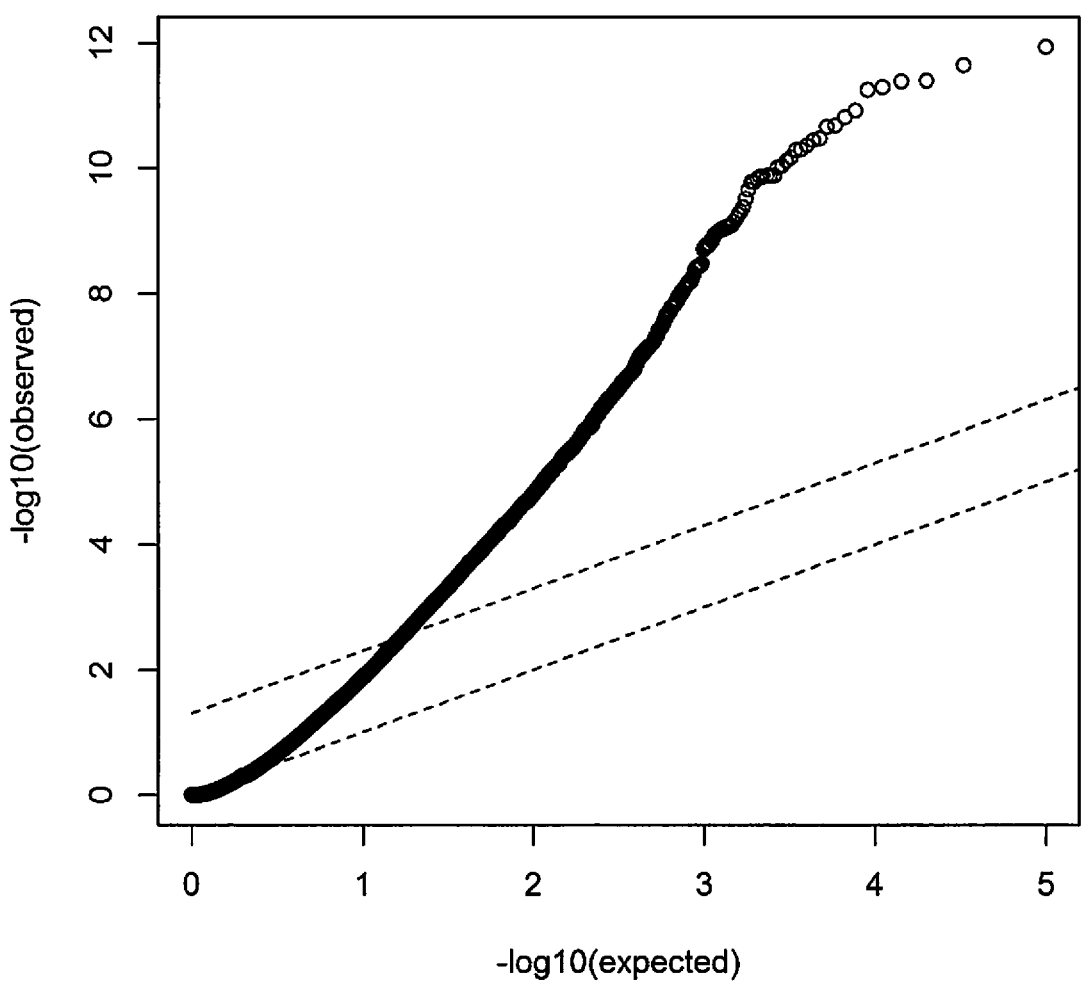
FIG. 8 shows a QQ-plot of test p-values from bootstrapped training samples for a T21 test. A QQ plot generally compares two distributions.

Due to residual correlations between portions, the test statistic was inflated in both the training and test samples. This inflation was estimated from bootstraps of the training set (FIG. 8).

The scores for test samples were corrected using this null distribution as an empirical background. Scores which are much larger than those in the empirical distribution were corrected using a Pareto extrapolation of the tail of the null distribution.

Calling Gender

Figure 9B:
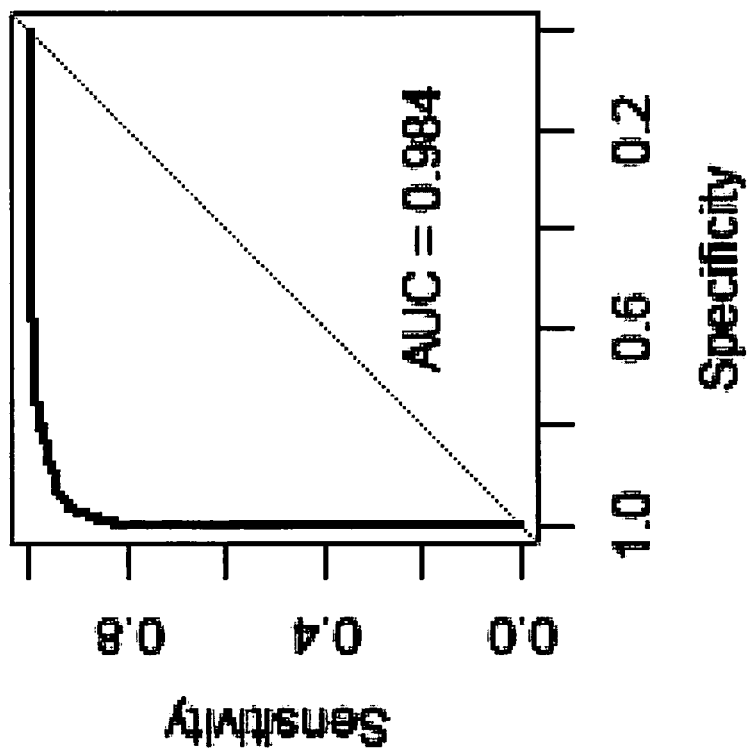
FIG. 9B shows a receiver operating characteristic (ROC) plot for gender calls with a PC2 coefficient. Gender calls performed by sequencing was used for the truth reference.
Figure 9A:
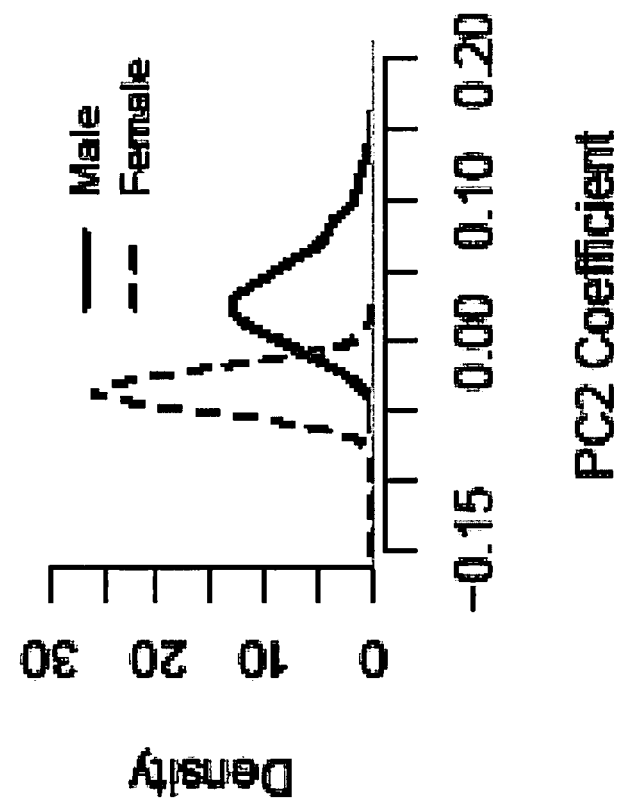
FIG. 9A shows a read density plot showing a difference in PC2 coefficients for men and women in a training set.

Gender was determined from a sample's principal component profile. In a training data set, the 2nd principal component (e.g., PC2) was highly correlated with gender. Using a regression coefficient of this component as a test statistic was a highly accurate test of gender (FIG. 9A-9B).

Removing Portion Dependencies

An additional step was taken during a ChAI run to improve the predictive power of the approach. This involved reducing the amount of correlation structure in the portion-sample matrix, which better supports the test assumption of variable independence and reduced the frequency of significant scores in the null permutations. The approach involved replacing the portions with orthogonal eigen-portions which contain nearly all of the same information, but without correlation structure.

The first step was to learn a transform matrix Meig for a set of training portions M:
1. SVD decomposition: M=U*D*VT
2. Choose the number of independent eigen-portions N: (e.g., Such that the cumulative fraction of the N diagonal elements of D is greater than 95%)
3. Compute the pseudoinverse: Meig=pinv(U[ . . . , 1:N]*D [1:N, 1:N])

Left-multiplication of any subset of the portion matrix M by its corresponding Meig resulted in a dimension-reduced correlation-free representation of that subset. In this way, Meig was derived on a training dataset and applied to test samples without further modification.

Meig was also used to transform the test variable. The test variable was represented as a vector consisting of all zeros, with ones at locations of expected deviations (e.g., Chr 21 portions). This vector was transformed with Meig through left-multiplication to appropriately match the transformed portion data.

This approach can only create as many independent eigen-portions as there are samples in the training set. For an example training set of 50,000 portions and 1,000 samples, the transformed data would contain, at most, 1,000 portions. This was likely an over-correction, reducing the number of portions drastically. The approach can be performed more loosely by computing separate Meig transforms for smaller subsets of the portion data and applying them separately. This was particularly useful for removing local correlation structure from neighboring portions. Other approaches can also be used to reduce portion correlation structure. For example, many clustering methods can be used to group portions and replace them with a smaller set of aggregate portions (e.g., based on group averages or centroids).

Example 2

Distribution/Profile Generation Module

A script was written in Java for generating read density profiles from sequence read data (e.g., BReads). The code below was designed to collect read data for each sequence read and update a density profile at the appropriate read density windows (e.g., individual read densities for a portion), weighted by the distance of a read from the median or middle point of a portion, and according to a sample's GC bias correction (see Example 4). The script below can call or utilize uses weighted and/or normalized counts generated from a relationship module or bias correction module (Example 4). In some embodiments a distribution module can comprise some or all, or a variation of the Java script shown below. In some embodiments a profile generation module can comprise some or all, or a variation of the Java script shown below:

```
package utilities.genome;
import java.util.Iterator;
import utilities.data.VectorUtil;
import utilities.text.DataFormatter;
public class ChromDensScaleRunnable implements Runnable{
    private GenomeScaleBoolean mask;
    private GenomeScaleFloat density;
    private final String modelPath;
    private final String brPath;
    private final int bandwidth;
    private final GenomeFloat gcdens;
    private final int stepSize;
    private final int sampleSize;
    private final int shift;
    private final String report;
    public ChromDensScaleRunnable(String modelPath, String brPath, int bandwidth,
GenomeFloat gcdens, int stepSize, GenomeScaleBoolean mask, String report, int sampleSize, int shift)
    {
        this.modelPath = modelPath;
        this.brPath = brPath;
        this.bandwidth = bandwidth;
        this.gcdens = gcdens;
        this.stepSize = stepSize;
        this.mask = mask;
        this.report = report;
        this.sampleSize = sampleSize;
        this.shift = shift;
    }
    public void run( )
    {
        double[ ] mdat = (gcdens==null) ? null : VectorUtil.loadDoubleFromFile(modelPath, 6);
        //Build density
        density = new GenomeScaleFloat(stepSize);
        double correction = 0;
        try
        {
            Iterator<GenomicPosition> readIterator = (sampleSize==-1) ?
GenomeIO.scanBReads(brPath) : new BReadsSampler(brPath, sampleSize,true);
            while (readIterator.hasNext( ))
            {
                GenomicPosition gp = readIterator.next( ).shift(shift);
                int pos = gp.pos;
                int start = Math.max(0, pos-bandwidth);
                int end = Math.min(pos+bandwidth, GenomeUtil.chromosomeSize(gp.chr)-1);
                int cindex = gp.chr.ordinal( );
                double weight;
                if (gcdens!=null)
                {
                    float gc = gcdens.values[cindex][pos-1];
                    if (gc==0) continue;
                    weight = modelWeight(mdat, gc);
                }else weight = 1;
                int[ ][ ] gpoints = density.getScalePoints(cindex, start, end, mask);
                if (gpoints[0].length==0 || Double.isNaN(weight)) continue;
                if (weight>2) weight = 2;
                if (weight<.5) weight = .5;
                correction += weight;
                for (int i=0;i<gpoints[0].length;i++)
                    density.values[cindex][gpoints[0][i]] += kernel((gpoints[1][i]-pos)/(double)bandwidth) * weight;
            }
        }catch (Exception e)
        {
            System.out.println("THROW!");
            e.printStackTrace( );
            System.exit(0);
        }
        //System.out.println(GenomeIO.countReadsFromBReads(brPath));
        //System.out.println(correction);
        //Normalize intensity
        for (int i=0;i<density.values.length;i++)
```

```
        for (int j=0;j<density.values[i].length;j++)
        {
            float blah = density.values[i][j];
            density.values[i][j] /= correction;
            if (Double.isNaN(density.values[i][j]) ||
Double.isInfinite(density.values[i][j]))
            {
                System.out.println("NA val2: "+modelPath+",
"+density.values[i][j]+", "+blah+", "+correction);
                System.exit(0);
            }
        }
        if (report!=null) System.out.println(report);
    }
    public GenomeScaleFloat density( )
    {
        return density;
    }
    private static double kernel(double x)
    {
        return .75 * (1.0 – x*x);
    }
    public static double modelWeight(double[ ] mdat, double gcdens)
    {
        if (mdat[5]==1) gcdens = Math.log(gcdens);
        double x2 = gcdens * gcdens;
        return Math.pow(2, mdat[0] + mdat[1] * gcdens + mdat[2] * x2 + mdat[3] * x2 *
gcdens);
    }
}
```

Example 3

Filtering Module

A script was written in R for filtering portions of a read density profile. This code examines a read density profile across all samples and identifies portions that are retained and/or portions that are discarded (e.g., removed from the analysis), based on an inter-quartile range. In some embodiments a filtering module comprises some or all, or a variation of the R script shown below:

```
rcodepath <- "l:/ghannum/Projects/Binless/RCode"
mdistpath <-
"l:/ghannum/Projects/Binless/Reference/MarkerDistribution__LDTv2__200__50000__50000.txt"
outpath <-
"l:/ghannum/Projects/Binless/Reference/LDTv2__200__50000__50000__MarkerMask.txt"
args <- commandArgs(trailingOnly = TRUE)
rcodepath <- args[1]
mdistpath <- args[2]
outpath <- args[3]
source(paste(rcodepath,"/src/utilities/scanmatrix.R",sep=""))
dat <- scanMatrix(mdistpath,rownames=FALSE,colnames=TRUE)
m <- apply(dat,1,median)
v <- apply(dat,1,mad)
qm <- quantile(m,c(.25,.75))
qv <- quantile(v,c(.25,.75))
scalem <- qm[2]-qm[1]
scalev <- qv[2]-qv[1]
ok <- m > qm[1]-4*scalem & m < qm[2]+4*scalem & v > qv[1]-4*scalev & v < qv[2]+4*scalev
write.table(matrix(as.integer(ok),1),row.names=F,col.names=F,quote=F,file=outpath,sep="")
```

Example 4

Bias Density Module, Relationship Module, Bias Correction Module & Plotting Module A script was written in R for generating bias densities, generating and comparing a relationship and for correcting bias in sequence reads. This code generally directs a microprocessor to analyze one or more samples and build a bias model (e.g., a relationship and/or a comparison of relationships) based on local genome bias estimations (e.g., GC densities) for each sample and a reference. The script below directs one or more processors, in part, to generate a relationship between (i) guanine and cytosine (GC) densities and (ii) GC density frequencies for sequence reads of a test sample, thereby generating a sample GC density relationship, (b) compare the sample GC density relationship and a reference GC density relationship, thereby generating a comparison, wherein, the reference GC density relationship is between (i) GC densities and (ii) the GC density frequencies for a reference and, with a suitable modification of the script, (c) normalize counts of the sequence reads for the sample according to the comparison determined in (b), where bias in the sequence reads for the sample is reduced. In some embodiments, a bias density module, a relationship module, a bias correction module and/or a plotting module comprises, some, all or a modification of some or all of the script shown below.

```
gcpath <- "l:/ghannum/Projects/Binless/Reference/BiasMaps/DnaseDensity_200_dist.txt"
inpath <- "l:/ghannum/Projects/Binless/Models/LDTv2_DNase-200"
outpath <- "l:/ghannum/Projects/Binless/Models/LDTv2_DNase-200"
makePlots <- TRUE
logTransform <- TRUE
args <- commandArgs(trailingOnly = TRUE)
gcpath <- args[1]
inpath <- args[2]
outpath <- args[3]
makePlots <- args[4]
logTransform <- as.logical(args[5])
paths <- dir(inpath)
paths <- paths[grep("_BiasDistr.txt$",paths)]
gcref <- scan(gcpath,0)
gcref <- gcref[gcref!=0]
if (logTransform) gcref <- log(gcref)
from <- quantile(gcref,.005)
to <- quantile(gcref,.995)
x <- seq(from,to,length.out=100);
d1y <- predict(smooth.spline(density(gcref,from=from,to=to)),x)$y
if (!logTransform) d1y <- sapply(d1y,function(x){max(x,0)})
print(paste("Processing",length(paths),"models."))
for (f in paths)
{
    distr <- scan(paste(inpath,"/",f,sep=""),0)
    distr <- distr[distr!=0]
    if (logTransform) distr <- log(distr)
    d2y <- predict(smooth.spline(density(distr,from=from,to=to)),x)$y
    if (!logTransform) d2y <- sapply(d2y,function(x){max(x,0)})
    pp <- log2(d1y / d2y)
    pp[pp > 2] <- 2; pp[pp < -2] <- -2
    ok <- !is.na(pp)
    mod <- lm(pp[ok]~x+I(x^2)+I(x^3), data=list(x=x[ok]), w=d2y[ok])
    w <- 2^predict(mod,list(x=distr))
    fname <- substr(f,1,nchar(f)-14)
    out <- c(mod$coefficients,mean(w))
    out[out==Inf] <- "Infinity"
    out[out==-Inf] <- "-Infinity"
    write.table(matrix(c(out,as.integer(logTransform)),ncol=1),file=paste(outpath,"/",fname,"_BiasMod.txt",sep=""),row.names=F,col.names=F,quote=F)
    if (makePlots)
    {
    png(units="in",height=4,width=4,res=300,file=paste(outpath,"/",fname,"_BiasMod.png",sep=""))
        if (logTransform)
        {
            plot(x[ok],pp[ok],ylim=c(-4,4),xlab="Bias Density",ylab="Log2 Ratio (Reference / Sample)")
        }else plot(x[ok],pp[ok],ylim=c(-4,4),xlab="Log-Bias Density",ylab="Log2 Ratio (Reference / Sample)")
        abline(h=0,lty=2)
        lines(x[ok],predict(mod),col=3)
        dev.off( )
    }
}
##Demo transformation
#load("l:/ghannum/Projects/Binless/2012_11_13_cewi_PERUN_19FCs_AltGCbias_chrFractions.RData")

#d <- dir("l:/ghannum/Projects/Binless/GCDistribution/LDTv2/")
#d <- d[grep("_GCDistr.txt",d)]
#v <- as.numeric(df.cewi.GCbiasTable[,"gcBiasRobust"])[1:length(d)]

#a <- scan(paste("l:/ghannum/Projects/Binless/GCDistribution/LDTv2/",d[which.min(v)],sep=""),0);
a <- sort(a)
#b <- scan(paste("l:/ghannum/Projects/Binless/GCDistribution/LDTv2/",d[which.max(v)],sep=""),0);
d <- sort(d)

#r <- scan("l:/ghannum/Projects/Binless/Reference/GCDensity_200_density.txt",0)

#plot(density(r),ylim=c(0,1e10),xlab="GC Density"); lines(density(a),col=3); lines(density(b),col=2)

#a <- a[a!=0]
#b <- b[b!=0]
#r <- r[r!=0]

#plot(density(r),ylim=c(0,1e10),xlab="GC Density"); lines(density(a),col=3); lines(density(b),col=2)
```

-continued

```

#modA <-
as.numeric(scan(paste("l:/ghannum/Projects/Binless/GCDistribution/LDTv2/",substr(d[which.
min(v)],1,nchar(d[which.min(v)])-12),"_GCMod.txt",sep=""),""))
#modB <-
as.numeric(scan(paste("l:/ghannum/Projects/Binless/GCDistribution/LDTv2/",substr(d[which.
max(v)],1,nchar(d[which.max(v)])-12),"_GCMod.txt",sep=""),""))

#wa <- sapply(a,function(x){2^sum(c(1,x,x^2,x^3)*modA[1:4])})
#wb <- sapply(b,function(x){2^sum(c(1,x,x^2,x^3)*modB[1:4])})

#wa <- wa/(length(wa)*modA[5])
#wb <- wb/(length(wb)*modB[5])

#plot(density(r),ylim=c(0,1e10),xlab="GC Density"); lines(density(a,weights=wa),col=3);
lines(density(b,weights=wb),col=2)
```

Example 5

Examples of Embodiments

The examples set forth below illustrate certain embodiments and do not limit the technology.

A1. A system comprising memory and one or more microprocessors, which one or more microprocessors are configured to perform, according to instructions in the memory, a process for reducing bias in sequence reads for a sample, which process comprises:

(a) generating a relationship between (i) guanine and cytosine (GC) densities and (ii) GC density frequencies for sequence reads of a test sample, thereby generating a sample GC density relationship, wherein, the sequence reads are of circulating cell-free nucleic acid from the test sample, and the sequence reads are mapped to a reference genome;

(b) comparing the sample GC density relationship and a reference GC density relationship, thereby generating a comparison, wherein, the reference GC density relationship is between (i) GC densities and (ii) the GC density frequencies for a reference; and (c) normalizing counts of the sequence reads for the sample according to the comparison determined in (b), whereby bias in the sequence reads for the sample is reduced.

A1.1. A system comprising a sequencing apparatus and one or more computing apparatus, which sequencing apparatus is configured to produce signals corresponding to nucleotide bases of a nucleic acid loaded in the sequencing apparatus, which nucleic acid is circulating cell-free nucleic acid from the blood of a pregnant female bearing a fetus, or which nucleic acid loaded in the sequencing apparatus is a modified variant of the circulating cell-free nucleic acid; and which one or more computing apparatus comprise memory and one or more processors, which memory comprises instructions executable by the one or more processors and which instructions executable by the one or more processors are configured to:

produce sequence reads from the signals and map the sequence reads to a reference genome;

(a) generate a relationship between (i) guanine and cytosine (GC) densities and (ii) GC density frequencies for sequence reads of a test sample, thereby generating a sample GC density relationship;

(b) compare the sample GC density relationship and a reference GC density relationship, thereby generating a comparison, wherein, the reference GC density relationship is between (i) GC densities and (ii) the GC density frequencies for a reference; and (c) normalize counts of the sequence reads for the sample according to the comparison determined in (b), whereby bias in the sequence reads for the sample is reduced.

A1.2. The system of embodiment A1 or A1.1, wherein the normalizing in (c) comprises providing normalized counts.

A2. The system of any one of embodiments A1 to A1.2, wherein each of the GC densities is determined by a process comprising use of a kernel density estimation.

A2.1. The system of any one of embodiments A1 to A2, wherein each of the GC densities for the reference GC density relationship and the sample GC density relationship is a representation of local GC content.

A2.2. The system of embodiment A2.1, wherein the local GC content is for a polynucleotide segment of 5000 bp or less.

A3. The system of any one of embodiments A1 to A2.2, wherein each of the GC densities is determined by a process comprising use of a sliding window analysis.

A4. The system of embodiment A3, wherein the window is about 5 contiguous nucleotides to about 5000 contiguous nucleotides and the window is slid about 1 base to about 10 bases at a time in the sliding window analysis.

A5. The system of embodiment A3, wherein the window is about 200 contiguous nucleotides and the window is slid about 1 base at a time in the sliding window analysis.

A6. The system of any one of embodiments A1 to A5, wherein (b) comprises generating a fitted relationship between (i) ratios, each of which ratios comprises a sample GC density relationship frequency and a reference GC density relationship frequency for each of the GC densities and (ii) GC densities.

A7. The system of embodiment A6, wherein the fitted relationship in (a) is obtained from a weighted fitting.

A8. The system of any one of embodiments A1 to A7, wherein each of the sequence reads for the sample is represented in a binary format and/or a text format.

A9. The system of embodiment A8, wherein the binary format for each of the sequence reads comprises a chromosome to which the read is mapped and a chromosome position to which the read is mapped.

A10. The system of embodiment A9, wherein the binary format is in a 5-byte format comprising a 1-byte chromosome ordinal and a 4-byte chromosome position.

A11. The system of any one of embodiments A8 to A10, wherein the binary format is 50 times smaller than a sequence alignment/map (SAM) format and/or about 13% smaller than a GZip format.

A12. The system of any one of embodiments A1 to A11, wherein the normalizing in (c) comprises factoring one or more features other than GC density, and normalizing the sequence reads.

A13. The system of embodiment A12, wherein the factoring one or more features is by a process comprising use of a multivariate model.

A14. The system of A13, wherein the process comprising use of the multivariate model is performed by a multivariate module.

A14.1. The system of any one of embodiments A12 to A14, wherein the counts of the sequence reads are normalized according to the normalizing in (c) and the factoring of the one or more features.

A15. The system of any one of embodiments A1 to A14.1, comprising, after (c), generating a read density for one or more portions of a genome, or a segment thereof, according to a process comprising generating a probability density estimation for each of the one or more portions comprising the counts of the sequence reads normalized in (c).

A16. The system of embodiment A15, wherein the probability density estimation is a kernel density estimation.

A17. The system of embodiment A15 or A16, comprising generating a read density profile for the genome or the segment thereof.

A18. The system of embodiment A17, wherein the read density profile comprises the read densities for the one or more portions of the genome, or the segment thereof.

A19. The system of any one of embodiments A15 to A18, comprises adjusting each of the read densities for the one or more portions.

A20. The system of any one of embodiments A15 to A19, wherein the one or more portions are filtered thereby providing filtered portions.

A21. The system of any one of embodiments A15 to A20, wherein the one or more portions are weighted thereby providing weighted portions.

A22. The system of embodiment A21, wherein the one or more portions are weighted by an eigen function.

A23. The system of any one of embodiments A1 to A22, comprising, prior to (a), obtaining the sequence reads.

A24. The system of embodiment A23, wherein the sequence reads are generated by massively parallel sequencing (MPS).

A25. The system of any one of embodiments A1 to A24, comprising obtaining sequence reads mapped to an entire reference genome or a segment of a genome.

A26. The system of embodiment A25, wherein the segment of the genome comprises a chromosome or a segment thereof.

A27. The system of embodiment A25 or A26, wherein the counts of the sequence reads mapped to the reference genome are normalized prior to (a).

A28. The system of embodiment A27, wherein the counts of the sequence reads mapped to the reference genome are normalized by GC content, bin-wise normalization, GC LOESS, PERUN, GCRM, or combinations thereof.

A29. The system of any one of embodiments A27 or A28, wherein the counts of the sequence reads mapped to the reference genome are raw counts.

A30. The system of any one of embodiments A15 to A29, wherein each portion of the reference genome comprises about an equal length of contiguous nucleotides.

A31. The system of any one of embodiments A15 or A30, wherein each portion of the reference genome comprises about 50 kb.

A32. The system of any one of embodiments A15 to A31, wherein each portion of the reference genome comprises about 100 kb.

A33. The system of any one of embodiments A15 to A32, wherein each portion of the reference genome comprises a segment of contiguous nucleotides in common with an adjacent portion of the reference genome.

A34. The system of any one of embodiments A1 to A33, wherein the test sample is obtained from a pregnant female.

A35. The system of any one of embodiments A1 to A34, wherein the test sample comprises blood from a pregnant female.

A36. The system of any one of embodiments A1 to A35, wherein the test sample comprises plasma from a pregnant female.

A37. The system of any one of embodiments A1 to A36, wherein the test sample comprises serum from a pregnant female.

A38. The system of any one of embodiments A1 to A37, wherein nucleic acids are isolated from the test sample.

A39. The system of any one of embodiments A8 to A38, comprising compressing the sequence reads mapped to a reference genome in (a) from a sequence alignment format into a binary format.

A40. The system of embodiment A39, wherein the compressing is performed by a compression module.

A41. The system of any one of embodiments A1 to A40, wherein the GC densities and the GC density frequencies for the sequence reads of the test sample and for the reference are provided by a bias density module.

A42. The system of any one of embodiments A1 to A41, wherein the comparison in (b) is generated by a relationship module.

A43. The system of any one of embodiments A1 to A42, wherein normalizing in (c) is performed by a bias correction module.

A44. The system of any one of embodiments A15 to A43, wherein the read densities are provided by a distribution module.

A45. The system of any one of embodiments A20 to A44, wherein filtered portions are provided by a filtering module.

A46. The system of any one of embodiments A21 to A45, wherein adjusted read densities are provided by a read density adjusting module.

A46.1. The system of any one of embodiments A21 to A46, wherein weighted portions are provided by a portion weighting module.

A47. The system of embodiment A46.1, comprising one or more of the compression module, the bias density module, the relationship module, the bias correction module, the distribution module, the filtering module, the read density adjusting module and the portion weighting module.

A48. The system of any one of embodiments A1 to A47, wherein the memory of the system comprises the sequence reads of circulating cell-free nucleic acid from the test sample that are mapped to the reference genome.

B1. A system comprising memory and one or more microprocessors, which one or more microprocessors are configured to perform, according to instructions in the memory, a process for determining the presence or absence of an aneuploidy for a sample, which process comprises:
    (a) filtering, according to a read density distribution, portions of a reference genome, thereby providing a read density profile for a test sample comprising read densities of filtered portions, wherein, the read densities comprise sequence reads of circulating cell-free nucleic acid from a test sample from a pregnant female, and the read density distribution is determined for read densities of portions for multiple samples;

(b) adjusting the read density profile for the test sample according to one or more principal components, which principal components are obtained from a set of known euploid samples by a principal component analysis, thereby providing a test sample profile comprising adjusted read densities;

(c) comparing the test sample profile to a reference profile, thereby providing a comparison; and (d) determining the presence or absence of a chromosome aneuploidy for the test sample according to the comparison.

B1.1. A system comprising a sequencing apparatus and one or more computing apparatus, which sequencing apparatus is configured to produce signals corresponding to nucleotide bases of a nucleic acid loaded in the sequencing apparatus, which nucleic acid is circulating cell-free nucleic acid from the blood of a pregnant female bearing a fetus, or which nucleic acid loaded in the sequencing apparatus is a modified variant of the circulating cell-free nucleic acid; and which one or more computing apparatus comprise memory and one or more processors, which memory comprises instructions executable by the one or more processors and which instructions executable by the one or more processors are configured to:

produce sequence reads from the signals and map the sequence reads to a reference genome;

a) filter, according to a read density distribution, portions of a reference genome, thereby providing a read density profile for a test sample comprising read densities of filtered portions, wherein, the read densities comprise sequence reads of circulating cell-free nucleic acid from a test sample from a pregnant female, and the read density distribution is determined for read densities of portions for multiple samples;

(b) adjust the read density profile for the test sample according to one or more principal components, which principal components are obtained from a set of known euploid samples by a principal component analysis, thereby providing a test sample profile comprising adjusted read densities;

(c) compare the test sample profile to a reference profile, thereby providing a comparison; and (d) determine the presence or absence of a chromosome aneuploidy for the test sample according to the comparison.

B2. The system of embodiment B1 or B1.1, wherein the comparison comprises determining a level of significance.

B3. The system of any one of embodiments B1 to B2, wherein determining the level of significance comprises determining a p-value.

B4. The system of any one of embodiments B1 to B3, wherein the reference profile comprises a read density profile obtained from a set of known euploid samples.

B5. The system of any one of embodiments B1 to B4, wherein the reference profile comprises read densities of filtered portions.

B6. The system of any one of embodiments B1 to B5, wherein the reference profile comprises read densities adjusted according to the one or more principle components.

B7. The system of any one of embodiments B2 to B6, wherein the level of significance indicates a statistically significantly difference between the test sample profile and the reference profile, and the presence of a chromosome aneuploidy is determined.

B8. The system of any one of embodiments B1 to B7, wherein the multiple samples comprise a set of known euploid samples.

B9. The system of any one of embodiments B1 to B8, wherein the read densities of portions for the multiple samples are median read densities.

B10. The system of any one of embodiments B1 to B9, wherein the read densities of filtered portions for the test sample are median read densities.

B11. The system of any one of embodiments B4 to B10, wherein the read density profile for the reference profile comprises median read densities.

B12. The system of any one of embodiments B4 to B11, wherein the read densities for the test sample profile, the multiple samples and the reference profile are determined according to a process comprising use of a kernel density estimation.

B13. The system of any one of embodiments B10 to B12, wherein the test sample profile is determined according to the median read densities for the test sample.

B14. The system of any one of embodiments B11 to B13, wherein the reference profile is determined according to the median read density distributions for the reference.

B15. The system of any one of embodiments B1 to B14, comprising filtering portions of a reference genome according to a measure of uncertainty for the read density distribution.

B16. The system of embodiment B15, wherein the measure of uncertainty is a MAD.

B17. The system of any one of embodiments B1 to B16, wherein the counts of sequence reads mapped to filtered portions for the test sample are normalized by a process performed prior to (a) comprising:

(I) generating a relationship between (i) local genome bias estimates and (ii) bias frequencies for sequence reads of a test sample, thereby generating a sample bias relationship, wherein, the sequence reads are of circulating cell-free nucleic acid from the test sample, and the sequence reads are mapped to a reference genome;

(II) comparing the sample bias relationship and a reference bias relationship, thereby generating a comparison, wherein, the reference bias relationship is between (i) local genome bias estimates and (ii) the bias frequencies for a reference; and (III) normalizing counts of the sequence reads for the sample according to the comparison determined in (II), whereby bias in the sequence reads for the sample is reduced.

B18. The system of embodiment B17, wherein the normalizing in (III) comprises providing normalized counts.

B19. The system of embodiment B17 or B18, wherein each of the local genome bias estimates is determined by a process comprising use of a kernel density estimation.

B20. The system of any one of embodiments B17 to B19, wherein each of the local genome bias estimates is determined by a process comprising use of a sliding window analysis.

B21. The system of embodiment B20, wherein the window is about 5 contiguous nucleotides to about 5000 contiguous nucleotides and the window is slid about 1 base to about 10 bases at a time in the sliding window analysis.

B22. The system of embodiment B20, wherein the window is about 200 contiguous nucleotides and the window is slid about 1 base at a time in the sliding window analysis.

B23. The system of any one of embodiments B17 to B22, wherein (II) comprises generating a fitted relationship between (i) ratios, each of which ratios comprises a sample bias relationship frequency and a reference bias relationship frequency for each of the local genome bias estimates and (ii) local genome bias estimates.

B24. The system of embodiment B23, wherein the fitted relationship in (I) is obtained from a weighted fitting.

B25. The system of any one of embodiments B17 to B24, wherein each of the sequence reads for the sample is represented in a binary format.

B26. The system of embodiment B25, wherein the binary format for each of the sequence reads comprises a chromosome to which the read is mapped and a chromosome position to which the read is mapped.

B27. The system of embodiment B26, wherein the binary format is in a 5-byte format comprising a 1-byte chromosome ordinal and a 4-byte chromosome position.

B28. The system of any one of embodiments B25 to B27, wherein the binary format is 50 times smaller than a sequence alignment/map (SAM) format and/or about 13% smaller than a GZip format.

B29. The system of any one of embodiments B17 to B28, wherein the normalizing in (III) comprises factoring one or more features other than bias, and normalizing the counts of sequence reads.

B30. The system of embodiment B29, wherein the factoring one or more features is by a process comprising use of a multivariate model.

B31. The system of B30, wherein the process comprising use of the multivariate model is performed by a multivariate module.

B32. The system of any one of embodiments B29 to B31, wherein the counts of the sequence reads are normalized according to the normalizing in (III) and the factoring of the one or more features.

B33. The system of any one of embodiments B17 to B32, comprising, after (III), generating a read density for one or more portions of a genome, or a segment thereof, according to a process comprising generating a probability density estimation for each of the one or more portions comprising the counts of the sequence reads normalized in (III).

B34. The system of embodiment B33, wherein the probability density estimation is a kernel density estimation.

B35. The system of embodiment B33 or B34, comprising generating a read density profile for the genome or the segment thereof.

B36. The system of embodiment B35, wherein the read density profile comprises the read densities for the one or more portions of the genome, or the segment thereof.

B37. The system of any one of embodiments B33 to B36, comprises adjusting each of the read densities for the one or more portions.

B38. The system of any one of embodiments B33 to B37, wherein the one or more portions are filtered thereby providing filtered portions.

B39. The system of any one of embodiments B33 to B38, wherein the one or more portions are weighted thereby providing weighted portions.

B40. The system of embodiment B39, wherein the one or more portions are weighted by an eigen function.

B41. The system of any one of embodiments B17 to B40, wherein the local genome bias estimates are local GC densities and the bias frequencies are GC bias frequencies.

B42. The system of any one of embodiments B1 to B16, wherein the counts of sequence reads mapped to filtered portions for the test sample are normalized by a process performed prior to (a) comprising:
(1) generating a fitted relationship between (i) guanine and cytosine (GC) densities and (ii) GC density frequencies for the sequence reads of the test sample, thereby generating a sample GC density relationship, wherein the sequence reads are mapped to the reference genome;
(2) comparing the sample GC density relationship and a reference GC density relationship, thereby generating a comparison, wherein,
the reference GC density relationship is between (i) GC densities and (ii) the GC density frequencies for a reference; and
(3) normalizing counts of the sequence reads for the sample according to the comparison determined in (b), whereby bias in the sequence reads for the sample is reduced.

B43. The system of embodiment B42, wherein the normalizing in (3) comprises providing normalized counts.

B44. The system of embodiment B42 or B43, wherein each of the GC densities is determined by a process comprising use of a kernel density estimation.

B44.1. The system of any one of embodiments B42 to B44, wherein each of the GC densities for the reference GC density relationship and the sample GC density relationship is a representation of local GC content.

B44.2. The system of embodiment B44.1, wherein the local GC content is for a polynucleotide segment of 5000 bp or less.

B45. The system of any one of embodiments B42 to B44.2, wherein each of the GC densities is determined by a process comprising use of a sliding window analysis.

B46. The system of embodiment B45, wherein the window is about 5 contiguous nucleotides to about 5000 contiguous nucleotides and the window is slid about 1 base to about 10 bases at a time in the sliding window analysis.

B47. The system of embodiment B46, wherein the window is about 200 contiguous nucleotides and the window is slid about 1 base at a time in the sliding window analysis.

B48. The system of any one of embodiments B42 to B47, wherein (2) comprises generating a fitted relationship between (i) ratios, each of which ratios comprises a sample GC density relationship frequency and a reference GC density relationship frequency for each of the GC densities and (ii) GC densities.

B49. The system of embodiment B48, wherein the fitted relationship in (1) is obtained from a weighted fitting.

B50. The system of any one of embodiments B42 to B49, wherein each of the sequence reads for the sample is represented in a binary format.

B51. The system of embodiment B50, wherein the binary format for each of the sequence reads comprises a chromosome to which the read is mapped and a chromosome position to which the read is mapped.

B52. The system of embodiment B51, wherein the binary format is in a 5-byte format comprising a 1-byte chromosome ordinal and a 4-byte chromosome position.

B53. The system of any one of embodiments B50 to B52, wherein the binary format is 50 times smaller than a sequence alignment/map (SAM) format and/or about 13% smaller than a GZip format.

B54. The system of any one of embodiments B42 to B53, wherein the normalizing in (c) comprises factoring one or more features other than GC density, and normalizing the sequence reads.

B55. The system of embodiment B54, wherein the factoring one or more features is by a process comprising use of a multivariate model.

B56. The system of embodiment B55, wherein the process comprising use of the multivariate model is performed by a multivariate module.

B57. The system of any one of embodiments B42 to B56, wherein the filtered portions for the test sample are weighted.

B58. The system of embodiment B57, wherein the filtered portions for the test sample are weighted by a process comprising an eigen function.

B59. The system of any one of embodiments B1 to B58, comprising, prior to (a), obtaining the sequence reads.

B60. The system of embodiment B59, wherein the sequence reads are generated by massively parallel sequencing (MPS).

B61. The system of any one of embodiments B1 to B60, comprising obtaining sequence reads mapped to an entire reference genome or a segment of a genome.

B62. The system of embodiment B61, wherein the segment of the genome comprises a chromosome or a segment thereof.

B63. The system of embodiment B61 or B62, wherein the counts of the sequence reads mapped to the reference genome are normalized prior to (1).

B64. The system of embodiment B63, wherein the counts of the sequence reads mapped to the reference genome are normalized by GC content, bin-wise normalization, GC LOESS, PERUN, GCRM, or combinations thereof.

B65. The system of embodiment B61 or B62, wherein the counts of the sequence reads mapped to the reference genome are raw counts.

B66. The system of any one of embodiments B1 to B65, wherein each portion of the reference genome comprises about an equal length of contiguous nucleotides.

B67. The system of any one of embodiments B1 to B66, wherein each portion of the reference genome comprises about 50 kb.

B68. The system of any one of embodiments B1 to B67, wherein each portion of the reference genome comprises about 100 kb.

B69. The system of any one of embodiments B1 to B68, wherein each portion of the reference genome comprises a segment of contiguous nucleotides in common with an adjacent portion of the reference genome.

B70. The system of any one of embodiments B1 to B69, wherein the test sample comprises blood from a pregnant female.

B71. The system of any one of embodiments B1 to B70, wherein the test sample comprises plasma from a pregnant female.

B72. The system of any one of embodiments B1 to B71, wherein the test sample comprises serum from a pregnant female.

B73. The system of any one of embodiments B1 to B72, wherein nucleic acids are isolated from the test sample.

B74. The system of any one of embodiments B50 to B73, comprising compressing the sequence reads mapped to the reference genome in (1) from a sequence alignment format into a binary format.

B75. The system of embodiment B74, wherein the compressing is performed by a compression module.

B76. The system of any one of embodiments B42 to B75, wherein the GC densities and the GC density frequencies for the sequence reads of the test sample and for the reference are provided by a bias density module.

B77. The system of any one of embodiments B42 to B76, wherein the comparison in (2) is generated by a relationship module.

B78. The system of any one of embodiments B44 to B77, wherein the normalizing in (3) is performed by a bias correction module.

B79. The system of any one of embodiments B1 to B78, wherein the read densities are provided by a distribution module.

B80. The system of any one of embodiments B1 to B79, wherein filtered portions are provided by a filtering module.

B81. The system of any one of embodiments B57 to B80, wherein the filtered portions for the test sample are weighted by a portion weighting module.

B81.1. The system of any one of embodiments B57 to B81, wherein the read densities are adjusted by a read density adjusting module.

B82. The system of embodiments B81.1, wherein an apparatus comprises one or more of the compression module, the bias density module, the relationship module, the bias correction module, the distribution module, the filtering module, the read density adjusting module and the portion weighting module.

B83. The system of any one of embodiments B1 to B82, wherein the test sample profile comprises a profile of a chromosome or a segment thereof.

B84. The system of any one of embodiments B1 to B83, wherein the reference profile comprises a profile of a chromosome or a segment thereof.

B85. The system of any one of embodiments B1 to B84, wherein the determining in (d) is provided with a specificity equal to or greater than 90% and a sensitivity equal to or greater than 90%.

B86. The system of any one of embodiments B1 to B85, wherein the aneuploidy is a trisomy.

B87. The system of embodiment B86, wherein the trisomy is trisomy 21, trisomy 18, or trisomy 13.

B88. The system of any one of embodiments B17 to B87, wherein the memory of the system comprises the sequence reads of circulating cell-free nucleic acid from the test sample that are mapped to the reference genome.

C1. The system of any one of embodiments A1 to A48 and B1 to B88, which is embodied in one or more machines.

C2. The system of embodiment C1, which is embodied in one machine.

C3. The system of embodiment C1 or C2, which comprises a machine configured to sequence nucleic acid and generate the sequence reads.

D1. A method for reducing bias in sequence reads for a sample comprising:
  (a) generating, using a microprocessor, a relationship between (i) guanine and cytosine (GC) densities and (ii) GC density frequencies for sequence reads of a test sample, thereby generating a sample GC density relationship, wherein,
    the sequence reads are of circulating cell-free nucleic acid from the test sample, and the sequence reads are mapped to a reference genome;
(b) comparing the sample GC density relationship and a reference GC density relationship, thereby generating a comparison, wherein,
the reference GC density relationship is between (i) GC densities and (ii) the GC density frequencies for a reference; and
(c) normalizing counts of the sequence reads for the sample according to the comparison determined in (b), whereby bias in the sequence reads for the sample is reduced.

D1.1. A method for reducing bias in sequence reads for a sample comprising:
loading a sequencing apparatus with circulating cell-free nucleic acid from the blood of a pregnant female bearing a fetus, or loading the sequencing apparatus with a modified variant of the nucleic acid, which sequencing apparatus produces signals corresponding to nucleotide bases of the nucleic acid;
generating sequence reads from the signals of the nucleic acid by, after optionally transferring the signals to, a system comprising one or more computing apparatus, wherein the one or more computing apparatus in the system comprise memory and one or more processors, and
wherein one computing apparatus, or combination of computing apparatus, in the system is configured to:
map the sequence reads to a reference genome;
(a) generate a relationship between (i) guanine and cytosine (GC) densities and (ii) GC density frequencies for sequence reads of a test sample, thereby generating a sample GC density relationship, wherein,
the sequence reads are of circulating cell-free nucleic acid from the test sample, and
the sequence reads are mapped to a reference genome;
(b) compare the sample GC density relationship and a reference GC density relationship, thereby generating a comparison, wherein,
the reference GC density relationship is between (i) GC densities and (ii) the GC density frequencies for a reference; and
(c) normalize counts of the sequence reads for the sample according to the comparison determined in (b), whereby bias in the sequence reads for the sample is reduced.

D1.2. The method of embodiment D1 or D1.1, wherein the normalizing in (c) comprises providing normalized counts.

D2. The method of any one of embodiments D1 to D1.2, wherein each of the GC densities is determined by a process comprising use of a kernel density estimation.

D2.1. The method of any one of embodiments D1 to D2, wherein each of the GC densities for the reference GC density relationship and the sample GC density relationship is a representation of local GC content.

D2.2. The method of embodiment D2.1, wherein the local GC content is for a polynucleotide segment of 5000 bp or less.

D3. The method of any one of embodiments D1 to D2.2, wherein each of the GC densities is determined by a process comprising use of a sliding window analysis.

D4. The method of embodiment D3, wherein the window is about 5 contiguous nucleotides to about 5000 contiguous nucleotides and the window is slid about 1 base to about 10 bases at a time in the sliding window analysis.

D5. The method of embodiment D3, wherein the window is about 200 contiguous nucleotides and the window is slid about 1 base at a time in the sliding window analysis.

D6. The method of any one of embodiments D1 to D5, wherein (b) comprises generating a fitted relationship between (i) ratios, each of which ratios comprises a sample GC density relationship frequency and a reference GC density relationship frequency for each of the GC densities and (ii) GC densities.

D7. The method of embodiment D6, wherein the fitted relationship in (a) is obtained from a weighted fitting.

D8. The method of any one of embodiments D1 to D7, wherein each of the sequence reads for the sample is represented in a binary format.

D9. The method of embodiment D8, wherein the binary format for each of the sequence reads comprises a chromosome to which the read is mapped and a chromosome position to which the read is mapped.

D10. The method of embodiment D9, wherein the binary format is in a 5-byte format comprising a 1-byte chromosome ordinal and a 4-byte chromosome position.

D11. The method of any one of embodiments D8 to D10, wherein the binary format is 50 times smaller than a sequence alignment/map (SAM) format and/or about 13% smaller than a GZip format.

D12. The method of any one of embodiments D1 to D11, wherein the normalizing in (c) comprises factoring one or more features other than GC density, and normalizing counts of the sequence reads.

D13. The method of embodiment D12, wherein the factoring one or more features is by a process comprising use of a multivariate model.

D14. The method of D13, wherein the process comprising use of the multivariate model is performed by a multivariate module.

D14.1. The method of any one of embodiments D12 to D14, wherein the counts of sequence reads are normalized according to the normalizing in (c) and the factoring of the one or more features.

D15. The method of any one of embodiments D1 to D14.1, comprising, after (c), generating a read density for one or more portions of a genome, or a segment thereof, according to a process comprising generating a probability density estimation for each of the one or more portions comprising the counts of the sequence reads normalized in (c).

D16. The method of embodiment D15, wherein the probability density estimation is a kernel density estimation.

D17. The method of embodiment D15 or D16, comprising generating a read density profile for the genome or the segment thereof.

D18. The method of embodiment D17, wherein the read density profile comprises the read densities for the one or more portions of the genome, or the segment thereof.

D19. The method of any one of embodiments D15 to D18, comprises adjusting each of the read densities for the one or more portions.

D20. The method of any one of embodiments D15 to D19, wherein the one or more portions are filtered thereby providing filtered portions.

D21. The method of any one of embodiments D15 to D20, wherein the one or more portions are weighted thereby providing weighted portions.

D22. The method of embodiment D21, wherein the one or more portions are weighted by an eigen function.

D23. The method of any one of embodiments D1 to D22, comprising, prior to (a), obtaining the sequence reads.

D24. The method of embodiment D23, wherein the sequence reads are generated by massively parallel sequencing (MPS).

D25. The method of any one of embodiments D1 to D24, comprising obtaining sequence reads mapped to an entire reference genome or a segment of a genome.

D26. The method of embodiment D25, wherein the segment of the genome comprises a chromosome or a segment thereof.

D27. The method of embodiment D25 or D26, wherein the counts of the sequence reads mapped to the reference genome are normalized prior to (a).

D28. The method of embodiment D27, wherein the counts of the sequence reads mapped to the reference genome are normalized by GC content, bin-wise normalization, GC LOESS, PERUN, GCRM, or combinations thereof.

D29. The method of any one of embodiments D27 or D28, wherein the counts of the sequence reads mapped to the reference genome are raw counts.

D30. The method of any one of embodiments D15 to D29, wherein each portion of the reference genome comprises about an equal length of contiguous nucleotides.

D31. The method of any one of embodiments D15 or D30, wherein each portion of the reference genome comprises about 50 kb.

D32. The method of any one of embodiments D15 to D31, wherein each portion of the reference genome comprises about 100 kb.

D33. The method of any one of embodiments D15 to D32, wherein each portion of the reference genome comprises a segment of contiguous nucleotides in common with an adjacent portion of the reference genome.

D34. The method of any one of embodiments D1 to D33, wherein the test sample is obtained from a pregnant female.

D35. The method of any one of embodiments D1 to D34, wherein the test sample comprises blood from a pregnant female.

D36. The method of any one of embodiments D1 to D35, wherein the test sample comprises plasma from a pregnant female.

D37. The method of any one of embodiments D1 to D36, wherein the test sample comprises serum from a pregnant female.

D38. The method of any one of embodiments D1 to D37, wherein nucleic acids are isolated from the test sample.

D39. The method of any one of embodiments D8 to D38, comprising compressing the sequence reads mapped to a reference genome in (a) from a sequence alignment format into a binary format.

D40. The method of embodiment D39, wherein the compressing is performed by a compression module.

D41. The method of any one of embodiments D1 to D40, wherein the GC densities and the GC density frequencies for the sequence reads of the test sample and for the reference are provided by a bias density module.

D42. The method of any one of embodiments D1 to D41, wherein the comparison in (b) is generated by a relationship module.

D43. The method of any one of embodiments D1 to D42, wherein normalizing in (c) is performed by a bias correction module.

D44. The method of any one of embodiments D15 to D43, wherein the read densities are provided by a distribution module.

D45. The method of any one of embodiments D20 to D44, wherein filtered portions are provided by a filtering module.

D46. The method of any one of embodiments D21 to D45, wherein weighted portions are provided by a portion weighting module.

D46.1. The method of any one of embodiments D21 to D46, wherein read densities are adjusted by a read density adjusting module.

D47. The method of embodiment D46.1, comprising one or more of the compression module, the bias density module, the relationship module, the bias correction module, the distribution module, the filtering module, the read density adjusting module and the portion weighting module.

E0. A method for determining the presence or absence of an aneuploidy for a sample comprising:
- (a) filtering, according to a read density distribution, portions of a reference genome, thereby providing a read density profile for a test sample comprising read densities of filtered portions, wherein,
  the read densities comprise sequence reads of circulating cell-free nucleic acid from a test sample from a pregnant female, and
  the read density distribution is determined for read densities of portions for multiple samples;
- (b) adjusting the read density profile for the test sample according to one or more principal components, which principal components are obtained from a set of known euploid samples by a principal component analysis, thereby providing a test sample profile comprising adjusted read densities;
- (c) comparing the test sample profile to a reference profile, thereby providing a comparison; and
- (d) determining the presence or absence of a chromosome aneuploidy for the test sample according to the comparison.

E0.1. A method for determining the presence or absence of an aneuploidy for a sample comprising:
- (a) filtering, according to a read density distribution, portions of a chromosome in a reference genome, thereby providing a read density profile for a test sample comprising read densities of filtered portions, wherein,
  the read densities comprise sequence reads of circulating cell-free nucleic acid from a test sample from a pregnant female, and
  the read density distribution is determined for read densities of portions for multiple samples;
- (b) adjusting the read density profile of a chromosome for the test sample according to one or more principal components, which principal components are obtained from a set of known euploid samples by a principal component analysis, thereby providing a test sample chromosome profile comprising adjusted read densities;
- (c) comparing the test sample chromosome profile to a reference profile, thereby providing a comparison; and
- (d) determining the presence or absence of a chromosome aneuploidy for the test sample according to the comparison.

E1. A method for determining the presence or absence of an aneuploidy for a sample comprising:
- (a) filtering, according to a read density distribution, portions of a reference genome, thereby providing a read density profile for a test sample comprising read densities of filtered portions, wherein,
  the read densities comprise sequence reads of circulating cell-free nucleic acid from a test sample from a pregnant female, and
  the read density distribution is determined for read densities of portions for multiple samples;
- (b) adjusting, using a microprocessor, the read density profile for the test sample according to one or more principal components, which principal components are obtained from a set of known euploid samples by a principal component analysis, thereby providing a test sample profile comprising adjusted read densities;

(c) comparing the test sample profile to a reference profile, thereby providing a comparison; and (d) determining the presence or absence of a chromosome aneuploidy for the test sample according to the comparison.

E1.1. A method for determining the presence or absence of an aneuploidy for a sample comprising:

loading a sequencing apparatus with circulating cell-free nucleic acid from the blood of a pregnant female bearing a fetus, or loading the sequencing apparatus with a modified variant of the nucleic acid, which sequencing apparatus produces signals corresponding to nucleotide bases of the nucleic acid;

generating sequence reads from the signals of the nucleic acid by, after optionally transferring the signals to, a system comprising one or more computing apparatus, wherein the one or more computing apparatus in the system comprise memory and one or more processors, and wherein one computing apparatus, or combination of computing apparatus, in the system is configured to:

map the sequence reads to a reference genome;

(a) filter, according to a read density distribution, portions of a reference genome, thereby providing a read density profile for a test sample comprising read densities of filtered portions, wherein, the read densities comprise sequence reads of circulating cell-free nucleic acid from a test sample from a pregnant female, and the read density distribution is determined for read densities of portions for multiple samples;

(b) adjust, using a microprocessor, the read density profile for the test sample according to one or more principal components, which principal components are obtained from a set of known euploid samples by a principal component analysis, thereby providing a test sample profile comprising adjusted read densities;

(c) compare the test sample profile to a reference profile, thereby providing a comparison; and (d) determine the presence or absence of a chromosome aneuploidy for the test sample according to the comparison.

E1.2. A method for reducing bias in sequence reads for a sample comprising:

loading a sequencing apparatus with circulating cell-free nucleic acid from the blood of a pregnant female bearing a fetus, or loading the sequencing apparatus with a modified variant of the nucleic acid, which sequencing apparatus produces signals corresponding to nucleotide bases of the nucleic acid;

generating sequence reads from the signals of the nucleic acid by, after optionally transferring the signals to, a system comprising one or more computing apparatus, wherein the one or more computing apparatus in the system comprise memory and one or more processors, and wherein one computing apparatus, or combination of computing apparatus, in the system is configured to:

map the sequence reads to a reference genome;

(a) filter, according to a read density distribution, portions of a reference genome, thereby providing a read density profile for a test sample comprising read densities of filtered portions, wherein, the read densities comprise sequence reads of circulating cell-free nucleic acid from a test sample from a pregnant female, and the read density distribution is determined for read densities of portions for multiple samples;

(b) adjust, using a microprocessor, the read density profile for the test sample according to one or more principal components, which principal components are obtained from a set of known euploid samples by a principal component analysis, thereby providing a test sample profile comprising adjusted read densities;

(c) compare the test sample profile to a reference profile, thereby providing a comparison; and (d) determine the presence or absence of a chromosome aneuploidy for the test sample according to the comparison.

E1.3. The method of any one of embodiments E0 to E1.2 wherein the read density profile is adjusted in (b) by 1 to 10 principal components.

E1.4. The method of any one of embodiments E0 to E1.3 wherein the read density profile is adjusted in (b) by 5 principal components.

E1.5. The method of any one of embodiments E0 to E1.4, wherein the one or more principal components adjust for one or more features in a read density profile, which features are selected from fetal gender, sequence bias, fetal fraction, bias correlated with DNase I sensitivity, entropy, repetitive sequence bias, chromatin structure bias, polymerase error-rate bias, palindrome bias, inverted repeat bias, PCR amplification bias, and hidden copy number variation.

E1.6. The method of embodiment E1.5 wherein sequence bias comprises guanine and cytosine (GC) bias.

E2. The method of any one of embodiments E0 to E1.6, wherein the comparison comprises determining a level of significance.

E3. The method of any one of embodiments E0 to E2, wherein determining the level of significance comprises determining a p-value.

E4. The method of any one of embodiments E0 to E3, wherein the reference profile comprises a read density profile obtained from a set of known euploid samples.

E5. The method of any one of embodiments E0 to E4, wherein the reference profile comprises read densities of filtered portions.

E6. The method of any one of embodiments E0 to E5, wherein the reference profile comprises read densities adjusted according to the one or more principle components.

E7. The method of any one of embodiments E2 to E6, wherein the level of significance indicates a statistically significantly difference between the test sample profile and the reference profile, and the presence of a chromosome aneuploidy is determined.

E8. The method of any one of embodiments E1 to E7, wherein the multiple samples comprise a set of known euploid samples.

E9. The method of any one of embodiments E0 to E8, wherein the read densities of portions for the multiple samples are median read densities.

E10. The method of any one of embodiments E0 to E9, wherein the read densities of filtered portions for the test sample are median read densities.

E11. The method of any one of embodiments E4 to E10, wherein the read density profile for the reference profile comprises median read densities.

E12. The method of any one of embodiments E4 to E11, wherein the read densities for the test sample profile, the multiple samples and the reference profile are determined according to a process comprising use of a kernel density estimation.

E13. The method of any one of embodiments E10 to E12, wherein the test sample profile is determined according to the median read densities for the test sample.

E14. The method of any one of embodiments E11 to E13, wherein the reference profile is determined according to the median read density distributions for the reference.

E15. The method of any one of embodiments E0 to E14, comprising filtering portions of a reference genome according to a measure of uncertainty for the read density distribution.

E16. The method of embodiment E15, wherein the measure of uncertainty is a MAD.

E16.1. The method of any one of embodiments E0 to E16, wherein the test sample profile is representative of chromosome dosage for the test sample.

E16.2. The method of embodiment E16.1, comprising comparing chromosome dosage for a test sample profile to chromosome dosage for a reference profile, thereby generating a chromosome dosage comparison.

E16.3. The method of embodiment E16.2, wherein determining the presence or absence of a chromosome aneuploidy for the test sample is according to the chromosome dosage comparison.

E16.4. The method of any one of embodiments E0 to E16.3, wherein determining the presence or absence of a chromosome aneuploidy for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

E17. The method of any one of embodiments E0 to E16.4, wherein counts of the sequence reads mapped to filtered portions for the test sample are normalized by a process performed prior to (a) comprising:
  (I) generating a relationship between (i) local genome bias estimates and (ii) bias frequencies for sequence reads of a test sample, thereby generating a sample bias relationship, wherein,
  the sequence reads are of circulating cell-free nucleic acid from the test sample, and
  the sequence reads are mapped to a reference genome;
  (II) comparing the sample bias relationship and a reference bias relationship, thereby generating a comparison, wherein,
  the reference bias relationship is between (i) local genome bias estimates and (ii) the bias frequencies for a reference; and
  (III) normalizing counts of the sequence reads for the sample according to the comparison determined in (II), whereby bias in the sequence reads for the sample is reduced.

E18. The method of embodiment E17, wherein the normalizing in (III) comprises providing normalized counts.

E19. The method of embodiment E17 or E18, wherein each of the local genome bias estimates is determined by a process comprising use of a kernel density estimation.

E19.1. The method of any one of embodiments E17 to E19, wherein each of the local genome bias estimates for the reference bias relationship and the sample bias relationship is a representation of local bias content.

E19.2. The method of embodiment E19.1, wherein the local bias content is for a polynucleotide segment of 5000 bp or less.

E20. The method of any one of embodiments E17 to E19.2, wherein each of the local genome bias estimates is determined by a process comprising use of a sliding window analysis.

E21. The method of embodiment E20, wherein the window is about 5 contiguous nucleotides to about 5000 contiguous nucleotides and the window is slid about 1 base to about 10 bases at a time in the sliding window analysis.

E22. The method of embodiment E20, wherein the window is about 200 contiguous nucleotides and the window is slid about 1 base at a time in the sliding window analysis.

E23. The method of any one of embodiments E17 to E22, wherein (II) comprises generating a fitted relationship between (i) ratios, each of which ratios comprises a sample bias relationship frequency and a reference bias relationship frequency for each of the local genome bias estimates and (ii) local genome bias estimates.

E24. The method of embodiment E23, wherein the fitted relationship in (I) is obtained from a weighted fitting.

E25. The method of any one of embodiments E17 to E24, wherein each of the sequence reads for the sample is represented in a binary format.

E26. The method of embodiment E25, wherein the binary format for each of the sequence reads comprises a chromosome to which the read is mapped and a chromosome position to which the read is mapped.

E27. The method of embodiment E26, wherein the binary format is in a 5-byte format comprising a 1-byte chromosome ordinal and a 4-byte chromosome position.

E28. The method of any one of embodiments E25 to E27, wherein the binary format is 50 times smaller than a sequence alignment/map (SAM) format and/or about 13% smaller than a GZip format.

E29. The method of any one of embodiments E17 to E28, wherein the normalizing in (III) comprises factoring one or more features other than bias, and normalizing counts of the sequence reads.

E30. The method of embodiment E29, wherein the factoring one or more features is by a process comprising use of a multivariate model.

E31. The method of E30, wherein the process comprising use of the multivariate model is performed by a multivariate module.

E32. The method of any one of embodiments E29 to E31, wherein counts of the sequence reads are normalized according to the normalizing in (III) and the factoring of the one or more features.

E33. The method of any one of embodiments E17 to E32, comprising, after (III), generating a read density for one or more portions of a genome, or a segment thereof, according to a process comprising generating a probability density estimation for each of the one or more portions comprising one or more of counts of sequence reads normalized in (III).

E34. The method of embodiment E33, wherein the probability density estimation is a kernel density estimation.

E35. The method of embodiment E33 or E34, comprising generating a read density profile for the genome or the segment thereof.

E36. The method of embodiment E35, wherein the read density profile comprises the read densities for the one or more portions of the genome, or the segment thereof.

E37. The method of any one of embodiments E33 to E36, comprises adjusting each of the read densities for the one or more portions.

E38. The method of any one of embodiments E33 to E37, wherein the one or more portions are filtered thereby providing filtered portions.

E39. The method of any one of embodiments E33 to E38, wherein the one or more portions are weighted thereby providing weighted portions.

E40. The method of embodiment E39, wherein the one or more portions are weighted by an eigen function.

E41. The method of any one of embodiments E17 to E40, wherein the local genome bias estimates are local GC densities and the bias frequencies are GC bias frequencies.

E42. The method of any one of embodiments E0 to E16, wherein counts of the sequence reads mapped to filtered portions for the test sample are normalized by a process performed prior to (a) comprising:
  (1) generating a fitted relationship between (i) guanine and cytosine (GC) densities and (ii) GC density frequencies for the sequence reads of the test sample, thereby generating a sample GC density relationship, wherein the sequence reads are mapped to the reference genome;
  (2) comparing the sample GC density relationship and a reference GC density relationship, thereby generating a comparison, wherein,
  the reference GC density relationship is between (i) GC densities and (ii) the GC density frequencies for a reference; and
  (3) normalizing counts of the sequence reads for the sample according to the comparison determined in (b), whereby bias in the sequence reads for the sample is reduced.

E43. The method of embodiment E42, wherein the normalizing in (3) comprises providing normalized counts.

E44. The method of embodiment E42 or E43, wherein each of the GC densities is determined by a process comprising use of a kernel density estimation.

E45. The method of any one of embodiments E42 to E44, wherein each of the GC densities is determined by a process comprising use of a sliding window analysis.

E46. The method of embodiment E45, wherein the window is about 5 contiguous nucleotides to about 5000 contiguous nucleotides and the window is slid about 1 base to about 10 bases at a time in the sliding window analysis.

E47. The method of embodiment E46, wherein the window is about 200 contiguous nucleotides and the window is slid about 1 base at a time in the sliding window analysis.

E48. The method of any one of embodiments E42 to E47, wherein (2) comprises generating a fitted relationship between (i) ratios, each of which ratios comprises a sample GC density relationship frequency and a reference GC density relationship frequency for each of the GC densities and (ii) GC densities.

E49. The method of embodiment E48, wherein the fitted relationship in (1) is obtained from a weighted fitting.

E50. The method of any one of embodiments E42 to E49, wherein each of the sequence reads for the sample is represented in a binary format.

E51. The method of embodiment E50, wherein the binary format for each of the sequence reads comprises a chromosome to which the read is mapped and a chromosome position to which the read is mapped.

E52. The method of embodiment E51, wherein the binary format is in a 5-byte format comprising a 1-byte chromosome ordinal and a 4-byte chromosome position.

E53. The method of any one of embodiments E50 to E52, wherein the binary format is 50 times smaller than a sequence alignment/map (SAM) format and/or about 13% smaller than a GZip format.

E54. The method of any one of embodiments E42 to E53, wherein the normalizing in (c) comprises factoring one or more features other than GC density, and normalizing the sequence reads.

E55. The method of embodiment E54, wherein the factoring one or more features is by a process comprising use of a multivariate model.

E56. The method of embodiment E55, wherein the process comprising use of the multivariate model is performed by a multivariate module.

E57. The method of any one of embodiments E42 to E56, wherein the filtered portions for the test sample are weighted.

E58. The method of embodiment E57, wherein the filtered portions for the test sample are weighted by a process comprising an eigen function.

E59. The method of any one of embodiments E0 to E58, comprising, prior to (a), obtaining the sequence reads.

E60. The method of embodiment E59, wherein the sequence reads are generated by massively parallel sequencing (MPS).

E61. The method of any one of embodiments E0 to E60, comprising obtaining sequence reads mapped to an entire reference genome or a segment of a genome.

E62. The method of embodiment E61, wherein the segment of the genome comprises a chromosome or a segment thereof.

E63. The method of embodiment E61 or E62, wherein the counts of the sequence reads mapped to the reference genome are normalized prior to (1).

E64. The method of embodiment E63, wherein the counts of the sequence reads mapped to the reference genome are normalized by GC content, bin-wise normalization, GC LOESS, PERUN, GCRM, or combinations thereof.

E65. The method of embodiment E61 or E62, wherein the counts of the sequence reads mapped to the reference genome are raw counts.

E66. The method of any one of embodiments E0 to E65, wherein each portion of the reference genome comprises about an equal length of contiguous nucleotides.

E67. The method of any one of embodiments E0 to E66, wherein each portion of the reference genome comprises about 50 kb.

E68. The method of any one of embodiments E0 to E67, wherein each portion of the reference genome comprises about 100 kb.

E69. The method of any one of embodiments E0 to E68, wherein each portion of the reference genome comprises a segment of contiguous nucleotides in common with an adjacent portion of the reference genome.

E70. The method of any one of embodiments E0 to E69, wherein the test sample comprises blood from a pregnant female.

E71. The method of any one of embodiments E0 to E70, wherein the test sample comprises plasma from a pregnant female.

E72. The method of any one of embodiments E0 to E71, wherein the test sample comprises serum from a pregnant female.

E73. The method of any one of embodiments E0 to E72, wherein nucleic acids are isolated from the test sample.

E74. The method of any one of embodiments E50 to E73, comprising compressing the sequence reads mapped to the reference genome in (1) from a sequence alignment format into a binary format.

E75. The method of embodiment E74, wherein the compressing is performed by a compression module.

E76. The method of any one of embodiments E42 to E75, wherein the GC densities and the GC density frequencies for the sequence reads of the test sample and for the reference are provided by a bias density module.

E77. The method of any one of embodiments E42 to E76, wherein the comparison in (2) is generated by a relationship module.

E78. The method of any one of embodiments E44 to E77, wherein the normalizing in (3) is performed by a bias correction module.

E79. The method of any one of embodiments E0 to E78, wherein the read densities are provided by a distribution module.

E80. The method of any one of embodiments E0 to E79, wherein filtered portions are provided by a filtering module.

E81. The method of any one of embodiments E57 to E80, wherein the filtered portions for the test sample are weighted by a portion weighting module.

E81.1. The method of any one of embodiments E57 to E81, wherein the read densities are adjusted by a read density adjusting module.

E82. The method of embodiments E81.1, wherein an apparatus comprises one or more of the compression module, the bias density module, the relationship module, the bias correction module, the distribution module, the filtering module, the read density adjusting module and the portion weighting module.

E83. The method of any one of embodiments E0 to E82, wherein the test sample profile comprises a profile of a chromosome or a segment thereof.

E84. The method of any one of embodiments E0 to E83, wherein the reference profile comprises a profile of a chromosome or a segment thereof.

E85. The method of any one of embodiments E0 to E84, wherein the determining in (d) is provided with a specificity equal to or greater than 90% and a sensitivity equal to or greater than 90%.

E86. The method of any one of embodiments E0 to E85, wherein the aneuploidy is a trisomy.

E87. The method of embodiment E86, wherein the trisomy is trisomy 21, trisomy 18, or trisomy 13.

F1. A non-transitory computer-readable storage medium comprising an executable program stored thereon, wherein the program instructs a microprocessor to perform the following:
(a) generate a relationship between (i) guanine and cytosine (GC) densities and (ii) GC density frequencies for sequence reads of a test sample, thereby generating a sample GC density relationship, wherein:
the sequence reads are of circulating cell-free nucleic acid from the test sample, and
the sequence reads are mapped to a reference genome;
(b) compare the sample GC density relationship and a reference GC density relationship, thereby generating a comparison, wherein,
the reference GC density relationship is between (i) GC densities and (ii) the GC density frequencies for a reference; and
(c) normalizing counts of the sequence reads for the sample according to the comparison determined in (b), whereby bias in the sequence reads for the sample is reduced.

F1.1. The storage medium of embodiment F1, wherein the normalizing in (c) comprises providing normalized counts of reads.

F2. The storage medium of embodiment F1 or F1.1, wherein each of the GC densities is determined by a process comprising use of a kernel density estimation.

F2.1. The storage medium of any one of embodiments F1 to F2, wherein each of the GC densities for the reference GC density relationship and the sample GC density relationship is a representation of local GC content.

F2.2. The storage medium of embodiment F2.1, wherein the local GC content is for a polynucleotide segment of 5000 bp or less.

F3. The storage medium of any one of embodiments F1 to F2.2, wherein each of the GC densities is determined by a process comprising use of a sliding window analysis.

F4. The storage medium of embodiment F3, wherein the window is about 5 contiguous nucleotides to about 5000 contiguous nucleotides and the window is slid about 1 base to about 10 bases at a time in the sliding window analysis.

F5. The storage medium of embodiment F3, wherein the window is about 200 contiguous nucleotides and the window is slid about 1 base at a time in the sliding window analysis.

F6. The storage medium of any one of embodiments F1 to F5, wherein (b) comprises generating a fitted relationship between (i) ratios, each of which ratios comprises a sample GC density relationship frequency and a reference GC density relationship frequency for each of the GC densities and (ii) GC densities.

F7. The storage medium of embodiment F6, wherein the fitted relationship in (a) is obtained from a weighted fitting.

F8. The storage medium of any one of embodiments F1 to F7, wherein each of the sequence reads for the sample is represented in a binary format.

F9. The storage medium of embodiment F8, wherein the binary format for each of the sequence reads comprises a chromosome to which the read is mapped and a chromosome position to which the read is mapped.

F10. The storage medium of embodiment F9, wherein the binary format is in a 5-byte format comprising a 1-byte chromosome ordinal and a 4-byte chromosome position.

F11. The storage medium of any one of embodiments F8 to F10, wherein the binary format is 50 times smaller than a sequence alignment/map (SAM) format and/or about 13% smaller than a GZip format.

F12. The storage medium of any one of embodiments F1 to F11, wherein the normalizing in (c) comprises factoring one or more features other than GC density, and normalizing the sequence reads.

F13. The storage medium of embodiment F12, wherein the factoring one or more features is by a process comprising use of a multivariate model.

F14. The storage medium of F13, wherein the process comprising use of the multivariate model is performed by a multivariate module.

F14.1. The storage medium of any one of embodiments F12 to F14, wherein counts of the sequence reads are normalized according to the normalizing in (c) and the factoring of the one or more features.

F15. The storage medium of any one of embodiments F1 to F14.1, wherein the program instructs a microprocessor to, after (c), generate a read density for one or more portions of a genome, or a segment thereof, according to a process comprising generating a probability density estimation for each of the one or more portions comprising the counts of the sequence reads normalized in (c).

F16. The storage medium of embodiment F15, wherein the probability density estimation is a kernel density estimation.

F17. The storage medium of embodiment F15 or F16, wherein the program instructs a microprocessor to generate a read density profile for the genome or the segment thereof.

F18. The storage medium of embodiment F17, wherein the read density profile comprises the read densities for the one or more portions of the genome, or the segment thereof.

F19. The storage medium of any one of embodiments F15 to F18, wherein the program instructs the microprocessor to adjust each of the read densities for the one or more portions.

F20. The storage medium of any one of embodiments F15 to F19, wherein the one or more portions are filtered thereby providing filtered portions.

F21. The storage medium of any one of embodiments F15 to F20, wherein the program instructs the microprocessor to weight the one or more portions thereby providing weighted portions.

F22. The storage medium of embodiment F21, wherein the one or more portions are weighted by an eigen function.

F23. The storage medium of any one of embodiments F1 to F22, wherein the program instructs the microprocessor, prior to (a), to obtain the sequence reads.

F24. The storage medium of embodiment F23, wherein the sequence reads are generated by massively parallel sequencing (MPS).

F25. The storage medium of embodiment F23 or F24, wherein the sequence reads obtained are sequence reads mapped to an entire reference genome or a segment of a genome.

F26. The storage medium of embodiment F25, wherein the segment of the genome comprises a chromosome or a segment thereof.

F27. The storage medium of embodiment F25 or F26, wherein the counts of the sequence reads mapped to the reference genome are normalized counts of sequence reads.

F28. The storage medium of embodiment F27, wherein the counts of the sequence reads mapped to the reference genome are normalized by GC content, bin-wise normalization, GC LOESS, PERUN, GCRM, or combinations thereof.

F29. The storage medium of embodiment F25 or F26, wherein the counts of the sequence reads mapped to the reference genome are raw counts.

F30. The storage medium of any one of embodiments F15 to F29, wherein each portion of the reference genome comprises about an equal length of contiguous nucleotides.

F31. The storage medium of any one of embodiments F15 or F30, wherein each portion of the reference genome comprises about 50 kb.

F32. The storage medium of any one of embodiments F15 to F31, wherein each portion of the reference genome comprises about 100 kb.

F33. The storage medium of any one of embodiments F15 to F32, wherein each portion of the reference genome comprises a segment of contiguous nucleotides in common with an adjacent portion of the reference genome.

F34. The storage medium of any one of embodiments F1 to F33, wherein the test sample is obtained from a pregnant female.

F35. The storage medium of any one of embodiments F1 to F34, wherein the test sample comprises blood from a pregnant female.

F36. The storage medium of any one of embodiments F1 to F35, wherein the test sample comprises plasma from a pregnant female.

F37. The storage medium of any one of embodiments F1 to F36, wherein the test sample comprises serum from a pregnant female.

F38. The storage medium of any one of embodiments F1 to F37, wherein the test sample comprises isolated nucleic acids.

F39. The storage medium of any one of embodiments F8 to F38, wherein the program instructs the microprocessor to compress the sequence reads mapped to a reference genome in (a) from a sequence alignment format into a binary format.

F40. The storage medium of embodiment F39, wherein the compressing is performed by a compression module.

F41. The storage medium of any one of embodiments F1 to F40, wherein the GC densities and the GC density frequencies for the sequence reads of the test sample and for the reference are provided by a bias density module.

F42. The storage medium of any one of embodiments F1 to F41, wherein the comparison in (b) is generated by a relationship module.

F43. The storage medium of any one of embodiments F1 to F42, wherein normalizing in (c) is performed by a bias correction module.

F44. The storage medium of any one of embodiments F15 to F43, wherein the read densities are provided by a distribution module.

F45. The storage medium of any one of embodiments F20 to F44, wherein filtered portions are provided by a filtering module.

F46. The storage medium of any one of embodiments F21 to F45, wherein weighted portions are provided by a portion weighting module.

F46.1. The storage medium of any one of embodiments F21 to F45, wherein the adjusted read densities are provided by a read density adjusting module.

F47. The storage medium of embodiment F46, comprising one or more of the compression module, the bias density module, the relationship module, the bias correction module, the distribution module, the filtering module, the read density adjusting module and the portion weighting module.

G1. A non-transitory computer-readable storage medium comprising an executable program stored thereon, wherein the program instructs a microprocessor to perform the following:
  (a) filter, according to a read density distribution, portions of a reference genome, thereby providing a read density profile for a test sample comprising read densities of filtered portions, wherein:
    the read densities comprise sequence reads of circulating cell-free nucleic acid from a test sample from a pregnant female, and
    the read density distribution is determined for read densities of portions for multiple samples;
  (b) adjust the read density profile for the test sample according to one or more principal components, which principal components are obtained from a set of known euploid samples by a principal component analysis, thereby providing a test sample profile comprising adjusted read densities;
  (c) compare the test sample profile to a reference profile, thereby providing a comparison; and
  (d) determine the presence or absence of a chromosome aneuploidy for the test sample according to the comparison.

G2. The storage medium of embodiment G1, wherein the comparison comprises determining a level of significance.

G3. The storage medium of embodiment G2, wherein determining the level of significance comprises determining a p-value.

G4. The storage medium of any one of embodiments G1 to G3, wherein the reference profile comprises a read density profile obtained from a set of known euploid samples.

G5. The storage medium of any one of embodiments G1 to G4, wherein the reference profile comprises read densities of filtered portions.

G6. The storage medium of any one of embodiments G1 to G5, wherein the reference profile comprises read densities adjusted according to the one or more principle components.

G7. The storage medium of any one of embodiments G2 to G6, wherein the level of significance indicates a statistically significantly difference between the test sample profile and the reference profile, and the presence of a chromosome aneuploidy is determined.

G8. The storage medium of any one of embodiments G1 to G7, wherein the multiple samples comprise a set of known euploid samples.

G9. The storage medium of any one of embodiments G1 to G8, wherein the read densities of portions for the multiple samples are median read densities.

G10. The storage medium of any one of embodiments G1 to G9, wherein the read densities of filtered portions for the test sample are median read densities.

G11. The storage medium of any one of embodiments G4 to G10, wherein the read density profile for the reference profile comprises median read densities.

G12. The storage medium of any one of embodiments G4 to G11, wherein the read densities for the test sample profile, the multiple samples and the reference profile are determined according to a process comprising use of a kernel density estimation.

G13. The storage medium of any one of embodiments G10 to G12, wherein the test sample profile is determined according to the median read densities for the test sample.

G14. The storage medium of any one of embodiments G11 to G13, wherein the reference profile is determined according to the median read density distributions for the reference.

G15. The storage medium of any one of embodiments G1 to G14, wherein the program instructs the microprocessor to filter portions of a reference genome according to a measure of uncertainty for the read density distribution.

G15.1. The storage medium of embodiment G14.1, wherein the measure of uncertainty is a MAD.

G16. The storage medium of any one of embodiments G1 to G15.1, wherein the program instructs the microprocessor to weight counts of sequence reads mapped to filtered portions for the test sample by a process performed prior to (a) comprising:
  (1) generating a fitted relationship between (i) guanine and cytosine (GC) densities and (ii) GC density frequencies for the sequence reads of the test sample, thereby generating a sample GC density relationship, wherein the sequence reads are mapped to the reference genome;
  (2) comparing the sample GC density relationship and a reference GC density relationship, thereby generating a comparison, wherein,
  the reference GC density relationship is between (i) GC densities and (ii) the GC density frequencies for a reference; and
  (3) normalizing the counts of the sequence reads for the sample according to the comparison determined in (b), whereby bias in the sequence reads for the sample is reduced.

G16.1. The storage medium of embodiment G16, wherein the normalizing in (3) comprises providing normalized counts.

G17. The storage medium of embodiment G16 or G16.1, wherein each of the GC densities is determined by a process comprising use of a kernel density estimation.

G17.1. The storage medium of any one of embodiments G16 to G17, wherein each of the GC densities for the reference GC density relationship and the sample GC density relationship is a representation of local GC content.

G17.2. The storage medium of embodiment G17.1, wherein the local GC content is for a polynucleotide segment of 5000 bp or less.

G18. The storage medium of any one of embodiments G16 to G17.2, wherein each of the GC densities is determined by a process comprising use of a sliding window analysis.

G19. The storage medium of embodiment G18, wherein the window is about 5 contiguous nucleotides to about 5000 contiguous nucleotides and the window is slid about 1 base to about 10 bases at a time in the sliding window analysis.

G20. The storage medium of embodiment G19, wherein the window is about 200 contiguous nucleotides and the window is slid about 1 base at a time in the sliding window analysis.

G21. The storage medium of any one of embodiments G16 to G20, wherein (2) comprises generating a fitted relationship between (i) ratios, each of which ratios comprises a sample GC density relationship frequency and a reference GC density relationship frequency for each of the GC densities and (ii) GC densities.

G22. The storage medium of embodiment G21, wherein the fitted relationship in (1) is obtained from a weighted fitting.

G23. The storage medium of any one of embodiments G16 to G22, wherein each of the sequence reads for the sample is represented in a binary format.

G24. The storage medium of embodiment G23, wherein the binary format for each of the sequence reads comprises a chromosome to which the read is mapped and a chromosome position to which the read is mapped.

G25. The storage medium of embodiment G24, wherein the binary format is in a 5-byte format comprising a 1-byte chromosome ordinal and a 4-byte chromosome position.

G26. The storage medium of any one of embodiments G23 to G25, wherein the binary format is 50 times smaller than a sequence alignment/map (SAM) format and/or about 13% smaller than a GZip format.

G27. The storage medium of any one of embodiments G16 to G26, wherein the normalizing in (c) comprises factoring one or more features other than GC density, and normalizing counts of the sequence reads.

G28. The storage medium of embodiment G27, wherein the factoring one or more features is by a process comprising use of a multivariate model.

G29. The storage medium of embodiment G28, wherein the process comprising use of the multivariate model is performed by a multivariate module.

G29.1. The storage medium of any one of embodiments G16 to G29, wherein the program instructs the microprocessor to weight the filtered portions for the test sample.

G29.2. The storage medium of embodiment G29.1, wherein the filtered portions for the test sample are weighted by a process comprising an eigen function.

G30. The storage medium of any one of embodiments G1 to G29.2, wherein the program instructs the microprocessor, prior to (a), to obtain the sequence reads.

G31. The storage medium of embodiment G30, wherein the sequence reads are generated by massively parallel sequencing (MPS).

G32. The storage medium of any one of embodiments G1 to G31, comprising obtaining sequence reads mapped to an entire reference genome or a segment of a genome.

G33. The storage medium of embodiment G32, wherein the segment of the genome comprises a chromosome or a segment thereof.

G34. The storage medium of embodiment G32 or G33, wherein the counts of the sequence reads mapped to the reference genome are normalized prior to (1).

G35. The storage medium of embodiment G34, wherein the counts of the sequence reads mapped to the reference genome are normalized by GC content, bin-wise normalization, GC LOESS, PERUN, GCRM, or combinations thereof.

G36. The storage medium of embodiment G32 or G33, wherein the counts of the sequence reads mapped to the reference genome are raw counts.

G37. The storage medium of any one of embodiments G1 to G36, wherein each portion of the reference genome comprises about an equal length of contiguous nucleotides.

G38. The storage medium of any one of embodiments G1 to G37, wherein each portion of the reference genome comprises about 50 kb.

G39. The storage medium of any one of embodiments G1 to G38, wherein each portion of the reference genome comprises about 100 kb.

G40. The storage medium of any one of embodiments G1 to G39, wherein each portion of the reference genome comprises a segment of contiguous nucleotides in common with an adjacent portion of the reference genome.

G41. The storage medium of any one of embodiments G1 to G40, wherein the test sample comprises blood from a pregnant female.

G42. The storage medium of any one of embodiments G1 to G41, wherein the test sample comprises plasma from a pregnant female.

G43. The storage medium of any one of embodiments G1 to G42, wherein the test sample comprises serum from a pregnant female.

G44 The storage medium of any one of embodiments G1 to G43, wherein nucleic acids are isolated from the test sample.

G45. The storage medium of any one of embodiments G23 to G44, wherein the program instructs a microprocessor to compress the sequence reads mapped to the reference genome in (1) from a sequence alignment format into a binary format.

G46. The storage medium of embodiment G45, wherein the compressing is performed by a compression module.

G47. The storage medium of any one of embodiments G16 to G46, wherein the GC densities and the GC density frequencies for the sequence reads of the test sample and for the reference are provided by a bias density module.

G48. The storage medium of any one of embodiments G16 to G47, wherein the comparison in (2) is generated by a relationship module.

G49. The storage medium of any one of embodiments G17 to G48, wherein the normalizing in (3) is performed by a bias correction module.

G50. The storage medium of any one of embodiments G1 to G49, wherein the read densities are provided by a distribution module.

G51. The storage medium of any one of embodiments G1 to G50, wherein filtered portions are provided by a filtering module.

G51.1. The storage medium of any one of embodiments G29.1 to G51, wherein the filtered portions for the test sample are weighted by a portion weighting module.

G51.1. The storage medium of any one of embodiments G29.1 to G51, wherein the adjusted read densities are provided by a read density adjusting module.

G52. The storage medium of embodiments G51.1, wherein an apparatus comprises one or more of the compression module, the bias density module, the relationship module, the bias correction module, the distribution module, the filtering module, the read density adjusting module and the portion weighting module.

G53. The storage medium of any one of embodiments G1 to G52, wherein the test sample profile comprises a profile of a chromosome or a segment thereof.

G54. The storage medium of any one of embodiments G1 to G53, wherein the reference profile comprises a profile of a chromosome or a segment thereof.

G55. The storage medium of any one of embodiments G1 to G54, wherein the determining in (d) is provided with a specificity equal to or greater than 90% and a sensitivity equal to or greater than 90%.

G56. The storage medium of any one of embodiments G1 to G55, wherein the aneuploidy is a trisomy.

G57. The storage medium of embodiment G56, wherein the trisomy is trisomy 21, trisomy 18, or trisomy 13.

H1. A system comprising memory and one or more microprocessors, which one or more microprocessors are configured to perform, according to instructions in the memory, a process for reducing bias in sequence reads for a sample, which process comprises:
 (a) generating a relationship between (i) local genome bias estimates and (ii) bias frequencies for sequence reads of a test sample, thereby generating a sample bias relationship, wherein,
 the sequence reads are of circulating cell-free nucleic acid from the test sample, and
 the sequence reads are mapped to a reference genome;
 (b) comparing the sample bias relationship and a reference bias relationship, thereby generating a comparison, wherein,
 the reference bias relationship is between (i) local genome bias estimates and (ii) the bias frequencies for a reference; and
 (c) normalizing counts of the sequence reads for the sample according to the comparison determined in (b), whereby bias in the sequence reads for the sample is reduced.

H1.1. A system comprising a sequencing apparatus and one or more computing apparatus,
 which sequencing apparatus is configured to produce signals corresponding to nucleotide bases of a nucleic acid loaded in the sequencing apparatus, which nucleic acid is circulating cell-free nucleic acid from the blood of a pregnant female bearing a fetus, or which nucleic acid loaded in the sequencing apparatus is a modified variant of the circulating cell-free nucleic acid; and
 which one or more computing apparatus comprise memory and one or more processors, which memory comprises instructions executable by the one or more processors and which instructions executable by the one or more processors are configured to:
 produce sequence reads from the signals and map the sequence reads;
 (a) generate a relationship between (i) local genome bias estimates and (ii) bias frequencies for sequence reads of a test sample, thereby generating a sample bias relationship;

(b) compare the sample bias relationship and a reference bias relationship, thereby generating a comparison, wherein, the reference bias relationship is between (i) local genome bias estimates and (ii) the bias frequencies for a reference; and (c) normalize counts of the sequence reads for the sample according to the comparison determined in (b), whereby bias in the sequence reads for the sample is reduced.

H1.2. The system of embodiment H1 or H1.1, wherein the normalizing in (c) comprises providing normalized counts.

H2. The system of any one of embodiments H1 to H1.2, wherein each of the local genome bias estimates is determined by a process comprising use of a kernel density estimation.

H2.1. The system of any one of embodiments H1 to H2, wherein each of the local genome bias estimates for the reference bias relationship and the sample bias relationship is a representation of local bias content.

H2.2. The system of embodiment H2.1, wherein the local bias content is for a polynucleotide segment of 5000 bp or less.

H3. The system of any one of embodiments H1 to H2.2, wherein each of the local genome bias estimates is determined by a process comprising use of a sliding window analysis.

H4. The system of embodiment H3, wherein the window is about 5 contiguous nucleotides to about 5000 contiguous nucleotides and the window is slid about 1 base to about 10 bases at a time in the sliding window analysis.

H5. The system of embodiment H3, wherein the window is about 200 contiguous nucleotides and the window is slid about 1 base at a time in the sliding window analysis.

H6. The system of any one of embodiments H1 to H5, wherein (b) comprises generating a fitted relationship between (i) ratios, each of which ratios comprises a sample bias relationship frequency and a reference bias relationship frequency for each of the local genome bias estimates and (ii) local genome bias estimates.

H7. The system of embodiment H6, wherein the fitted relationship in (a) is obtained from a weighted fitting.

H8. The system of any one of embodiments H1 to H7, wherein each of the sequence reads for the sample is represented in a binary format.

H9. The system of embodiment H8, wherein the binary format for each of the sequence reads comprises a chromosome to which the read is mapped and a chromosome position to which the read is mapped.

H10. The system of embodiment H9, wherein the binary format is in a 5-byte format comprising a 1-byte chromosome ordinal and a 4-byte chromosome position.

H11. The system of any one of embodiments H8 to H10, wherein the binary format is 50 times smaller than a sequence alignment/map (SAM) format and/or about 13% smaller than a GZip format.

H12. The system of any one of embodiments H1 to H11, wherein the normalizing in (c) comprises factoring one or more features other than bias, and normalizing counts of the sequence reads.

H13. The system of embodiment H12, wherein the factoring one or more features is by a process comprising use of a multivariate model.

H14. The system of embodiment H13, wherein the process comprising use of the multivariate model is performed by a multivariate module.

H14.1. The system of any one of embodiments H12 to H14, wherein counts of the sequence reads are normalized according to the normalizing in (c) and the factoring of the one or more features.

H15. The system of any one of embodiments H1 to H14.1, comprising, after (c), generating a read density for one or more portions of a genome, or a segment thereof, according to a process comprising generating a probability density estimation for each of the one or more portions comprising the counts of the sequence reads normalized in (c).

H16. The system of embodiment H15, wherein the probability density estimation is a kernel density estimation.

H17. The system of embodiment H15 or H16, comprising generating a read density profile for the genome or the segment thereof.

H18. The system of embodiment H17, wherein the read density profile comprises the read densities for the one or more portions of the genome, or the segment thereof.

H19. The system of any one of embodiments H15 to H18, comprises adjusting each of the read densities for the one or more portions.

H20. The system of any one of embodiments H15 to H19, wherein the one or more portions are filtered thereby providing filtered portions.

H21. The system of any one of embodiments H15 to H20, wherein the one or more portions are weighted thereby providing weighted portions.

H22. The system of embodiment H21, wherein the one or more portions are weighted by an eigen function.

H23. The system of any one of embodiments H1 to H22, wherein the local genome bias estimates comprise local GC densities and the bias frequencies comprise GC bias frequencies.

H24. The system of any one of embodiments H1 to H23 comprising:

(a) filtering, according to a read density distribution, portions of a reference genome, thereby providing a read density profile for a test sample comprising read densities of filtered portions, wherein, the read densities comprise sequence reads of circulating cell-free nucleic acid from a test sample from a pregnant female, and the read density distribution is determined for read densities of portions for multiple samples;

(b) adjusting the read density profile for the test sample according to one or more principal components, which principal components are obtained from a set of known euploid samples by a principal component analysis, thereby providing a test sample profile comprising adjusted read densities;

(c) comparing the test sample profile to a reference profile, thereby providing a comparison; and (d) determining the presence or absence of a chromosome aneuploidy for the test sample according to the comparison.

H25. The system of embodiment H24, wherein the comparison comprises determining a level of significance.

H26. The system of embodiment H25, wherein determining the level of significance comprises determining a p-value.

H27. The system of any one of embodiments H24 to H26, wherein the reference profile comprises a read density profile obtained from a set of known euploid samples.

H28. The system of any one of embodiments H24 to H27, wherein the reference profile comprises read densities of filtered portions.

H29. The system of any one of embodiments H24 to H28, wherein the reference profile comprises read densities adjusted according to the one or more principle components.

H30. The system of any one of embodiments H25 to H29, wherein the level of significance indicates a statistically significantly difference between the test sample profile and the reference profile, and the presence of a chromosome aneuploidy is determined.

H31. The system of any one of embodiments H24 to H30, wherein the multiple samples comprise a set of known euploid samples.

H32. The system of any one of embodiments H24 to H31, wherein the read densities of portions for the multiple samples are median read densities.

H33. The system of any one of embodiments H24 to H32, wherein the read densities of filtered portions for the test sample are median read densities.

H34. The system of any one of embodiments H27 to H33, wherein the read density profile for the reference profile comprises median read densities.

H35. The system of any one of embodiments H27 to H34, wherein the read densities for the test sample profile, the multiple samples and the reference profile are determined according to a process comprising use of a kernel density estimation.

H36. The system of any one of embodiments H33 to H35, wherein the test sample profile is determined according to the median read densities for the test sample.

H37. The system of any one of embodiments H34 to H36, wherein the reference profile is determined according to the median read density distributions for the reference.

H38. The system of any one of embodiments H24 to H37, comprising filtering portions of a reference genome according to a measure of uncertainty for the read density distribution.

H39. The system of embodiment H38, wherein the measure of uncertainty is a MAD.

H40. The system of any one of embodiments H1 to H39, wherein the memory of the system comprises the sequence reads of circulating cell-free nucleic acid from the test sample that are mapped to the reference genome.

I1. A method for reducing bias in sequence reads for a sample comprising:
  (a) generating, using a microprocessor, a relationship between (i) local genome bias estimates and (ii) bias frequencies for sequence reads of a test sample, thereby generating a sample bias relationship, wherein,
  the sequence reads are of circulating cell-free nucleic acid from the test sample, and
  the sequence reads are mapped to a reference genome;
  (b) comparing the sample bias relationship and a reference bias relationship, thereby generating a comparison, wherein,
  the reference bias relationship is between (i) local genome bias estimates and (ii) the bias frequencies for a reference; and
  (c) normalizing counts of the sequence reads for the sample according to the comparison determined in (b), whereby bias in the sequence reads for the sample is reduced.

I1.1. A method for reducing bias in sequence reads for a sample comprising:
  loading a sequencing apparatus with circulating cell-free nucleic acid from the blood of a pregnant female bearing a fetus, or loading the sequencing apparatus with a modified variant of the nucleic acid, which sequencing apparatus produces signals corresponding to nucleotide bases of the nucleic acid;
  generating sequence reads from the signals of the nucleic acid by, after optionally transferring the signals to, a system comprising one or more computing apparatus, wherein the one or more computing apparatus in the system comprise memory and one or more processors, and
  wherein one computing apparatus, or combination of computing apparatus, in the system is configured to:
  map the sequence reads to a reference genome;
  (a) generate, using a microprocessor, a relationship between (i) local genome bias estimates and (ii) bias frequencies for sequence reads of a test sample, thereby generating a sample bias relationship, wherein,
  the sequence reads are of circulating cell-free nucleic acid from the test sample, and
  the sequence reads are mapped to a reference genome;
  (b) compare the sample bias relationship and a reference bias relationship, thereby generating a comparison, wherein,
  the reference bias relationship is between (i) local genome bias estimates and (ii) the bias frequencies for a reference; and
  (c) normalize counts of the sequence reads for the sample according to the comparison determined in (b), whereby bias in the sequence reads for the sample is reduced.

I1.2. The method of embodiment I1 or I1.1, wherein the normalizing in (c) comprises providing normalized counts.

I2. The method of embodiment I1, I1.1 or I1.2, wherein each of the local genome bias estimates is determined by a process comprising use of a kernel density estimation.

I2.1. The method of any one of embodiments I1 to I2, wherein each of the local genome bias estimates for the reference bias relationship and the sample bias relationship is a representation of local bias content.

I2.2. The method of embodiment I2.1, wherein the local bias content is for a polynucleotide segment of 5000 bp or less.

I3. The method of any one of embodiments I1 to I2.2, wherein each of the local genome bias estimates is determined by a process comprising use of a sliding window analysis.

I4. The method of embodiment I3, wherein the window is about 5 contiguous nucleotides to about 5000 contiguous nucleotides and the window is slid about 1 base to about 10 bases at a time in the sliding window analysis.

I5. The method of embodiment I3, wherein the window is about 200 contiguous nucleotides and the window is slid about 1 base at a time in the sliding window analysis.

I6. The method of any one of embodiments I1 to I5, wherein (b) comprises generating a fitted relationship between (i) ratios, each of which ratios comprises a sample bias relationship frequency and a reference bias relationship frequency for each of the local genome bias estimates and (ii) local genome bias estimates.

I7. The method of embodiment I6, wherein the fitted relationship in (a) is obtained from a weighted fitting.

I8. The method of any one of embodiments I1 to I7, wherein each of the sequence reads for the sample is represented in a binary format.

I9. The method of embodiment I8, wherein the binary format for each of the sequence reads comprises a chromosome to which the read is mapped and a chromosome position to which the read is mapped.

I10. The method of embodiment I9, wherein the binary format is in a 5-byte format comprising a 1-byte chromosome ordinal and a 4-byte chromosome position.

I11. The method of any one of embodiments I8 to I10, wherein the binary format is 50 times smaller than a sequence alignment/map (SAM) format and/or about 13% smaller than a GZip format.

I12. The method of any one of embodiments I1 to I11, wherein the normalizing in (c) comprises factoring one or more features other than bias, and normalizing counts of the sequence reads.

I13. The method of embodiment I12, wherein the factoring one or more features is by a process comprising use of a multivariate model.

I14. The method embodiment of I13, wherein the process comprising use of the multivariate model is performed by a multivariate module.

I14.1. The method of any one of embodiments I12 to I14, wherein counts of the sequence reads are normalized according to the normalizing in (c) and the factoring of the one or more features.

I15. The method of any one of embodiments I1 to I14.1, comprising, after (c), generating a read density for one or more portions of a genome, or a segment thereof, according to a process comprising generating a probability density estimation for each of the one or more portions comprising the counts of the sequence reads normalized in (c).

I16. The method of embodiment I15, wherein the probability density estimation is a kernel density estimation.

I17. The method of embodiment I15 or I16, comprising generating a read density profile for the genome or the segment thereof.

I18. The method of embodiment I17, wherein the read density profile comprises the read densities for the one or more portions of the genome, or the segment thereof.

I19. The method of any one of embodiments I15 to I18, comprises adjusting each of the read densities for the one or more portions.

I20. The method of any one of embodiments I15 to I19, wherein the one or more portions are filtered thereby providing filtered portions.

I21. The method of any one of embodiments I15 to I20, wherein the one or more portions are weighted thereby providing weighted portions.

I22. The method of embodiment I21, wherein the one or more portions are weighted by an eigen function.

I23. The method of any one of embodiments I1 to I22, wherein the local genome bias estimates comprise local GC densities and the bias frequencies comprise GC bias frequencies.

I23.1. The method of any one of embodiments I1 to I23 comprising:
  (a) filtering, according to a read density distribution, portions of a chromosome in a reference genome, thereby providing a read density profile for a test sample comprising read densities of filtered portions, wherein,
  the read densities comprise sequence reads of circulating cell-free nucleic acid from a test sample from a pregnant female, and
  the read density distribution is determined for read densities of portions for multiple samples;
  (b) adjusting the read density profile of a chromosome for the test sample according to one or more principal components, which principal components are obtained from a set of known euploid samples by a principal component analysis, thereby providing a test sample chromosome profile comprising adjusted read densities;
  (c) comparing the test sample chromosome profile to a reference profile, thereby providing a comparison; and
  (d) determining the presence or absence of a chromosome aneuploidy for the test sample according to the comparison.

I24. The method of any one of embodiments I1 to I23 comprising:
  (a) filtering, according to a read density distribution, portions of a reference genome, thereby providing a read density profile for a test sample comprising read densities of filtered portions, wherein,
  the read densities comprise sequence reads of circulating cell-free nucleic acid from a test sample from a pregnant female, and
  the read density distribution is determined for read densities of portions for multiple samples;
  (b) adjusting the read density profile for the test sample according to one or more principal components, which principal components are obtained from a set of known euploid samples by a principal component analysis, thereby providing a test sample profile comprising adjusted read densities;
  (c) comparing the test sample profile to a reference profile, thereby providing a comparison; and
  (d) determining the presence or absence of a chromosome aneuploidy for the test sample according to the comparison.

I24.1. The method of embodiment I23.1 or I24, wherein the read density profile is adjusted in (b) by 1 to 10 principal components.

I24.2. The method of embodiment I23.1, I24 or I24.1, wherein the read density profile is adjusted in (b) by 5 principal components.

I24.3. The method of any one of embodiments I23.1 to I24.2, wherein the one or more principal components adjust for one or more features in a read density profile, which features are selected from fetal gender, sequence bias, fetal fraction, bias correlated with DNase I sensitivity, entropy, repetitive sequence bias, chromatin structure bias, polymerase error-rate bias, palindrome bias, inverted repeat bias, PCR amplification bias, and hidden copy number variation.

I24.4. The method of embodiment I24.3, wherein sequence bias comprises guanine and cytosine (GC) bias.

I25. The method of any one of embodiments I23.1 to I24.4, wherein the comparison comprises determining a level of significance.

I26. The method of embodiment I25, wherein determining the level of significance comprises determining a p-value.

I27. The method of any one of embodiments I23.1 to I26, wherein the reference profile comprises a read density profile obtained from a set of known euploid samples.

I28. The method of any one of embodiments I23.1 to I27, wherein the reference profile comprises read densities of filtered portions.

I29. The method of any one of embodiments I23.1 to I28, wherein the reference profile comprises read densities adjusted according to the one or more principle components.

I30. The method of any one of embodiments I25 to I29, wherein the level of significance indicates a statistically significantly difference between the test sample profile and the reference profile, and the presence of a chromosome aneuploidy is determined.

I31. The method of any one of embodiments I23.1 to I30, wherein the multiple samples comprise a set of known euploid samples.

I32. The method of any one of embodiments I23.1 to I31, wherein the read densities of portions for the multiple samples are median read densities.

I33. The method of any one of embodiments I23.1 to I32, wherein the read densities of filtered portions for the test sample are median read densities.

I34. The method of any one of embodiments I27 to I33, wherein the read density profile for the reference profile comprises median read densities.

I35. The method of any one of embodiments I27 to I34, wherein the read densities for the test sample profile, the multiple samples and the reference profile are determined according to a process comprising use of a kernel density estimation.

I36. The method of any one of embodiments I33 to I35, wherein the test sample profile is determined according to the median read densities for the test sample.

I37. The method of any one of embodiments I34 to I36, wherein the reference profile is determined according to the median read density distributions for the reference.

I38. The method of any one of embodiments I23.1 to I37, comprising filtering portions of a reference genome according to a measure of uncertainty for the read density distribution.

I39. The method of embodiment I38, wherein the measure of uncertainty is a MAD.

I40. The method of any one of embodiments I23.1 to I39, wherein the test sample profile is representative of chromosome dosage for the test sample.

I41. The method of embodiment I40, comprising comparing chromosome dosage for a test sample profile to chromosome dosage for a reference profile, thereby generating a chromosome dosage comparison.

I42. The method of embodiment I41, comprising determining the presence or absence of a chromosome aneuploidy for the test sample is according to the chromosome dosage comparison.

I43. The method of embodiment I42, wherein determining the presence or absence of a chromosome aneuploidy for the test sample comprises identifying the presence or absence of one copy of a chromosome, two copies of a chromosome, three copies of a chromosome, four copies of a chromosome, five copies of a chromosome, a deletion of one or more segments of a chromosome or an insertion of one or more segments of chromosome.

J1. A method for determining the presence or absence of an aneuploidy, comprising:
(a) obtaining counts of partial nucleotide sequence reads mapped to genomic portions of a reference genome, which partial nucleotide sequence reads are reads of circulating cell-free nucleic acid from a test sample from a pregnant female, wherein at least some of the partial nucleotide sequence reads comprise:
  i) multiple nucleobase gaps between identified nucleobases, or
  ii) one or more nucleobase classes, wherein each nucleobase class comprises a subset of nucleobases present in the sample nucleic acid, or
  a combination of (i) and (ii),
(b) filtering, according to a read density distribution, portions of a reference genome, thereby providing a read density profile for the test sample comprising read densities of filtered portions, wherein,
  the read densities comprise partial nucleotide sequence reads from the test sample, and
  the read density distribution is determined for read densities of portions for multiple samples;
(c) adjusting the read density profile for the test sample according to one or more principal components, which principal components are obtained from a set of known euploid samples by a principal component analysis, thereby providing a test sample profile comprising adjusted read densities;
(d) comparing the test sample profile to a reference profile, thereby providing a comparison; and
(e) determining the presence or absence of an aneuploidy for the test sample according to the comparison.

J2. A method for determining fetal fraction based on a copy number variation, comprising:
(a) obtaining counts of nucleic acid sequence reads mapped to genomic portions of a reference genome, which sequence reads are reads of circulating cell-free nucleic acid from a test sample from a pregnant female;
(b) normalizing the counts mapped to the genomic portions of the reference genome, thereby providing normalized counts for the genomic portions; wherein the normalizing comprises:
  (i) filtering, according to a read density distribution, portions of the reference genome, thereby providing a read density profile for the test sample comprising read densities of filtered portions, wherein,
  the read densities comprise nucleotide sequence reads from the test sample, and
  the read density distribution is determined for read densities of portions for multiple samples; and
  (ii) adjusting the read density profile for the test sample according to one or more principal components, which principal components are obtained from a set of known euploid samples by a principal component analysis, thereby providing a test sample profile comprising adjusted read densities
(c) identifying a first level of the normalized counts significantly different than a second level of the normalized counts, which first level is for a first set of genomic portions, and which second level is for a second set of genomic portions;
(d) assigning a copy number variation to the first level, thereby providing a categorization; and
(e) determining a fetal fraction of the circulating cell-free nucleic acid according to the categorization, whereby the fetal fraction is generated from the nucleic acid sequence reads.

J3. A method for determining the fraction of fetal nucleic acid in circulating cell-free nucleic acid from the blood of a pregnant female, comprising:
(a) obtaining counts of nucleic acid sequence reads mapped to genomic portions of a reference genome, which sequence reads are reads of circulating cell-free nucleic acid from a test sample from a pregnant female bearing a male fetus;
(b) generating an experimental X chromosome representation, which experimental X chromosome representation is a ratio of (i) counts of sequence reads mapped to the genomic portions of the reference genome in the X chromosome, and (ii) counts of sequence reads mapped to genomic portions of the reference genome in the genome or segment thereof; and
(c) from the experimental X chromosome representation, determining the fraction of fetal nucleic acid in the blood of the pregnant female according to the experimental X chromosome representation and an expected X chromosome representation, which expected X chromosome representation is a ratio of (i) the number of the genomic portions of the reference genome in the X chromosome, and (ii) the number of the genomic portions of the reference genome in the genome or segment thereof, wherein the counts in (b) are normalized by a process comprising:
(1) filtering, according to a read density distribution, portions of the reference genome, thereby providing a read density profile for the test sample comprising read densities of filtered portions, wherein,
the read densities comprise nucleotide sequence reads from the test sample, and
the read density distribution is determined for read densities of portions for multiple samples; and
(2) adjusting the read density profile for the test sample according to one or more principal components, which principal components are obtained from a set of known euploid samples by a principal component analysis, thereby providing a test sample profile comprising adjusted read densities.

J4. A method for determining fetal ploidy according to nucleic acid sequence reads, comprising:
(a) determining a fraction of fetal nucleic acid in a test sample, which test sample comprises circulating cell-free nucleic acid from a pregnant female;
(b) obtaining counts of sequence reads mapped to portions of a reference genome, which sequence reads are from the nucleic acid in the sample;
(c) calculating a genomic section level for each of the portions of the reference genome, thereby providing calculated genomic section levels; and
(d) determining fetal ploidy according to a relationship between (i) the calculated genomic section levels for a subset of portions of the reference genome and (ii) the fraction of fetal nucleic acid determined in (a), wherein the counts in (b) are normalized by a process comprising:
(1) filtering, according to a read density distribution, portions of the reference genome, thereby providing a read density profile for the test sample comprising read densities of filtered portions, wherein,
the read densities comprise nucleotide sequence reads from the test sample, and
the read density distribution is determined for read densities of portions for multiple samples; and
(2) adjusting the read density profile for the test sample according to one or more principal components, which principal components are obtained from a set of known euploid samples by a principal component analysis, thereby providing a test sample profile comprising adjusted read densities.

J5. A method for determining the presence or absence of a fetal aneuploidy, comprising:
(a) obtaining counts of nucleotide sequence reads mapped to reference genome portions, wherein the nucleotide sequence reads are reads of circulating cell-free nucleic acid from a test sample from a pregnant female;
(b) normalizing the counts for a first genome portion by a process comprising subtracting the expected count from the counts for the first genome portion, thereby generating a subtraction value, and dividing the subtraction value by an estimate of the variability of the counts, or normalizing, using a microprocessor, a derivative of the counts for the first genome portion, thereby obtaining a normalized sample count, which expected count, or derivative of the expected count, is obtained for a group comprising samples, references, or samples and references, exposed to one or more common experimental conditions; and
(c) determining the presence or absence of a fetal aneuploidy based on the normalized sample count, wherein normalizing the counts in (b) further comprises:
(1) filtering, according to a read density distribution, portions of the reference genome, thereby providing a read density profile for the test sample comprising read densities of filtered portions, wherein,
the read densities comprise nucleotide sequence reads from the test sample, and
the read density distribution is determined for read densities of portions for multiple samples; and
(2) adjusting the read density profile for the test sample according to one or more principal components, which principal components are obtained from a set of known euploid samples by a principal component analysis, thereby providing a test sample profile comprising adjusted read densities.

J6. A method for determining sex chromosome karyotype in a fetus, comprising:
(a) obtaining counts of nucleotide sequence reads mapped to portions of a reference genome, which sequence reads are reads of circulating cell-free nucleic acid from a test sample from a pregnant female;
(b) determining an experimental bias for each of the portions of the reference genome for multiple samples from a fitted relation for each sample between (i) the counts of the sequence reads mapped to each of the portions of the reference genome, and (ii) a mapping feature for each of the portions;
(c) calculating a genomic section level for each of the portions of the reference genome from a fitted relation between the experimental bias and the counts of the sequence reads mapped to each of the portions of the reference genome, thereby providing calculated genomic section levels; and
(d) determining sex chromosome karyotype for the fetus according to the calculated genomic section levels, wherein determining an experimental bias in (b) further comprises:
(1) filtering, according to a read density distribution, portions of the reference genome, thereby providing a read density profile for the test sample comprising read densities of filtered portions, wherein,
the read densities comprise nucleotide sequence reads from the test sample, and
the read density distribution is determined for read densities of portions for multiple samples; and
(2) adjusting the read density profile for the test sample according to one or more principal components, which principal components are obtained from a set of known euploid samples by a principal component analysis, thereby providing a test sample profile comprising adjusted read densities.

J7. A method for determining the presence or absence of an aneuploidy, comprising:
(a) obtaining counts of sequence reads mapped to chromosomes 13, 18 and 21, or segments thereof, in a reference genome, which sequence reads are reads of circulating cell-free nucleic acid from a test sample from a pregnant female;
(b) determining three ratios or ratio values, each of which three ratios is a ratio of (i) counts mapped to each of chromosomes 13, 18 and 21, or segments thereof, to (ii)

counts mapped to each of the other chromosomes 13, 18 and 21, or segments thereof;

(c) comparing the three ratios or ratio values, thereby generating a comparison; and (d) determining the presence or absence of a chromosome aneuploidy based on the comparison generated in (c), with the proviso that the comparison generated in (c) and the determination in (d) are not based on segments of the genome other than in chromosomes 13, 18 and 21; whereby the determination of the presence or absence of the chromosome aneuploidy is generated from the sequence reads, wherein the counts of sequence reads mapped to chromosomes 13, 18, and 21 or segments thereof are normalized by a process comprising:

(1) filtering, according to a read density distribution, portions of the reference genome, thereby providing a read density profile for the test sample comprising read densities of filtered portions, wherein, the read densities comprise nucleotide sequence reads from the test sample, and the read density distribution is determined for read densities of portions for multiple samples; and (2) adjusting the read density profile for the test sample according to one or more principal components, which principal components are obtained from a set of known euploid samples by a principal component analysis, thereby providing a test sample profile comprising adjusted read densities.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (e.g., plus or minus 10%), and use of the term "about" at the beginning of a string of values modifies each of the values (e.g., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed can be resorted to by those skilled in the art, and such modifications and variations are considered within the scope of this technology.

Certain embodiments of the technology are set forth in the claim(s) that follow(s).

What is claimed is:

1. A computer-implemented method for reducing bias in sequence reads for a test sample, the method comprising:

(a) sequencing circulating cell-free nucleic acid from a test sample by a non-targeted multiplexed massively parallel sequencing process, thereby generating at least one million sequence reads for the test sample, and mapping the sequence reads to a complete reference genome thereby generating mapped sequence reads:

(b) normalizing, using a microprocessor, counts of the mapped sequence reads by a process comprising:

(1) fitting (i) guanine and cytosine (GC) densities and (ii) GC density frequencies; for the mapped sequence reads of the test sample; thereby generating a test sample GC density fit; and (2) adjusting counts of the mapped sequence reads for the test sample by comparing the test sample GC density fit with a second GC density relationship, wherein the second GC density relationship is between (i) GC densities and (ii) GC density frequencies for a complete reference genome, wherein the adjusted sequence read counts have different GC bias compared with GC bias in the sequence read counts for the test sample prior to normalization;

(c) generating; using the microprocessor, (i) read densities from the normalized mapped sequence read counts using a probability density estimation, and (ii) a read density profile from the read densities; and (d) removing a plurality of biases from the read density profile for the test sample using a principal component analysis by:

(i) fitting a multivariate model between differences in the read density profile for the test sample with a training set density profile that includes a plurality of identified principal components, wherein the training set density profile is obtained from a training set of samples; and (ii) adjusting counts of the read density profile for the test sample to remove principal components from the read density profile that correspond to the identified principal components of the training set density profile, thereby generating an adjusted read density profile for the test sample that excludes the plurality of biases from the read density profile.

2. The method of claim 1, wherein the read density profile is adjusted in (d)(ii) by 2 to 10 principal components.

3. The method of claim 1, wherein the read density profile is adjusted in (d)(ii) by 5 principal components.

4. The method of claim 1, wherein the plurality of principal components represent a plurality of biases in a read density profile, which biases are selected from fetal gender, sequence bias, fetal fraction, bias correlated with DNase I sensitivity, entropy, repetitive sequence bias, chromatin structure bias, polymerase error-rate bias, palindrome bias, inverted repeat bias, PCR amplification bias, and hidden copy number variation.

5. The method of claim 4, wherein the sequence bias comprises guanine and cytosine (GC) bias.

6. The method of claim 1, further comprising determining a presence or absence of a chromosome aneuploidy according to the adjusted read density profile and a reference profile that is obtained from one or more reference samples, by comparing the adjusted read density profile to the reference profile, wherein the comparing comprises determining a level of significance.

7. The method of claim 6, wherein determining the level of significance comprises determining a p-value.

8. The method of claim 6, wherein the level of significance indicates a statistically significant difference between the adjusted read density profile and the reference profile, and the presence of a chromosome aneuploidy is determined.

9. The method of claim 1, wherein the reference profile in (e) comprises:
(i) a read density profile obtained from the one or more reference samples, wherein the one or more reference samples are known euploid samples; and
(ii) read densities adjusted according to the plurality of principal components.

10. The method of claim 9, wherein:
(i) the principal components are obtained from median read densities for the samples in the training set; and
(ii) the read density profile for the reference profile comprises median read densities.

11. The method of claim 10, wherein the read densities for the read density profile for the test sample, the read densities for the samples in the training set, and the read densities for the reference profile are determined according to a process comprising use of a kernel density estimation.

12. The method claim 10, wherein the read density profile for the test sample is determined according to median read densities for the test sample; and the reference profile is determined according to median read density distributions for the one or more reference samples.

13. The method of claim 1, wherein the read density profile for the test sample is representative of chromosome dosage for the test sample.

14. The method of claim 13, further comprising comparing chromosome dosage for the read density profile for the test sample to chromosome dosage for the reference profile, thereby generating a chromosome dosage comparison.

15. The method of claim 14, further comprising determining presence or absence of a chromosome aneuploidy by using the chromosome dosage comparison.

16. The method of claim 14, wherein the chromosome dosage comparison is for the same chromosome.

17. The method of claim 14, wherein the chromosome dosage comparison is for different chromosomes.

18. The method of claim 1, further comprising determining presence or absence of a chromosome aneuploidy by identifying presence or absence of one or more copies of a chromosome, a deletion of one or more segments of a chromosome, or an insertion of one or more segments of a chromosome.

19. The method of claim 1, wherein GC bias in the adjusted sequence read counts for the test sample is reduced compared to the sequence read counts before normalizing in (b).

20. The method of claim 1, wherein (c) comprises filtering, according to a read density distribution, portions of the reference genome, thereby providing the read density profile for the test sample comprising read densities of filtered portions, wherein:
(1) the read densities comprise the sequence reads of circulating cell-free nucleic acid from the test sample, and
(2) the read density distribution is determined for read densities of portions for multiple samples.

21. The method of claim 20, wherein the multiple samples comprise a set of known euploid samples.

22. The method of claim 20, comprising filtering portions of the reference genome according to a measure of uncertainty for the read density distribution.

23. The method of claim 22, wherein the measure of uncertainty is a median absolute deviation (MAD).

24. The method of claim 1, wherein the training set of samples comprises known euploid samples.

25. The method of claim 1, wherein the sequencing process in (a) is performed with 1-fold coverage or fraction thereof.

26. The method of claim 1, wherein the reference genome or part thereof in (b)(2)(ii) comprises a reference sequence or reference sequences from one or more reference samples.

27. The method of claim 1, wherein the reference genome or part thereof in (b)(2)(ii) comprises a reference sequence or reference sequences from an external reference.

28. The method of claim 1, wherein millions of nucleic acid fragments are sequenced in (a).

29. The method of claim 1, wherein the training set of samples comprises at least 500 known euploid samples.

* * * * *